(12) United States Patent
Molinero et al.

(10) Patent No.: US 11,236,394 B2
(45) Date of Patent: Feb. 1, 2022

(54) METHODS AND COMPOSITIONS FOR PROGNOSIS AND TREATMENT OF CANCERS

(71) Applicant: Genentech, Inc., South San Francisco, CA (US)

(72) Inventors: Luciana Molinero, South San Francisco, CA (US); Priti Hegde, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 15/609,473

(22) Filed: May 31, 2017

(65) Prior Publication Data

US 2017/0260594 A1  Sep. 14, 2017

Related U.S. Application Data

(63) Continuation of application No. PCT/US2015/067878, filed on Dec. 29, 2015.

(60) Provisional application No. 62/098,055, filed on Dec. 30, 2014.

(51) Int. Cl.
*C12Q 1/6886* (2018.01)

(52) U.S. Cl.
CPC ..... *C12Q 1/6886* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| 2011/0070268 | A1  | 3/2011  | Brichard et al. | |
|---|---|---|---|---|
| 2012/0219559 | A1* | 8/2012  | Chen | C07K 14/70521 424/152.1 |
| 2012/0258878 | A1* | 10/2012 | Saad | G01N 33/57423 506/9 |
| 2013/0309250 | A1* | 11/2013 | Cogswell | C07K 16/2827 424/172.1 |

FOREIGN PATENT DOCUMENTS

| EP | 2484762 A1 | 8/2012 |
|---|---|---|
| EP | 2615181 A1 | 7/2013 |
| JP | 2013-505008 A | 2/2013 |
| WO | WO-2011/033095 A1 | 3/2011 |
| WO | WO-2011/094483 A2 | 8/2011 |
| WO | WO-2014/023706 A1 | 2/2014 |
| WO | WO-2014/078468 A2 | 5/2014 |

OTHER PUBLICATIONS

Enard et al. (Science 2002 vol. 296 p. 340) (Year: 2002).*
Cobb et al. (Crit Care Med 2002 vol. 30 p. 2711) (Year: 2002).*
Quezada et al. (J clin Invest 2006 vol. 116 p. 1935) (Year: 2006).*
Affymetrix U133 Microarray (www.affymetrix.com downloaded Jan. 17, 2021). (Year: 2021).*
International Search Report and Written Opinion for International Patent Application No. PCT/US2015/067878, dated Jul. 11, 2016 (15 pages).
Invitation to Pay Additional Fees for International Patent Application No. PCT/US2015/067878, dated May 2, 2016 (6 pages).
International Preliminary Report on Patentability for International Patent Application No. PCT/US2015/067878 dated Jul. 4, 2017 (8 pages).
Onishi et al., "New Immunotherapy Against Cancer: A Therapy to Control Regulatory T Cell," Fukuoka Igaku Zasshi. 101(10):207-14 (2010) (20 pages).
Notice of Reasons for Rejection for Japanese Patent Application No. 2017-534648, dated Nov. 26, 2019 (8 pages).
English Translation of First Office Action for Chinese Patent Application No. 201580070110.8, dated Nov. 4, 2020 (9 pages).
Notice of Reasons for Rejection for Japanese Patent Application No. 2017-534648, dated Sep. 1, 2020 (3 pages).
Generali et al., "Immunomodulation of FOXP3+ Regulatory T Cells by the Aromatase Inhibitor Letrozole in Breast Cancer Patients," Clin. Cancer. Res. 15(3): 1046-1051 (2009) (6 pages).
Yuan et al., "Elevated Expression of Foxp3 in tumor-infiltrating Treg Cells suppresses T-cell proliferation and contributes to gastric cancer progression in a COX-2-dependent manner," Clinical Immunology. 134(3):277-288 (2010) (13 pages).
Tsai et al., "Lentiviral-mediated Foxp3 RNAi suppresses tumor growth of regulatory T cell-like leukemia in a murine tumor model," Gene Therapy. 17:972-979 (2010) (9 pages).
Decision of Rejection for Japanese Patent Application No. 2017-534648, dated Aug. 3, 2021 (4 pages).

* cited by examiner

*Primary Examiner* — Katherine D Salmon
(74) *Attorney, Agent, or Firm* — Clark & Elbing LLP; Karen L. Elbing

(57) ABSTRACT

The invention provides methods of using expression levels of one or more immune cell gene signatures and/or combinations of immune cell gene signatures as selection criteria for selecting a patient having cancer for treatment with an immunotherapy. The invention further provides methods for selecting a patient having cancer who may benefit from a particular immunotherapy, such as an activating immunotherapy or a suppressing immunotherapy and administering to the patient the activating immunotherapy or suppressing immunotherapy to treat the cancer.

13 Claims, 49 Drawing Sheets

(17 of 49 Drawing Sheet(s) Filed in Color)

METHODS AND COMPOSITIONS FOR PROGNOSIS AND TREATMENT OF CANCERS

FIELD OF INVENTION

The present invention is directed to methods for selecting cancer patients for treatment with an immunotherapy.

BACKGROUND OF THE INVENTION

Studies in humans with immune checkpoint inhibitors have demonstrated the promise of harnessing the immune system to control and eradicate tumor growth in difficult to treat indications including melanoma, renal cell carcinoma, lung cancer, breast cancer, ovarian cancer, colorectal cancer, gastric cancer, liver cancer, and bladder cancer.

Tumors arise from normal cells that accumulate mutations leading to uncontrolled cellular proliferation and survival under conditions of stress. In normal circumstances, the immune system, mainly through cytotoxic CD8 T cells, recognizes these transformed cells and prevents the invasion into normal tissue. In certain circumstances, tumor cells escape immune control and progress to disease. The mechanisms of tumor escape may be the product of one or more of the following mechanisms: inability of tumor cells to present neo-antigens on MHC Class I molecules, down-regulation of MHC Class I molecules on tumor cells, inability of T cells to infiltrate the tumor, increased presence of immunosuppressive regulatory T cells or myeloid suppressor cells, enhanced expression of immune checkpoint inhibitors, or increased Th2 and Th17 mediators. The relative contributions of these various immune cell subsets across cancer types and their affects on tumor progression, treatment response, and clinical outcomes are poorly studied.

Accordingly, there is a need for methods for selecting patients who are likely to respond to immuno-based therapies and to develop alternative strategies for the treatment of cancer.

SUMMARY OF THE INVENTION

In one aspect, the invention features a method of selecting a patient having cancer for treatment with an immunotherapy, the method comprising determining the expression level of an immune cell gene signature in a biological sample obtained from the patient, the immune cell gene signature comprising one or more of the following genes (e.g., 1, 2, 3, 4, 5, 6, 7, 8, 9, 10, 11, 12, 13, 14, 15, 16, 17, 18, 19, or 20 or more of the following genes): CD8A, GZMA, GZMB, IFNγ, EOMES, or PRF1; FOXP3; MS4A1 or CD48; CD79A, MS4A1, CD19, STAP1, KIAA0125, POU2AF1, or FCRL5; NCAM1 or NKP46; KLRC3, KLRK1, KLRC2, or KLRD1; ITGAM, ITGAX, CD1C, or CLEC4C; CD68, CD163, ITGAM, ITGAX, or CD14; LAPTM5, LAIR1, CD4, CSF1R, CD163, ADAP2, CD68, MRC1, CD45RO, SLA, MSR1, FPR3, FCGR2A, or FCGR3A; IL17A or IL17F; CCL2, IL1B, IL8, IL6, or PTGS2; CD3D, CD3E, CD2, CD3G, CD6, TRAT1, CD28, or LCK; CTLA4, BTLA, LAG3, HAVCR2, or PDCD1; CTLA4, BTLA, LAG3, HAVCR2, PDCD1, or TIGIT; CD276, PDL1, PDL2, or IDO1; CD274, PDL2, IDO1, or PVR; CX3CL1, CXCL9, CXCL10, CXCR3, CCL21, or CCL22; CD4, IL2RA, or CD69; TAPBP, TAP1, TAP2, PSMB9, or PSMB8; CD40, CD80, CD86, CD70, or GITRL; CD27, CD28, ICOS, TNFRSF4, TNFRSF14, TNFRSF18, TNFSF14, or CD226; GNLY, KLRK1, KLRB1, GZMH, GZMA, KLRD1, or NKG7; or FAP, FN1, MMP2, BGN, LOXL2, PDPN, PDGFRB, COL4A1, COL4A2, COL5A1, or COL8A1, wherein a change in the level of expression of the one or more genes in the immune cell gene signature relative to a median level identifies a patient for treatment with an immunotherapy.

In some embodiments, the method further comprises the step of informing the patient that they have an increased likelihood of being responsive to the immunotherapy. In some embodiments, the method further comprises the step of providing a recommendation to the patient for a particular immunotherapy. In some embodiments, the method further comprises the step of administering an immunotherapy to the patient if it is determined that the patient may benefit from the immunotherapy. In some embodiments, the immunotherapy is an activating immunotherapy or a suppressing immunotherapy.

In some embodiments, the expression level of one or more of CD8A, GZMA, GZMB, IFNγ, EOMES, or PRF1 is correlated with the presence of T effector ($T_{eff}$) cells in the tumor microenvironment. In some embodiments, an increase in expression level of one or more of CD8A, GZMA, GZMB, IFNγ, EOMES, or PRF1 indicates that the patient is likely to benefit from an activating immunotherapy. In some embodiments, the activating immunotherapy comprises a CD28, OX40, GITR, CD137, CD27, ICOS, HVEM, NKG2D, MICA, or 2B4 agonist.

In some embodiments, the expression level of FOXP3 is correlated to the presence of T regulatory ($T_{reg}$) cells in the tumor microenvironment. In some embodiments, an increase in expression level of FOXP3 indicates that the patient is likely to benefit from a suppressing immunotherapy. In some embodiments, the suppressing immunotherapy comprises a CTLA-4, PD-1 axis, TIM-3, BTLA, VISTA, LAG-3, B7H4, CD96, TIGIT, or CD226 antagonist.

In some embodiments, the expression level of (a) one or more of MS3A1 or CD48 and/or (b) one or more of CD79A, MS4A1, CD19, STAP1, KIAA0125, POU2AF1, or FCRL5 is correlated with the presence of B cells in the tumor microenvironment. In some embodiments, the expression level of (a) one or more of NCAM1 or NKP46 and/or (b) KLRC3, KLRK1, KLRC2, or KLRD1 is correlated with the presence of NK cells in the tumor microenvironment. In some embodiments, the expression level of one or more of ITGAM, ITGAX, CD1C, or CLEC4C is correlated with the presence of myeloid cells in the tumor microenvironment. In some embodiments, the expression level of one or more of CD68, CD163, ITGAM, ITGAX, or CD14 is correlated with the presence of macrophage cells in the tumor microenvironment. In some embodiments, the expression level of one or more of LAPTM5, LAIR1, CD4, CSF1R, CD163, ADAP2, CD68, MRC1, CD45RO, SLA, MSR1, FPR3, FCGR2A, or FCGR3A is correlated with the presence of M2 macrophage cells in the tumor microenvironment. In some embodiments, the expression level of one or more of IL17A or IL17F is correlated with the presence of Th17 cells in the tumor microenvironment. In some embodiments, the expression level of one or more of CCL2, IL1B, IL8, IL6, or PTGS2 is correlated with the presence of inflammatory cells in the tumor microenvironment. In some embodiments, the expression level of (a) one or more of CTLA4, BTLA, LAG3, HAVCR2, or PDCD1 and/or (b) one or more of CTLA4, BTLA, LAG3, HAVCR2, PDCD1, or TIGIT is correlated with the presence of T cell immune blockers in the tumor microenvironment. In some embodiments, the expression level of (a) one or more of CD276, PDL1, PDL2, or IDO1 and/or (b) one or more of CD274, PDL2, IDO1, or PVR is correlated to the presence of antigen presenting cell (APC) immune blockers in the tumor microenvironment. In some embodiments, the expression level of one or more of CX3CL1, CXCL9, CXCL10, CXCR3, CCL21, or CCL22 is correlated to T cell chemotaxis. In some embodiments, the expression level of one or more of CD4, IL2RA, or CD69 is correlated with the presence of activated CD4 T cells in the tumor microenvironment. In some embodiments, the expression level of one or more of TAPBP, TAP1, TAP2, PSMB9, or PSMB8 is correlated with the presence of antigen processing in the tumor microenvironment. In some embodiments, the expression level of one or more of CD40, CD80, CD86, CD70, or GITRL is correlated with the presence of costimulatory ligands in the tumor microenvironment. In some embodiments, the expression level of one or more of CD27, CD28, ICOS, TNFRSF4, TNFRSF14, TNFRSF18, TNFSF14, or CD226 is correlated with the presence of costimulatory receptors in the tumor microenvironment. In some embodiments, the expression level of one or more of GNLY, KLRK1, KLRB1, GZMH, GZMA, KLRD1, or NKG7 is correlated with cytolytic activity and/or the presence of cytolytic cells in the tumor microenvironment. In some embodiments, the expression level of one or more of FAP, FN1, MMP2, BGN, LOXL2, PDPN, PDGFRB, COL4A1, COL4A2, COL5A1, or COL8A1 is correlated with the presence of active fibroblasts in the tumor microenvironment. In some embodiments, the expression level of one or more of CD3D, CD3E, CD2, CD3G, CD6, TRAT1, CD28, or LCK is correlated with the presence of T cells in the tumor microenvironment.

In other embodiments of any of the above methods, the expression level is one or more (e.g., 1, 2, 3, 4, 5, or 6) of CD8A, GZMA, GZMB, IFNγ, EOMES, or PRF1 is determined. In some embodiments, the expression level of FOXP3 is determined. In some embodiments, the expression level of one or more (e.g., 1 or 2) of MS4A1 or CD48 and/or one or more (e.g., 1, 2, 3, 4, 5, 6, or 7) of CD79A, MS4A1, CD19, STAP1, KIAA0125, POU2AF1, or FCRL5 is determined. In some embodiments, the expression level of one or more (e.g., 1 or 2) of NCAM1 and NKP46 and/or one or more (e.g., 1, 2, 3, or 4) of KLRC3, KLRK1, KLRC2, or KLRD1 is determined. In some embodiments, the expression level of one or more (e.g., 1, 2, 3, or 4) of ITGAM, ITGAX, CD1C, or CLEC4C is determined. In some embodiments, the expression level of one or more (e.g., 1, 2, 3, 4, or 5) of CD68, CD163, ITGAM, ITGAX, or CD14 is determined. In some embodiments, the expression level of one or more (e.g., 1, 2, 3, 4, 5, 6, 7, 8, 9, 10, 11, 12, 13, or 14) of LAPTM5, LAIR1, CD4, CSF1R, CD163, ADAP2, CD68, MRC1, CD45RO, SLA, MSR1, FPR3, FCGR2A, or FCGR3A is determined. In some embodiments, the expression level of one or more (e.g., 1 or 2) of IL17A or IL17B is determined. In some embodiments, the expression level of one or more (e.g., 1, 2, 3, 4, 5, 6, 7, or 8) of CD3D, CD3E, CD2, CD3G, CD6, TRAT1, CD28, or LCK is determined. In some embodiments, the expression level of one or more (e.g., 1, 2, 3, 4, or 5) of CCL2, IL1B, IL8, IL6, or PTGS2 is determined. In some embodiments, the expression level of one or more (e.g., 1, 2, 3, 4, or 5) of CTLA4, BTLA, LAG3, HAVCR2, or PDCD1 and/or one or more (e.g., 1, 2, 3, 4, 5, or 6) of CTLA4, BTLA, LAG3, HAVCR2, PDCD1, or TIGIT is determined. In some embodiments, the expression level of one or more (e.g., 1, 2, 3, or 4) of CD276, PDL1, PDL2, or IDO1 and/or one or more (e.g., 1, 2, 3, or 4) of CD274, PDL2, IDO1, or PVR is determined. In some embodiments, the expression level of one or more (e.g., 1, 2, 3, 4, 5, or 6) of CX3CL1, CXCL9, CXCL10, CXCR3, CCL21, or CCL22 is determined. In some embodiments, the expression level of one or more (e.g., 1, 2, or 3) of CD4, IL2RA, or CD69 is determined. In some embodiments, the expression level of one or more (e.g., 1, 2, 3, 4, or 5) of TAPBP, TAP1, TAP2, PSMB9, or PSMB8 is determined. In some embodiments, the expression level of one or more (e.g., 1, 2, 3, 4, or 5) of CD40, CD80, CD86, CD70, or GITRL is determined. In some embodiments, the expression level of one or more (e.g., 1, 2, 3, 4, 5, 6, 7, or 8) of CD27, CD28, ICOS, TNFRSF4, TNFRSF14, TNFRSF18, TNFSF14, or CD226 is determined. In some embodiments, the expression level of one or more (e.g., 1, 2, 3, 4, 5, 6, or 7) of GNLY, KLRK1, KLRB1, GZMH, GZMA, KLRD1, or NKG7 is determined. In some embodiments, the expression level of one or more (e.g., 1, 2, 3, 4, 5, 6, 7, 8, 9, 10, or 11) of FAP, FN1, MMP2, BGN, LOXL2, PDPN, PDGFRB, COL4A1, COL4A2, COL5A1, or COL8A1 is determined.

In some embodiments of any of the above methods, the expression level of one or more of the genes in Table 2 are determined.

In some embodiments of any of the above methods, the expression level of one or more of the genes in Table 3 are determined.

In some embodiments of any of the above methods, the expression level of one or more of the genes in Table 4 are determined.

In some embodiments of any of the above methods, the expression level of one or more of the genes in Table 5 are determined.

In some embodiments of any of the above methods, the expression level of one or more of the genes in Table 6 are determined.

In some embodiments of any of the above methods, the expression level of one or more of the genes in Table 7 are determined.

In some embodiments of any of the above methods, the expression level of one or more of the genes in Table 8 are determined.

In some embodiments of any of the above methods, the expression level of one or more of the genes in Table 9 are determined.

In some embodiments of any of the above methods, the expression level of one or more of the genes from each of the following gene signatures CD8A, GZMA, GZMB, IFNγ, EOMES, or PRF1; FOXP3; MS4A1 or CD48; CD79A, MS4A1, CD19, STAP1, KIAA0125, POU2AF1, or FCRL5; NCAM1 or NKP46; KLRC3, KLRK1, KLRC2, or KLRD1; ITGAM, ITGAX, CD1C, or CLEC4C; CD68, CD163, ITGAM, ITGAX, or CD14; LAPTM5, LAIR1, CD4, CSF1R, CD163, ADAP2, CD68, MRC1, CD45RO, SLA, MSR1, FPR3, FCGR2A, or FCGR3A; IL17A or IL17F; CCL2, IL1B, IL8, IL6, or PTGS2; CD3D, CD3E, CD2, CD3G, CD6, TRAT1, CD28, or LCK; CTLA4, BTLA, LAG3, HAVCR2, or PDCD1; CTLA4, BTLA, LAG3, HAVCR2, PDCD1, or TIGIT; CD276, PDL1, PDL2, or IDO1; CD274, PDL2, IDO1, or PVR; CX3CL1, CXCL9, CXCL10, CXCR3, CCL21, or CCL22; CD4, IL2RA, or CD69; TAPBP, TAP1, TAP2, PSMB9, or PSMB8; CD40, CD80, CD86, CD70, or GITRL; CD27, CD28, ICOS, TNFRSF4, TNFRSF14, TNFRSF18, TNFSF14, or CD226; GNLY, KLRK1, KLRB1, GZMH, GZMA, KLRD1, or NKG7; and FAP, FN1, MMP2, BGN, LOXL2, PDPN, PDGFRB, COL4A1, COL4A2, COL5A1, or COL8A1 are determined.

In some embodiments of any of the above methods, the method further comprises determining the ratio of expression level of one or more of CD8A, GZMA, GZMB, IFNγ, EOMES, or PRF1 to the expression level of FOXP3. In some embodiments, if the ratio of expression level of one or more of CD8A, GZMA, GZMB, IFNγ, EOMES, or PRF1 to the expression level of FOXP3 is high, the patient will likely benefit from an activating immunotherapy. In some embodiments, wherein if the ratio of expression level of one or more of CD8A, GZMA, GZMB, IFNγ, EOMES, or PRF1 to the expression level of FOXP3 is low, the patient will likely benefit from a suppressing immunotherapy.

In some embodiments of any of the above methods, the method further comprises determining the ratio of $T_{eff}$ to $T_{reg}$ cells. In some embodiments, if the ratio of $T_{eff}$ to $T_{reg}$ is high, the patient will likely benefit from an activating immunotherapy. In some embodiments, if the ratio of $T_{eff}$ to $T_{reg}$ is low, the patient will likely benefit from a suppressing immunotherapy. In some embodiments, the activating immunotherapy comprises a CD28, OX40, GITR, CD137, CD27, ICOS, HVEM, NKG2D, MICA, or 2B4 agonist. In some embodiments, the suppressing immunotherapy comprises a CTLA-4, PD-1 axis, TIM-3, BTLA, VISTA, LAG-3, B7H4, CD96, TIGIT, or CD226 antagonist.

In some embodiments of any of the above methods, the method is carried out prior to administering an immunotherapy in order to provide a patient with a pre-administration prognosis for response.

In some embodiments of any of the above methods, the cancer is a breast cancer, melanoma, non-small cell lung cancer (NSCLC), bladder cancer, renal cell carcinoma, colorectal cancer, ovarian cancer, gastric cancer, or liver cancer. In some embodiments, the cancer is primary, advanced, refractory, or recurrent. In some embodiments, the breast cancer is hormone receptor+(HR+), HER2+, or triple negative (TN) breast cancer. In some embodiments, the NSCLC is non-squamous NSCLC or squamous NSCLC.

In some embodiments of any of the above methods, expression of the immune cell gene signature in the biological sample obtained from the patient is detected by measuring mRNA.

In some embodiments of any of the above methods, expression of the immune cell gene signature in the biological sample obtained from the patient is detected by measuring plasma protein levels.

BRIEF DESCRIPTION OF THE DRAWINGS

The application file contains at least one drawing executed in color. Copies of this patent or patent application with color drawings will be provided by the Office upon request and payment of the necessary fee.

DETAILED DESCRIPTION OF THE INVENTION

I. Introduction

Figure 1A:
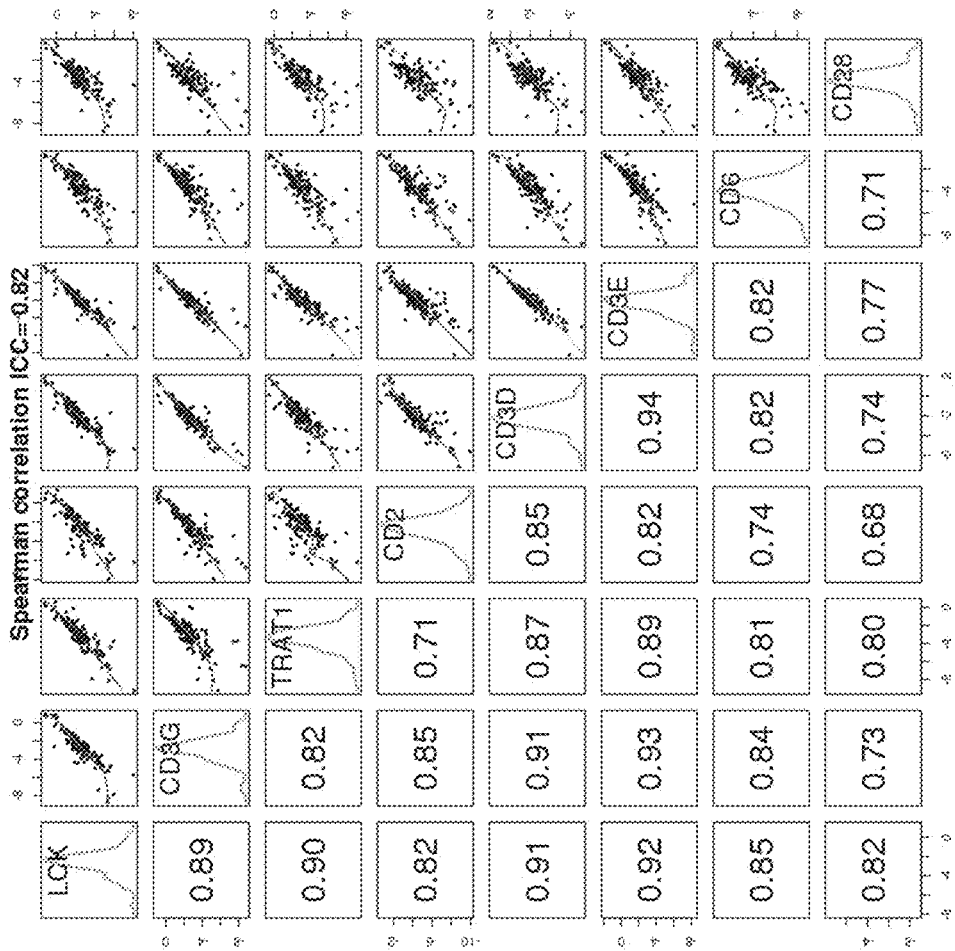
FIG. 1A is a Scattermatrix plot of T cell signature genes.
Figure 1B:
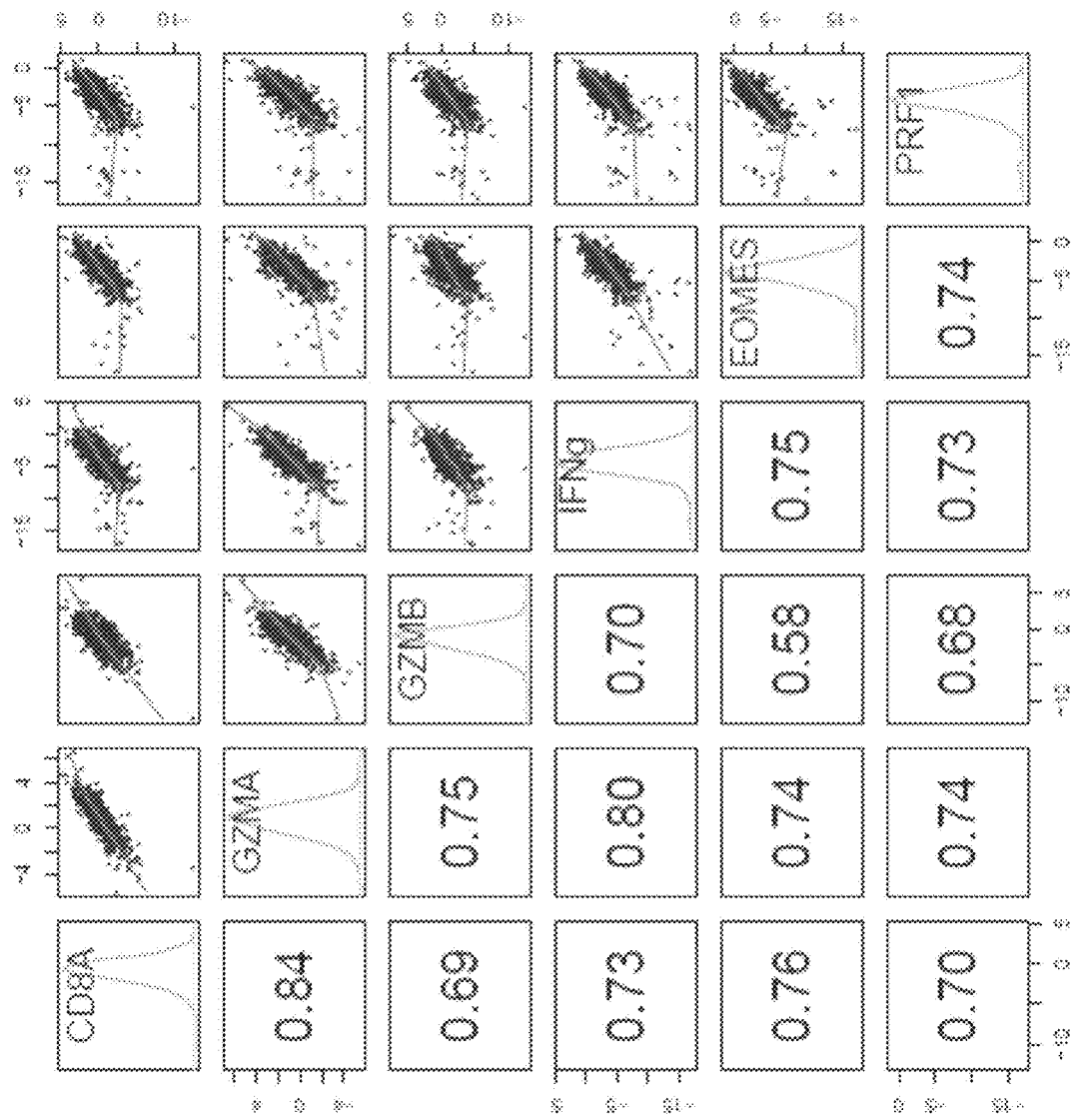
FIG. 1B is a Scattermatrix plot of T effector signature genes.
Figure 1C:
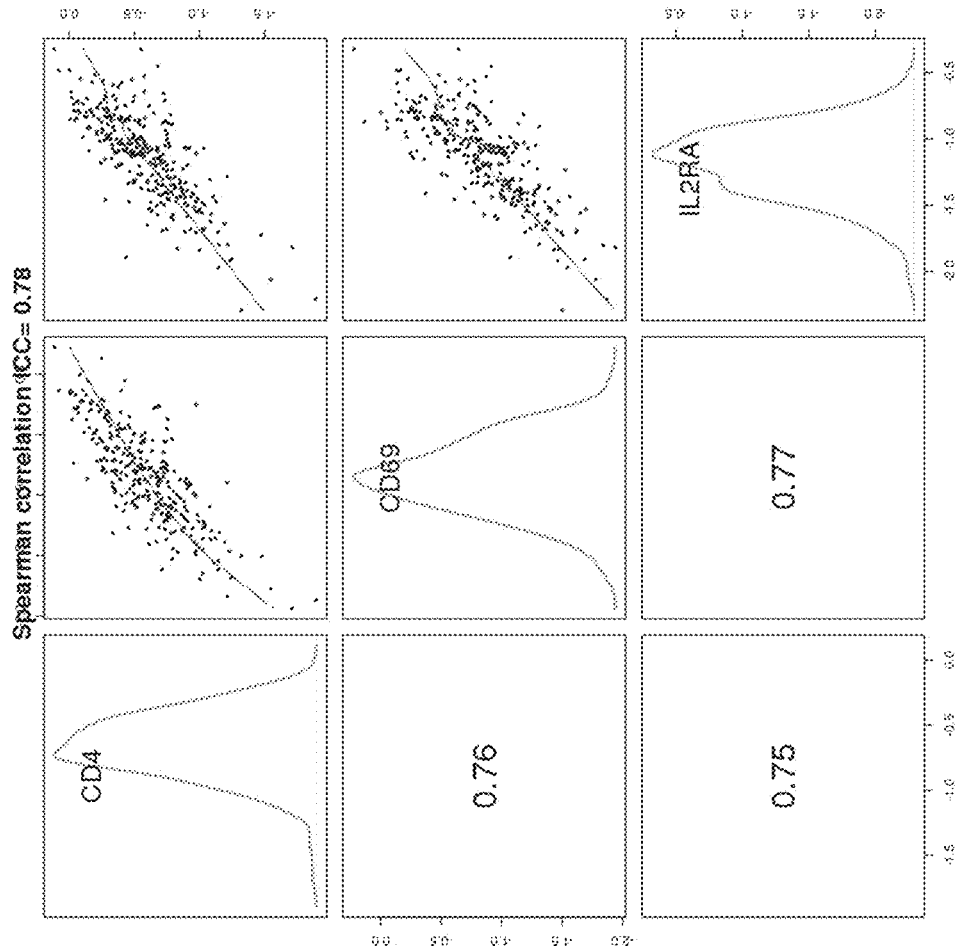
FIG. 1C is a Scattermatrix plot of activated CD4 T cell signature genes.

The tumor immune microenvironment consists of a host of immunosuppressive factors that allow the tumor cells to keep the resident T cells in check and to evade anti-tumor immunity. A study of the factors in the tumor stroma or secreted by the tumor cells to keep the T cells from infiltrating the tumor provides a tool for understanding how to convert aggressive tumors into immunogenic tumors capable of responding to immunotherapy. In the present invention, gene expression was used to evaluate the prevalence of gene signatures that represent immune cell subsets across seven different cancer types. This analysis provides insight into the tumor immune microenvironment of nine different cancer indications and various tumor subtypes to identify the drivers of tumor immune biology that dictate response to immunotherapy.

Accordingly, the invention provides methods for selecting a patient having cancer (e.g., bladder cancer, breast cancer, colorectal cancer, gastric cancer, liver cancer, melanoma, lung cancer (e.g., non-small cell lung carcinoma), ovarian cancer, or renal cell carcinoma) for treatment with an immunotherapy by determining the expression level of one or more immune cell gene signatures, and comparing this level of expression to the median level of expression of the one or more immune cell gene signatures. Detection of increased expression of the one or more immune cell gene signatures relative to a median level (i.e., higher expression of the one or more immune cell gene signatures relative to the median level in the cancer type) identifies the patient for treatment with an immunotherapy. The invention also provides methods for treating a patient having cancer (e.g., bladder cancer, breast cancer, colorectal cancer, gastric cancer, liver cancer, melanoma, lung cancer (e.g., non-small cell lung carcinoma), ovarian cancer, or renal cell carcinoma) who may benefit from immunotherapy by administering an activating immunotherapy or a suppressing immunotherapy alone or in combination with a chemotherapy regimen and/or other anti-cancer therapy regimen by determining the expression level of one or more immune cell gene signatures in the patient.

II. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), and March, Advanced Organic Chemistry Reactions, Mechanisms and Structure 4th ed., John Wiley & Sons (New York, N.Y. 1992), provide one skilled in the art with a general guide to many of the terms used in the present application.

For purposes of interpreting this specification, the following definitions will apply and whenever appropriate, terms used in the singular will also include the plural and vice versa. In the event that any definition set forth below conflicts with any document incorporated herein by reference, the definition set forth below shall control.

The term "antagonist" is used in the broadest sense, and includes any molecule that partially or fully blocks, inhibits, interferes, or neutralizes a normal biological activity of a native polypeptide disclosed herein (e.g., an immune cell receptor or ligand, such as CTLA-4, PD-1, TIM-3, BTLA, VISTA, LAG-3, B7H4, CD96, TIGIT, or CD226), either by decreasing transcription or translation of the nucleic acid encoding the native polypeptide, or by inhibiting or blocking the native polypeptide activity, or both. It will be understood by one of ordinary skill in the art that, in some instances, an antagonist may antagonize one activity of the native polypeptide without affecting another activity of the native polypeptide. It will also be understood by one of ordinary skill in the art that, in some instances, an antagonist may be a therapeutic agent that is considered an activating or suppressing immunotherapy depending on the native polypeptide that it binds, interacts, or associates with. Examples of antagonists include, but are not limited to, antisense polynucleotides, interfering RNAs, catalytic RNAs, RNA-DNA chimeras, native polypeptide-specific aptamers, antibodies, antigen-binding fragments of antibodies, native polypeptide-binding small molecules, native polypeptide-binding peptides, and other peptides that specifically bind the native polypeptide (including, but not limited to native polypeptide-binding fragments of one or more native polypeptide ligands, optionally fused to one or more additional domains), such that the interaction between the antagonist and the native polypeptide results in a reduction or cessation of native polypeptide activity or expression.

In a similar manner, the term "agonist" is used in the broadest sense and includes any molecule that mimics, promotes, stimulates, or enhances a normal biological activity of a native polypeptide disclosed herein (e.g., an immune cell receptor or ligand, such as CD28, OX40, GITR, CD137, CD27, ICOS, HVEM, NKG2D, MICA, or 2B4), by increasing transcription or translation of the nucleic acid encoding the native polypeptide, and/or by inhibiting or blocking activity of a molecule that inhibits the expression or activity of the native polypeptide, and/or by enhancing normal native polypeptide activity (including, but not limited to, enhancing the stability of the native polypeptide, or enhancing binding of the native polypeptide to one or more target ligands). It will be understood by one of ordinary skill in the art that, in some instances, an agonist may agonize one activity of the native polypeptide without affecting another activity of the native polypeptide. It will also be understood by one of ordinary skill in the art that, in some instances, an agonist may be a therapeutic agent that is considered an activating or suppressing immunotherapy depending on the native polypeptide that it binds, interacts, or associates with. The agonist can be selected from an antibody, an antigen-binding fragment, an aptamer, an interfering RNA, a small molecule, a peptide, an antisense molecule, and another binding polypeptide. In another example, the agonist can be a polynucleotide selected from an aptamer, interfering RNA, or antisense molecule that interferes with the transcription and/or translation of a native polypeptide-inhibitory molecule. Methods for identifying agonists or antagonists of a polypeptide may comprise contacting a polypeptide with a candidate agonist or antagonist molecule and measuring a detectable change in one or more biological activities normally associated with the polypeptide.

The term "activating immunotherapy" refers to the use of a therapeutic agent that induces, enhances, or promotes an immune response, including, e.g., a T cell response. The term "suppressing immunotherapy" refers to the use of a therapeutic agent that interferes with, suppresses, or inhibits an immune response, including, e.g., a T cell response.

"Human effector cells" refer to leukocytes that express one or more FcRs and perform effector functions. In certain embodiments, the cells express at least FcγRIII and perform ADCC effector function(s). Examples of human leukocytes which mediate ADCC include peripheral blood mononuclear cells (PBMC), natural killer (NK) cells, monocytes, cytotoxic T cells, and neutrophils. The effector cells may be isolated from a native source, e.g., from blood.

"Regulatory T cells ($T_{reg}$)" refer to a subset of helper T cells that play a role in inhibition of self-reactive immune responses and are often found in sites of chronic inflammation such as in tumor tissue. In certain embodiments, $T_{regs}$ are defined phenotypically by high cell surface expression of CD25, CLTA4, GITR, and neuropilin-1 and are under the control of transcription factor FOXP3. In other embodiments, $T_{regs}$ perform their suppressive function on activated T cells through contact-dependent mechanisms and cytokine production. In some embodiments, $T_{regs}$ also modulate immune responses by direct interaction with ligands on dendritic cells (DC), such as, e.g., CTLA4 interaction with B7 molecules on DC that elicits the induction of indoleamine 2,3-dioxygenase (IDO).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (RIA) or biacore assay. In certain embodiments, an antibody that binds to a target has a dissociation constant (Kd) of <1 μM, <100 nM, <10 nM, <1 nM, <0.1 nM, <0.01 nM, or <0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

As used herein, the term "binds," "specifically binds to," or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, for example, by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

The term "biological sample" or "sample" as used herein includes, but is not limited to, blood, serum, plasma, sputum, tissue biopsies, tumor tissue, and nasal samples including nasal swabs or nasal polyps.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

An "advanced" cancer is one which has spread outside the site or organ of origin, either by local invasion or metastasis.

A "refractory" cancer is one which progresses even though an anti-tumor agent, such as a chemotherapeutic agent, is being administered to the cancer patient. An example of a refractory cancer is one which is platinum refractory.

A "recurrent" cancer is one which has regrown, either at the initial site or at a distant site, after a response to initial therapy.

By "platinum-resistant" cancer is meant cancer in a patient that has progressed while the patient was receiving platinum-based chemotherapy or cancer in a patient that has progressed within, e.g., 12 months (for instance, within 6 months) after the completion of platinum-based chemotherapy. Such a cancer can be said to have or exhibit "platinum-resistance."

By "chemotherapy-resistant" cancer is meant cancer in a patient that has progressed while the patient is receiving a chemotherapy regimen or cancer in a patient that has progressed within, e.g., 12 months (for instance, within 6 months) after the completion of a chemotherapy regimen. Such a cancer can be said to have or exhibit "chemotherapy-resistance."

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

As used herein, "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and µ, respectively.

A "chemotherapeutic agent" includes chemical compounds useful in the treatment of cancer. Examples of chemotherapeutic agents include erlotinib (TARCEVA®, Genentech/OSI Pharm.), bortezomib (VELCADE®, Millennium Pharm.), disulfiram, epigallocatechin gallate, salinosporamide A, carfilzomib, 17-AAG (geldanamycin), radicicol, lactate dehydrogenase A (LDH-A), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, Rapamycin (Sirolimus, RAPAMUNE®, Wyeth), Lapatinib (TYKERB®, GSK572016, Glaxo Smith Kline), Lonafamib (SCH 66336), sorafenib (NEXAVAR®, Bayer Labs), gefitinib (IRESSA®, AstraZeneca), AG1478, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including topotecan and irinotecan); bryostatin; callystatin; CC-1065 (including its adozelesin, carzelesin and bizelesin synthetic analogs); cryptophycins (particularly cryptophycin 1 and cryptophycin 8); adrenocorticosteroids (including prednisone and prednisolone); cyproterone acetate; 5α-reductases including finasteride and dutasteride); vorinostat, romidepsin, panobinostat, valproic acid, mocetinostat dolastatin; aldesleukin, talc duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ11 and calicheamicin ω11 (Angew Chem. Intl. Ed. Engl. 1994 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidamnol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (docetaxel, doxetaxel; Sanofi-Aventis); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Chemotherapeutic agent also includes (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, iodoxyfene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide and goserelin; buserelin, tripterelin, medroxyprogesterone acetate, diethylstilbestrol, premarin, fluoxymesterone, all transretionic acid, fenretinide, as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN®, rIL-2; a topoisomerase 1 inhibitor such as LURTOTECAN®; ABARELIX® rmRH; and (ix) pharmaceutically acceptable salts, acids and derivatives of any of the above.

Chemotherapeutic agent also includes antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agent also includes "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/ Amgen); EMD 55900 (Stragliotto et al. Eur. J. Cancer 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc.); and mAb 806 or humanized mAb 806 (Johns et al., J. Biol. Chem. 279(29): 30375-30384 (2004)). The anti-EGFR antibody may be conjugated with a cytotoxic agent, thus generating an immunoconjugate (see, e.g., EP659,439A2, Merck Patent GmbH). EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include OSI-774 (CP-358774, erlotinib, TARCEVA® Genentech/OSI Pharmaceuticals); PD 183805 (CI 1033, 2-propenamide, N-[4-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenylamino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N-[4-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); dual EGFR/HER2 tyrosine kinase inhibitors such as lapatinib (TYKERB®, GSK572016 or N-[3-chloro-4-[(3 fluorophenyl)methoxy]phenyl]-6[5[[[2 methylsulfonyl) ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitor such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (CI-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor CI-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d]pyrimidines; curcumin (diferuloyl methane, 4,5-bis(4-fluoroanilino)phthalimide); tyrphostines containing nitrothiophene moieties; PD-0183805 (Warner-Lamber); antisense molecules (e.g. those that bind to HER-encoding nucleic acid); quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as CI-1033 (Pfizer); Affinitac (ISIS 3521; Isis/Lilly); imatinib mesylate (GLEEVEC®); PKI 166 (Novartis); GW2016 (Glaxo SmithKline); CI-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

By "platinum-based chemotherapeutic agent" or "platin" is meant an antineoplastic drug that is a coordination complex of platinum. Examples of platinum-based chemotherapeutic agents include carboplatin, cisplatin, satraplatin, picoplatin, nedaplatin, triplatin, lipoplatin, and oxaliplatinum.

By "platinum-based chemotherapy" is meant therapy with one or more platinum-based chemotherapeutic agent, optionally in combination with one or more other chemotherapeutic agents.

By "correlate" or "correlation" is meant comparing, in any way, the performance and/or results of a first analysis or protocol with the performance and/or results of a second analysis or protocol. For example, one may use the results of a first analysis or protocol to determine the outcome or result of a second analysis or protocol. Or one may use the results of a first analysis or protocol to determine whether a second analysis or protocol should be performed. For example, with respect to the embodiment of gene expression analysis or protocol, one may use the results of the gene expression analysis or protocol to determine whether a specific immune cell type or subset is present.

"Effector functions" refer to those biological activities attributable to the Fc region of an antibody, which vary with the antibody isotype. Examples of antibody effector functions include: Clq binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

"Enhancing T cell function" means to induce, cause or stimulate an effector or memory T cell to have a renewed, sustained or amplified biological function. Examples of enhancing T cell function include: increased secretion of γ-interferon from CD8 effector T cells, increased secretion of γ-interferon from CD4+ memory and/or effector T cells, increased proliferation of CD4+ effector and/or memory T cells, increased proliferation of CD8 effector T cells, increased antigen responsiveness (e.g., clearance), relative to such levels before the intervention. In one embodiment, the level of enhancement is at least 50%, alternatively 60%, 70%, 80%, 90%, 100%, 120%, 150%, 200%. The manner of measuring this enhancement is known to one of ordinary skill in the art.

A sample, cell, tumor, or cancer which "expresses" one or more immune cell gene signatures at an increased expression level relative to a median level of expression (e.g., the median level of expression of the one or more immune cell gene signatures in the type of cancer (or in a cancer type, wherein the "cancer type" is meant to include cancerous cells (e.g., tumor cells, tumor tissues) as well as non-cancerous cells (e.g., stromal cells, stromal tissues) that surround the cancerous/tumor environment) is one in which the expression level of one or more immune cell gene signatures is considered to be a "high immune cell gene signature expression level" to a skilled person for that type of cancer. Generally, such a level will be in the range from about 50% up to about 100% or more (e.g., 50%, 55%, 60%, 65%, 70%, 75%, 80%, 85%, 90%, 95%, 100%, or more) relative to immune cell gene signature levels in a population of samples, cells, tumors, or cancers of the same cancer type. For instance, the population that is used to arrive at the median expression level may be particular cancer samples (e.g., bladder cancer, breast cancer, colorectal cancer, gastric cancer, liver cancer, melanoma, lung cancer (e.g., non-small cell lung carcinoma), ovarian cancer, or renal cell carcinoma) generally, or subgroupings thereof, such as chemotherapy-resistant cancer, platinum-resistant cancer, as well as advanced, refractory, or recurrent cancer samples.

By "determining the expression level" used in reference to a particular biomarker (e.g., one or more immune cell gene signatures), means expression of the biomarker(s) (e.g., one or more immune cell gene signatures) in a cancer-associated biological environment (e.g., expression of the biomarker(s) in the tumor cells), tumor-associated cells (e.g., tumor-associated stromal cells), as determined using a diagnostic test, any of the detection methods described herein, or the similar.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al, Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4.

Accordingly, the HVR and FR sequences generally appear in the following sequence in VH (or VL): FR1-H1 (L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al, Sequences of Proteins of Immunological Interest, Fifth Edition, NIH Publication 91-3242, Bethesda Md. (1991), vols. 1-3. In one embodiment, for the VL, the subgroup is subgroup kappa I as in Kabat et al, supra. In one embodiment, for the VH, the subgroup is subgroup III as in Kabat et al, supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (HI, H2, H3), and three in the VL (LI, L2, L3). HVRs generally comprise amino acid residues from the hypervariable loops and/or from the "complementarity determining regions" (CDRs), the latter typically being of highest sequence variability and/or involved in antigen recognition. An HVR region as used herein comprise any number of residues located within positions 24-36 (for HVRL1), 46-56 (for HVRL2), 89-97 (for HVRL3), 26-35B (for HVRH1), 47-65 (for HVRH2), and 93-102 (for HVRH3).

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage, and tumor clearance. "Immunogenicity" refers to the ability of a particular substance to provoke an immune response. Tumors are immunogenic and enhancing tumor immunogenicity aids in the clearance of the tumor cells by the immune response. Examples of enhancing tumor immunogenicity include but are not limited to treatment with a CD28, OX40, GITR, CD137, CD27, ICOS, HVEM, NKG2D, MICA, or 2B4 agonist or treatment with a CTLA-4, PD-1 axis, TIM-3, BTLA, VISTA, LAG-3, B7H4, CD96, TIGIT, or CD226 antagonist.

An "immunoconjugate" is an antibody conjugated to one or more heterologous molecule(s), including but not limited to a cytotoxic agent.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). F or review of methods for assessment of antibody purity, see, e.g., Flatman et al, J. Chromatogr. B 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-target antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

A "loading" dose herein generally comprises an initial dose of a therapeutic agent administered to a patient, and is followed by one or more maintenance dose(s) thereof. Generally, a single loading dose is administered, but multiple loading doses are contemplated herein. Usually, the amount of loading dose(s) administered exceeds the amount of the maintenance dose(s) administered and/or the loading dose(s) are administered more frequently than the maintenance dose(s), so as to achieve the desired steady-state concentration of the therapeutic agent earlier than can be achieved with the maintenance dose(s).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used according to the methods provided herein may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CHI, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Patient response" or "response" (and grammatical variations thereof) can be assessed using any endpoint indicating a benefit to the patient, including, without limitation, (1) inhibition, to some extent, of disease progression, including slowing down and complete arrest; (2) reduction in the number of disease episodes and/or symptoms; (3) reduction in lesional size; (4) inhibition (i.e., reduction, slowing down or complete stopping) of disease cell infiltration into adjacent peripheral organs and/or tissues; (5) inhibition (i.e. reduction, slowing down or complete stopping) of disease spread; (6) decrease of auto-immune response, which may, but does not have to, result in the regression or ablation of the disease lesion; (7) relief, to some extent, of one or more symptoms associated with the disorder; (8) increase in the length of disease-free presentation following treatment; and/or (9) decreased mortality at a given point of time following treatment.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one-time administration and typical dosages range from 10 to 200 units (Grays) per day.

The term "small molecule" refers to an organic molecule having a molecular weight between 50 Daltons to 2500 Daltons.

The terms "immune cell gene signature" and "immune cell signature" refer to any one or a combination or sub-combination of the 31 genes set forth in Table 1. Such sub-combinations of these 31 genes are sometimes referred to as "gene sets," and exemplary "gene sets" are set forth in Tables 2-8. The gene expression pattern of an immune cell gene signature in a patient correlates with the presence of an immune cell subtype (e.g., T effector cells, T regulatory cells, B cells, NK cells, myeloid cells, Th17 cells, inflammatory cells, T cell immune blockers, and antigen presenting cell (APC) immune blockers). Each individual gene or member of an immune cell gene signature is an "immune cell signature gene." These genes include, without limitation: CD8A, GZMA, GZMB, IFNγ, EOMES, PRF1, FOXP3, MS4A1, CD48, NCAM1, NKP46, ITGAM, ITGAX, CD1C, CLEC4C, IL17A, IL17F, CCL2, IL1B, IL8, IL6, PTGS2, CTLA4, BTLA, LAG3, HAVCR2, PDCD1, CD276, PDL1, PDL2, and IDO1.

The term "PD1-axis antagonist" refers to a molecule that inhibits the interaction of a PD-1 axis binding partner with either one or more of its binding partner, so as to remove T cell dysfunction resulting from signaling on the PD-1 signaling axis—with a result being to restore or enhance T cell function (e.g., proliferation, cytokine production, target cell killing). As used herein, a PD-1 axis antagonist includes a PD-1 binding antagonist, a PD-L1 binding antagonist, and a PD-L2 binding antagonist.

"Survival" refers to the patient remaining alive, and includes overall survival as well as progression free survival.

"Overall survival" refers to the patient remaining alive for a defined period of time, such as 1 year, 5 years, etc. from the time of diagnosis or treatment.

The phrase "progression-free survival" in the context of the present invention refers to the length of time during and after treatment during which, according to the assessment of the treating physician or investigator, a patient's disease does not become worse, i.e., does not progress. As the skilled person will appreciate, a patient's progression-free survival is improved or enhanced if the patient experiences a longer length of time during which the disease does not progress as compared to the average or mean progression free survival time of a control group of similarly situated patients.

By "standard of care" herein is intended the anti-tumor/anti-cancer agent or agents that are routinely used to treat a particular form of cancer.

The terms "therapeutically effective amount" or "effective amount" refer to an amount of a drug effective to treat cancer in the patient. The effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. The effective amount may extend progression free survival (e.g. as measured by Response Evaluation Criteria for Solid Tumors, RECIST, or CA-125 changes), result in an objective response (including a partial response, PR, or complete response, CR), improve survival (including overall survival and progression free survival) and/or improve one or more symptoms of cancer (e.g. as assessed by FOSI). Most preferably, the therapeutically effective amount of the drug is effective to improve progression free survival (PFS) and/or overall survival (OS).

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. In some embodiments, methods and compositions of the invention are useful in attempts to delay development of a disease or disorder.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al, J. Immunol. 150:880-887 (1993); Clarkson et al, Nature 352:624-628 (1991).

III. Methods of Prognosis and Detection

The present invention relates to the identification, selection, and use of biomarkers of cancer (e.g., bladder cancer, breast cancer, colorectal cancer, gastric cancer, liver cancer, melanoma, lung cancer (e.g., non-small cell lung carcinoma), ovarian cancer, or renal cell carcinoma) that are correlated with an immune cell subtype (e.g., T effector cells, T regulatory cells, B cells, NK cells, myeloid cells, Th17 cells, inflammatory cells, T cell immune blockers, antigen presenting cell (APC) immune blockers). In this respect, the invention relates to analysis of expression profile(s) in samples from patients with cancer (e.g., bladder cancer, breast cancer, colorectal cancer, gastric cancer, liver cancer, melanoma, lung cancer (e.g., non-small cell lung carcinoma), ovarian cancer, or renal cell carcinoma), to identify biomarkers correlated with an immune cell subtype (e.g., T effector cells, T regulatory cells, B cells, NK cells, myeloid cells, Th17 cells, inflammatory cells, T cell immune blockers, and antigen presenting cell (APC) immune blockers) involved in tumor immunity and the use of these biomarkers in selecting patients for treatment with immunotherapy. The biomarkers of the invention are listed herein, e.g., in Table 1.

TABLE 1

Gene signature sets and immune cell gene signature set members

| Gene signature sets | Gene signature set members |
| --- | --- |
| T effector ($T_{eff}$) | CD8A, GZMA, GZMB, IFNγ, EOMES, PRF1 |
| T regulatory ($T_{reg}$) | FOXP3 |
| B cell Signature 1 | MS4A1, CD48 |
| B cell Signature 2# | CD79A, MS4A1, CD19, STAP1, KIAA0125, POU2AF1, FCRL5 |
| NK cell Signature 1 | NCAM1, NKP46 |
| NK cell Signature 2# | KLRC3, KLRK1, KLRC2, KLRD1 |
| Myeloid cell | ITGAM, ITGAX, CD1C, CLEC4C |
| Macrophage# | CD68, CD163, ITGAM, ITGAX, CD14 |
| M2 Macrophage# | LAPTM5, LAIR1, CD4, CSF1R, CD163, ADAP2, CD68, MRC1, CD45RO, SLA, MSR1, FPR3, FCGR2A, FCGR3A |
| Th17* | IL17A, IL17F |
| Inflammatory# | CCL2, IL1B, IL8 (CXCL8), IL6, PTGS2 |
| T cell# | CD3D, CD3E, CD2, CD3G, CD6, TRAT1, CD28, LCK |
| T cell immune blockers (IB T cell) Signature 1 | CTLA4, BTLA, LAG3, HAVCR2, PDCD1 |
| IB T cell Signature 2# | CTLA4, BTLA, LAG3, HAVCR2, PDCD1, TIGIT |

TABLE 1-continued

Gene signature sets and immune cell gene signature set members

| Gene signature sets | Gene signature set members |
|---|---|
| Antigen presenting cell immune blockers (IB APC) Signature 1 | CD276, PDL1, PDL2, IDO1 |
| IB APC Signature 2# | CD274, PDL2, IDO1, PVR |
| T cell chemotaxis | CX3CL1, CXCL9, CXCL10, CXCR3, CCL21, CCL22 |
| Activated CD4 T cell** | CD4, IL2RA, CD69 |
| Antigen processing** | TAPBP, TAP1, TAP2, PSMB9, PSMB8 |
| Costimulatory ligand# | CD40, CD80, CD86, CD70, GITRL |
| Costimulatory receptor# | CD27, CD28, ICOS, TNFRSF4, TNFRSF14, TNFRSF18, TNFSF14, CD226 |
| Cytolytic# | GNLY, KLRK1, KLRB1, GZMH, GZMA, KLRD1, NKG7 |
| Active fibroblast## | FAP, FN1, MMP2, BGN, LOXL2, PDPN, PDGFRB, COL4A1, COL4A2, COL5A1, COL8A1 |

All unmarked gene signature sets were derived from analysis of data using a 90-gene PCR based FLUIDIGM ™ panel.
*The Th17 gene signature set is also described herein as the IL17 gene set and was derived from analysis of data using a 90-gene PCR based FLUIDIGM ™ panel.. Th17 gene set and IL17 gene set are used interchangeably throughout the application and refer to the same gene set.
**Gene signature sets that were derived from analysis of data using an 800-gene custom Nanostring panel (instead of the 90-gene PCR based FLUIDIGM ™ panel) in urothelial bladder cancer (UBC) samples.
Gene signature sets that were derived from analysis of data using an 800-gene custom Nanostring panel (instead of the 90-gene PCR based FLUIDIGM ™ panel) in non-small cell lung carcinoma (NSCLC) samples.
Gene signature set that was derived from a targeted RNA-Seq Access in UBC samples.

The invention provides methods for selecting patients with cancer (e.g., bladder cancer, breast cancer, colorectal cancer, gastric cancer, liver cancer, melanoma, lung cancer (e.g., non-small cell lung carcinoma), ovarian cancer, or renal cell carcinoma) for treatment with immunotherapy by determining the expression level of one or more immune cell gene signatures (e.g., one or more of the genes listed in Table 1 or combinations thereof, e.g., as listed in Tables 2-8), and comparing the expression level of the immune cell gene signature to a median level for expression of the immune cell gene signature (e.g., the median level for expression of the immune cell gene signature in the cancer type), where a change in the level of expression of the immune cell gene signature identifies patients for treatment with an immunotherapy. Optionally, the methods include the step of informing the patient that they have an increased likelihood of being responsive to an immunotherapy and/or proving a recommendation to the patient for a particular immunotherapy based on the expression level of one or more immune cell gene signatures (e.g., one or more of the genes listed in Table 1 or combinations thereof, e.g., as listed in Tables 2-8).

In some embodiments, the patient is identified for treatment with an activating immunotherapy or selected as having the likelihood of benefiting from an activating immunotherapy regimen if there is an increase in expression level of one or more immune cell gene signatures in the $T_{eff}$ gene set (i.e., one or more of CD8A, GZMA, GZMB, IFNγ, EOMES, or PRF1) or a decrease in expression level of one or more immune cell gene signatures in the $T_{reg}$ gene set. In other embodiments, the patient is identified for treatment with a suppressing immunotherapy or selected as having the likelihood of benefiting from a suppressing immunotherapy if there is an increase in expression level of one or more immune cell gene signatures in the $T_{reg}$ gene set (i.e., FOXP3) or a decrease in expression level of one or more immune cell gene signatures in the $T_{eff}$ gene set (i.e., one or more of CD8A, GZMA, GZMB, IFNγ, EOMES, or PRF1). In other embodiments, in addition to determining the expression levels of one or more immune cell gene signatures in the $T_{eff}$ and/or $T_{reg}$ gene sets, expression levels of one or more immune cell gene signatures in combinations of any one of the gene sets as set forth in Tables 2-8 can be determined in order to identify a patient for a particular immunotherapy regimen (e.g., an activating immunotherapy regimen or a suppressing immunotherapy regimen). Optionally, these methods are carried out prior to administering an immunotherapy regimen in order to provide the patient with a pre-administration prognosis for response to immunotherapy.

In certain embodiments, the expression level of one or more of the genes in an immune cell gene signature in any one particular gene signature set is determined. For example:
  CD8A, GZMA, GZMB, IFNγ, EOMES, or PRF1; or
  FOXP3; or
  MS4A1 or CD48; or
  CD79A, MS4A1, CD19, STAP1, KIAA0125, POU2AF1, or FCRL5; or
  NCAM1 or NKP46; or
  KLRC3, KLRK1, KLRC2, or KLRD1; or
  ITGAM, ITGAX, CD1C, or CLEC4C; or
  CD68, CD163, ITGAM, ITGAX, or CD14; or
  LAPTM5, LAIR1, CD4, CSF1R, CD163, ADAP2, CD68, MRC1, CD45RO, SLA, MSR1, FPR3, FCGR2A, or FCGR3A; or
  IL17A or IL17F; or
  CCL2, IL1B, IL8, IL6, or PTGS2; or
  CD3D, CD3E, CD2, CD3G, CD6, TRAT1, CD28, or LCK; or
  CTLA4, BTLA, LAG3, HAVCR2, or PDCD1; or
  CTLA4, BTLA, LAG3, HAVCR2, PDCD1, or TIGIT; or
  CD276, PDL1, PDL2, or IDO1; or
  CD274, PDL2, IDO1, or PVR; or
  CX3CL1, CXCL9, CXCL10, CXCR3, CCL21, or CCL22; or
  CD4, IL2RA, or CD69; or
  TAPBP, TAP1, TAP2, PSMB9, or PSMB8; or
  CD40, CD80, CD86, CD70, or GITRL; or
  CD27, CD28, ICOS, TNFRSF4, TNFRSF14, TNFRSF18, TNFSF14, or CD226; or
  GNLY, KLRK1, KLRB1, GZMH, GZMA, KLRD1, or NKG7; or
  FAP, FN1, MMP2, BGN, LOXL2, PDPN, PDGFRB, COL4A1, COL4A2, COL5A1, or COL8A1 is determined. In another embodiment, the expression levels of one or more of the genes in an immune cell gene signature in two particular gene signature sets are determined. For example, combinations of two particular gene signature sets are set forth in Table 2 below.

TABLE 2

Combinations of two gene signature sets

CD8A, GZMA, GZMB, IFNγ, EOMES, or PRF1; and MS4A1 or CD48.
CD8A, GZMA, GZMB, IFNγ, EOMES, or PRF1; and NCAM1 or NKP46.
CD8A, GZMA, GZMB, IFNγ, EOMES, or PRF1; and FOXP3.
CD8A, GZMA, GZMB, IFNγ, EOMES, or PRF1; and ITGAM, ITGAX, CD1C, or CLEC4C.
CD8A, GZMA, GZMB, IFNγ, EOMES, or PRF1; and IL17A or IL17F.
CD8A, GZMA, GZMB, IFNγ, EOMES, or PRF1; and CCL2, IL1B, IL8, IL6, or PTGS2.
CD8A, GZMA, GZMB, IFNγ, EOMES, or PRF1; and TABLE 2-continued

| Combinations of two gene signature sets |
|---|
| CTLA4, BTLA, LAG3, HAVCR2, or PDCD1. |
| CD8A, GZMA, GZMB, IFNγ, EOMES, or PRF1; and |
| CD276, PDL1, PDL2, or IDO1. |
| FOXP3; and |
| MS4A1 or CD48. |
| FOXP3; and |
| NCAM1 or NKP46. |
| FOXP3; and |
| ITGAM, ITGAX, CD1C, or CLEC4C. |
| FOXP3; and |
| IL17A or IL17F. |
| FOXP3; and |
| CCL2, IL1B, IL8, IL6, or PTGS2. |
| FOXP3; and |
| CTLA4, BTLA, LAG3, HAVCR2, or PDCD1. |
| FOXP3; and |
| CD276, PDL1, PDL2, or IDO1. |
| MS4A1 or CD48; and |
| NCAM1 or NKP46. |
| MS4A1 or CD48; and |
| ITGAM, ITGAX, CD1C, or CLEC4C. |
| MS4A1 or CD48; and |
| IL17A or IL17F. |
| MS4A1 or CD48; and |
| CCL2, IL1B, IL8, IL6, or PTGS2. |
| MS4A1 or CD48; and |
| CTLA4, BTLA, LAG3, HAVCR2, or PDCD1. |
| MS4A1 or CD48; and |
| CD276, PDL1, PDL2, or IDO1. |
| NCAM1 or NKP46; and |
| ITGAM, ITGAX, CD1C, or CLEC4C. |
| NCAM1 or NKP46; and |
| IL17A or IL17F. |
| NCAM1 or NKP46; and |
| CCL2, IL1B, IL8, IL6, or PTGS2. |
| NCAM1 or NKP46; and |
| CTLA4, BTLA, LAG3, HAVCR2, or PDCD1. |
| NCAM1 or NKP46; and |
| CD276, PDL1, PDL2, or IDO1. |
| ITGAM, ITGAX, CD1C, or CLEC4C; and |
| IL17A or IL17F. |
| ITGAM, ITGAX, CD1C, or CLEC4C; and |
| CCL2, IL1B, IL8, IL6, or PTGS2. |
| ITGAM, ITGAX, CD1C, or CLEC4C; and |
| CTLA4, BTLA, LAG3, HAVCR2, or PDCD1. |
| ITGAM, ITGAX, CD1C, or CLEC4C; and |
| CD276, PDL1, PDL2, or IDO1. |
| IL17A or IL17F; and |
| CCL2, IL1B, IL8, IL6, or PTGS2. |
| IL17A or IL17F; and |
| CTLA4, BTLA, LAG3, HAVCR2, or PDCD1. |
| IL17A or IL17F; and |
| CD276, PDL1, PDL2, or IDO1. |
| CCL2, IL1B, IL8, IL6, or PTGS2; and |
| CTLA4, BTLA, LAG3, HAVCR2, or PDCD1. |
| CCL2, IL1B, IL8, IL6, or PTGS2; and |
| CD276, PDL1, PDL2, or IDO1. |
| CTLA4, BTLA, LAG3, HAVCR2, or PDCD1; and |
| CD276, PDL1, PDL2, or IDO1. |
| CD8A, GZMA, GZMB, IFNγ, EOMES, or PRF1; and CX3CL1, CXCL9, CXCL10, CXCR3, CCL21, CCL22. |
| FOXP3; and |
| CX3CL1, CXCL9, CXCL10, CXCR3, CCL21, CCL22. |
| MS4A1 or CD48; and |
| CX3CL1, CXCL9, CXCL10, CXCR3, CCL21, CCL22. |
| NCAM1 or NKP46; and |
| CX3CL1, CXCL9, CXCL10, CXCR3, CCL21, CCL22. |
| ITGAM, ITGAX, CD1C, or CLEC4C; and |
| CX3CL1, CXCL9, CXCL10, CXCR3, CCL21, CCL22. |
| IL17A or IL17F; and |
| CX3CL1, CXCL9, CXCL10, CXCR3, CCL21, CCL22. |
| CCL2, IL1B, IL8, IL6, or PTGS2; and |
| CX3CL1, CXCL9, CXCL10, CXCR3, CCL21, CCL22. |
| CTLA4, BTLA, LAG3, HAVCR2, or PDCD1; and CX3CL1, CXCL9, CXCL10, CXCR3, CCL21, CCL22. |
| CD276, PDL1, PDL2, or IDO1; and |
| CX3CL1, CXCL9, CXCL10, CXCR3, CCL21, CCL22. |
| CD8A, GZMA, GZMB, IFNγ, EOMES, or PRF1; and |
| CD79A, MS4A1, CD19, STAP1, KIAA0125, POU2AF1, FCRL5 |
| CD8A, GZMA, GZMB, IFNγ, EOMES, or PRF1; and |
| KLRC3, KLRK1, KLRC2, KLRD1 |
| CD8A, GZMA, GZMB, IFNγ, EOMES, or PRF1; and |
| CD68, CD163, ITGAM, ITGAX, CD14 |
| CD8A, GZMA, GZMB, IFNγ, EOMES, or PRF1; and |
| LAPTM5, LAIR1, CD4, CSF1R, CD163, ADAP2, CD68, MRC1, CD45RO, SLA, MSR1, FPR3, FCGR2A, FCGR3A |
| CD8A, GZMA, GZMB, IFNγ, EOMES, or PRF1; and |
| CD3D, CD3E, CD2, CD3G, CD6, TRAT1, CD28, LCK |
| CD8A, GZMA, GZMB, IFNγ, EOMES, or PRF1; and |
| CTLA4, BTLA, LAG3, HAVCR2, PDCD1, TIGIT |
| CD8A, GZMA, GZMB, IFNγ, EOMES, or PRF1; and |
| CD274, PDL2, IDO1, PVR |
| CD8A, GZMA, GZMB, IFNγ, EOMES, or PRF1; and |
| CD4, IL2RA, CD69 |
| CD8A, GZMA, GZMB, IFNγ, EOMES, or PRF1; and |
| TAPBP, TAP1, TAP2, PSMB9, PSMB8 |
| CD8A, GZMA, GZMB, IFNγ, EOMES, or PRF1; and |
| CD40, CD80, CD86, CD70, GITRL |
| CD8A, GZMA, GZMB, IFNγ, EOMES, or PRF1; and |
| CD27, CD28, ICOS, TNFRSF4, TNFRSF14, TNFRSF18, TNFRSF14, TNFSF14, CD226 |
| CD8A, GZMA, GZMB, IFNγ, EOMES, or PRF1; and |
| GNLY, KLRK1, KLRB1, GZMH, GZMA, KLRD1, NKG7 |
| CD8A, GZMA, GZMB, IFNγ, EOMES, or PRF1; and |
| FAP, FN1, MMP2, BGN, LOXL2, PDPN, PDGFRB, COL4A1, COL4A2, COL5A1, COL8A1 |
| FOXP3; and |
| CD79A, MS4A1, CD19, STAP1, KIAA0125, POU2AF1, FCRL5 |
| FOXP3; and |
| KLRC3, KLRK1, KLRC2, KLRD1 |
| FOXP3; and |
| CD68, CD163, ITGAM, ITGAX, CD14 |
| FOXP3; and |
| LAPTM5, LAIR1, CD4, CSF1R, CD163, ADAP2, CD68, MRC1, CD45RO, SLA, MSR1, FPR3, FCGR2A, FCGR3A |
| FOXP3; and |
| CD3D, CD3E, CD2, CD3G, CD6, TRAT1, CD28, LCK |
| FOXP3; and |
| CTLA4, BTLA, LAG3, HAVCR2, PDCD1, TIGIT |
| FOXP3; and |
| CD274, PDL2, IDO1, PVR |
| FOXP3; and |
| CD4, IL2RA, CD69 |
| FOXP3; and |
| TAPBP, TAP1, TAP2, PSMB9, PSMB8 |
| FOXP3; and |
| CD40, CD80, CD86, CD70, GITRL |
| FOXP3; and |
| CD27, CD28, ICOS, TNFRSF4, TNFRSF14, TNFRSF18, TNFRSF14, TNFSF14, CD226 |
| FOXP3; and |
| GNLY, KLRK1, KLRB1, GZMH, GZMA, KLRD1, NKG7 |
| FOXP3; and |
| FAP, FN1, MMP2, BGN, LOXL2, PDPN, PDGFRB, COL4A1, COL4A2, COL5A1, COL8A1 |
| MS4A1 or CD48; and |
| CD79A, MS4A1, CD19, STAP1, KIAA0125, POU2AF1, FCRL5 |
| MS4A1 or CD48; and |
| KLRC3, KLRK1, KLRC2, KLRD1 |
| MS4A1 or CD48; and |
| CD68, CD163, ITGAM, ITGAX, CD14 |
| MS4A1 or CD48; and |
| LAPTM5, LAIR1, CD4, CSF1R, CD163, ADAP2, CD68, MRC1, CD45RO, SLA, MSR1, FPR3, FCGR2A, FCGR3A |
| MS4A1 or CD48; and |
| CD3D, CD3E, CD2, CD3G, CD6, TRAT1, CD28, LCK |
| MS4A1 or CD48; and |
| CTLA4, BTLA, LAG3, HAVCR2, PDCD1, TIGIT |
| MS4A1 or CD48; and |
| CD274, PDL2, IDO1, PVR |
| MS4A1 or CD48; and |
| CD4, IL2RA, CD69 |
| MS4A1 or CD48; and |
| TAPBP, TAP1, TAP2, PSMB9, PSMB8 |
| MS4A1 or CD48; and |
| CD40, CD80, CD86, CD70, GITRL |

TABLE 2-continued

| Combinations of two gene signature sets |
|---|
| MS4A1 or CD48; and<br>CD27, CD28, ICOS, TNFRSF4, TNFRSF14, TNFRSF18, TNFSF14, CD226 |
| MS4A1 or CD48; and<br>GNLY, KLRK1, KLRB1, GZMH, GZMA, KLRD1, NKG7 |
| MS4A1 or CD48; and<br>FAP, FN1, MMP2, BGN, LOXL2, PDPN, PDGFRB, COL4A1, COL4A2, COL5A1, COL8A1 |
| NCAM1 or NKP46; and<br>CD79A, MS4A1, CD19, STAP1, KIAA0125, POU2AF1, FCRL5 |
| NCAM1 or NKP46; and<br>KLRC3, KLRK1, KLRC2, KLRD1 |
| NCAM1 or NKP46; and<br>CD68, CD163, ITGAM, ITGAX, CD14 |
| NCAM1 or NKP46; and<br>LAPTM5, LAIR1, CD4, CSF1R, CD163, ADAP2, CD68, MRC1, CD45RO, SLA, MSR1, FPR3, FCGR2A, FCGR3A |
| NCAM1 or NKP46; and<br>CD3D, CD3E, CD2, CD3G, CD6, TRAT1, CD28, LCK |
| NCAM1 or NKP46; and<br>CTLA4, BTLA, LAG3, HAVCR2, PDCD1, TIGIT |
| NCAM1 or NKP46; and<br>CD274, PDL2, IDO1, PVR |
| NCAM1 or NKP46; and<br>CD4, IL2RA, CD69 |
| NCAM1 or NKP46; and<br>TAPBP, TAP1, TAP2, PSMB9, PSMB8 |
| NCAM1 or NKP46; and<br>CD40, CD80, CD86, CD70, GITRL |
| NCAM1 or NKP46; and<br>CD27, CD28, ICOS, TNFRSF4, TNFRSF14, TNFRSF18, TNFSF14, CD226 |
| NCAM1 or NKP46; and<br>GNLY, KLRK1, KLRB1, GZMH, GZMA, KLRD1, NKG7 |
| NCAM1 or NKP46; and<br>FAP, FN1, MMP2, BGN, LOXL2, PDPN, PDGFRB, COL4A1, COL4A2, COL5A1, COL8A1 |
| ITGAM, ITGAX, CD1C, or CLEC4C; and<br>CD79A, MS4A1, CD19, STAP1, KIAA0125, POU2AF1, FCRL5 |
| ITGAM, ITGAX, CD1C, or CLEC4C; and<br>KLRC3, KLRK1, KLRC2, KLRD1 |
| ITGAM, ITGAX, CD1C, or CLEC4C; and<br>CD68, CD163, ITGAM, ITGAX, CD14 |
| ITGAM, ITGAX, CD1C, or CLEC4C; and<br>LAPTM5, LAIR1, CD4, CSF1R, CD163, ADAP2, CD68, MRC1, CD45RO, SLA, MSR1, FPR3, FCGR2A, FCGR3A |
| ITGAM, ITGAX, CD1C, or CLEC4C; and<br>CD3D, CD3E, CD2, CD3G, CD6, TRAT1, CD28, LCK |
| ITGAM, ITGAX, CD1C, or CLEC4C; and<br>CTLA4, BTLA, LAG3, HAVCR2, PDCD1, TIGIT |
| ITGAM, ITGAX, CD1C, or CLEC4C; and<br>CD274, PDL2, IDO1, PVR |
| ITGAM, ITGAX, CD1C, or CLEC4C; and<br>CD4, IL2RA, CD69 |
| ITGAM, ITGAX, CD1C, or CLEC4C; and<br>TAPBP, TAP1, TAP2, PSMB9, PSMB8 |
| ITGAM, ITGAX, CD1C, or CLEC4C; and<br>CD40, CD80, CD86, CD70, GITRL |
| ITGAM, ITGAX, CD1C, or CLEC4C; and<br>CD27, CD28, ICOS, TNFRSF4, TNFRSF14, TNFRSF18, TNFSF14, CD226 |
| ITGAM, ITGAX, CD1C, or CLEC4C; and<br>GNLY, KLRK1, KLRB1, GZMH, GZMA, KLRD1, NKG7 |
| ITGAM, ITGAX, CD1C, or CLEC4C; and<br>FAP, FN1, MMP2, BGN, LOXL2, PDPN, PDGFRB, COL4A1, COL4A2, COL5A1, COL8A1 |
| IL17A or IL17F; and<br>CD79A, MS4A1, CD19, STAP1, KIAA0125, POU2AF1, FCRL5 |
| IL17A or IL17F; and<br>KLRC3, KLRK1, KLRC2, KLRD1 |
| IL17A or IL17F; and<br>CD68, CD163, ITGAM, ITGAX, CD14 |
| IL17A or IL17F; and<br>LAPTM5, LAIR1, CD4, CSF1R, CD163, ADAP2, CD68, MRC1, CD45RO, SLA, MSR1, FPR3, FCGR2A, FCGR3A |
| IL17A or IL17F; and<br>CD3D, CD3E, CD2, CD3G, CD6, TRAT1, CD28, LCK |
| IL17A or IL17F; and<br>CTLA4, BTLA, LAG3, HAVCR2, PDCD1, TIGIT |
| IL17A or IL17F; and<br>CD274, PDL2, IDO1, PVR |
| IL17A or IL17F; and<br>CD4, IL2RA, CD69 |
| IL17A or IL17F; and<br>TAPBP, TAP1, TAP2, PSMB9, PSMB8 |
| IL17A or IL17F; and<br>CD40, CD80, CD86, CD70, GITRL |
| IL17A or IL17F; and<br>CD27, CD28, ICOS, TNFRSF4, TNFRSF14, TNFRSF18, TNFSF14, CD226 |
| IL17A or IL17F; and<br>GNLY, KLRK1, KLRB1, GZMH, GZMA, KLRD1, NKG7 |
| IL17A or IL17F; and<br>FAP, FN1, MMP2, BGN, LOXL2, PDPN, PDGFRB, COL4A1, COL4A2, COL5A1, COL8A1 |
| CCL2, IL1B, IL8 (CXCL8), IL6, or PTGS2; and<br>CD79A, MS4A1, CD19, STAP1, KIAA0125, POU2AF1, FCRL5 |
| CCL2, IL1B, IL8 (CXCL8), IL6, or PTGS2; and<br>KLRC3, KLRK1, KLRC2, KLRD1 |
| CCL2, IL1B, IL8 (CXCL8), IL6, or PTGS2; and<br>CD68, CD163, ITGAM, ITGAX, CD14 |
| CCL2, IL1B, IL8 (CXCL8), IL6, or PTGS2; and<br>LAPTM5, LAIR1, CD4, CSF1R, CD163, ADAP2, CD68, MRC1, CD45RO, SLA, MSR1, FPR3, FCGR2A, FCGR3A |
| CCL2, IL1B, IL8 (CXCL8), IL6, or PTGS2; and<br>CD3D, CD3E, CD2, CD3G, CD6, TRAT1, CD28, LCK |
| CCL2, IL1B, IL8 (CXCL8), IL6, or PTGS2; and<br>CTLA4, BTLA, LAG3, HAVCR2, PDCD1, TIGIT |
| CCL2, IL1B, IL8 (CXCL8), IL6, or PTGS2; and<br>CD274, PDL2, IDO1, PVR |
| CCL2, IL1B, IL8 (CXCL8), IL6, or PTGS2; and<br>CD4, IL2RA, CD69 |
| CCL2, IL1B, IL8 (CXCL8), IL6, or PTGS2; and<br>TAPBP, TAP1, TAP2, PSMB9, PSMB8 |
| CCL2, IL1B, IL8 (CXCL8), IL6, or PTGS2; and<br>CD40, CD80, CD86, CD70, GITRL |
| CCL2, IL1B, IL8 (CXCL8), IL6, or PTGS2; and<br>CD27, CD28, ICOS, TNFRSF4, TNFRSF14, TNFRSF18, TNFSF14, CD226 |
| CCL2, IL1B, IL8 (CXCL8), IL6, or PTGS2; and<br>GNLY, KLRK1, KLRB1, GZMH, GZMA, KLRD1, NKG7 |
| CCL2, IL1B, IL8 (CXCL8), IL6, or PTGS2; and<br>FAP, FN1, MMP2, BGN, LOXL2, PDPN, PDGFRB, COL4A1, COL4A2, COL5A1, COL8A1 |
| CTLA4, BTLA, LAG3, HAVCR2, or PDCD1; and<br>CD79A, MS4A1, CD19, STAP1, KIAA0125, POU2AF1, FCRL5 |
| CTLA4, BTLA, LAG3, HAVCR2, or PDCD1; and<br>KLRC3, KLRK1, KLRC2, KLRD1 |
| CTLA4, BTLA, LAG3, HAVCR2, or PDCD1; and<br>CD68, CD163, ITGAM, ITGAX, CD14 |
| CTLA4, BTLA, LAG3, HAVCR2, or PDCD1; and<br>LAPTM5, LAIR1, CD4, CSF1R, CD163, ADAP2, CD68, MRC1, CD45RO, SLA, MSR1, FPR3, FCGR2A, FCGR3A |
| CTLA4, BTLA, LAG3, HAVCR2, or PDCD1; and<br>CD3D, CD3E, CD2, CD3G, CD6, TRAT1, CD28, LCK |
| CTLA4, BTLA, LAG3, HAVCR2, or PDCD1; and<br>CTLA4, BTLA, LAG3, HAVCR2, PDCD1, TIGIT |
| CTLA4, BTLA, LAG3, HAVCR2, or PDCD1; and<br>CD274, PDL2, IDO1, PVR |
| CTLA4, BTLA, LAG3, HAVCR2, or PDCD1; and<br>CD4, IL2RA, CD69 |
| CTLA4, BTLA, LAG3, HAVCR2, or PDCD1; and<br>TAPBP, TAP1, TAP2, PSMB9, PSMB8 |
| CTLA4, BTLA, LAG3, HAVCR2, or PDCD1; and<br>CD40, CD80, CD86, CD70, GITRL |
| CTLA4, BTLA, LAG3, HAVCR2, or PDCD1; and<br>CD27, CD28, ICOS, TNFRSF4, TNFRSF14, TNFRSF18, TNFSF14, CD226 |
| CTLA4, BTLA, LAG3, HAVCR2, or PDCD1; and<br>GNLY, KLRK1, KLRB1, GZMH, GZMA, KLRD1, NKG7 |
| CTLA4, BTLA, LAG3, HAVCR2, or PDCD1; and<br>FAP, FN1, MMP2, BGN, LOXL2, PDPN, PDGFRB, COL4A1, COL4A2, COL5A1, COL8A1 |
| CD276, PDL1, PDL2, or IDO1; and<br>CD79A, MS4A1, CD19, STAP1, KIAA0125, POU2AF1, FCRL5 |
| CD276, PDL1, PDL2, or IDO1; and |

TABLE 2-continued

| Combinations of two gene signature sets |
|---|
| KLRC3, KLRK1, KLRC2, KLRD1 |
| CD276, PDL1, PDL2, or IDO1; and |
| CD68, CD163, ITGAM, ITGAX, CD14 |
| CD276, PDL1, PDL2, or IDO1; and |
| LAPTM5, LAIR1, CD4, CSF1R, CD163, ADAP2, CD68, MRC1, CD45RO, SLA, MSR1, FPR3, FCGR2A, FCGR3A |
| CD276, PDL1, PDL2, or IDO1; and |
| CD3D, CD3E, CD2, CD3G, CD6, TRAT1, CD28, LCK |
| CD276, PDL1, PDL2, or IDO1; and |
| CTLA4, BTLA, LAG3, HAVCR2, PDCD1, TIGIT |
| CD276, PDL1, PDL2, or IDO1; and |
| CD274, PDL2, IDO1, PVR |
| CD276, PDL1, PDL2, or IDO1; and |
| CD4, IL2RA, CD69 |
| CD276, PDL1, PDL2, or IDO1; and |
| TAPBP, TAP1, TAP2, PSMB9, PSMB8 |
| CD276, PDL1, PDL2, or IDO1; and |
| CD40, CD80, CD86, CD70, GITRL |
| CD276, PDL1, PDL2, or IDO1; and |
| CD27, CD28, ICOS, TNFRSF4, TNFRSF14, TNFRSF18, TNFRSF14, TNFSF14, CD226 |
| CD276, PDL1, PDL2, or IDO1; and |
| GNLY, KLRK1, KLRB1, GZMH, GZMA, KLRD1, NKG7 |
| CD276, PDL1, PDL2, or IDO1; and |
| FAP, FN1, MMP2, BGN, LOXL2, PDPN, PDGFRB, COL4A1, COL4A2, COL5A1, COL8A1 |
| CX3CL1, CXCL9, CXCL10, CXCR3, CCL21, or CCL22; and |
| CD79A, MS4A1, CD19, STAP1, KIAA0125, POU2AF1, FCRL5 |
| CX3CL1, CXCL9, CXCL10, CXCR3, CCL21, or CCL22; and |
| KLRC3, KLRK1, KLRC2, KLRD1 |
| CX3CL1, CXCL9, CXCL10, CXCR3, CCL21, or CCL22; and |
| CD68, CD163, ITGAM, ITGAX, CD14 |
| CX3CL1, CXCL9, CXCL10, CXCR3, CCL21, or CCL22; and |
| LAPTM5, LAIR1, CD4, CSF1R, CD163, ADAP2, CD68, MRC1, CD45RO, SLA, MSR1, FPR3, FCGR2A, FCGR3A |
| CX3CL1, CXCL9, CXCL10, CXCR3, CCL21, or CCL22; and |
| CD3D, CD3E, CD2, CD3G, CD6, TRAT1, CD28, LCK |
| CX3CL1, CXCL9, CXCL10, CXCR3, CCL21, or CCL22; and |
| CTLA4, BTLA, LAG3, HAVCR2, PDCD1, TIGIT |
| CX3CL1, CXCL9, CXCL10, CXCR3, CCL21, or CCL22; and |
| CD274, PDL2, IDO1, PVR |
| CX3CL1, CXCL9, CXCL10, CXCR3, CCL21, or CCL22; and |
| CD4, IL2RA, CD69 |
| CX3CL1, CXCL9, CXCL10, CXCR3, CCL21, or CCL22; and |
| TAPBP, TAP1, TAP2, PSMB9, PSMB8 |
| CX3CL1, CXCL9, CXCL10, CXCR3, CCL21, or CCL22; and |
| CD40, CD80, CD86, CD70, GITRL |
| CX3CL1, CXCL9, CXCL10, CXCR3, CCL21, or CCL22; and |
| CD27, CD28, ICOS, TNFRSF4, TNFRSF14, TNFRSF18, TNFRSF14, TNFSF14, CD226 |
| CX3CL1, CXCL9, CXCL10, CXCR3, CCL21, or CCL22; and |
| GNLY, KLRK1, KLRB1, GZMH, GZMA, KLRD1, NKG7 |
| CX3CL1, CXCL9, CXCL10, CXCR3, CCL21, or CCL22; and |
| FAP, FN1, MMP2, BGN, LOXL2, PDPN, PDGFRB, COL4A1, COL4A2, COL5A1, COL8A1 |
| CD79A, MS4A1, CD19, STAP1, KIAA0125, POU2AF1, or FCRL5; and |
| KLRC3, KLRK1, KLRC2, KLRD1 |
| CD79A, MS4A1, CD19, STAP1, KIAA0125, POU2AF1, or FCRL5; and |
| CD68, CD163, ITGAM, ITGAX, CD14 |
| CD79A, MS4A1, CD19, STAP1, KIAA0125, POU2AF1, or FCRL5; and |
| LAPTM5, LAIR1, CD4, CSF1R, CD163, ADAP2, CD68, MRC1, CD45RO, SLA, MSR1, FPR3, FCGR2A, FCGR3A |
| CD79A, MS4A1, CD19, STAP1, KIAA0125, POU2AF1, or FCRL5; and |
| CD3D, CD3E, CD2, CD3G, CD6, TRAT1, CD28, LCK |
| CD79A, MS4A1, CD19, STAP1, KIAA0125, POU2AF1, or FCRL5; and |
| CTLA4, BTLA, LAG3, HAVCR2, PDCD1, TIGIT |
| CD79A, MS4A1, CD19, STAP1, KIAA0125, POU2AF1, or FCRL5; and |
| CD274, PDL2, IDO1, PVR |
| CD79A, MS4A1, CD19, STAP1, KIAA0125, POU2AF1, or FCRL5; and |
| CD4, IL2RA, CD69 |
| CD79A, MS4A1, CD19, STAP1, KIAA0125, POU2AF1, or FCRL5; and |
| TAPBP, TAP1, TAP2, PSMB9, PSMB8 |
| CD79A, MS4A1, CD19, STAP1, KIAA0125, POU2AF1, or FCRL5; and |
| CD40, CD80, CD86, CD70, GITRL |
| CD79A, MS4A1, CD19, STAP1, KIAA0125, POU2AF1, or FCRL5; and |
| CD27, CD28, ICOS, TNFRSF4, TNFRSF14, TNFRSF18, TNFRSF14, TNFSF14, CD226 |
| CD79A, MS4A1, CD19, STAP1, KIAA0125, POU2AF1, or FCRL5; and |
| GNLY, KLRK1, KLRB1, GZMH, GZMA, KLRD1, NKG7 |
| CD79A, MS4A1, CD19, STAP1, KIAA0125, POU2AF1, or FCRL5; and |
| FAP, FN1, MMP2, BGN, LOXL2, PDPN, PDGFRB, COL4A1, COL4A2, COL5A1, COL8A1 |
| KLRC3, KLRK1, KLRC2, or KLRD1; and |
| CD68, CD163, ITGAM, ITGAX, CD14 |
| KLRC3, KLRK1, KLRC2, or KLRD1; and |
| LAPTM5, LAIR1, CD4, CSF1R, CD163, ADAP2, CD68, MRC1, CD45RO, SLA, MSR1, FPR3, FCGR2A, FCGR3A |
| KLRC3, KLRK1, KLRC2, or KLRD1; and |
| CD3D, CD3E, CD2, CD3G, CD6, TRAT1, CD28, LCK |
| KLRC3, KLRK1, KLRC2, or KLRD1; and |
| CTLA4, BTLA, LAG3, HAVCR2, PDCD1, TIGIT |
| KLRC3, KLRK1, KLRC2, or KLRD1; and |
| CD274, PDL2, IDO1, PVR |
| KLRC3, KLRK1, KLRC2, or KLRD1; and |
| CD4, IL2RA, CD69 |
| KLRC3, KLRK1, KLRC2, or KLRD1; and |
| TAPBP, TAP1, TAP2, PSMB9, PSMB8 |
| KLRC3, KLRK1, KLRC2, or KLRD1; and |
| CD40, CD80, CD86, CD70, GITRL |
| KLRC3, KLRK1, KLRC2, or KLRD1; and |
| CD27, CD28, ICOS, TNFRSF4, TNFRSF14, TNFRSF18, TNFRSF14, TNFSF14, CD226 |
| KLRC3, KLRK1, KLRC2, or KLRD1; and |
| GNLY, KLRK1, KLRB1, GZMH, GZMA, KLRD1, NKG7 |
| KLRC3, KLRK1, KLRC2, or KLRD1; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; and |
| LAPTM5, LAIR1, CD4, CSF1R, CD163, ADAP2, CD68, MRC1, CD45RO, SLA, MSR1, FPR3, FCGR2A, FCGR3A |
| CD68, CD163, ITGAM, ITGAX, or CD14; and |
| CD3D, CD3E, CD2, CD3G, CD6, TRAT1, CD28, LCK |
| CD68, CD163, ITGAM, ITGAX, or CD14; and |
| CTLA4, BTLA, LAG3, HAVCR2, PDCD1, TIGIT |
| CD68, CD163, ITGAM, ITGAX, or CD14; and |
| CD274, PDL2, IDO1, PVR |
| CD68, CD163, ITGAM, ITGAX, or CD14; and |
| CD4, IL2RA, CD69 |
| CD68, CD163, ITGAM, ITGAX, or CD14; and |
| TAPBP, TAP1, TAP2, PSMB9, PSMB8 |
| CD68, CD163, ITGAM, ITGAX, or CD14; and |
| CD40, CD80, CD86, CD70, GITRL |
| CD68, CD163, ITGAM, ITGAX, or CD14; and |
| CD27, CD28, ICOS, TNFRSF4, TNFRSF14, TNFRSF18, TNFRSF14, TNFSF14, CD226 |
| CD68, CD163, ITGAM, ITGAX, or CD14; and |
| GNLY, KLRK1, KLRB1, GZMH, GZMA, KLRD1, NKG7 |
| CD68, CD163, ITGAM, ITGAX, or CD14; and |
| FAP, FN1, MMP2, BGN, LOXL2, PDPN, PDGFRB, COL4A1, COL4A2, COL5A1, COL8A1 |
| LAPTM5, LAIR1, CD4, CSF1R, CD163, ADAP2, CD68, MRC1, CD45RO, SLA, MSR1, FPR3, FCGR2A, or FCGR3A; and |
| CD3D, CD3E, CD2, CD3G, CD6, TRAT1, CD28, LCK |
| LAPTM5, LAIR1, CD4, CSF1R, CD163, ADAP2, CD68, MRC1, CD45RO, SLA, MSR1, FPR3, FCGR2A, or FCGR3A; and |
| CTLA4, BTLA, LAG3, HAVCR2, PDCD1, TIGIT |
| LAPTM5, LAIR1, CD4, CSF1R, CD163, ADAP2, CD68, MRC1, CD45RO, SLA, MSR1, FPR3, FCGR2A, or FCGR3A; and |
| CD274, PDL2, IDO1, PVR |
| LAPTM5, LAIR1, CD4, CSF1R, CD163, ADAP2, CD68, MRC1, CD45RO, SLA, MSR1, FPR3, FCGR2A, or FCGR3A; and |
| CD4, IL2RA, CD69 |
| LAPTM5, LAIR1, CD4, CSF1R, CD163, ADAP2, CD68, MRC1, CD45RO, SLA, MSR1, FPR3, FCGR2A, or FCGR3A; and |

TABLE 2-continued

Combinations of two gene signature sets

TAPBP, TAP1, TAP2, PSMB9, PSMB8
LAPTM5, LAIR1, CD4, CSF1R, CD163, ADAP2, CD68, MRC1, CD45RO, SLA, MSR1, FPR3, FCGR2A, or FCGR3A; and
CD40, CD80, CD86, CD70, GITRL
LAPTM5, LAIR1, CD4, CSF1R, CD163, ADAP2, CD68, MRC1, CD45RO, SLA, MSR1, FPR3, FCGR2A, or FCGR3A; and
CD27, CD28, ICOS, TNFRSF4, TNFRSF14, TNFRSF18, TNFRSF14, TNFSF14, CD226
LAPTM5, LAIR1, CD4, CSF1R, CD163, ADAP2, CD68, MRC1, CD45RO, SLA, MSR1, FPR3, FCGR2A, or FCGR3A; and
GNLY, KLRK1, KLRB1, GZMH, GZMA, KLRD1, NKG7
LAPTM5, LAIR1, CD4, CSF1R, CD163, ADAP2, CD68, MRC1, CD45RO, SLA, MSR1, FPR3, FCGR2A, or FCGR3A; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK; and
CTLA4, BTLA, LAG3, HAVCR2, PDCD1, TIGIT
CD3D, CD3E, CD2, CD3G, CD6, TRAT1, CD28, or LCK; and
CD274, PDL2, IDO1, PVR
CD3D, CD3E, CD2, CD3G, CD6, TRAT1, CD28, or LCK; and
CD4, IL2RA, CD69
CD3D, CD3E, CD2, CD3G, CD6, TRAT1, CD28, or LCK; and
TAPBP, TAP1, TAP2, PSMB9, PSMB8
CD3D, CD3E, CD2, CD3G, CD6, TRAT1, CD28, or LCK; and
CD40, CD80, CD86, CD70, GITRL
CD3D, CD3E, CD2, CD3G, CD6, TRAT1, CD28, or LCK; and
CD27, CD28, ICOS, TNFRSF4, TNFRSF14, TNFRSF18, TNFRSF14, TNFSF14, CD226
CD3D, CD3E, CD2, CD3G, CD6, TRAT1, CD28, or LCK; and
GNLY, KLRK1, KLRB1, GZMH, GZMA, KLRD1, NKG7
CD3D, CD3E, CD2, CD3G, CD6, TRAT1, CD28, or LCK; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT; and
CD274, PDL2, IDO1, PVR
CTLA4, BTLA, LAG3, HAVCR2, PDCD1, or TIGIT; and
CD4, IL2RA, CD69
CTLA4, BTLA, LAG3, HAVCR2, PDCD1, or TIGIT; and
TAPBP, TAP1, TAP2, PSMB9, PSMB8
CTLA4, BTLA, LAG3, HAVCR2, PDCD1, or TIGIT; and
CD40, CD80, CD86, CD70, GITRL
CTLA4, BTLA, LAG3, HAVCR2, PDCD1, or TIGIT; and
CD27, CD28, ICOS, TNFRSF4, TNFRSF14, TNFRSF18, TNFRSF14, TNFSF14, CD226
CTLA4, BTLA, LAG3, HAVCR2, PDCD1, or TIGIT; and
GNLY, KLRK1, KLRB1, GZMH, GZMA, KLRD1, NKG7
CTLA4, BTLA, LAG3, HAVCR2, PDCD1, or TIGIT; and
FAP, FN1, MMP2, BGN, LOXL2, PDPN, PDGFRB, COL4A1, COL4A2, COL5A1, COL8A1
CD274, PDL2, IDO1, or PVR; and
CD4, IL2RA, CD69
CD274, PDL2, IDO1, or PVR; and
TAPBP, TAP1, TAP2, PSMB9, PSMB8
CD274, PDL2, IDO1, or PVR; and
CD40, CD80, CD86, CD70, GITRL
CD274, PDL2, IDO1, or PVR; and
CD27, CD28, ICOS, TNFRSF4, TNFRSF14, TNFRSF18, TNFRSF14, TNFSF14, CD226
CD274, PDL2, IDO1, or PVR; and
GNLY, KLRK1, KLRB1, GZMH, GZMA, KLRD1, NKG7
CD274, PDL2, IDO1, or PVR; and
FAP, FN1, MMP2, BGN, LOXL2, PDPN, PDGFRB, COL4A1, COL4A2, COL5A1, COL8A1
CD4, IL2RA, or CD69; and
TAPBP, TAP1, TAP2, PSMB9, PSMB8
CD4, IL2RA, or CD69; and
CD40, CD80, CD86, CD70, GITRL
CD4, IL2RA, or CD69; and
CD27, CD28, ICOS, TNFRSF4, TNFRSF14, TNFRSF18, TNFRSF14, TNFSF14, CD226
CD4, IL2RA, or CD69; and
GNLY, KLRK1, KLRB1, GZMH, GZMA, KLRD1, NKG7
CD4, IL2RA, or CD69; and
FAP, FN1, MMP2, BGN, LOXL2, PDPN, PDGFRB, COL4A1, COL4A2, COL5A1, COL8A1
TAPBP, TAP1, TAP2, PSMB9, or PSMB8; and
CD40, CD80, CD86, CD70, GITRL
TAPBP, TAP1, TAP2, PSMB9, or PSMB8; and
CD27, CD28, ICOS, TNFRSF4, TNFRSF14, TNFRSF18, TNFRSF14, TNFSF14, CD226
TAPBP, TAP1, TAP2, PSMB9, or PSMB8; and
GNLY, KLRK1, KLRB1, GZMH, GZMA, KLRD1, NKG7
TAPBP, TAP1, TAP2, PSMB9, or PSMB8; and
FAP, FN1, MMP2, BGN, LOXL2, PDPN, PDGFRB, COL4A1, COL4A2, COL5A1, COL8A1
CD40, CD80, CD86, CD70, or GITRL; and
CD27, CD28, ICOS, TNFRSF4, TNFRSF14, TNFRSF18, TNFRSF14, TNFSF14, CD226
CD40, CD80, CD86, CD70, or GITRL; and
GNLY, KLRK1, KLRB1, GZMH, GZMA, KLRD1, NKG7
CD40, CD80, CD86, CD70, or GITRL; and
FAP, FN1, MMP2, BGN, LOXL2, PDPN, PDGFRB, COL4A1, COL4A2, COL5A1, COL8A1
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1

In another embodiment, the expression levels of one or more of the genes in an immune cell gene signature in three particular gene signature sets are determined. For example, combinations of three particular gene signature sets are set forth in Table 3 below.

TABLE 3

Combinations of three gene signature sets

CD8A, GZMA, GZMB, IFNγ, EOMES, or PRF1;
FOXP3; and
MS4A1 or CD48.
CD8A, GZMA, GZMB, IFNγ, EOMES, or PRF1;
FOXP3; and
NCAM1 or NKP46.
CD8A, GZMA, GZMB, IFNγ, EOMES, or PRF1;
FOXP3; and
ITGAM, ITGAX, CD1C, or CLEC4C.
CD8A, GZMA, GZMB, IFNγ, EOMES, or PRF1;
FOXP3; and
IL17A or IL17F.
CD8A, GZMA, GZMB, IFNγ, EOMES, or PRF1;
FOXP3; and
CCL2, IL1B, IL8, IL6, or PTGS2.
CD8A, GZMA, GZMB, IFNγ, EOMES, or PRF1;
FOXP3; and
CTLA4, BTLA, LAG3, HAVCR2, or PDCD1.
CD8A, GZMA, GZMB, IFNγ, EOMES, or PRF1;
FOXP3; and
CD276, PDL1, PDL2, or IDO1.
CD8A, GZMA, GZMB, IFNγ, EOMES, or PRF1;
MS4A1 or CD48; and
NCAM1 or NKP46.
CD8A, GZMA, GZMB, IFNγ, EOMES, or PRF1;
MS4A1 or CD48; and
ITGAM, ITGAX, CD1C, or CLEC4C.
CD8A, GZMA, GZMB, IFNγ, EOMES, or PRF1;
MS4A1 or CD48; and
IL17A or IL17F.
CD8A, GZMA, GZMB, IFNγ, EOMES, or PRF1;
MS4A1 or CD48; and
CCL2, IL1B, IL8, IL6, or PTGS2.
CD8A, GZMA, GZMB, IFNγ, EOMES, or PRF1;
MS4A1 or CD48; and
CTLA4, BTLA, LAG3, HAVCR2, or PDCD1.
CD8A, GZMA, GZMB, IFNγ, EOMES, or PRF1;
MS4A1 or CD48; and
CD276, PDL1, PDL2, or IDO1.

TABLE 3-continued

Combinations of three gene signature sets

CD8A, GZMA, GZMB, IFNγ, EOMES, or PRF1;
NCAM1 or NKP46; and
ITGAM, ITGAX, CD1C, or CLEC4C.
CD8A, GZMA, GZMB, IFNγ, EOMES, or PRF1;
NCAM1 or NKP46; and
IL17A or IL17F.
CD8A, GZMA, GZMB, IFNγ, EOMES, or PRF1;
NCAM1 or NKP46; and
CCL2, IL1B, IL8, IL6, or PTGS2.
CD8A, GZMA, GZMB, IFNγ, EOMES, or PRF1;
NCAM1 or NKP46; and
CTLA4, BTLA, LAG3, HAVCR2, or PDCD1.
CD8A, GZMA, GZMB, IFNγ, EOMES, or PRF1;
NCAM1 or NKP46; and
CD276, PDL1, PDL2, or IDO1.
CD8A, GZMA, GZMB, IFNγ, EOMES, or PRF1;
ITGAM, ITGAX, CD1C, or CLEC4C; and
IL17A or IL17F.
CD8A, GZMA, GZMB, IFNγ, EOMES, or PRF1;
ITGAM, ITGAX, CD1C, or CLEC4C; and
CCL2, IL1B, IL8, IL6, or PTGS2.
CD8A, GZMA, GZMB, IFNγ, EOMES, or PRF1;
ITGAM, ITGAX, CD1C, or CLEC4C; and
CTLA4, BTLA, LAG3, HAVCR2, or PDCD1.
CD8A, GZMA, GZMB, IFNγ, EOMES, or PRF1;
ITGAM, ITGAX, CD1C, or CLEC4C; and
CD276, PDL1, PDL2, or IDO1.
CD8A, GZMA, GZMB, IFNγ, EOMES, or PRF1;
IL17A or IL17F; and
CCL2, IL1B, IL8, IL6, or PTGS2.
CD8A, GZMA, GZMB, IFNγ, EOMES, or PRF1;
IL17A or IL17F; and
CTLA4, BTLA, LAG3, HAVCR2, or PDCD1.
CD8A, GZMA, GZMB, IFNγ, EOMES, or PRF1;
IL17A or IL17F; and
CD276, PDL1, PDL2, or IDO1.
CD8A, GZMA, GZMB, IFNγ, EOMES, or PRF1;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
CCL2, IL1B, IL8, IL6, or PTGS2; and
CD276, PDL1, PDL2, or IDO1.
CD8A, GZMA, GZMB, IFNγ, EOMES, or PRF1;
CTLA4, BTLA, LAG3, HAVCR2, or PDCD1; and
CD276, PDL1, PDL2, or IDO1.
FOXP3;
MS4A1 or CD48; and
NCAM1 or NKP46.
FOXP3;
MS4A1 or CD48; and
ITGAM, ITGAX, CD1C, or CLEC4C.
FOXP3;
MS4A1 or CD48; and
IL17A or IL17F.
FOXP3;
MS4A1 or CD48; and
CCL2, IL1B, IL8, IL6, or PTGS2.
FOXP3;
MS4A1 or CD48; and
CTLA4, BTLA, LAG3, HAVCR2, or PDCD1.
FOXP3;
MS4A1 or CD48; and
CD276, PDL1, PDL2, or IDO1.
FOXP3;
NCAM1 or NKP46; and
ITGAM, ITGAX, CD1C, or CLEC4C.
FOXP3;
NCAM1 or NKP46; and
IL17A or IL17F.
FOXP3;
NCAM1 or NKP46; and
CCL2, IL1B, IL8, IL6, or PTGS2.
FOXP3;
NCAM1 or NKP46; and
CTLA4, BTLA, LAG3, HAVCR2, or PDCD1.
FOXP3;
NCAM1 or NKP46; and
CD276, PDL1, PDL2, or IDO1.
FOXP3;
ITGAM, ITGAX, CD1C, or CLEC4C; and
IL17A or IL17F.
FOXP3;
ITGAM, ITGAX, CD1C, or CLEC4C; and
CCL2, IL1B, IL8, IL6, or PTGS2.
FOXP3;
ITGAM, ITGAX, CD1C, or CLEC4C; and
CTLA4, BTLA, LAG3, HAVCR2, or PDCD1.
FOXP3;
ITGAM, ITGAX, CD1C, or CLEC4C; and
CD276, PDL1, PDL2, or IDO1.
FOXP3;
IL17A or IL17F; and
CCL2, IL1B, IL8, IL6, or PTGS2.
FOXP3;
IL17A or IL17F; and
CTLA4, BTLA, LAG3, HAVCR2, or PDCD1.
FOXP3;
IL17A or IL17F; and
CD276, PDL1, PDL2, or IDO1.
FOXP3;
CCL2, IL1B, IL8, IL6, or PTGS2; and
CTLA4, BTLA, LAG3, HAVCR2, or PDCD1.
FOXP3;
CCL2, IL1B, IL8, IL6, or PTGS2; and
CD276, PDL1, PDL2, or IDO1.
FOXP3;
CTLA4, BTLA, LAG3, HAVCR2, or PDCD1; and
CD276, PDL1, PDL2, or IDO1.
MS4A1 or CD48;
NCAM1 or NKP46; and
ITGAM, ITGAX, CD1C, or CLEC4C.
MS4A1 or CD48;
NCAM1 or NKP46; and
IL17A or IL17F.
MS4A1 or CD48;
NCAM1 or NKP46; and
CCL2, IL1B, IL8, IL6, or PTGS2.
MS4A1 or CD48;
NCAM1 or NKP46; and
CTLA4, BTLA, LAG3, HAVCR2, or PDCD1.
MS4A1 or CD48;
NCAM1 or NKP46; and
CD276, PDL1, PDL2, or IDO1.
MS4A1 or CD48;
ITGAM, ITGAX, CD1C, or CLEC4C; and
IL17A or IL17F.
MS4A1 or CD48;
ITGAM, ITGAX, CD1C, or CLEC4C; and
CCL2, IL1B, IL8, IL6, or PTGS2.
MS4A1 or CD48;
ITGAM, ITGAX, CD1C, or CLEC4C; and
CTLA4, BTLA, LAG3, HAVCR2, or PDCD1.
MS4A1 or CD48;
ITGAM, ITGAX, CD1C, or CLEC4C; and
CD276, PDL1, PDL2, or IDO1.
MS4A1 or CD48;
IL17A or IL17F; and
CCL2, IL1B, IL8, IL6, or PTGS2.
MS4A1 or CD48;
IL17A or IL17F; and
CTLA4, BTLA, LAG3, HAVCR2, or PDCD1.
MS4A1 or CD48;
IL17A or IL17F; and
CD276, PDL1, PDL2, or IDO1.
MS4A1 or CD48;
CCL2, IL1B, IL8, IL6, or PTGS2; and
CTLA4, BTLA, LAG3, HAVCR2, or PDCD1.
MS4A1 or CD48;
CCL2, IL1B, IL8, IL6, or PTGS2; and
CD276, PDL1, PDL2, or IDO1.
MS4A1 or CD48;
CTLA4, BTLA, LAG3, HAVCR2, or PDCD1; and
CD276, PDL1, PDL2, or IDO1.
NCAM1 or NKP46;
ITGAM, ITGAX, CD1C, or CLEC4C; and
IL17A or IL17F.

TABLE 3-continued

Combinations of three gene signature sets

NCAM1 or NKP46;
ITGAM, ITGAX, CD1C, or CLEC4C; and
CCL2, IL1B, IL8, IL6, or PTGS2.
NCAM1 or NKP46;
ITGAM, ITGAX, CD1C, or CLEC4C; and
CTLA4, BTLA, LAG3, HAVCR2, or PDCD1.
NCAM1 or NKP46;
ITGAM, ITGAX, CD1C, or CLEC4C; and
CD276, PDL1, PDL2, or IDO1.
NCAM1 or NKP46;
IL17A or IL17F; and
CCL2, IL1B, IL8, IL6, or PTGS2.
NCAM1 or NKP46;
IL17A or IL17F; and
CTLA4, BTLA, LAG3, HAVCR2, or PDCD1.
NCAM1 or NKP46;
IL17A or IL17F; and
CD276, PDL1, PDL2, or IDO1.
NCAM1 or NKP46;
CCL2, IL1B, IL8, IL6, or PTGS2; and
CTLA4, BTLA, LAG3, HAVCR2, or PDCD1.
NCAM1 or NKP46;
CCL2, IL1B, IL8, IL6, or PTGS2; and
CD276, PDL1, PDL2, or IDO1.
NCAM1 or NKP46;
CTLA4, BTLA, LAG3, HAVCR2, or PDCD1; and
CD276, PDL1, PDL2, or IDO1.
ITGAM, ITGAX, CD1C, or CLEC4C;
IL17A or IL17F; and
CCL2, IL1B, IL8, IL6, or PTGS2.
ITGAM, ITGAX, CD1C, or CLEC4C;
IL17A or IL17F; and
CTLA4, BTLA, LAG3, HAVCR2, or PDCD1.
ITGAM, ITGAX, CD1C, or CLEC4C;
IL17A or IL17F; and
CD276, PDL1, PDL2, or IDO1.
ITGAM, ITGAX, CD1C, or CLEC4C;
CCL2, IL1B, IL8, IL6, or PTGS2; and
CTLA4, BTLA, LAG3, HAVCR2, or PDCD1.
ITGAM, ITGAX, CD1C, or CLEC4C;
CCL2, IL1B, IL8, IL6, or PTGS2; and
CD276, PDL1, PDL2, or IDO1.
ITGAM, ITGAX, CD1C, or CLEC4C;
CTLA4, BTLA, LAG3, HAVCR2, or PDCD1; and
CD276, PDL1, PDL2, or IDO1.
IL17A or IL17F;
CCL2, IL1B, IL8, IL6, or PTGS2; and
CTLA4, BTLA, LAG3, HAVCR2, or PDCD1.
IL17A or IL17F;
CCL2, IL1B, IL8, IL6, or PTGS2; and
CD276, PDL1, PDL2, or IDO1.
IL17A or IL17F;
CTLA4, BTLA, LAG3, HAVCR2, or PDCD1; and
CD276, PDL1, PDL2, or IDO1.
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3; and
CX3CL1, CXCL9, CXCL10, CXCR3, CCL21, CCL22.
CD8A, GZMA, GZMB, IFNγ, EOMES, or PRF1;
MS4A1 or CD48; and
CX3CL1, CXCL9, CXCL10, CXCR3, CCL21, CCL22.
CD8A, GZMA, GZMB, IFNγ, EOMES, or PRF1;
NCAM1 or NKP46; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C; and
CX3CL1, CXCL9, CXCL10, CXCR3, CCL21, CCL22.
CD8A, GZMA, GZMB, IFNγ, EOMES, or PRF1;
IL17A or IL17F; and
CX3CL1, CXCL9, CXCL10, CXCR3, CCL21, CCL22.
CD8A, GZMA, GZMB, IFNγ, EOMES, or PRF1;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
CD276, PDL1, PDL2, or IDO1; and
CX3CL1, CXCL9, CXCL10, CXCR3, CCL21, CCL22.
FOXP3;
MS4A1 or CD48; and
CX3CL1, CXCL9, CXCL10, CXCR3, CCL21, CCL22.
FOXP3;
NCAM1 or NKP46; and
CX3CL1, CXCL9, CXCL10, CXCR3, CCL21, CCL22.
FOXP3;
ITGAM, ITGAX, CD1C, or CLEC4C; and
CX3CL1, CXCL9, CXCL10, CXCR3, CCL21, CCL22.
FOXP3;
IL17A or IL17F; and
CX3CL1, CXCL9, CXCL10, CXCR3, CCL21, CCL22.
FOXP3;
CCL2, IL1B, IL8, IL6, or PTGS2; and
CX3CL1, CXCL9, CXCL10, CXCR3, CCL21, CCL22.
FOXP3;
CTLA4, BTLA, LAG3, HAVCR2, or PDCD1; and
CX3CL1, CXCL9, CXCL10, CXCR3, CCL21, CCL22.
FOXP3;
CD276, PDL1, PDL2, or IDO1; and
CX3CL1, CXCL9, CXCL10, CXCR3, CCL21, CCL22.
MS4A1 or CD48;
NCAM1 or NKP46; and
CX3CL1, CXCL9, CXCL10, CXCR3, CCL21, CCL22.
MS4A1 or CD48;
ITGAM, ITGAX, CD1C, or CLEC4C; and
CX3CL1, CXCL9, CXCL10, CXCR3, CCL21, CCL22.
MS4A1 or CD48;
IL17A or IL17F; and
CX3CL1, CXCL9, CXCL10, CXCR3, CCL21, CCL22.
MS4A1 or CD48;
CCL2, IL1B, IL8, IL6, or PTGS2; and
CX3CL1, CXCL9, CXCL10, CXCR3, CCL21, CCL22.
MS4A1 or CD48;
CTLA4, BTLA, LAG3, HAVCR2, or PDCD1; and
CX3CL1, CXCL9, CXCL10, CXCR3, CCL21, CCL22.
MS4A1 or CD48;
CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C; and
CX3CL1, CXCL9, CXCL10, CXCR3, CCL21, CCL22.
NCAM1 or NKP46;
IL17A or IL17F; and
CX3CL1, CXCL9, CXCL10, CXCR3, CCL21, CCL22.
NCAM1 or NKP46;
CCL2, IL1B, IL8, IL6, or PTGS2; and
CX3CL1, CXCL9, CXCL10, CXCR3, CCL21, CCL22.
NCAM1 or NKP46;
CTLA4, BTLA, LAG3, HAVCR2, or PDCD1; and
CX3CL1, CXCL9, CXCL10, CXCR3, CCL21, CCL22.
NCAM1 or NKP46;
CD276, PDL1, PDL2, or IDO1; and
CX3CL1, CXCL9, CXCL10, CXCR3, CCL21, CCL22.
ITGAM, ITGAX, CD1C, or CLEC4C;
IL17A or IL17F; and
CX3CL1, CXCL9, CXCL10, CXCR3, CCL21, CCL22.
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
ITGAM, ITGAX, CD1C, or CLEC4C;
CD276, PDL1, PDL2, or IDO1; and
CX3CL1, CXCL9, CXCL10, CXCR3, CCL21, CCL22.
IL17A or IL17F;
CCL2, IL1B, IL8, IL6, or PTGS2; and
CX3CL1, CXCL9, CXCL10, CXCR3, CCL21, CCL22.
IL17A or IL17F;
CTLA4, BTLA, LAG3, HAVCR2, or PDCD1; and
CX3CL1, CXCL9, CXCL10, CXCR3, CCL21, CCL22.
IL17A or IL17F;
CD276, PDL1, PDL2, or IDO1; and
CX3CL1, CXCL9, CXCL10, CXCR3, CCL21, CCL22.

TABLE 3-continued

Combinations of three gene signature sets

CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CCL2, IL1B, IL8, IL6, or PTGS2;
CD276, PDL1, PDL2, or IDO1; and
CX3CL1, CXCL9, CXCL10, CXCR3, CCL21, CCL22.
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3; and
CD79A, MS4A1, CD19, STAP1, KIAA0125, POU2AF1, FCRL5
CD8A, GZMA, GZMB, IFNγ, EOMES, or PRF1;
MS4A1 or CD48; and
CD79A, MS4A1, CD19, STAP1, KIAA0125, POU2AF1, FCRL5
CD8A, GZMA, GZMB, IFNγ, EOMES, or PRF1;
NCAM1 or NKP46; and
CD79A, MS4A1, CD19, STAP1, KIAA0125, POU2AF1, FCRL5
CD8A, GZMA, GZMB, IFNγ, EOMES, or PRF1;
ITGAM, ITGAX, CD1C, or CLEC4C; and
CD79A, MS4A1, CD19, STAP1, KIAA0125, POU2AF1, FCRL5
CD8A, GZMA, GZMB, IFNγ, EOMES, or PRF1;
IL17A or IL17F; and
CD79A, MS4A1, CD19, STAP1, KIAA0125, POU2AF1, FCRL5
CD8A, GZMA, GZMB, IFNγ, EOMES, or PRF1;
CCL2, IL1B, IL8 (CXCL8), IL6, or PTGS2; and
CD79A, MS4A1, CD19, STAP1, KIAA0125, POU2AF1, FCRL5
CD8A, GZMA, GZMB, IFNγ, EOMES, or PRF1;
CTLA4, BTLA, LAG3, HAVCR2, or PDCD1; and
CD79A, MS4A1, CD19, STAP1, KIAA0125, POU2AF1, FCRL5
CD8A, GZMA, GZMB, IFNγ, EOMES, or PRF1;
CD276, PDL1, PDL2, or IDO1; and
CD79A, MS4A1, CD19, STAP1, KIAA0125, POU2AF1, FCRL5
CD8A, GZMA, GZMB, IFNγ, EOMES, or PRF1;
CX3CL1, CXCL9, CXCL10, CXCR3, CCL21, or CCL22; and
CD79A, MS4A1, CD19, STAP1, KIAA0125, POU2AF1, FCRL5
CD8A, GZMA, GZMB, IFNγ, EOMES, or PRF1;
FOXP3; and
KLRC3, KLRK1, KLRC2, KLRD1
CD8A, GZMA, GZMB, IFNγ, EOMES, or PRF1;
MS4A1 or CD48; and
KLRC3, KLRK1, KLRC2, KLRD1
CD8A, GZMA, GZMB, IFNγ, EOMES, or PRF1;
NCAM1 or NKP46; and
KLRC3, KLRK1, KLRC2, KLRD1
CD8A, GZMA, GZMB, IFNγ, EOMES, or PRF1;
ITGAM, ITGAX, CD1C, or CLEC4C; and
KLRC3, KLRK1, KLRC2, KLRD1
CD8A, GZMA, GZMB, IFNγ, EOMES, or PRF1;
IL17A or IL17F; and
KLRC3, KLRK1, KLRC2, KLRD1
CD8A, GZMA, GZMB, IFNγ, EOMES, or PRF1;
CCL2, IL1B, IL8 (CXCL8), IL6, or PTGS2; and
KLRC3, KLRK1, KLRC2, KLRD1
CD8A, GZMA, GZMB, IFNγ, EOMES, or PRF1;
CTLA4, BTLA, LAG3, HAVCR2, or PDCD1; and
KLRC3, KLRK1, KLRC2, KLRD1
CD8A, GZMA, GZMB, IFNγ, EOMES, or PRF1;
CD276, PDL1, PDL2, or IDO1; and
KLRC3, KLRK1, KLRC2, KLRD1
CD8A, GZMA, GZMB, IFNγ, EOMES, or PRF1;
CX3CL1, CXCL9, CXCL10, CXCR3, CCL21, or CCL22; and
KLRC3, KLRK1, KLRC2, KLRD1
CD8A, GZMA, GZMB, IFNγ, EOMES, or PRF1;
FOXP3; and
CD68, CD163, ITGAM, ITGAX, CD14
CD8A, GZMA, GZMB, IFNγ, EOMES, or PRF1;
MS4A1 or CD48; and
CD68, CD163, ITGAM, ITGAX, CD14
CD8A, GZMA, GZMB, IFNγ, EOMES, or PRF1;
NCAM1 or NKP46; and
CD68, CD163, ITGAM, ITGAX, CD14
CD8A, GZMA, GZMB, IFNγ, EOMES, or PRF1;
ITGAM, ITGAX, CD1C, or CLEC4C; and
CD68, CD163, ITGAM, ITGAX, CD14
CD8A, GZMA, GZMB, IFNγ, EOMES, or PRF1;
IL17A or IL17F; and
CD68, CD163, ITGAM, ITGAX, CD14
CD8A, GZMA, GZMB, IFNγ, EOMES, or PRF1;
CCL2, IL1B, IL8 (CXCL8), IL6, or PTGS2; and
CD68, CD163, ITGAM, ITGAX, CD14
CD8A, GZMA, GZMB, IFNγ, EOMES, or PRF1;
CTLA4, BTLA, LAG3, HAVCR2, or PDCD1; and
CD68, CD163, ITGAM, ITGAX, CD14
CD8A, GZMA, GZMB, IFNγ, EOMES, or PRF1;
CD276, PDL1, PDL2, or IDO1; and
CD68, CD163, ITGAM, ITGAX, CD14
CD8A, GZMA, GZMB, IFNγ, EOMES, or PRF1;
CX3CL1, CXCL9, CXCL10, CXCR3, CCL21, or CCL22; and
CD68, CD163, ITGAM, ITGAX, CD14
CD8A, GZMA, GZMB, IFNγ, EOMES, or PRF1;
FOXP3; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
MS4A1 or CD48; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
NCAM1 or NKP46; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
ITGAM, ITGAX, CD1C, or CLEC4C; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
IL17A or IL17F; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
CCL2, IL1B, IL8 (CXCL8), IL6, or PTGS2; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
CTLA4, BTLA, LAG3, HAVCR2, or PDCD1; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
CD276, PDL1, PDL2, or IDO1; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
CX3CL1, CXCL9, CXCL10, CXCR3, CCL21, or CCL22; and
LAPTM5, LAIR1, CD4, CSF1R, CD163, ADAP2, CD68, MRC1, CD45RO, SLA, MSR1, FPR3, FCGR2A, FCGR3A
CD8A, GZMA, GZMB, IFNγ, EOMES, or PRF1;
FOXP3; and
CD3D, CD3E, CD2, CD3G, CD6, TRAT1, CD28, LCK
CD8A, GZMA, GZMB, IFNγ, EOMES, or PRF1;
MS4A1 or CD48; and
CD3D, CD3E, CD2, CD3G, CD6, TRAT1, CD28, LCK
CD8A, GZMA, GZMB, IFNγ, EOMES, or PRF1;
NCAM1 or NKP46; and
CD3D, CD3E, CD2, CD3G, CD6, TRAT1, CD28, LCK
CD8A, GZMA, GZMB, IFNγ, EOMES, or PRF1;
ITGAM, ITGAX, CD1C, or CLEC4C; and
CD3D, CD3E, CD2, CD3G, CD6, TRAT1, CD28, LCK
CD8A, GZMA, GZMB, IFNγ, EOMES, or PRF1;
IL17A or IL17F; and
CD3D, CD3E, CD2, CD3G, CD6, TRAT1, CD28, LCK
CD8A, GZMA, GZMB, IFNγ, EOMES, or PRF1;
CCL2, IL1B, IL8 (CXCL8), IL6, or PTGS2; and
CD3D, CD3E, CD2, CD3G, CD6, TRAT1, CD28, LCK
CD8A, GZMA, GZMB, IFNγ, EOMES, or PRF1;
CTLA4, BTLA, LAG3, HAVCR2, or PDCD1; and
CD3D, CD3E, CD2, CD3G, CD6, TRAT1, CD28, LCK
CD8A, GZMA, GZMB, IFNγ, EOMES, or PRF1;
CD276, PDL1, PDL2, or IDO1; and
CD3D, CD3E, CD2, CD3G, CD6, TRAT1, CD28, LCK
CD8A, GZMA, GZMB, IFNγ, EOMES, or PRF1;
CX3CL1, CXCL9, CXCL10, CXCR3, CCL21, or CCL22; and
CD3D, CD3E, CD2, CD3G, CD6, TRAT1, CD28, LCK
CD8A, GZMA, GZMB, IFNγ, EOMES, or PRF1;
FOXP3; and
CTLA4, BTLA, LAG3, HAVCR2, PDCD1, TIGIT TABLE 3-continued

| Combinations of three gene signature sets |
|---|
| CD8A, GZMA, GZMB, IFNγ, EOMES, or PRF1; MS4A1 or CD48; and CTLA4, BTLA, LAG3, HAVCR2, PDCD1, TIGIT |
| CD8A, GZMA, GZMB, IFNγ, EOMES, or PRF1; NCAM1 or NKP46; and CTLA4, BTLA, LAG3, HAVCR2, PDCD1, TIGIT |
| CD8A, GZMA, GZMB, IFNγ, EOMES, or PRF1; ITGAM, ITGAX, CD1C, or CLEC4C; and CTLA4, BTLA, LAG3, HAVCR2, PDCD1, TIGIT |
| CD8A, GZMA, GZMB, IFNγ, EOMES, or PRF1; IL17A or IL17F; and CTLA4, BTLA, LAG3, HAVCR2, PDCD1, TIGIT |
| CD8A, GZMA, GZMB, IFNγ, EOMES, or PRF1; CCL2, IL1B, IL8 (CXCL8), IL6, or PTGS2; and CTLA4, BTLA, LAG3, HAVCR2, PDCD1, TIGIT |
| CD8A, GZMA, GZMB, IFNγ, EOMES, or PRF1; CTLA4, BTLA, LAG3, HAVCR2, or PDCD1; and CTLA4, BTLA, LAG3, HAVCR2, PDCD1, TIGIT |
| CD8A, GZMA, GZMB, IFNγ, EOMES, or PRF1; CD276, PDL1, PDL2, or IDO1; and CTLA4, BTLA, LAG3, HAVCR2, PDCD1, TIGIT |
| CD8A, GZMA, GZMB, IFNγ, EOMES, or PRF1; CX3CL1, CXCL9, CXCL10, CXCR3, CCL21, or CCL22; and CTLA4, BTLA, LAG3, HAVCR2, PDCD1, TIGIT |
| CD8A, GZMA, GZMB, IFNγ, EOMES, or PRF1; FOXP3; and CD274, PDL2, IDO1, PVR |
| CD8A, GZMA, GZMB, IFNγ, EOMES, or PRF1; MS4A1 or CD48; and CD274, PDL2, IDO1, PVR |
| CD8A, GZMA, GZMB, IFNγ, EOMES, or PRF1; NCAM1 or NKP46; and CD274, PDL2, IDO1, PVR |
| CD8A, GZMA, GZMB, IFNγ, EOMES, or PRF1; ITGAM, ITGAX, CD1C, or CLEC4C; and CD274, PDL2, IDO1, PVR |
| CD8A, GZMA, GZMB, IFNγ, EOMES, or PRF1; IL17A or IL17F; and CD274, PDL2, IDO1, PVR |
| CD8A, GZMA, GZMB, IFNγ, EOMES, or PRF1; CCL2, IL1B, IL8 (CXCL8), IL6, or PTGS2; and CD274, PDL2, IDO1, PVR |
| CD8A, GZMA, GZMB, IFNγ, EOMES, or PRF1; CTLA4, BTLA, LAG3, HAVCR2, or PDCD1; and CD274, PDL2, IDO1, PVR |
| CD8A, GZMA, GZMB, IFNγ, EOMES, or PRF1; CD276, PDL1, PDL2, or IDO1; and CD274, PDL2, IDO1, PVR |
| CD8A, GZMA, GZMB, IFNγ, EOMES, or PRF1; CX3CL1, CXCL9, CXCL10, CXCR3, CCL21, or CCL22; and CD274, PDL2, IDO1, PVR |
| CD8A, GZMA, GZMB, IFNγ, EOMES, or PRF1; FOXP3; and CD4, IL2RA, CD69 |
| CD8A, GZMA, GZMB, IFNγ, EOMES, or PRF1; MS4A1 or CD48; and CD4, IL2RA, CD69 |
| CD8A, GZMA, GZMB, IFNγ, EOMES, or PRF1; NCAM1 or NKP46; and CD4, IL2RA, CD69 |
| CD8A, GZMA, GZMB, IFNγ, EOMES, or PRF1; ITGAM, ITGAX, CD1C, or CLEC4C; and CD4, IL2RA, CD69 |
| CD8A, GZMA, GZMB, IFNγ, EOMES, or PRF1; IL17A or IL17F; and CD4, IL2RA, CD69 |
| CD8A, GZMA, GZMB, IFNγ, EOMES, or PRF1; CCL2, IL1B, IL8 (CXCL8), IL6, or PTGS2; and CD4, IL2RA, CD69 |
| CD8A, GZMA, GZMB, IFNγ, EOMES, or PRF1; CTLA4, BTLA, LAG3, HAVCR2, or PDCD1; and CD4, IL2RA, CD69 |
| CD8A, GZMA, GZMB, IFNγ, EOMES, or PRF1; CD276, PDL1, PDL2, or IDO1; and CD4, IL2RA, CD69 |
| CD8A, GZMA, GZMB, IFNγ, EOMES, or PRF1; CX3CL1, CXCL9, CXCL10, CXCR3, CCL21, or CCL22; and CD4, IL2RA, CD69 |
| CD8A, GZMA, GZMB, IFNγ, EOMES, or PRF1; FOXP3; and TAPBP, TAP1, TAP2, PSMB9, PSMB8 |
| CD8A, GZMA, GZMB, IFNγ, EOMES, or PRF1; MS4A1 or CD48; and TAPBP, TAP1, TAP2, PSMB9, PSMB8 |
| CD8A, GZMA, GZMB, IFNγ, EOMES, or PRF1; NCAM1 or NKP46; and TAPBP, TAP1, TAP2, PSMB9, PSMB8 |
| CD8A, GZMA, GZMB, IFNγ, EOMES, or PRF1; ITGAM, ITGAX, CD1C, or CLEC4C; and TAPBP, TAP1, TAP2, PSMB9, PSMB8 |
| CD8A, GZMA, GZMB, IFNγ, EOMES, or PRF1; IL17A or IL17F; and TAPBP, TAP1, TAP2, PSMB9, PSMB8 |
| CD8A, GZMA, GZMB, IFNγ, EOMES, or PRF1; CCL2, IL1B, IL8 (CXCL8), IL6, or PTGS2; and TAPBP, TAP1, TAP2, PSMB9, PSMB8 |
| CD8A, GZMA, GZMB, IFNγ, EOMES, or PRF1; CTLA4, BTLA, LAG3, HAVCR2, or PDCD1; and TAPBP, TAP1, TAP2, PSMB9, PSMB8 |
| CD8A, GZMA, GZMB, IFNγ, EOMES, or PRF1; CD276, PDL1, PDL2, or IDO1; and TAPBP, TAP1, TAP2, PSMB9, PSMB8 |
| CD8A, GZMA, GZMB, IFNγ, EOMES, or PRF1; CX3CL1, CXCL9, CXCL10, CXCR3, CCL21, or CCL22; and TAPBP, TAP1, TAP2, PSMB9, PSMB8 |
| CD8A, GZMA, GZMB, IFNγ, EOMES, or PRF1; FOXP3; and CD40, CD80, CD86, CD70, GITRL |
| CD8A, GZMA, GZMB, IFNγ, EOMES, or PRF1; MS4A1 or CD48; and CD40, CD80, CD86, CD70, GITRL |
| CD8A, GZMA, GZMB, IFNγ, EOMES, or PRF1; NCAM1 or NKP46; and CD40, CD80, CD86, CD70, GITRL |
| CD8A, GZMA, GZMB, IFNγ, EOMES, or PRF1; ITGAM, ITGAX, CD1C, or CLEC4C; and CD40, CD80, CD86, CD70, GITRL |
| CD8A, GZMA, GZMB, IFNγ, EOMES, or PRF1; IL17A or IL17F; and CD40, CD80, CD86, CD70, GITRL |
| CD8A, GZMA, GZMB, IFNγ, EOMES, or PRF1; CCL2, IL1B, IL8 (CXCL8), IL6, or PTGS2; and CD40, CD80, CD86, CD70, GITRL |
| CD8A, GZMA, GZMB, IFNγ, EOMES, or PRF1; CTLA4, BTLA, LAG3, HAVCR2, or PDCD1; and CD40, CD80, CD86, CD70, GITRL |
| CD8A, GZMA, GZMB, IFNγ, EOMES, or PRF1; CD276, PDL1, PDL2, or IDO1; and CD40, CD80, CD86, CD70, GITRL |
| CD8A, GZMA, GZMB, IFNγ, EOMES, or PRF1; CX3CL1, CXCL9, CXCL10, CXCR3, CCL21, or CCL22; and CD40, CD80, CD86, CD70, GITRL |
| CD8A, GZMA, GZMB, IFNγ, EOMES, or PRF1; FOXP3; and CD27, CD28, ICOS, TNFRSF4, TNFRSF14, TNFRSF18, TNFRSF14, TNFSF14, CD226 |
| CD8A, GZMA, GZMB, IFNγ, EOMES, or PRF1; MS4A1 or CD48; and CD27, CD28, ICOS, TNFRSF4, TNFRSF14, TNFRSF18, TNFRSF14, TNFSF14, CD226 |
| CD8A, GZMA, GZMB, IFNγ, EOMES, or PRF1; NCAM1 or NKP46; and CD27, CD28, ICOS, TNFRSF4, TNFRSF14, TNFRSF18, TNFRSF14, TNFSF14, CD226 |
| CD8A, GZMA, GZMB, IFNγ, EOMES, or PRF1; ITGAM, ITGAX, CD1C, or CLEC4C; and CD27, CD28, ICOS, TNFRSF4, TNFRSF14, TNFRSF18, TNFRSF14, TNFSF14, CD226 |
| CD8A, GZMA, GZMB, IFNγ, EOMES, or PRF1; IL17A or IL17F; and CD27, CD28, ICOS, TNFRSF4, TNFRSF14, TNFRSF18, TNFRSF14, TNFSF14, CD226 |
| CD8A, GZMA, GZMB, IFNγ, EOMES, or PRF1; CCL2, IL1B, IL8 (CXCL8), IL6, or PTGS2; and CD27, CD28, ICOS, TNFRSF4, TNFRSF14, TNFRSF18, TNFRSF14, TNFSF14, CD226 |

TABLE 3-continued

Combinations of three gene signature sets

CD8A, GZMA, GZMB, IFNγ, EOMES, or PRF1;
CTLA4, BTLA, LAG3, HAVCR2, or PDCD1; and
CD27, CD28, ICOS, TNFRSF4, TNFRSF14, TNFRSF18, TNFRSF14, TNFSF14, CD226
CD8A, GZMA, GZMB, IFNγ, EOMES, or PRF1;
CD276, PDL1, PDL2, or IDO1; and
CD27, CD28, ICOS, TNFRSF4, TNFRSF14, TNFRSF18, TNFRSF14, TNFSF14, CD226
CD8A, GZMA, GZMB, IFNγ, EOMES, or PRF1;
CX3CL1, CXCL9, CXCL10, CXCR3, CCL21, or CCL22; and
CD27, CD28, ICOS, TNFRSF4, TNFRSF14, TNFRSF18, TNFRSF14, TNFSF14, CD226
CD8A, GZMA, GZMB, IFNγ, EOMES, or PRF1;
FOXP3; and
GNLY, KLRK1, KLRB1, GZMH, GZMA, KLRD1, NKG7
CD8A, GZMA, GZMB, IFNγ, EOMES, or PRF1;
MS4A1 or CD48; and
GNLY, KLRK1, KLRB1, GZMH, GZMA, KLRD1, NKG7
CD8A, GZMA, GZMB, IFNγ, EOMES, or PRF1;
NCAM1 or NKP46; and
GNLY, KLRK1, KLRB1, GZMH, GZMA, KLRD1, NKG7
CD8A, GZMA, GZMB, IFNγ, EOMES, or PRF1;
ITGAM, ITGAX, CD1C, or CLEC4C; and
GNLY, KLRK1, KLRB1, GZMH, GZMA, KLRD1, NKG7
CD8A, GZMA, GZMB, IFNγ, EOMES, or PRF1;
IL17A or IL17F; and
GNLY, KLRK1, KLRB1, GZMH, GZMA, KLRD1, NKG7
CD8A, GZMA, GZMB, IFNγ, EOMES, or PRF1;
CCL2, IL1B, IL8 (CXCL8), IL6, or PTGS2; and
GNLY, KLRK1, KLRB1, GZMH, GZMA, KLRD1, NKG7
CD8A, GZMA, GZMB, IFNγ, EOMES, or PRF1;
CTLA4, BTLA, LAG3, HAVCR2, or PDCD1; and
GNLY, KLRK1, KLRB1, GZMH, GZMA, KLRD1, NKG7
CD8A, GZMA, GZMB, IFNγ, EOMES, or PRF1;
CD276, PDL1, PDL2, or IDO1; and
GNLY, KLRK1, KLRB1, GZMH, GZMA, KLRD1, NKG7
CD8A, GZMA, GZMB, IFNγ, EOMES, or PRF1;
CX3CL1, CXCL9, CXCL10, CXCR3, CCL21, or CCL22; and
GNLY, KLRK1, KLRB1, GZMH, GZMA, KLRD1, NKG7
CD8A, GZMA, GZMB, IFNγ, EOMES, or PRF1;
FOXP3; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
MS4A1 or CD48; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
NCAM1 or NKP46; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
ITGAM, ITGAX, CD1C, or CLEC4C; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
IL17A or IL17F; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
CCL2, IL1B, IL8 (CXCL8), IL6, or PTGS2; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
CTLA4, BTLA, LAG3, HAVCR2, or PDCD1; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
CD276, PDL1, PDL2, or IDO1; and
FAP, FN1, MMP2, BGN, LOXL2, PDPN, PDGFRB, COL4A1, COL4A2, COL5A1, COL8A1
CD8A, GZMA, GZMB, IFNγ, EOMES, or PRF1;
CX3CL1, CXCL9, CXCL10, CXCR3, CCL21, or CCL22; and
FAP, FN1, MMP2, BGN, LOXL2, PDPN, PDGFRB, COL4A1, COL4A2, COL5A1, COL8A1
FOXP3;
MS4A1 or CD48; and
CD79A, MS4A1, CD19, STAP1, KIAA0125, POU2AF1, FCRL5
FOXP3;
NCAM1 or NKP46; and
CD79A, MS4A1, CD19, STAP1, KIAA0125, POU2AF1, FCRL5
FOXP3;
ITGAM, ITGAX, CD1C, or CLEC4C; and
CD79A, MS4A1, CD19, STAP1, KIAA0125, POU2AF1, FCRL5
FOXP3;
IL17A or IL17F; and
CD79A, MS4A1, CD19, STAP1, KIAA0125, POU2AF1, FCRL5
FOXP3;
CCL2, IL1B, IL8 (CXCL8), IL6, or PTGS2; and
CD79A, MS4A1, CD19, STAP1, KIAA0125, POU2AF1, FCRL5
FOXP3;
CTLA4, BTLA, LAG3, HAVCR2, or PDCD1; and
CD79A, MS4A1, CD19, STAP1, KIAA0125, POU2AF1, FCRL5
FOXP3;
CD276, PDL1, PDL2, or IDO1; and
CD79A, MS4A1, CD19, STAP1, KIAA0125, POU2AF1, FCRL5
FOXP3;
CX3CL1, CXCL9, CXCL10, CXCR3, CCL21, or CCL22; and
CD79A, MS4A1, CD19, STAP1, KIAA0125, POU2AF1, FCRL5
FOXP3;
MS4A1 or CD48; and
KLRC3, KLRK1, KLRC2, KLRD1
FOXP3;
NCAM1 or NKP46; and
KLRC3, KLRK1, KLRC2, KLRD1
FOXP3;
ITGAM, ITGAX, CD1C, or CLEC4C; and
KLRC3, KLRK1, KLRC2, KLRD1
FOXP3;
IL17A or IL17F; and
KLRC3, KLRK1, KLRC2, KLRD1
FOXP3;
CCL2, IL1B, IL8 (CXCL8), IL6, or PTGS2; and
KLRC3, KLRK1, KLRC2, KLRD1
FOXP3;
CTLA4, BTLA, LAG3, HAVCR2, or PDCD1; and
KLRC3, KLRK1, KLRC2, KLRD1
FOXP3;
CD276, PDL1, PDL2, or IDO1; and
KLRC3, KLRK1, KLRC2, KLRD1
FOXP3;
CX3CL1, CXCL9, CXCL10, CXCR3, CCL21, or CCL22; and
KLRC3, KLRK1, KLRC2, KLRD1
FOXP3;
MS4A1 or CD48; and
CD68, CD163, ITGAM, ITGAX, CD14
FOXP3;
NCAM1 or NKP46; and
CD68, CD163, ITGAM, ITGAX, CD14
FOXP3;
ITGAM, ITGAX, CD1C, or CLEC4C; and
CD68, CD163, ITGAM, ITGAX, CD14
FOXP3;
IL17A or IL17F; and
CD68, CD163, ITGAM, ITGAX, CD14
FOXP3;
CCL2, IL1B, IL8 (CXCL8), IL6, or PTGS2; and
CD68, CD163, ITGAM, ITGAX, CD14
FOXP3;
CTLA4, BTLA, LAG3, HAVCR2, or PDCD1; and
CD68, CD163, ITGAM, ITGAX, CD14
FOXP3;
CD276, PDL1, PDL2, or IDO1; and
CD68, CD163, ITGAM, ITGAX, CD14
FOXP3;
CX3CL1, CXCL9, CXCL10, CXCR3, CCL21, or CCL22; and
CD68, CD163, ITGAM, ITGAX, CD14
FOXP3;
MS4A1 or CD48; and
LAPTM5, LAIR1, CD4, CSF1R, CD163, ADAP2, CD68, MRC1, CD45RO, SLA, MSR1, FPR3, FCGR2A, FCGR3A
FOXP3;
NCAM1 or NKP46; and
LAPTM5, LAIR1, CD4, CSF1R, CD163, ADAP2, CD68, MRC1, CD45RO, SLA, MSR1, FPR3, FCGR2A, FCGR3A
FOXP3;

TABLE 3-continued

Combinations of three gene signature sets

ITGAM, ITGAX, CD1C, or CLEC4C; and
LAPTM5, LAIR1, CD4, CSF1R, CD163, ADAP2, CD68, MRC1,
CD45RO, SLA, MSR1, FPR3, FCGR2A, FCGR3A
FOXP3;
IL17A or IL17F; and
LAPTM5, LAIR1, CD4, CSF1R, CD163, ADAP2, CD68, MRC1,
CD45RO, SLA, MSR1, FPR3, FCGR2A, FCGR3A
FOXP3;
CCL2, IL1B, IL8 (CXCL8), IL6, or PTGS2; and
LAPTM5, LAIR1, CD4, CSF1R, CD163, ADAP2, CD68, MRC1,
CD45RO, SLA, MSR1, FPR3, FCGR2A, FCGR3A
FOXP3;
CTLA4, BTLA, LAG3, HAVCR2, or PDCD1; and
LAPTM5, LAIR1, CD4, CSF1R, CD163, ADAP2, CD68, MRC1,
CD45RO, SLA, MSR1, FPR3, FCGR2A, FCGR3A
FOXP3;
CD276, PDL1, PDL2, or IDO1; and
LAPTM5, LAIR1, CD4, CSF1R, CD163, ADAP2, CD68, MRC1,
CD45RO, SLA, MSR1, FPR3, FCGR2A, FCGR3A
FOXP3;
CX3CL1, CXCL9, CXCL10, CXCR3, CCL21, or CCL22; and
LAPTM5, LAIR1, CD4, CSF1R, CD163, ADAP2, CD68, MRC1,
CD45RO, SLA, MSR1, FPR3, FCGR2A, FCGR3A
FOXP3;
MS4A1 or CD48; and
CD3D, CD3E, CD2, CD3G, CD6, TRAT1, CD28, LCK
FOXP3;
NCAM1 or NKP46; and
CD3D, CD3E, CD2, CD3G, CD6, TRAT1, CD28, LCK
FOXP3;
ITGAM, ITGAX, CD1C, or CLEC4C; and
CD3D, CD3E, CD2, CD3G, CD6, TRAT1, CD28, LCK
FOXP3;
IL17A or IL17F; and
CD3D, CD3E, CD2, CD3G, CD6, TRAT1, CD28, LCK
FOXP3;
CCL2, IL1B, IL8 (CXCL8), IL6, or PTGS2; and
CD3D, CD3E, CD2, CD3G, CD6, TRAT1, CD28, LCK
FOXP3;
CTLA4, BTLA, LAG3, HAVCR2, or PDCD1; and
CD3D, CD3E, CD2, CD3G, CD6, TRAT1, CD28, LCK
FOXP3;
CD276, PDL1, PDL2, or IDO1; and
CD3D, CD3E, CD2, CD3G, CD6, TRAT1, CD28, LCK
FOXP3;
CX3CL1, CXCL9, CXCL10, CXCR3, CCL21, or CCL22; and
CD3D, CD3E, CD2, CD3G, CD6, TRAT1, CD28, LCK
FOXP3;
MS4A1 or CD48; and
CTLA4, BTLA, LAG3, HAVCR2, PDCD1, TIGIT
FOXP3;
NCAM1 or NKP46; and
CTLA4, BTLA, LAG3, HAVCR2, PDCD1, TIGIT
FOXP3;
ITGAM, ITGAX, CD1C, or CLEC4C; and
CTLA4, BTLA, LAG3, HAVCR2, PDCD1, TIGIT
FOXP3;
IL17A or IL17F; and
CTLA4, BTLA, LAG3, HAVCR2, PDCD1, TIGIT
FOXP3;
CCL2, IL1B, IL8 (CXCL8), IL6, or PTGS2; and
CTLA4, BTLA, LAG3, HAVCR2, PDCD1, TIGIT
FOXP3;
CTLA4, BTLA, LAG3, HAVCR2, or PDCD1; and
CTLA4, BTLA, LAG3, HAVCR2, PDCD1, TIGIT
FOXP3;
CD276, PDL1, PDL2, or IDO1; and
CTLA4, BTLA, LAG3, HAVCR2, PDCD1, TIGIT
FOXP3;
CX3CL1, CXCL9, CXCL10, CXCR3, CCL21, or CCL22; and
CTLA4, BTLA, LAG3, HAVCR2, PDCD1, TIGIT
FOXP3;
MS4A1 or CD48; and
CD274, PDL2, IDO1, PVR
FOXP3;
NCAM1 or NKP46; and
CD274, PDL2, IDO1, PVR
FOXP3;
ITGAM, ITGAX, CD1C, or CLEC4C; and
CD274, PDL2, IDO1, PVR
FOXP3;
IL17A or IL17F; and
CD274, PDL2, IDO1, PVR
FOXP3;
CCL2, IL1B, IL8 (CXCL8), IL6, or PTGS2; and
CD274, PDL2, IDO1, PVR
FOXP3;
CTLA4, BTLA, LAG3, HAVCR2, or PDCD1; and
CD274, PDL2, IDO1, PVR
FOXP3;
CD276, PDL1, PDL2, or IDO1; and
CD274, PDL2, IDO1, PVR
FOXP3;
CX3CL1, CXCL9, CXCL10, CXCR3, CCL21, or CCL22; and
CD274, PDL2, IDO1, PVR
FOXP3;
MS4A1 or CD48; and
CD4, IL2RA, CD69
FOXP3;
NCAM1 or NKP46; and
CD4, IL2RA, CD69
FOXP3;
ITGAM, ITGAX, CD1C, or CLEC4C; and
CD4, IL2RA, CD69
FOXP3;
IL17A or IL17F; and
CD4, IL2RA, CD69
FOXP3;
CCL2, IL1B, IL8 (CXCL8), IL6, or PTGS2; and
CD4, IL2RA, CD69
FOXP3;
CTLA4, BTLA, LAG3, HAVCR2, or PDCD1; and
CD4, IL2RA, CD69
FOXP3;
CD276, PDL1, PDL2, or IDO1; and
CD4, IL2RA, CD69
FOXP3;
CX3CL1, CXCL9, CXCL10, CXCR3, CCL21, or CCL22; and
CD4, IL2RA, CD69
FOXP3;
MS4A1 or CD48; and
TAPBP, TAP1, TAP2, PSMB9, PSMB8
FOXP3;
NCAM1 or NKP46; and
TAPBP, TAP1, TAP2, PSMB9, PSMB8
FOXP3;
ITGAM, ITGAX, CD1C, or CLEC4C; and
TAPBP, TAP1, TAP2, PSMB9, PSMB8
FOXP3;
IL17A or IL17F; and
TAPBP, TAP1, TAP2, PSMB9, PSMB8
FOXP3;
CCL2, IL1B, IL8 (CXCL8), IL6, or PTGS2; and
TAPBP, TAP1, TAP2, PSMB9, PSMB8
FOXP3;
CTLA4, BTLA, LAG3, HAVCR2, or PDCD1; and
TAPBP, TAP1, TAP2, PSMB9, PSMB8
FOXP3;
CD276, PDL1, PDL2, or IDO1; and
TAPBP, TAP1, TAP2, PSMB9, PSMB8
FOXP3;
CX3CL1, CXCL9, CXCL10, CXCR3, CCL21, or CCL22; and
TAPBP, TAP1, TAP2, PSMB9, PSMB8
FOXP3;
MS4A1 or CD48; and
CD40, CD80, CD86, CD70, GITRL
FOXP3;
NCAM1 or NKP46; and
CD40, CD80, CD86, CD70, GITRL
FOXP3;
ITGAM, ITGAX, CD1C, or CLEC4C; and
CD40, CD80, CD86, CD70, GITRL
FOXP3;
IL17A or IL17F; and
CD40, CD80, CD86, CD70, GITRL
FOXP3;

TABLE 3-continued

Combinations of three gene signature sets

CCL2, IL1B, IL8 (CXCL8), IL6, or PTGS2; and
CD40, CD80, CD86, CD70, GITRL
FOXP3;
CTLA4, BTLA, LAG3, HAVCR2, or PDCD1; and
CD40, CD80, CD86, CD70, GITRL
FOXP3;
CD276, PDL1, PDL2, or IDO1; and
CD40, CD80, CD86, CD70, GITRL
FOXP3;
CX3CL1, CXCL9, CXCL10, CXCR3, CCL21, or CCL22; and
CD40, CD80, CD86, CD70, GITRL
FOXP3;
MS4A1 or CD48; and
CD27, CD28, ICOS, TNFRSF4, TNFRSF14, TNFRSF18, TNFRSF14, TNFSF14, CD226
FOXP3;
NCAM1 or NKP46; and
CD27, CD28, ICOS, TNFRSF4, TNFRSF14, TNFRSF18, TNFRSF14, TNFSF14, CD226
FOXP3;
ITGAM, ITGAX, CD1C, or CLEC4C; and
CD27, CD28, ICOS, TNFRSF4, TNFRSF14, TNFRSF18, TNFRSF14, TNFSF14, CD226
FOXP3;
IL17A or IL17F; and
CD27, CD28, ICOS, TNFRSF4, TNFRSF14, TNFRSF18, TNFRSF14, TNFSF14, CD226
FOXP3;
CCL2, IL1B, IL8 (CXCL8), IL6, or PTGS2; and
CD27, CD28, ICOS, TNFRSF4, TNFRSF14, TNFRSF18, TNFRSF14, TNFSF14, CD226
FOXP3;
CTLA4, BTLA, LAG3, HAVCR2, or PDCD1; and
CD27, CD28, ICOS, TNFRSF4, TNFRSF14, TNFRSF18, TNFRSF14, TNFSF14, CD226
FOXP3;
CD276, PDL1, PDL2, or IDO1; and
CD27, CD28, ICOS, TNFRSF4, TNFRSF14, TNFRSF18, TNFRSF14, TNFSF14, CD226
FOXP3;
CX3CL1, CXCL9, CXCL10, CXCR3, CCL21, or CCL22; and
CD27, CD28, ICOS, TNFRSF4, TNFRSF14, TNFRSF18, TNFRSF14, TNFSF14, CD226
FOXP3;
MS4A1 or CD48; and
GNLY, KLRK1, KLRB1, GZMH, GZMA, KLRD1, NKG7
FOXP3;
NCAM1 or NKP46; and
GNLY, KLRK1, KLRB1, GZMH, GZMA, KLRD1, NKG7
FOXP3;
ITGAM, ITGAX, CD1C, or CLEC4C; and
GNLY, KLRK1, KLRB1, GZMH, GZMA, KLRD1, NKG7
FOXP3;
IL17A or IL17F; and
GNLY, KLRK1, KLRB1, GZMH, GZMA, KLRD1, NKG7
FOXP3;
CCL2, IL1B, IL8 (CXCL8), IL6, or PTGS2; and
GNLY, KLRK1, KLRB1, GZMH, GZMA, KLRD1, NKG7
FOXP3;
CTLA4, BTLA, LAG3, HAVCR2, or PDCD1; and
GNLY, KLRK1, KLRB1, GZMH, GZMA, KLRD1, NKG7
FOXP3;
CD276, PDL1, PDL2, or IDO1; and
GNLY, KLRK1, KLRB1, GZMH, GZMA, KLRD1, NKG7
FOXP3;
CX3CL1, CXCL9, CXCL10, CXCR3, CCL21, or CCL22; and
GNLY, KLRK1, KLRB1, GZMH, GZMA, KLRD1, NKG7
FOXP3;
MS4A1 or CD48; and
FAP, FN1, MMP2, BGN, LOXL2, PDPN, PDGFRB, COL4A1, COL4A2, COL5A1, COL8A1
FOXP3;
NCAM1 or NKP46; and
FAP, FN1, MMP2, BGN, LOXL2, PDPN, PDGFRB, COL4A1, COL4A2, COL5A1, COL8A1
FOXP3;
ITGAM, ITGAX, CD1C, or CLEC4C; and
FAP, FN1, MMP2, BGN, LOXL2, PDPN, PDGFRB, COL4A1, COL4A2, COL5A1, COL8A1
FOXP3;
IL17A or IL17F; and
FAP, FN1, MMP2, BGN, LOXL2, PDPN, PDGFRB, COL4A1, COL4A2, COL5A1, COL8A1
FOXP3;
CCL2, IL1B, IL8 (CXCL8), IL6, or PTGS2; and
FAP, FN1, MMP2, BGN, LOXL2, PDPN, PDGFRB, COL4A1, COL4A2, COL5A1, COL8A1
FOXP3;
CTLA4, BTLA, LAG3, HAVCR2, or PDCD1; and
FAP, FN1, MMP2, BGN, LOXL2, PDPN, PDGFRB, COL4A1, COL4A2, COL5A1, COL8A1
FOXP3;
CD276, PDL1, PDL2, or IDO1; and
FAP, FN1, MMP2, BGN, LOXL2, PDPN, PDGFRB, COL4A1, COL4A2, COL5A1, COL8A1
FOXP3;
CX3CL1, CXCL9, CXCL10, CXCR3, CCL21, or CCL22; and
FAP, FN1, MMP2, BGN, LOXL2, PDPN, PDGFRB, COL4A1, COL4A2, COL5A1, COL8A1
MS4A1 OR CD48;
NCAM1 or NKP46; and
CD79A, MS4A1, CD19, STAP1, KIAA0125, POU2AF1, FCRL5
MS4A1 OR CD48;
ITGAM, ITGAX, CD1C, or CLEC4C; and
CD79A, MS4A1, CD19, STAP1, KIAA0125, POU2AF1, FCRL5
MS4A1 OR CD48;
IL17A or IL17F; and
CD79A, MS4A1, CD19, STAP1, KIAA0125, POU2AF1, FCRL5
MS4A1 OR CD48;
CCL2, IL1B, IL8 (CXCL8), IL6, or PTGS2; and
CD79A, MS4A1, CD19, STAP1, KIAA0125, POU2AF1, FCRL5
MS4A1 OR CD48;
CTLA4, BTLA, LAG3, HAVCR2, or PDCD1; and
CD79A, MS4A1, CD19, STAP1, KIAA0125, POU2AF1, FCRL5
MS4A1 OR CD48;
CD276, PDL1, PDL2, or IDO1; and
CD79A, MS4A1, CD19, STAP1, KIAA0125, POU2AF1, FCRL5
MS4A1 OR CD48;
CX3CL1, CXCL9, CXCL10, CXCR3, CCL21, or CCL22; and
CD79A, MS4A1, CD19, STAP1, KIAA0125, POU2AF1, FCRL5
MS4A1 OR CD48;
NCAM1 or NKP46; and
KLRC3, KLRK1, KLRC2, KLRD1
MS4A1 OR CD48;
ITGAM, ITGAX, CD1C, or CLEC4C; and
KLRC3, KLRK1, KLRC2, KLRD1
MS4A1 OR CD48;
IL17A or IL17F; and
KLRC3, KLRK1, KLRC2, KLRD1
MS4A1 OR CD48;
CCL2, IL1B, IL8 (CXCL8), IL6, or PTGS2; and
KLRC3, KLRK1, KLRC2, KLRD1
MS4A1 OR CD48;
CTLA4, BTLA, LAG3, HAVCR2, or PDCD1; and
KLRC3, KLRK1, KLRC2, KLRD1
MS4A1 OR CD48;
CD276, PDL1, PDL2, or IDO1; and
KLRC3, KLRK1, KLRC2, KLRD1
MS4A1 OR CD48;
CX3CL1, CXCL9, CXCL10, CXCR3, CCL21, or CCL22; and
KLRC3, KLRK1, KLRC2, KLRD1
MS4A1 OR CD48;
NCAM1 or NKP46; and
CD68, CD163, ITGAM, ITGAX, CD14
MS4A1 OR CD48;
ITGAM, ITGAX, CD1C, or CLEC4C; and
CD68, CD163, ITGAM, ITGAX, CD14
MS4A1 OR CD48;
IL17A or IL17F; and
CD68, CD163, ITGAM, ITGAX, CD14
MS4A1 OR CD48;
CCL2, IL1B, IL8 (CXCL8), IL6, or PTGS2; and
CD68, CD163, ITGAM, ITGAX, CD14
MS4A1 OR CD48;
CTLA4, BTLA, LAG3, HAVCR2, or PDCD1; and
CD68, CD163, ITGAM, ITGAX, CD14

TABLE 3-continued

Combinations of three gene signature sets

MS4A1 OR CD48;
CD276, PDL1, PDL2, or IDO1; and
CD68, CD163, ITGAM, ITGAX, CD14
MS4A1 OR CD48;
CX3CL1, CXCL9, CXCL10, CXCR3, CCL21, or CCL22; and
CD68, CD163, ITGAM, ITGAX, CD14
MS4A1 OR CD48;
NCAM1 or NKP46; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
ITGAM, ITGAX, CD1C, or CLEC4C; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
IL17A or IL17F; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
CCL2, IL1B, IL8 (CXCL8), IL6, or PTGS2; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
CTLA4, BTLA, LAG3, HAVCR2, or PDCD1; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
CD276, PDL1, PDL2, or IDO1; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
CX3CL1, CXCL9, CXCL10, CXCR3, CCL21, or CCL22; and
LAPTM5, LAIR1, CD4, CSF1R, CD163, ADAP2, CD68, MRC1, CD45RO, SLA, MSR1, FPR3, FCGR2A, FCGR3A
MS4A1 OR CD48;
NCAM1 or NKP46; and
CD3D, CD3E, CD2, CD3G, CD6, TRAT1, CD28, LCK
MS4A1 OR CD48;
ITGAM, ITGAX, CD1C, or CLEC4C; and
CD3D, CD3E, CD2, CD3G, CD6, TRAT1, CD28, LCK
MS4A1 OR CD48;
IL17A or IL17F; and
CD3D, CD3E, CD2, CD3G, CD6, TRAT1, CD28, LCK
MS4A1 OR CD48;
CCL2, IL1B, IL8 (CXCL8), IL6, or PTGS2; and
CD3D, CD3E, CD2, CD3G, CD6, TRAT1, CD28, LCK
MS4A1 OR CD48;
CTLA4, BTLA, LAG3, HAVCR2, or PDCD1; and
CD3D, CD3E, CD2, CD3G, CD6, TRAT1, CD28, LCK
MS4A1 OR CD48;
CD276, PDL1, PDL2, or IDO1; and
CD3D, CD3E, CD2, CD3G, CD6, TRAT1, CD28, LCK
MS4A1 OR CD48;
CX3CL1, CXCL9, CXCL10, CXCR3, CCL21, or CCL22; and
CD3D, CD3E, CD2, CD3G, CD6, TRAT1, CD28, LCK
MS4A1 OR CD48;
NCAM1 or NKP46; and
CTLA4, BTLA, LAG3, HAVCR2, PDCD1, TIGIT
MS4A1 OR CD48;
ITGAM, ITGAX, CD1C, or CLEC4C; and
CTLA4, BTLA, LAG3, HAVCR2, PDCD1, TIGIT
MS4A1 OR CD48;
IL17A or IL17F; and
CTLA4, BTLA, LAG3, HAVCR2, PDCD1, TIGIT
MS4A1 OR CD48;
CCL2, IL1B, IL8 (CXCL8), IL6, or PTGS2; and
CTLA4, BTLA, LAG3, HAVCR2, PDCD1, TIGIT
MS4A1 OR CD48;
CTLA4, BTLA, LAG3, HAVCR2, or PDCD1; and
CTLA4, BTLA, LAG3, HAVCR2, PDCD1, TIGIT
MS4A1 OR CD48;
CD276, PDL1, PDL2, or IDO1; and
CTLA4, BTLA, LAG3, HAVCR2, PDCD1, TIGIT
MS4A1 OR CD48;
CX3CL1, CXCL9, CXCL10, CXCR3, CCL21, or CCL22; and
CTLA4, BTLA, LAG3, HAVCR2, PDCD1, TIGIT
MS4A1 OR CD48;
NCAM1 or NKP46; and
CD274, PDL2, IDO1, PVR
MS4A1 OR CD48;
ITGAM, ITGAX, CD1C, or CLEC4C; and
CD274, PDL2, IDO1, PVR
MS4A1 OR CD48;
IL17A or IL17F; and
CD274, PDL2, IDO1, PVR
MS4A1 OR CD48;
CCL2, IL1B, IL8 (CXCL8), IL6, or PTGS2; and
CD274, PDL2, IDO1, PVR
MS4A1 OR CD48;
CTLA4, BTLA, LAG3, HAVCR2, or PDCD1; and
CD274, PDL2, IDO1, PVR
MS4A1 OR CD48;
CD276, PDL1, PDL2, or IDO1; and
CD274, PDL2, IDO1, PVR
MS4A1 OR CD48;
CX3CL1, CXCL9, CXCL10, CXCR3, CCL21, or CCL22; and
CD274, PDL2, IDO1, PVR
MS4A1 OR CD48;
NCAM1 or NKP46; and
CD4, IL2RA, CD69
MS4A1 OR CD48;
ITGAM, ITGAX, CD1C, or CLEC4C; and
CD4, IL2RA, CD69
MS4A1 OR CD48;
IL17A or IL17F; and
CD4, IL2RA, CD69
MS4A1 OR CD48;
CCL2, IL1B, IL8 (CXCL8), IL6, or PTGS2; and
CD4, IL2RA, CD69
MS4A1 OR CD48;
CTLA4, BTLA, LAG3, HAVCR2, or PDCD1; and
CD4, IL2RA, CD69
MS4A1 OR CD48;
CD276, PDL1, PDL2, or IDO1; and
CD4, IL2RA, CD69
MS4A1 OR CD48;
CX3CL1, CXCL9, CXCL10, CXCR3, CCL21, or CCL22; and
CD4, IL2RA, CD69
MS4A1 OR CD48;
NCAM1 or NKP46; and
TAPBP, TAP1, TAP2, PSMB9, PSMB8
MS4A1 OR CD48;
ITGAM, ITGAX, CD1C, or CLEC4C; and
TAPBP, TAP1, TAP2, PSMB9, PSMB8
MS4A1 OR CD48;
IL17A or IL17F; and
TAPBP, TAP1, TAP2, PSMB9, PSMB8
MS4A1 OR CD48;
CCL2, IL1B, IL8 (CXCL8), IL6, or PTGS2; and
TAPBP, TAP1, TAP2, PSMB9, PSMB8
MS4A1 OR CD48;
CTLA4, BTLA, LAG3, HAVCR2, or PDCD1; and
TAPBP, TAP1, TAP2, PSMB9, PSMB8
MS4A1 OR CD48;
CD276, PDL1, PDL2, or IDO1; and
TAPBP, TAP1, TAP2, PSMB9, PSMB8
MS4A1 OR CD48;
CX3CL1, CXCL9, CXCL10, CXCR3, CCL21, or CCL22; and
TAPBP, TAP1, TAP2, PSMB9, PSMB8
MS4A1 OR CD48;
NCAM1 or NKP46; and
CD40, CD80, CD86, CD70, GITRL
MS4A1 OR CD48;
ITGAM, ITGAX, CD1C, or CLEC4C; and
CD40, CD80, CD86, CD70, GITRL
MS4A1 OR CD48;
IL17A or IL17F; and
CD40, CD80, CD86, CD70, GITRL
MS4A1 OR CD48;
CCL2, IL1B, IL8 (CXCL8), IL6, or PTGS2; and
CD40, CD80, CD86, CD70, GITRL
MS4A1 OR CD48;
CTLA4, BTLA, LAG3, HAVCR2, or PDCD1; and
CD40, CD80, CD86, CD70, GITRL
MS4A1 OR CD48;
CD276, PDL1, PDL2, or IDO1; and TABLE 3-continued

| Combinations of three gene signature sets |
|---|
| CD40, CD80, CD86, CD70, GITRL |
| MS4A1 OR CD48; |
| CX3CL1, CXCL9, CXCL10, CXCR3, CCL21, or CCL22; and |
| CD40, CD80, CD86, CD70, GITRL |
| MS4A1 OR CD48; |
| NCAM1 or NKP46; and |
| CD27, CD28, ICOS, TNFRSF4, TNFRSF14, TNFRSF18, |
| TNFRSF14, TNFSF14, CD226 |
| MS4A1 OR CD48; |
| ITGAM, ITGAX, CD1C, or CLEC4C; and |
| CD27, CD28, ICOS, TNFRSF4, TNFRSF14, TNFRSF18, |
| TNFRSF14, TNFSF14, CD226 |
| MS4A1 OR CD48; |
| IL17A or IL17F; and |
| CD27, CD28, ICOS, TNFRSF4, TNFRSF14, TNFRSF18, |
| TNFRSF14, TNFSF14, CD226 |
| MS4A1 OR CD48; |
| CCL2, IL1B, IL8 (CXCL8), IL6, or PTGS2; and |
| CD27, CD28, ICOS, TNFRSF4, TNFRSF14, TNFRSF18, |
| TNFRSF14, TNFSF14, CD226 |
| MS4A1 OR CD48; |
| CTLA4, BTLA, LAG3, HAVCR2, or PDCD1; and |
| CD27, CD28, ICOS, TNFRSF4, TNFRSF14, TNFRSF18, |
| TNFRSF14, TNFSF14, CD226 |
| MS4A1 OR CD48; |
| CD276, PDL1, PDL2, or IDO1; and |
| CD27, CD28, ICOS, TNFRSF4, TNFRSF14, TNFRSF18, |
| TNFRSF14, TNFSF14, CD226 |
| MS4A1 OR CD48; |
| CX3CL1, CXCL9, CXCL10, CXCR3, CCL21, or CCL22; and |
| CD27, CD28, ICOS, TNFRSF4, TNFRSF14, TNFRSF18, |
| TNFRSF14, TNFSF14, CD226 |
| MS4A1 OR CD48; |
| NCAM1 or NKP46; and |
| GNLY, KLRK1, KLRB1, GZMH, GZMA, KLRD1, NKG7 |
| MS4A1 OR CD48; |
| ITGAM, ITGAX, CD1C, or CLEC4C; and |
| GNLY, KLRK1, KLRB1, GZMH, GZMA, KLRD1, NKG7 |
| MS4A1 OR CD48; |
| IL17A or IL17F; and |
| GNLY, KLRK1, KLRB1, GZMH, GZMA, KLRD1, NKG7 |
| MS4A1 OR CD48; |
| CCL2, IL1B, IL8 (CXCL8), IL6, or PTGS2; and |
| GNLY, KLRK1, KLRB1, GZMH, GZMA, KLRD1, NKG7 |
| MS4A1 OR CD48; |
| CTLA4, BTLA, LAG3, HAVCR2, or PDCD1; and |
| GNLY, KLRK1, KLRB1, GZMH, GZMA, KLRD1, NKG7 |
| MS4A1 OR CD48; |
| CD276, PDL1, PDL2, or IDO1; and |
| GNLY, KLRK1, KLRB1, GZMH, GZMA, KLRD1, NKG7 |
| MS4A1 OR CD48; |
| CX3CL1, CXCL9, CXCL10, CXCR3, CCL21, or CCL22; and |
| GNLY, KLRK1, KLRB1, GZMH, GZMA, KLRD1, NKG7 |
| MS4A1 OR CD48; |
| NCAM1 or NKP46; and |
| FAP, FN1, MMP2, BGN, LOXL2, PDPN, PDGFRB, |
| COL4A1, COL4A2, COL5A1, COL8A1 |
| MS4A1 OR CD48; |
| ITGAM, ITGAX, CD1C, or CLEC4C; and |
| FAP, FN1, MMP2, BGN, LOXL2, PDPN, PDGFRB, |
| COL4A1, COL4A2, COL5A1, COL8A1 |
| MS4A1 OR CD48; |
| IL17A or IL17F; and |
| FAP, FN1, MMP2, BGN, LOXL2, PDPN, PDGFRB, |
| COL4A1, COL4A2, COL5A1, COL8A1 |
| MS4A1 OR CD48; |
| CCL2, IL1B, IL8 (CXCL8), IL6, or PTGS2; and |
| FAP, FN1, MMP2, BGN, LOXL2, PDPN, PDGFRB, |
| COL4A1, COL4A2, COL5A1, COL8A1 |
| MS4A1 OR CD48; |
| CTLA4, BTLA, LAG3, HAVCR2, or PDCD1; and |
| FAP, FN1, MMP2, BGN, LOXL2, PDPN, PDGFRB, |
| COL4A1, COL4A2, COL5A1, COL8A1 |
| MS4A1 OR CD48; |
| CD276, PDL1, PDL2, or IDO1; and |
| FAP, FN1, MMP2, BGN, LOXL2, PDPN, PDGFRB, |
| COL4A1, COL4A2, COL5A1, COL8A1 |
| MS4A1 OR CD48; |

TABLE 3-continued

| Combinations of three gene signature sets |
|---|
| CX3CL1, CXCL9, CXCL10, CXCR3, CCL21, or CCL22; and |
| FAP, FN1, MMP2, BGN, LOXL2, PDPN, PDGFRB, |
| COL4A1, COL4A2, COL5A1, COL8A1 |
| NCAM1 or NKP46; |
| ITGAM, ITGAX, CD1C, or CLEC4C; and |
| CD79A, MS4A1, CD19, STAP1, KIAA0125, POU2AF1, FCRL5 |
| NCAM1 or NKP46; |
| IL17A or IL17F; and |
| CD79A, MS4A1, CD19, STAP1, KIAA0125, POU2AF1, FCRL5 |
| NCAM1 or NKP46; |
| CCL2, IL1B, IL8 (CXCL8), IL6, or PTGS2; and |
| CD79A, MS4A1, CD19, STAP1, KIAA0125, POU2AF1, FCRL5 |
| NCAM1 or NKP46; |
| CTLA4, BTLA, LAG3, HAVCR2, or PDCD1; and |
| CD79A, MS4A1, CD19, STAP1, KIAA0125, POU2AF1, FCRL5 |
| NCAM1 or NKP46; |
| CD276, PDL1, PDL2, or IDO1; and |
| CD79A, MS4A1, CD19, STAP1, KIAA0125, POU2AF1, FCRL5 |
| NCAM1 or NKP46; |
| CX3CL1, CXCL9, CXCL10, CXCR3, CCL21, or CCL22; and |
| CD79A, MS4A1, CD19, STAP1, KIAA0125, POU2AF1, FCRL5 |
| NCAM1 or NKP46; |
| ITGAM, ITGAX, CD1C, or CLEC4C; and |
| KLRC3, KLRK1, KLRC2, KLRD1 |
| NCAM1 or NKP46; |
| IL17A or IL17F; and |
| KLRC3, KLRK1, KLRC2, KLRD1 |
| NCAM1 or NKP46; |
| CCL2, IL1B, IL8 (CXCL8), IL6, or PTGS2; and |
| KLRC3, KLRK1, KLRC2, KLRD1 |
| NCAM1 or NKP46; |
| CTLA4, BTLA, LAG3, HAVCR2, or PDCD1; and |
| KLRC3, KLRK1, KLRC2, KLRD1 |
| NCAM1 or NKP46; |
| CD276, PDL1, PDL2, or IDO1; and |
| KLRC3, KLRK1, KLRC2, KLRD1 |
| NCAM1 or NKP46; |
| CX3CL1, CXCL9, CXCL10, CXCR3, CCL21, or CCL22; and |
| KLRC3, KLRK1, KLRC2, KLRD1 |
| NCAM1 or NKP46; |
| ITGAM, ITGAX, CD1C, or CLEC4C; and |
| CD68, CD163, ITGAM, ITGAX, CD14 |
| NCAM1 or NKP46; |
| IL17A or IL17F; and |
| CD68, CD163, ITGAM, ITGAX, CD14 |
| NCAM1 or NKP46; |
| CCL2, IL1B, IL8 (CXCL8), IL6, or PTGS2; and |
| CD68, CD163, ITGAM, ITGAX, CD14 |
| NCAM1 or NKP46; |
| CTLA4, BTLA, LAG3, HAVCR2, or PDCD1; and |
| CD68, CD163, ITGAM, ITGAX, CD14 |
| NCAM1 or NKP46; |
| CD276, PDL1, PDL2, or IDO1; and |
| CD68, CD163, ITGAM, ITGAX, CD14 |
| NCAM1 or NKP46; |
| CX3CL1, CXCL9, CXCL10, CXCR3, CCL21, or CCL22; and |
| CD68, CD163, ITGAM, ITGAX, CD14 |
| NCAM1 or NKP46; |
| ITGAM, ITGAX, CD1C, or CLEC4C; and |
| LAPTM5, LAIR1, CD4, CSF1R, CD163, ADAP2, CD68, MRC1, |
| CD45RO, SLA, MSR1, FPR3, FCGR2A, FCGR3A |
| NCAM1 or NKP46; |
| IL17A or IL17F; and |
| LAPTM5, LAIR1, CD4, CSF1R, CD163, ADAP2, CD68, MRC1, |
| CD45RO, SLA, MSR1, FPR3, FCGR2A, FCGR3A |
| NCAM1 or NKP46; |
| CCL2, IL1B, IL8 (CXCL8), IL6, or PTGS2; and |
| LAPTM5, LAIR1, CD4, CSF1R, CD163, ADAP2, CD68, MRC1, |
| CD45RO, SLA, MSR1, FPR3, FCGR2A, FCGR3A |
| NCAM1 or NKP46; |
| CTLA4, BTLA, LAG3, HAVCR2, or PDCD1; and |
| LAPTM5, LAIR1, CD4, CSF1R, CD163, ADAP2, CD68, MRC1, |
| CD45RO, SLA, MSR1, FPR3, FCGR2A, FCGR3A |
| NCAM1 or NKP46; |
| CD276, PDL1, PDL2, or IDO1; and |
| LAPTM5, LAIR1, CD4, CSF1R, CD163, ADAP2, CD68, MRC1, |
| CD45RO, SLA, MSR1, FPR3, FCGR2A, FCGR3A |
| NCAM1 or NKP46; |

TABLE 3-continued

Combinations of three gene signature sets

CX3CL1, CXCL9, CXCL10, CXCR3, CCL21, or CCL22; and
LAPTM5, LAIR1, CD4, CSF1R, CD163, ADAP2, CD68, MRC1,
CD45RO, SLA, MSR1, FPR3, FCGR2A, FCGR3A
NCAM1 or NKP46;
ITGAM, ITGAX, CD1C, or CLEC4C; and
CD3D, CD3E, CD2, CD3G, CD6, TRAT1, CD28, LCK
NCAM1 or NKP46;
IL17A or IL17F; and
CD3D, CD3E, CD2, CD3G, CD6, TRAT1, CD28, LCK
NCAM1 or NKP46;
CCL2, IL1B, IL8 (CXCL8), IL6, or PTGS2; and
CD3D, CD3E, CD2, CD3G, CD6, TRAT1, CD28, LCK
NCAM1 or NKP46;
CTLA4, BTLA, LAG3, HAVCR2, or PDCD1; and
CD3D, CD3E, CD2, CD3G, CD6, TRAT1, CD28, LCK
NCAM1 or NKP46;
CD276, PDL1, PDL2, or IDO1; and
CD3D, CD3E, CD2, CD3G, CD6, TRAT1, CD28, LCK
NCAM1 or NKP46;
CX3CL1, CXCL9, CXCL10, CXCR3, CCL21, or CCL22; and
CD3D, CD3E, CD2, CD3G, CD6, TRAT1, CD28, LCK
NCAM1 or NKP46;
ITGAM, ITGAX, CD1C, or CLEC4C; and
CTLA4, BTLA, LAG3, HAVCR2, PDCD1, TIGIT
NCAM1 or NKP46;
IL17A or IL17F; and
CTLA4, BTLA, LAG3, HAVCR2, PDCD1, TIGIT
NCAM1 or NKP46;
CCL2, IL1B, IL8 (CXCL8), IL6, or PTGS2; and
CTLA4, BTLA, LAG3, HAVCR2, PDCD1, TIGIT
NCAM1 or NKP46;
CTLA4, BTLA, LAG3, HAVCR2, or PDCD1; and
CTLA4, BTLA, LAG3, HAVCR2, PDCD1, TIGIT
NCAM1 or NKP46;
CD276, PDL1, PDL2, or IDO1; and
CTLA4, BTLA, LAG3, HAVCR2, PDCD1, TIGIT
NCAM1 or NKP46;
CX3CL1, CXCL9, CXCL10, CXCR3, CCL21, or CCL22; and
CTLA4, BTLA, LAG3, HAVCR2, PDCD1, TIGIT
NCAM1 or NKP46;
ITGAM, ITGAX, CD1C, or CLEC4C; and
CD274, PDL2, IDO1, PVR
NCAM1 or NKP46;
IL17A or IL17F; and
CD274, PDL2, IDO1, PVR
NCAM1 or NKP46;
CCL2, IL1B, IL8 (CXCL8), IL6, or PTGS2; and
CD274, PDL2, IDO1, PVR
NCAM1 or NKP46;
CTLA4, BTLA, LAG3, HAVCR2, or PDCD1; and
CD274, PDL2, IDO1, PVR
NCAM1 or NKP46;
CD276, PDL1, PDL2, or IDO1; and
CD274, PDL2, IDO1, PVR
NCAM1 or NKP46;
CX3CL1, CXCL9, CXCL10, CXCR3, CCL21, or CCL22; and
CD274, PDL2, IDO1, PVR
NCAM1 or NKP46;
ITGAM, ITGAX, CD1C, or CLEC4C; and
CD4, IL2RA, CD69
NCAM1 or NKP46;
IL17A or IL17F; and
CD4, IL2RA, CD69
NCAM1 or NKP46;
CCL2, IL1B, IL8 (CXCL8), IL6, or PTGS2; and
CD4, IL2RA, CD69
NCAM1 or NKP46;
CTLA4, BTLA, LAG3, HAVCR2, or PDCD1; and
CD4, IL2RA, CD69
NCAM1 or NKP46;
CD276, PDL1, PDL2, or IDO1; and
CD4, IL2RA, CD69
NCAM1 or NKP46;
CX3CL1, CXCL9, CXCL10, CXCR3, CCL21, or CCL22; and
CD4, IL2RA, CD69
NCAM1 or NKP46;
ITGAM, ITGAX, CD1C, or CLEC4C; and
TAPBP, TAP1, TAP2, PSMB9, PSMB8
NCAM1 or NKP46;
IL17A or IL17F; and
TAPBP, TAP1, TAP2, PSMB9, PSMB8
NCAM1 or NKP46;
CCL2, IL1B, IL8 (CXCL8), IL6, or PTGS2; and
TAPBP, TAP1, TAP2, PSMB9, PSMB8
NCAM1 or NKP46;
CTLA4, BTLA, LAG3, HAVCR2, or PDCD1; and
TAPBP, TAP1, TAP2, PSMB9, PSMB8
NCAM1 or NKP46;
CD276, PDL1, PDL2, or IDO1; and
TAPBP, TAP1, TAP2, PSMB9, PSMB8
NCAM1 or NKP46;
CX3CL1, CXCL9, CXCL10, CXCR3, CCL21, or CCL22; and
TAPBP, TAP1, TAP2, PSMB9, PSMB8
NCAM1 or NKP46;
ITGAM, ITGAX, CD1C, or CLEC4C; and
CD40, CD80, CD86, CD70, GITRL
NCAM1 or NKP46;
IL17A or IL17F; and
CD40, CD80, CD86, CD70, GITRL
NCAM1 or NKP46;
CCL2, IL1B, IL8 (CXCL8), IL6, or PTGS2; and
CD40, CD80, CD86, CD70, GITRL
NCAM1 or NKP46;
CTLA4, BTLA, LAG3, HAVCR2, or PDCD1; and
CD40, CD80, CD86, CD70, GITRL
NCAM1 or NKP46;
CD276, PDL1, PDL2, or IDO1; and
CD40, CD80, CD86, CD70, GITRL
NCAM1 or NKP46;
CX3CL1, CXCL9, CXCL10, CXCR3, CCL21, or CCL22; and
CD40, CD80, CD86, CD70, GITRL
NCAM1 or NKP46;
ITGAM, ITGAX, CD1C, or CLEC4C; and
CD27, CD28, ICOS, TNFRSF4, TNFRSF14, TNFRSF18,
TNFRSF14, TNFSF14, CD226
NCAM1 or NKP46;
IL17A or IL17F; and
CD27, CD28, ICOS, TNFRSF4, TNFRSF14, TNFRSF18,
TNFRSF14, TNFSF14, CD226
NCAM1 or NKP46;
CCL2, IL1B, IL8 (CXCL8), IL6, or PTGS2; and
CD27, CD28, ICOS, TNFRSF4, TNFRSF14, TNFRSF18,
TNFRSF14, TNFSF14, CD226
NCAM1 or NKP46;
CTLA4, BTLA, LAG3, HAVCR2, or PDCD1; and
CD27, CD28, ICOS, TNFRSF4, TNFRSF14, TNFRSF18,
TNFRSF14, TNFSF14, CD226
NCAM1 or NKP46;
CD276, PDL1, PDL2, or IDO1; and
CD27, CD28, ICOS, TNFRSF4, TNFRSF14, TNFRSF18,
TNFRSF14, TNFSF14, CD226
NCAM1 or NKP46;
CX3CL1, CXCL9, CXCL10, CXCR3, CCL21, or CCL22; and
CD27, CD28, ICOS, TNFRSF4, TNFRSF14, TNFRSF18,
TNFRSF14, TNFSF14, CD226
NCAM1 or NKP46;
ITGAM, ITGAX, CD1C, or CLEC4C; and
GNLY, KLRK1, KLRB1, GZMH, GZMA, KLRD1, NKG7
NCAM1 or NKP46;
IL17A or IL17F; and
GNLY, KLRK1, KLRB1, GZMH, GZMA, KLRD1, NKG7
NCAM1 or NKP46;
CCL2, IL1B, IL8 (CXCL8), IL6, or PTGS2; and
GNLY, KLRK1, KLRB1, GZMH, GZMA, KLRD1, NKG7
NCAM1 or NKP46;
CTLA4, BTLA, LAG3, HAVCR2, or PDCD1; and
GNLY, KLRK1, KLRB1, GZMH, GZMA, KLRD1, NKG7
NCAM1 or NKP46;
CD276, PDL1, PDL2, or IDO1; and
GNLY, KLRK1, KLRB1, GZMH, GZMA, KLRD1, NKG7
NCAM1 or NKP46;
CX3CL1, CXCL9, CXCL10, CXCR3, CCL21, or CCL22; and
GNLY, KLRK1, KLRB1, GZMH, GZMA, KLRD1, NKG7
NCAM1 or NKP46;
ITGAM, ITGAX, CD1C, or CLEC4C; and
FAP, FN1, MMP2, BGN, LOXL2, PDPN, PDGFRB,

TABLE 3-continued

Combinations of three gene signature sets

COL4A1, COL4A2, COL5A1, COL8A1
NCAM1 or NKP46;
IL17A or IL17F; and
FAP, FN1, MMP2, BGN, LOXL2, PDPN, PDGFRB,
COL4A1, COL4A2, COL5A1, COL8A1
NCAM1 or NKP46;
CCL2, IL1B, IL8 (CXCL8), IL6, or PTGS2; and
FAP, FN1, MMP2, BGN, LOXL2, PDPN, PDGFRB,
COL4A1, COL4A2, COL5A1, COL8A1
NCAM1 or NKP46;
CTLA4, BTLA, LAG3, HAVCR2, or PDCD1; and
FAP, FN1, MMP2, BGN, LOXL2, PDPN, PDGFRB,
COL4A1, COL4A2, COL5A1, COL8A1
NCAM1 or NKP46;
CD276, PDL1, PDL2, or IDO1; and
FAP, FN1, MMP2, BGN, LOXL2, PDPN, PDGFRB,
COL4A1, COL4A2, COL5A1, COL8A1
NCAM1 or NKP46;
CX3CL1, CXCL9, CXCL10, CXCR3, CCL21, or CCL22; and
FAP, FN1, MMP2, BGN, LOXL2, PDPN, PDGFRB,
COL4A1, COL4A2, COL5A1, COL8A1
ITGAM, ITGAX, CD1C, or CLEC4C;
IL17A or IL17F; and
CD79A, MS4A1, CD19, STAP1, KIAA0125, POU2AF1, FCRL5
ITGAM, ITGAX, CD1C, or CLEC4C;
CCL2, IL1B, IL8 (CXCL8), IL6, or PTGS2; and
CD79A, MS4A1, CD19, STAP1, KIAA0125, POU2AF1, FCRL5
ITGAM, ITGAX, CD1C, or CLEC4C;
CTLA4, BTLA, LAG3, HAVCR2, or PDCD1; and
CD79A, MS4A1, CD19, STAP1, KIAA0125, POU2AF1, FCRL5
ITGAM, ITGAX, CD1C, or CLEC4C;
CD276, PDL1, PDL2, or IDO1; and
CD79A, MS4A1, CD19, STAP1, KIAA0125, POU2AF1, FCRL5
ITGAM, ITGAX, CD1C, or CLEC4C;
CX3CL1, CXCL9, CXCL10, CXCR3, CCL21, or CCL22; and
CD79A, MS4A1, CD19, STAP1, KIAA0125, POU2AF1, FCRL5
ITGAM, ITGAX, CD1C, or CLEC4C;
IL17A or IL17F; and
KLRC3, KLRK1, KLRC2, KLRD1
ITGAM, ITGAX, CD1C, or CLEC4C;
CCL2, IL1B, IL8 (CXCL8), IL6, or PTGS2; and
KLRC3, KLRK1, KLRC2, KLRD1
ITGAM, ITGAX, CD1C, or CLEC4C;
CTLA4, BTLA, LAG3, HAVCR2, or PDCD1; and
KLRC3, KLRK1, KLRC2, KLRD1
ITGAM, ITGAX, CD1C, or CLEC4C;
CD276, PDL1, PDL2, or IDO1; and
KLRC3, KLRK1, KLRC2, KLRD1
ITGAM, ITGAX, CD1C, or CLEC4C;
CX3CL1, CXCL9, CXCL10, CXCR3, CCL21, or CCL22; and
KLRC3, KLRK1, KLRC2, KLRD1
ITGAM, ITGAX, CD1C, or CLEC4C;
IL17A or IL17F; and
CD68, CD163, ITGAM, ITGAX, CD14
ITGAM, ITGAX, CD1C, or CLEC4C;
CCL2, IL1B, IL8 (CXCL8), IL6, or PTGS2; and
CD68, CD163, ITGAM, ITGAX, CD14
ITGAM, ITGAX, CD1C, or CLEC4C;
CTLA4, BTLA, LAG3, HAVCR2, or PDCD1; and
CD68, CD163, ITGAM, ITGAX, CD14
ITGAM, ITGAX, CD1C, or CLEC4C;
CD276, PDL1, PDL2, or IDO1; and
CD68, CD163, ITGAM, ITGAX, CD14
ITGAM, ITGAX, CD1C, or CLEC4C;
CX3CL1, CXCL9, CXCR3, CCL21, or CCL22; and
CD68, CD163, ITGAM, ITGAX, CD14
ITGAM, ITGAX, CD1C, or CLEC4C;
IL17A or IL17F; and
LAPTM5, LAIR1, CD4, CSF1R, CD163, ADAP2, CD68, MRC1,
CD45RO, SLA, MSR1, FPR3, FCGR2A, FCGR3A
ITGAM, ITGAX, CD1C, or CLEC4C;
CCL2, IL1B, IL8 (CXCL8), IL6, or PTGS2; and
LAPTM5, LAIR1, CD4, CSF1R, CD163, ADAP2, CD68, MRC1,
CD45RO, SLA, MSR1, FPR3, FCGR2A, FCGR3A
ITGAM, ITGAX, CD1C, or CLEC4C;
CTLA4, BTLA, LAG3, HAVCR2, or PDCD1; and
LAPTM5, LAIR1, CD4, CSF1R, CD163, ADAP2, CD68, MRC1,
CD45RO, SLA, MSR1, FPR3, FCGR2A, FCGR3A
ITGAM, ITGAX, CD1C, or CLEC4C;
CD276, PDL1, PDL2, or IDO1; and
LAPTM5, LAIR1, CD4, CSF1R, CD163, ADAP2, CD68, MRC1,
CD45RO, SLA, MSR1, FPR3, FCGR2A, FCGR3A
ITGAM, ITGAX, CD1C, or CLEC4C;
CX3CL1, CXCL9, CXCL10, CXCR3, CCL21, or CCL22; and
LAPTM5, LAIR1, CD4, CSF1R, CD163, ADAP2, CD68, MRC1,
CD45RO, SLA, MSR1, FPR3, FCGR2A, FCGR3A
ITGAM, ITGAX, CD1C, or CLEC4C;
IL17A or IL17F; and
CD3D, CD3E, CD2, CD3G, CD6, TRAT1, CD28, LCK
ITGAM, ITGAX, CD1C, or CLEC4C;
CCL2, IL1B, IL8 (CXCL8), IL6, or PTGS2; and
CD3D, CD3E, CD2, CD3G, CD6, TRAT1, CD28, LCK
ITGAM, ITGAX, CD1C, or CLEC4C;
CTLA4, BTLA, LAG3, HAVCR2, or PDCD1; and
CD3D, CD3E, CD2, CD3G, CD6, TRAT1, CD28, LCK
ITGAM, ITGAX, CD1C, or CLEC4C;
CD276, PDL1, PDL2, or IDO1; and
CD3D, CD3E, CD2, CD3G, CD6, TRAT1, CD28, LCK
ITGAM, ITGAX, CD1C, or CLEC4C;
CX3CL1, CXCL9, CXCL10, CXCR3, CCL21, or CCL22; and
CD3D, CD3E, CD2, CD3G, CD6, TRAT1, CD28, LCK
ITGAM, ITGAX, CD1C, or CLEC4C;
IL17A or IL17F; and
CTLA4, BTLA, LAG3, HAVCR2, PDCD1, TIGIT
ITGAM, ITGAX, CD1C, or CLEC4C;
CCL2, IL1B, IL8 (CXCL8), IL6, or PTGS2; and
CTLA4, BTLA, LAG3, HAVCR2, PDCD1, TIGIT
ITGAM, ITGAX, CD1C, or CLEC4C;
CTLA4, BTLA, LAG3, HAVCR2, or PDCD1; and
CTLA4, BTLA, LAG3, HAVCR2, PDCD1, TIGIT
ITGAM, ITGAX, CD1C, or CLEC4C;
CD276, PDL1, PDL2, or IDO1; and
CTLA4, BTLA, LAG3, HAVCR2, PDCD1, TIGIT
ITGAM, ITGAX, CD1C, or CLEC4C;
CX3CL1, CXCL9, CXCL10, CXCR3, CCL21, or CCL22; and
CTLA4, BTLA, LAG3, HAVCR2, PDCD1, TIGIT
ITGAM, ITGAX, CD1C, or CLEC4C;
IL17A or IL17F; and
CD274, PDL2, IDO1, PVR
ITGAM, ITGAX, CD1C, or CLEC4C;
CCL2, IL1B, IL8 (CXCL8), IL6, or PTGS2; and
CD274, PDL2, IDO1, PVR
ITGAM, ITGAX, CD1C, or CLEC4C;
CTLA4, BTLA, LAG3, HAVCR2, or PDCD1; and
CD274, PDL2, IDO1, PVR
ITGAM, ITGAX, CD1C, or CLEC4C;
CD276, PDL1, PDL2, or IDO1; and
CD274, PDL2, IDO1, PVR
ITGAM, ITGAX, CD1C, or CLEC4C;
CX3CL1, CXCL9, CXCL10, CXCR3, CCL21, or CCL22; and
CD274, PDL2, IDO1, PVR
ITGAM, ITGAX, CD1C, or CLEC4C;
IL17A or IL17F; and
CD4, IL2RA, CD69
ITGAM, ITGAX, CD1C, or CLEC4C;
CCL2, IL1B, IL8 (CXCL8), IL6, or PTGS2; and
CD4, IL2RA, CD69
ITGAM, ITGAX, CD1C, or CLEC4C;
CTLA4, BTLA, LAG3, HAVCR2, or PDCD1; and
CD4, IL2RA, CD69
ITGAM, ITGAX, CD1C, or CLEC4C;
CD276, PDL1, PDL2, or IDO1; and
CD4, IL2RA, CD69
ITGAM, ITGAX, CD1C, or CLEC4C;
CX3CL1, CXCL9, CXCL10, CXCR3, CCL21, or CCL22; and
CD4, IL2RA, CD69
ITGAM, ITGAX, CD1C, or CLEC4C;
IL17A or IL17F; and
TAPBP, TAP1, TAP2, PSMB9, PSMB8
ITGAM, ITGAX, CD1C, or CLEC4C;
CCL2, IL1B, IL8 (CXCL8), IL6, or PTGS2; and
TAPBP, TAP1, TAP2, PSMB9, PSMB8
ITGAM, ITGAX, CD1C, or CLEC4C;
CTLA4, BTLA, LAG3, HAVCR2, or PDCD1; and
TAPBP, TAP1, TAP2, PSMB9, PSMB8
ITGAM, ITGAX, CD1C, or CLEC4C;

TABLE 3-continued

Combinations of three gene signature sets

CD276, PDL1, PDL2, or IDO1; and
TAPBP, TAP1, TAP2, PSMB9, PSMB8
ITGAM, ITGAX, CD1C, or CLEC4C;
CX3CL1, CXCL9, CXCL10, CXCR3, CCL21, or CCL22; and
TAPBP, TAP1, TAP2, PSMB9, PSMB8
ITGAM, ITGAX, CD1C, or CLEC4C;
IL17A or IL17F; and
CD40, CD80, CD86, CD70, GITRL
ITGAM, ITGAX, CD1C, or CLEC4C;
CCL2, IL1B, IL8 (CXCL8), IL6, or PTGS2; and
CD40, CD80, CD86, CD70, GITRL
ITGAM, ITGAX, CD1C, or CLEC4C;
CTLA4, BTLA, LAG3, HAVCR2, or PDCD1; and
CD40, CD80, CD86, CD70, GITRL
ITGAM, ITGAX, CD1C, or CLEC4C;
CD276, PDL1, PDL2, or IDO1; and
CD40, CD80, CD86, CD70, GITRL
ITGAM, ITGAX, CD1C, or CLEC4C;
CX3CL1, CXCL9, CXCL10, CXCR3, CCL21, or CCL22; and
CD40, CD80, CD86, CD70, GITRL
ITGAM, ITGAX, CD1C, or CLEC4C;
IL17A or IL17F; and
CD27, CD28, ICOS, TNFRSF4, TNFRSF14, TNFRSF18, TNFRSF14, TNFSF14, CD226
ITGAM, ITGAX, CD1C, or CLEC4C;
CCL2, IL1B, IL8 (CXCL8), IL6, or PTGS2; and
CD27, CD28, ICOS, TNFRSF4, TNFRSF14, TNFRSF18, TNFRSF14, TNFSF14, CD226
ITGAM, ITGAX, CD1C, or CLEC4C;
CTLA4, BTLA, LAG3, HAVCR2, or PDCD1; and
CD27, CD28, ICOS, TNFRSF4, TNFRSF14, TNFRSF18, TNFRSF14, TNFSF14, CD226
ITGAM, ITGAX, CD1C, or CLEC4C;
CD276, PDL1, PDL2, or IDO1; and
CD27, CD28, ICOS, TNFRSF4, TNFRSF14, TNFRSF18, TNFRSF14, TNFSF14, CD226
ITGAM, ITGAX, CD1C, or CLEC4C;
CX3CL1, CXCL9, CXCL10, CXCR3, CCL21, or CCL22; and
CD27, CD28, ICOS, TNFRSF4, TNFRSF14, TNFRSF18, TNFRSF14, TNFSF14, CD226
ITGAM, ITGAX, CD1C, or CLEC4C;
IL17A or IL17F; and
GNLY, KLRK1, KLRB1, GZMH, GZMA, KLRD1, NKG7
ITGAM, ITGAX, CD1C, or CLEC4C;
CCL2, IL1B, IL8 (CXCL8), IL6, or PTGS2; and
GNLY, KLRK1, KLRB1, GZMH, GZMA, KLRD1, NKG7
ITGAM, ITGAX, CD1C, or CLEC4C;
CTLA4, BTLA, LAG3, HAVCR2, or PDCD1; and
GNLY, KLRK1, KLRB1, GZMH, GZMA, KLRD1, NKG7
ITGAM, ITGAX, CD1C, or CLEC4C;
CD276, PDL1, PDL2, or IDO1; and
GNLY, KLRK1, KLRB1, GZMH, GZMA, KLRD1, NKG7
ITGAM, ITGAX, CD1C, or CLEC4C;
CX3CL1, CXCL9, CXCL10, CXCR3, CCL21, or CCL22; and
GNLY, KLRK1, KLRB1, GZMH, GZMA, KLRD1, NKG7
ITGAM, ITGAX, CD1C, or CLEC4C;
IL17A or IL17F; and
FAP, FN1, MMP2, BGN, LOXL2, PDPN, PDGFRB, COL4A1, COL4A2, COL5A1, COL8A1
ITGAM, ITGAX, CD1C, or CLEC4C;
CCL2, IL1B, IL8 (CXCL8), IL6, or PTGS2; and
FAP, FN1, MMP2, BGN, LOXL2, PDPN, PDGFRB, COL4A1, COL4A2, COL5A1, COL8A1
ITGAM, ITGAX, CD1C, or CLEC4C;
CTLA4, BTLA, LAG3, HAVCR2, or PDCD1; and
FAP, FN1, MMP2, BGN, LOXL2, PDPN, PDGFRB, COL4A1, COL4A2, COL5A1, COL8A1
ITGAM, ITGAX, CD1C, or CLEC4C;
CD276, PDL1, PDL2, or IDO1; and
FAP, FN1, MMP2, BGN, LOXL2, PDPN, PDGFRB, COL4A1, COL4A2, COL5A1, COL8A1
ITGAM, ITGAX, CD1C, or CLEC4C;
CX3CL1, CXCL9, CXCL10, CXCR3, CCL21, or CCL22; and
FAP, FN1, MMP2, BGN, LOXL2, PDPN, PDGFRB, COL4A1, COL4A2, COL5A1, COL8A1
IL17A or IL17F;
CCL2, IL1B, IL8 (CXCL8), IL6, or PTGS2; and
CD79A, MS4A1, CD19, STAP1, KIAA0125, POU2AF1, FCRL5
IL17A or IL17F;
CTLA4, BTLA, LAG3, HAVCR2, or PDCD1; and
CD79A, MS4A1, CD19, STAP1, KIAA0125, POU2AF1, FCRL5
IL17A or IL17F;
CD276, PDL1, PDL2, or IDO1; and
CD79A, MS4A1, CD19, STAP1, KIAA0125, POU2AF1, FCRL5
IL17A or IL17F;
CX3CL1, CXCL9, CXCL10, CXCR3, CCL21, or CCL22; and
CD79A, MS4A1, CD19, STAP1, KIAA0125, POU2AF1, FCRL5
IL17A or IL17F;
CCL2, IL1B, IL8 (CXCL8), IL6, or PTGS2; and
KLRC3, KLRK1, KLRC2, KLRD1
IL17A or IL17F;
CTLA4, BTLA, LAG3, HAVCR2, or PDCD1; and
KLRC3, KLRK1, KLRC2, KLRD1
IL17A or IL17F;
CD276, PDL1, PDL2, or IDO1; and
KLRC3, KLRK1, KLRC2, KLRD1
IL17A or IL17F;
CX3CL1, CXCL9, CXCL10, CXCR3, CCL21, or CCL22; and
KLRC3, KLRK1, KLRC2, KLRD1
IL17A or IL17F;
CCL2, IL1B, IL8 (CXCL8), IL6, or PTGS2; and
CD68, CD163, ITGAM, ITGAX, CD14
IL17A or IL17F;
CTLA4, BTLA, LAG3, HAVCR2, or PDCD1; and
CD68, CD163, ITGAM, ITGAX, CD14
IL17A or IL17F;
CD276, PDL1, PDL2, or IDO1; and
CD68, CD163, ITGAM, ITGAX, CD14
IL17A or IL17F;
CX3CL1, CXCL9, CXCL10, CXCR3, CCL21, or CCL22; and
CD68, CD163, ITGAM, ITGAX, CD14
IL17A or IL17F;
CCL2, IL1B, IL8 (CXCL8), IL6, or PTGS2; and
LAPTM5, LAIR1, CD4, CSF1R, CD163, ADAP2, CD68, MRC1, CD45RO, SLA, MSR1, FPR3, FCGR2A, FCGR3A
IL17A or IL17F;
CTLA4, BTLA, LAG3, HAVCR2, or PDCD1; and
LAPTM5, LAIR1, CD4, CSF1R, CD163, ADAP2, CD68, MRC1, CD45RO, SLA, MSR1, FPR3, FCGR2A, FCGR3A
IL17A or IL17F;
CD276, PDL1, PDL2, or IDO1; and
LAPTM5, LAIR1, CD4, CSF1R, CD163, ADAP2, CD68, MRC1, CD45RO, SLA, MSR1, FPR3, FCGR2A, FCGR3A
IL17A or IL17F;
CX3CL1, CXCL9, CXCL10, CXCR3, CCL21, or CCL22; and
LAPTM5, LAIR1, CD4, CSF1R, CD163, ADAP2, CD68, MRC1, CD45RO, SLA, MSR1, FPR3, FCGR2A, FCGR3A
IL17A or IL17F;
CCL2, IL1B, IL8 (CXCL8), IL6, or PTGS2; and
CD3D, CD3E, CD2, CD3G, CD6, TRAT1, CD28, LCK
IL17A or IL17F;
CTLA4, BTLA, LAG3, HAVCR2, or PDCD1; and
CD3D, CD3E, CD2, CD3G, CD6, TRAT1, CD28, LCK
IL17A or IL17F;
CD276, PDL1, PDL2, or IDO1; and
CD3D, CD3E, CD2, CD3G, CD6, TRAT1, CD28, LCK
IL17A or IL17F;
CX3CL1, CXCL9, CXCL10, CXCR3, CCL21, or CCL22; and
CD3D, CD3E, CD2, CD3G, CD6, TRAT1, CD28, LCK
IL17A or IL17F;
CCL2, IL1B, IL8 (CXCL8), IL6, or PTGS2; and
CTLA4, BTLA, LAG3, HAVCR2, PDCD1, TIGIT
IL17A or IL17F;
CTLA4, BTLA, LAG3, HAVCR2, or PDCD1; and
CTLA4, BTLA, LAG3, HAVCR2, PDCD1, TIGIT
IL17A or IL17F;
CD276, PDL1, PDL2, or IDO1; and
CTLA4, BTLA, LAG3, HAVCR2, PDCD1, TIGIT
IL17A or IL17F;
CX3CL1, CXCL9, CXCL10, CXCR3, CCL21, or CCL22; and
CTLA4, BTLA, LAG3, HAVCR2, PDCD1, TIGIT
IL17A or IL17F;
CCL2, IL1B, IL8 (CXCL8), IL6, or PTGS2; and
CD274, PDL2, IDO1, PVR
IL17A or IL17F;
CTLA4, BTLA, LAG3, HAVCR2, or PDCD1; and

TABLE 3-continued

| Combinations of three gene signature sets |
|---|
| CD274, PDL2, IDO1, PVR |
| IL17A or IL17F; |
| CD276, PDL1, PDL2, or IDO1; and |
| CD274, PDL2, IDO1, PVR |
| IL17A or IL17F; |
| CX3CL1, CXCL9, CXCL10, CXCR3, CCL21, or CCL22; and |
| CD274, PDL2, IDO1, PVR |
| IL17A or IL17F; |
| CCL2, IL1B, IL8 (CXCL8), IL6, or PTGS2; and |
| CD4, IL2RA, CD69 |
| IL17A or IL17F; |
| CTLA4, BTLA, LAG3, HAVCR2, or PDCD1; and |
| CD4, IL2RA, CD69 |
| IL17A or IL17F; |
| CD276, PDL1, PDL2, or IDO1; and |
| CD4, IL2RA, CD69 |
| IL17A or IL17F; |
| CX3CL1, CXCL9, CXCL10, CXCR3, CCL21, or CCL22; and |
| CD4, IL2RA, CD69 |
| IL17A or IL17F; |
| CCL2, IL1B, IL8 (CXCL8), IL6, or PTGS2; and |
| TAPBP, TAP1, TAP2, PSMB9, PSMB8 |
| IL17A or IL17F; |
| CTLA4, BTLA, LAG3, HAVCR2, or PDCD1; and |
| TAPBP, TAP1, TAP2, PSMB9, PSMB8 |
| IL17A or IL17F; |
| CD276, PDL1, PDL2, or IDO1; and |
| TAPBP, TAP1, TAP2, PSMB9, PSMB8 |
| IL17A or IL17F; |
| CX3CL1, CXCL9, CXCL10, CXCR3, CCL21, or CCL22; and |
| TAPBP, TAP1, TAP2, PSMB9, PSMB8 |
| IL17A or IL17F; |
| CCL2, IL1B, IL8 (CXCL8), IL6, or PTGS2; and |
| CD40, CD80, CD86, CD70, GITRL |
| IL17A or IL17F; |
| CTLA4, BTLA, LAG3, HAVCR2, or PDCD1; and |
| CD40, CD80, CD86, CD70, GITRL |
| IL17A or IL17F; |
| CD276, PDL1, PDL2, or IDO1; and |
| CD40, CD80, CD86, CD70, GITRL |
| IL17A or IL17F; |
| CX3CL1, CXCL9, CXCL10, CXCR3, CCL21, or CCL22; and |
| CD40, CD80, CD86, CD70, GITRL |
| IL17A or IL17F; |
| CCL2, IL1B, IL8 (CXCL8), IL6, or PTGS2; and |
| CD27, CD28, ICOS, TNFRSF4, TNFRSF14, TNFRSF18, TNFRSF14, TNFSF14, CD226 |
| IL17A or IL17F; |
| CTLA4, BTLA, LAG3, HAVCR2, or PDCD1; and |
| CD27, CD28, ICOS, TNFRSF4, TNFRSF14, TNFRSF18, TNFRSF14, TNFSF14, CD226 |
| IL17A or IL17F; |
| CD276, PDL1, PDL2, or IDO1; and |
| CD27, CD28, ICOS, TNFRSF4, TNFRSF14, TNFRSF18, TNFRSF14, TNFSF14, CD226 |
| IL17A or IL17F; |
| CX3CL1, CXCL9, CXCL10, CXCR3, CCL21, or CCL22; and |
| CD27, CD28, ICOS, TNFRSF4, TNFRSF14, TNFRSF18, TNFRSF14, TNFSF14, CD226 |
| IL17A or IL17F; |
| CCL2, IL1B, IL8 (CXCL8), IL6, or PTGS2; and |
| GNLY, KLRK1, KLRB1, GZMH, GZMA, KLRD1, NKG7 |
| IL17A or IL17F; |
| CTLA4, BTLA, LAG3, HAVCR2, or PDCD1; and |
| GNLY, KLRK1, KLRB1, GZMH, GZMA, KLRD1, NKG7 |
| IL17A or IL17F; |
| CD276, PDL1, PDL2, or IDO1; and |
| GNLY, KLRK1, KLRB1, GZMH, GZMA, KLRD1, NKG7 |
| IL17A or IL17F; |
| CX3CL1, CXCL9, CXCL10, CXCR3, CCL21, or CCL22; and |
| GNLY, KLRK1, KLRB1, GZMH, GZMA, KLRD1, NKG7 |
| IL17A or IL17F; |
| CCL2, IL1B, IL8 (CXCL8), IL6, or PTGS2; and |
| FAP, FN1, MMP2, BGN, LOXL2, PDPN, PDGFRB, COL4A1, COL4A2, COL5A1, COL8A1 |
| IL17A or IL17F; |
| CTLA4, BTLA, LAG3, HAVCR2, or PDCD1; and |
| FAP, FN1, MMP2, BGN, LOXL2, PDPN, PDGFRB, COL4A1, COL4A2, COL5A1, COL8A1 |
| IL17A or IL17F; |
| CD276, PDL1, PDL2, or IDO1; and |
| FAP, FN1, MMP2, BGN, LOXL2, PDPN, PDGFRB, COL4A1, COL4A2, COL5A1, COL8A1 |
| IL17A or IL17F; |
| CX3CL1, CXCL9, CXCL10, CXCR3, CCL21, or CCL22; and |
| FAP, FN1, MMP2, BGN, LOXL2, PDPN, PDGFRB, COL4A1, COL4A2, COL5A1, COL8A1 |
| CCL2, IL1B, IL8 (CXCL8), IL6, or PTGS2; |
| CTLA4, BTLA, LAG3, HAVCR2, or PDCD1; and |
| CD79A, MS4A1, CD19, STAP1, KIAA0125, POU2AF1, FCRL5 |
| CCL2, IL1B, IL8 (CXCL8), IL6, or PTGS2; |
| CD276, PDL1, PDL2, or IDO1; and |
| CD79A, MS4A1, CD19, STAP1, KIAA0125, POU2AF1, FCRL5 |
| CCL2, IL1B, IL8 (CXCL8), IL6, or PTGS2; |
| CX3CL1, CXCL9, CXCL10, CXCR3, CCL21, or CCL22; and |
| CD79A, MS4A1, CD19, STAP1, KIAA0125, POU2AF1, FCRL5 |
| CCL2, IL1B, IL8 (CXCL8), IL6, or PTGS2; |
| CTLA4, BTLA, LAG3, HAVCR2, or PDCD1; and |
| KLRC3, KLRK1, KLRC2, KLRD1 |
| CCL2, IL1B, IL8 (CXCL8), IL6, or PTGS2; |
| CD276, PDL1, PDL2, or IDO1; and |
| KLRC3, KLRK1, KLRC2, KLRD1 |
| CCL2, IL1B, IL8 (CXCL8), IL6, or PTGS2; |
| CX3CL1, CXCL9, CXCL10, CXCR3, CCL21, or CCL22; and |
| KLRC3, KLRK1, KLRC2, KLRD1 |
| CCL2, IL1B, IL8 (CXCL8), IL6, or PTGS2; |
| CTLA4, BTLA, LAG3, HAVCR2, or PDCD1; and |
| CD68, CD163, ITGAM, ITGAX, CD14 |
| CCL2, IL1B, IL8 (CXCL8), IL6, or PTGS2; |
| CD276, PDL1, PDL2, or IDO1; and |
| CD68, CD163, ITGAM, ITGAX, CD14 |
| CCL2, IL1B, IL8 (CXCL8), IL6, or PTGS2; |
| CX3CL1, CXCL9, CXCL10, CXCR3, CCL21, or CCL22; and |
| CD68, CD163, ITGAM, ITGAX, CD14 |
| CCL2, IL1B, IL8 (CXCL8), IL6, or PTGS2; |
| CTLA4, BTLA, LAG3, HAVCR2, or PDCD1; and |
| LAPTM5, LAIR1, CD4, CSF1R, CD163, ADAP2, CD68, MRC1, CD45RO, SLA, MSR1, FPR3, FCGR2A, FCGR3A |
| CCL2, IL1B, IL8 (CXCL8), IL6, or PTGS2; |
| CD276, PDL1, PDL2, or IDO1; and |
| LAPTM5, LAIR1, CD4, CSF1R, CD163, ADAP2, CD68, MRC1, CD45RO, SLA, MSR1, FPR3, FCGR2A, FCGR3A |
| CCL2, IL1B, IL8 (CXCL8), IL6, or PTGS2; |
| CX3CL1, CXCL9, CXCL10, CXCR3, CCL21, or CCL22; and |
| LAPTM5, LAIR1, CD4, CSF1R, CD163, ADAP2, CD68, MRC1, CD45RO, SLA, MSR1, FPR3, FCGR2A, FCGR3A |
| CCL2, IL1B, IL8 (CXCL8), IL6, or PTGS2; |
| CTLA4, BTLA, LAG3, HAVCR2, or PDCD1; and |
| CD3D, CD3E, CD2, CD3G, CD6, TRAT1, CD28, LCK |
| CCL2, IL1B, IL8 (CXCL8), IL6, or PTGS2; |
| CD276, PDL1, PDL2, or IDO1; and |
| CD3D, CD3E, CD2, CD3G, CD6, TRAT1, CD28, LCK |
| CCL2, IL1B, IL8 (CXCL8), IL6, or PTGS2; |
| CX3CL1, CXCL9, CXCL10, CXCR3, CCL21, or CCL22; and |
| CD3D, CD3E, CD2, CD3G, CD6, TRAT1, CD28, LCK |
| CCL2, IL1B, IL8 (CXCL8), IL6, or PTGS2; |
| CTLA4, BTLA, LAG3, HAVCR2, PDCD1, TIGIT |
| CCL2, IL1B, IL8 (CXCL8), IL6, or PTGS2; |
| CD276, PDL1, PDL2, or IDO1; and |
| CTLA4, BTLA, LAG3, HAVCR2, PDCD1, TIGIT |
| CCL2, IL1B, IL8 (CXCL8), IL6, or PTGS2; |
| CX3CL1, CXCL9, CXCL10, CXCR3, CCL21, or CCL22; and |
| CTLA4, BTLA, LAG3, HAVCR2, PDCD1, TIGIT |
| CCL2, IL1B, IL8 (CXCL8), IL6, or PTGS2; |
| CTLA4, BTLA, LAG3, HAVCR2, or PDCD1; and |
| CD274, PDL2, IDO1, PVR |
| CCL2, IL1B, IL8 (CXCL8), IL6, or PTGS2; |
| CD276, PDL1, PDL2, or IDO1; and |
| CD274, PDL2, IDO1, PVR |
| CCL2, IL1B, IL8 (CXCL8), IL6, or PTGS2; |
| CX3CL1, CXCL9, CXCL10, CXCR3, CCL21, or CCL22; and |
| CD274, PDL2, IDO1, PVR |
| CCL2, IL1B, IL8 (CXCL8), IL6, or PTGS2; |
| CTLA4, BTLA, LAG3, HAVCR2, or PDCD1; and |
| CD4, IL2RA, CD69 |

TABLE 3-continued

Combinations of three gene signature sets

CCL2, IL1B, IL8 (CXCL8), IL6, or PTGS2;
CD276, PDL1, PDL2, or IDO1; and
CD4, IL2RA, CD69
CCL2, IL1B, IL8 (CXCL8), IL6, or PTGS2;
CX3CL1, CXCL9, CXCL10, CXCR3, CCL21, or CCL22; and
CD4, IL2RA, CD69
CCL2, IL1B, IL8 (CXCL8), IL6, or PTGS2;
CTLA4, BTLA, LAG3, HAVCR2, or PDCD1; and
TAPBP, TAP1, TAP2, PSMB9, PSMB8
CCL2, IL1B, IL8 (CXCL8), IL6, or PTGS2;
CD276, PDL1, PDL2, or IDO1; and
TAPBP, TAP1, TAP2, PSMB9, PSMB8
CCL2, IL1B, IL8 (CXCL8), IL6, or PTGS2;
CX3CL1, CXCL9, CXCL10, CXCR3, CCL21, or CCL22; and
TAPBP, TAP1, TAP2, PSMB9, PSMB8
CCL2, IL1B, IL8 (CXCL8), IL6, or PTGS2;
CTLA4, BTLA, LAG3, HAVCR2, or PDCD1; and
CD40, CD80, CD86, CD70, GITRL
CCL2, IL1B, IL8 (CXCL8), IL6, or PTGS2;
CD276, PDL1, PDL2, or IDO1; and
CD40, CD80, CD86, CD70, GITRL
CCL2, IL1B, IL8 (CXCL8), IL6, or PTGS2;
CX3CL1, CXCL9, CXCL10, CXCR3, CCL21, or CCL22; and
CD40, CD80, CD86, CD70, GITRL
CCL2, IL1B, IL8 (CXCL8), IL6, or PTGS2;
CTLA4, BTLA, LAG3, HAVCR2, or PDCD1; and
CD27, CD28, ICOS, TNFRSF4, TNFRSF14, TNFRSF18,
TNFRSF14, TNFSF14, CD226
CCL2, IL1B, IL8 (CXCL8), IL6, or PTGS2;
CD276, PDL1, PDL2, or IDO1; and
CD27, CD28, ICOS, TNFRSF4, TNFRSF14, TNFRSF18,
TNFRSF14, TNFSF14, CD226
CCL2, IL1B, IL8 (CXCL8), IL6, or PTGS2;
CX3CL1, CXCL9, CXCL10, CXCR3, CCL21, or CCL22; and
CD27, CD28, ICOS, TNFRSF4, TNFRSF14, TNFRSF18,
TNFRSF14, TNFSF14, CD226
CCL2, IL1B, IL8 (CXCL8), IL6, or PTGS2;
CTLA4, BTLA, LAG3, HAVCR2, or PDCD1; and
GNLY, KLRK1, KLRB1, GZMH, GZMA, KLRD1, NKG7
CCL2, IL1B, IL8 (CXCL8), IL6, or PTGS2;
CD276, PDL1, PDL2, or IDO1; and
GNLY, KLRK1, KLRB1, GZMH, GZMA, KLRD1, NKG7
CCL2, IL1B, IL8 (CXCL8), IL6, or PTGS2;
CX3CL1, CXCL9, CXCL10, CXCR3, CCL21, or CCL22; and
GNLY, KLRK1, KLRB1, GZMH, GZMA, KLRD1, NKG7
CCL2, IL1B, IL8 (CXCL8), IL6, or PTGS2;
CTLA4, BTLA, LAG3, HAVCR2, or PDCD1; and
FAP, FN1, MMP2, BGN, LOXL2, PDPN, PDGFRB,
COL4A1, COL4A2, COL5A1, COL8A1
CCL2, IL1B, IL8 (CXCL8), IL6, or PTGS2;
CD276, PDL1, PDL2, or IDO1; and
FAP, FN1, MMP2, BGN, LOXL2, PDPN, PDGFRB,
COL4A1, COL4A2, COL5A1, COL8A1
CCL2, IL1B, IL8 (CXCL8), IL6, or PTGS2;
CX3CL1, CXCL9, CXCL10, CXCR3, CCL21, or CCL22; and
FAP, FN1, MMP2, BGN, LOXL2, PDPN, PDGFRB,
COL4A1, COL4A2, COL5A1, COL8A1
CTLA4, BTLA, LAG3, HAVCR2, or PDCD1;
CD276, PDL1, PDL2, or IDO1; and
CD79A, MS4A1, CD19, STAP1, KIAA0125, POU2AF1, FCRL5
CTLA4, BTLA, LAG3, HAVCR2, or PDCD1;
CX3CL1, CXCL9, CXCL10, CXCR3, CCL21, or CCL22; and
CD79A, MS4A1, CD19, STAP1, KIAA0125, POU2AF1, FCRL5
CTLA4, BTLA, LAG3, HAVCR2, or PDCD1;
CD276, PDL1, PDL2, or IDO1; and
KLRC3, KLRK1, KLRC2, KLRD1
CTLA4, BTLA, LAG3, HAVCR2, or PDCD1;
CX3CL1, CXCL9, CXCL10, CXCR3, CCL21, or CCL22; and
KLRC3, KLRK1, KLRC2, KLRD1
CTLA4, BTLA, LAG3, HAVCR2, or PDCD1;
CD276, PDL1, PDL2, or IDO1; and
CD68, CD163, ITGAM, ITGAX, CD14
CTLA4, BTLA, LAG3, HAVCR2, or PDCD1;
CX3CL1, CXCL9, CXCL10, CXCR3, CCL21, or CCL22; and
CD68, CD163, ITGAM, ITGAX, CD14
CTLA4, BTLA, LAG3, HAVCR2, or PDCD1;
CD276, PDL1, PDL2, or IDO1; and
LAPTM5, LAIR1, CD4, CSF1R, CD163, ADAP2, CD68, MRC1, CD45RO, SLA, MSR1, FPR3, FCGR2A, FCGR3A
CTLA4, BTLA, LAG3, HAVCR2, or PDCD1;
CX3CL1, CXCL9, CXCL10, CXCR3, CCL21, or CCL22; and
LAPTM5, LAIR1, CD4, CSF1R, CD163, ADAP2, CD68, MRC1,
CD45RO, SLA, MSR1, FPR3, FCGR2A, FCGR3A
CTLA4, BTLA, LAG3, HAVCR2, or PDCD1;
CD276, PDL1, PDL2, or IDO1; and
CD3D, CD3E, CD2, CD3G, CD6, TRAT1, CD28, LCK
CTLA4, BTLA, LAG3, HAVCR2, or PDCD1;
CX3CL1, CXCL9, CXCL10, CXCR3, CCL21, or CCL22; and
CD3D, CD3E, CD2, CD3G, CD6, TRAT1, CD28, LCK
CTLA4, BTLA, LAG3, HAVCR2, or PDCD1;
CD276, PDL1, PDL2, or IDO1; and
CTLA4, BTLA, LAG3, HAVCR2, PDCD1, TIGIT
CTLA4, BTLA, LAG3, HAVCR2, or PDCD1;
CX3CL1, CXCL9, CXCL10, CXCR3, CCL21, or CCL22; and
CTLA4, BTLA, LAG3, HAVCR2, PDCD1, TIGIT
CTLA4, BTLA, LAG3, HAVCR2, or PDCD1;
CD276, PDL1, PDL2, or IDO1; and
CD274, PDL2, IDO1, PVR
CTLA4, BTLA, LAG3, HAVCR2, or PDCD1;
CX3CL1, CXCL9, CXCL10, CXCR3, CCL21, or CCL22; and
CD274, PDL2, IDO1, PVR
CTLA4, BTLA, LAG3, HAVCR2, or PDCD1;
CD276, PDL1, PDL2, or IDO1; and
CD4, IL2RA, CD69
CTLA4, BTLA, LAG3, HAVCR2, or PDCD1;
CX3CL1, CXCL9, CXCL10, CXCR3, CCL21, or CCL22; and
CD4, IL2RA, CD69
CTLA4, BTLA, LAG3, HAVCR2, or PDCD1;
CD276, PDL1, PDL2, or IDO1; and
TAPBP, TAP1, TAP2, PSMB9, PSMB8
CTLA4, BTLA, LAG3, HAVCR2, or PDCD1;
CX3CL1, CXCL9, CXCL10, CXCR3, CCL21, or CCL22; and
TAPBP, TAP1, TAP2, PSMB9, PSMB8
CTLA4, BTLA, LAG3, HAVCR2, or PDCD1;
CD276, PDL1, PDL2, or IDO1; and
CD40, CD80, CD86, CD70, GITRL
CTLA4, BTLA, LAG3, HAVCR2, or PDCD1;
CX3CL1, CXCL9, CXCL10, CXCR3, CCL21, or CCL22; and
CD40, CD80, CD86, CD70, GITRL
CTLA4, BTLA, LAG3, HAVCR2, or PDCD1;
CD276, PDL1, PDL2, or IDO1; and
CD27, CD28, ICOS, TNFRSF4, TNFRSF14, TNFRSF18,
TNFRSF14, TNFSF14, CD226
CTLA4, BTLA, LAG3, HAVCR2, or PDCD1;
CX3CL1, CXCL9, CXCL10, CXCR3, CCL21, or CCL22; and
CD27, CD28, ICOS, TNFRSF4, TNFRSF14, TNFRSF18,
TNFRSF14, TNFSF14, CD226
CTLA4, BTLA, LAG3, HAVCR2, or PDCD1;
CD276, PDL1, PDL2, or IDO1; and
GNLY, KLRK1, KLRB1, GZMH, GZMA, KLRD1, NKG7
CTLA4, BTLA, LAG3, HAVCR2, or PDCD1;
CX3CL1, CXCL9, CXCL10, CXCR3, CCL21, or CCL22; and
GNLY, KLRK1, KLRB1, GZMH, GZMA, KLRD1, NKG7
CTLA4, BTLA, LAG3, HAVCR2, or PDCD1;
CD276, PDL1, PDL2, or IDO1; and
FAP, FN1, MMP2, BGN, LOXL2, PDPN, PDGFRB,
COL4A1, COL4A2, COL5A1, COL8A1
CTLA4, BTLA, LAG3, HAVCR2, or PDCD1;
CX3CL1, CXCL9, CXCL10, CXCR3, CCL21, or CCL22; and
FAP, FN1, MMP2, BGN, LOXL2, PDPN, PDGFRB,
COL4A1, COL4A2, COL5A1, COL8A1
CD79A, MS4A1, CD19, STAP1, KIAA0125, POU2AF1, or
FCRL5;
KLRC3, KLRK1, KLRC2, or KLRD1; and
CD68, CD163, ITGAM, ITGAX, CD14
CD79A, MS4A1, CD19, STAP1, KIAA0125, POU2AF1, or
FCRL5;
KLRC3, KLRK1, KLRC2, or KLRD1; and
LAPTM5, LAIR1, CD4, CSF1R, CD163, ADAP2, CD68, MRC1,
CD45RO, SLA, MSR1, FPR3, FCGR2A, FCGR3A
CD79A, MS4A1, CD19, STAP1, KIAA0125, POU2AF1, or
FCRL5;
KLRC3, KLRK1, KLRC2, or KLRD1; and
CD3D, CD3E, CD2, CD3G, CD6, TRAT1, CD28, LCK
CD79A, MS4A1, CD19, STAP1, KIAA0125, POU2AF1, or
FCRL5;

TABLE 3-continued

Combinations of three gene signature sets

KLRC3, KLRK1, KLRC2, or KLRD1; and
CTLA4, BTLA, LAG3, HAVCR2, PDCD1, TIGIT
CD79A, MS4A1, CD19, STAP1, KIAA0125, POU2AF1, or FCRL5;
KLRC3, KLRK1, KLRC2, or KLRD1; and
CD274, PDL2, IDO1, PVR
CD79A, MS4A1, CD19, STAP1, KIAA0125, POU2AF1, or FCRL5;
KLRC3, KLRK1, KLRC2, or KLRD1; and
CD4, IL2RA, CD69
CD79A, MS4A1, CD19, STAP1, KIAA0125, POU2AF1, or FCRL5;
KLRC3, KLRK1, KLRC2, or KLRD1; and
TAPBP, TAP1, TAP2, PSMB9, PSMB8
CD79A, MS4A1, CD19, STAP1, KIAA0125, POU2AF1, or FCRL5;
KLRC3, KLRK1, KLRC2, or KLRD1; and
CD40, CD80, CD86, CD70, GITRL
CD79A, MS4A1, CD19, STAP1, KIAA0125, POU2AF1, or FCRL5;
KLRC3, KLRK1, KLRC2, or KLRD1; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
KLRC3, KLRK1, KLRC2, or KLRD1; and
GNLY, KLRK1, KLRB1, GZMH, GZMA, KLRD1, NKG7
CD79A, MS4A1, CD19, STAP1, KIAA0125, POU2AF1, or FCRL5;
KLRC3, KLRK1, KLRC2, or KLRD1; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
CD68, CD163, ITGAM, ITGAX, or CD14; and
LAPTM5, LAIR1, CD4, CSF1R, CD163, ADAP2, CD68, MRC1, CD45RO, SLA, MSR1, FPR3, FCGR2A, FCGR3A
CD79A, MS4A1, CD19, STAP1, KIAA0125, POU2AF1, or FCRL5;
CD68, CD163, ITGAM, ITGAX, or CD14; and
CD3D, CD3E, CD2, CD3G, CD6, TRAT1, CD28, LCK
CD79A, MS4A1, CD19, STAP1, KIAA0125, POU2AF1, or FCRL5;
CD68, CD163, ITGAM, ITGAX, or CD14; and
CTLA4, BTLA, LAG3, HAVCR2, PDCD1, TIGIT
CD79A, MS4A1, CD19, STAP1, KIAA0125, POU2AF1, or FCRL5;
CD68, CD163, ITGAM, ITGAX, or CD14; and
CD274, PDL2, IDO1, PVR
CD79A, MS4A1, CD19, STAP1, KIAA0125, POU2AF1, or FCRL5;
CD68, CD163, ITGAM, ITGAX, or CD14; and
CD4, IL2RA, CD69
CD79A, MS4A1, CD19, STAP1, KIAA0125, POU2AF1, or FCRL5;
CD68, CD163, ITGAM, ITGAX, or CD14; and
TAPBP, TAP1, TAP2, PSMB9, PSMB8
CD79A, MS4A1, CD19, STAP1, KIAA0125, POU2AF1, or FCRL5;
CD68, CD163, ITGAM, ITGAX, or CD14; and
CD40, CD80, CD86, CD70, GITRL
CD79A, MS4A1, CD19, STAP1, KIAA0125, POU2AF1, or FCRL5;
CD68, CD163, ITGAM, ITGAX, or CD14; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
CD68, CD163, ITGAM, ITGAX, or CD14; and
GNLY, KLRK1, KLRB1, GZMH, GZMA, KLRD1, NKG7
CD79A, MS4A1, CD19, STAP1, KIAA0125, POU2AF1, or FCRL5;
CD68, CD163, ITGAM, ITGAX, or CD14; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
CD3D, CD3E, CD2, CD3G, CD6, TRAT1, CD28, LCK
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
CTLA4, BTLA, LAG3, HAVCR2, PDCD1, TIGIT
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
CD274, PDL2, IDO1, PVR
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
CD4, IL2RA, CD69
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
TAPBP, TAP1, TAP2, PSMB9, PSMB8
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
CD40, CD80, CD86, CD70, GITRL
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
GNLY, KLRK1, KLRB1, GZMH, GZMA, KLRD1, NKG7
CD79A, MS4A1, CD19, STAP1, KIAA0125, POU2AF1, or FCRL5;
LAPTM5, LAIR1, CD4, CSF1R, CD163, ADAP2, CD68, MRC1, CD45RO, SLA, MSR1, FPR3, FCGR2A, or FCGR3A; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
CD3D, CD3E, CD2, CD3G, CD6, TRAT1, CD28, or LCK; and
CTLA4, BTLA, LAG3, HAVCR2, PDCD1, TIGIT
CD79A, MS4A1, CD19, STAP1, KIAA0125, POU2AF1, or FCRL5;
CD3D, CD3E, CD2, CD3G, CD6, TRAT1, CD28, or LCK; and
CD274, PDL2, IDO1, PVR
CD79A, MS4A1, CD19, STAP1, KIAA0125, POU2AF1, or FCRL5;
CD3D, CD3E, CD2, CD3G, CD6, TRAT1, CD28, or LCK; and
CD4, IL2RA, CD69
CD79A, MS4A1, CD19, STAP1, KIAA0125, POU2AF1, or FCRL5;
CD3D, CD3E, CD2, CD3G, CD6, TRAT1, CD28, or LCK; and
TAPBP, TAP1, TAP2, PSMB9, PSMB8
CD79A, MS4A1, CD19, STAP1, KIAA0125, POU2AF1, or FCRL5;
CD3D, CD3E, CD2, CD3G, CD6, TRAT1, CD28, or LCK; and
CD40, CD80, CD86, CD70, GITRL
CD79A, MS4A1, CD19, STAP1, KIAA0125, POU2AF1, or FCRL5;
CD3D, CD3E, CD2, CD3G, CD6, TRAT1, CD28, or LCK; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
CD3D, CD3E, CD2, CD3G, CD6, TRAT1, CD28, or LCK; and
GNLY, KLRK1, KLRB1, GZMH, GZMA, KLRD1, NKG7
CD79A, MS4A1, CD19, STAP1, KIAA0125, POU2AF1, or FCRL5;
CD3D, CD3E, CD2, CD3G, CD6, TRAT1, CD28, or LCK; and
FAP, FN1, MMP2, BGN, LOXL2, PDPN, PDGFRB, COL4A1, COL4A2, COL5A1, COL8A1

TABLE 3-continued

Combinations of three gene signature sets

CD79A, MS4A1, CD19, STAP1, KIAA0125, POU2AF1, or FCRL5;
CTLA4, BTLA, LAG3, HAVCR2, PDCD1, or TIGIT; and
CD274, PDL2, IDO1, PVR
CD79A, MS4A1, CD19, STAP1, KIAA0125, POU2AF1, or FCRL5;
CTLA4, BTLA, LAG3, HAVCR2, PDCD1, or TIGIT; and
CD4, IL2RA, CD69
CD79A, MS4A1, CD19, STAP1, KIAA0125, POU2AF1, or FCRL5;
CTLA4, BTLA, LAG3, HAVCR2, PDCD1, or TIGIT; and
TAPBP, TAP1, TAP2, PSMB9, PSMB8
CD79A, MS4A1, CD19, STAP1, KIAA0125, POU2AF1, or FCRL5;
CTLA4, BTLA, LAG3, HAVCR2, PDCD1, or TIGIT; and
CD40, CD80, CD86, CD70, GITRL
CD79A, MS4A1, CD19, STAP1, KIAA0125, POU2AF1, or FCRL5;
CTLA4, BTLA, LAG3, HAVCR2, PDCD1, or TIGIT; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
CTLA4, BTLA, LAG3, HAVCR2, PDCD1, or TIGIT; and
GNLY, KLRK1, KLRB1, GZMH, GZMA, KLRD1, NKG7
CD79A, MS4A1, CD19, STAP1, KIAA0125, POU2AF1, or FCRL5;
CTLA4, BTLA, LAG3, HAVCR2, PDCD1, or TIGIT; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
CD274, PDL2, IDO1, or PVR; and
CD4, IL2RA, CD69
CD79A, MS4A1, CD19, STAP1, KIAA0125, POU2AF1, or FCRL5;
CD274, PDL2, IDO1, or PVR; and
TAPBP, TAP1, TAP2, PSMB9, PSMB8
CD79A, MS4A1, CD19, STAP1, KIAA0125, POU2AF1, or FCRL5;
CD274, PDL2, IDO1, or PVR; and
CD40, CD80, CD86, CD70, GITRL
CD79A, MS4A1, CD19, STAP1, KIAA0125, POU2AF1, or FCRL5;
CD274, PDL2, IDO1, or PVR; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
CD274, PDL2, IDO1, or PVR; and
GNLY, KLRK1, KLRB1, GZMH, GZMA, KLRD1, NKG7
CD79A, MS4A1, CD19, STAP1, KIAA0125, POU2AF1, or FCRL5;
CD274, PDL2, IDO1, or PVR; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
CD4, IL2RA, or CD69; and
TAPBP, TAP1, TAP2, PSMB9, PSMB8
CD79A, MS4A1, CD19, STAP1, KIAA0125, POU2AF1, or FCRL5;
CD4, IL2RA, or CD69; and
CD40, CD80, CD86, CD70, GITRL
CD79A, MS4A1, CD19, STAP1, KIAA0125, POU2AF1, or FCRL5;
CD4, IL2RA, or CD69; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
CD4, IL2RA, or CD69; and
GNLY, KLRK1, KLRB1, GZMH, GZMA, KLRD1, NKG7
CD79A, MS4A1, CD19, STAP1, KIAA0125, POU2AF1, or FCRL5;
CD4, IL2RA, or CD69; and
FAP, FN1, MMP2, BGN, LOXL2, PDPN, PDGFRB, COL4A1, COL4A2, COL5A1, COL8A1

TABLE 3-continued

Combinations of three gene signature sets

CD79A, MS4A1, CD19, STAP1, KIAA0125, POU2AF1, or FCRL5;
TAPBP, TAP1, TAP2, PSMB9, or PSMB8; and
CD40, CD80, CD86, CD70, GITRL
CD79A, MS4A1, CD19, STAP1, KIAA0125, POU2AF1, or FCRL5;
TAPBP, TAP1, TAP2, PSMB9, or PSMB8; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
TAPBP, TAP1, TAP2, PSMB9, or PSMB8; and
GNLY, KLRK1, KLRB1, GZMH, GZMA, KLRD1, NKG7
CD79A, MS4A1, CD19, STAP1, KIAA0125, POU2AF1, or FCRL5;
TAPBP, TAP1, TAP2, PSMB9, or PSMB8; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
CD40, CD80, CD86, CD70, or GITRL; and
CD27, CD28, ICOS, TNFRSF4, TNFRSF14, TNFRSF18, TNFRSF14, TNFSF14, CD226
CD79A, MS4A1, CD19, STAP1, KIAA0125, POU2AF1, or FCRL5;
CD40, CD80, CD86, CD70, or GITRL; and
GNLY, KLRK1, KLRB1, GZMH, GZMA, KLRD1, NKG7
CD79A, MS4A1, CD19, STAP1, KIAA0125, POU2AF1, or FCRL5;
CD40, CD80, CD86, CD70, or GITRL; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
CD79A, MS4A1, CD19, STAP1, KIAA0125, POU2AF1, or FCRL5;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
CD79A, MS4A1, CD19, STAP1, KIAA0125, POU2AF1, or FCRL5;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
KLRC3, KLRK1, KLRC2, or KLRD1;
CD68, CD163, ITGAM, ITGAX, or CD14; and
LAPTM5, LAIR1, CD4, CSF1R, CD163, ADAP2, CD68, MRC1, CD45RO, SLA, MSR1, FPR3, FCGR2A, FCGR3A
KLRC3, KLRK1, KLRC2, or KLRD1;
CD68, CD163, ITGAM, ITGAX, or CD14; and
CD3D, CD3E, CD2, CD3G, CD6, TRAT1, CD28, LCK
KLRC3, KLRK1, KLRC2, or KLRD1;
CD68, CD163, ITGAM, ITGAX, or CD14; and
CTLA4, BTLA, LAG3, HAVCR2, PDCD1, TIGIT
KLRC3, KLRK1, KLRC2, or KLRD1;
CD68, CD163, ITGAM, ITGAX, or CD14; and
CD274, PDL2, IDO1, PVR
KLRC3, KLRK1, KLRC2, or KLRD1;
CD68, CD163, ITGAM, ITGAX, or CD14; and
CD4, IL2RA, CD69
KLRC3, KLRK1, KLRC2, or KLRD1;
CD68, CD163, ITGAM, ITGAX, or CD14; and
TAPBP, TAP1, TAP2, PSMB9, PSMB8
KLRC3, KLRK1, KLRC2, or KLRD1;
CD68, CD163, ITGAM, ITGAX, or CD14; and
CD40, CD80, CD86, CD70, GITRL
KLRC3, KLRK1, KLRC2, or KLRD1;
CD68, CD163, ITGAM, ITGAX, or CD14; and
CD27, CD28, ICOS, TNFRSF4, TNFRSF14, TNFRSF18, TNFRSF14, TNFSF14, CD226
KLRC3, KLRK1, KLRC2, or KLRD1;
CD68, CD163, ITGAM, ITGAX, or CD14; and
GNLY, KLRK1, KLRB1, GZMH, GZMA, KLRD1, NKG7
KLRC3, KLRK1, KLRC2, or KLRD1;

TABLE 3-continued

Combinations of three gene signature sets

CD68, CD163, ITGAM, ITGAX, or CD14; and
FAP, FN1, MMP2, BGN, LOXL2, PDPN, PDGFRB,
COL4A1, COL4A2, COL5A1, COL8A1
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
CD3D, CD3E, CD2, CD3G, CD6, TRAT1, CD28, LCK
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
CTLA4, BTLA, LAG3, HAVCR2, PDCD1, TIGIT
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
CD274, PDL2, IDO1, PVR
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
CD4, IL2RA, CD69
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
TAPBP, TAP1, TAP2, PSMB9, PSMB8
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
CD40, CD80, CD86, CD70, GITRL
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
CD27, CD28, ICOS, TNFRSF4, TNFRSF14, TNFRSF18,
TNFRSF14, TNFSF14, CD226
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
GNLY, KLRK1, KLRB1, GZMH, GZMA, KLRD1, NKG7
KLRC3, KLRK1, KLRC2, or KLRD1;
LAPTM5, LAIR1, CD4, CSF1R, CD163, ADAP2, CD68, MRC1,
CD45RO, SLA, MSR1, FPR3, FCGR2A, or FCGR3A; and
FAP, FN1, MMP2, BGN, LOXL2, PDPN, PDGFRB,
COL4A1, COL4A2, COL5A1, COL8A1
KLRC3, KLRK1, KLRC2, or KLRD1;
CD3D, CD3E, CD2, CD3G, CD6, TRAT1, CD28, or LCK; and
CTLA4, BTLA, LAG3, HAVCR2, PDCD1, TIGIT
KLRC3, KLRK1, KLRC2, or KLRD1;
CD3D, CD3E, CD2, CD3G, CD6, TRAT1, CD28, or LCK; and
CD274, PDL2, IDO1, PVR
KLRC3, KLRK1, KLRC2, or KLRD1;
CD3D, CD3E, CD2, CD3G, CD6, TRAT1, CD28, or LCK; and
CD4, IL2RA, CD69
KLRC3, KLRK1, KLRC2, or KLRD1;
CD3D, CD3E, CD2, CD3G, CD6, TRAT1, CD28, or LCK; and
TAPBP, TAP1, TAP2, PSMB9, PSMB8
KLRC3, KLRK1, KLRC2, or KLRD1;
CD3D, CD3E, CD2, CD3G, CD6, TRAT1, CD28, or LCK; and
CD40, CD80, CD86, CD70, GITRL
KLRC3, KLRK1, KLRC2, or KLRD1;
CD3D, CD3E, CD2, CD3G, CD6, TRAT1, CD28, or LCK; and
CD27, CD28, ICOS, TNFRSF4, TNFRSF14, TNFRSF18,
TNFRSF14, TNFSF14, CD226
KLRC3, KLRK1, KLRC2, or KLRD1;
CD3D, CD3E, CD2, CD3G, CD6, TRAT1, CD28, or LCK; and
GNLY, KLRK1, KLRB1, GZMH, GZMA, KLRD1, NKG7
KLRC3, KLRK1, KLRC2, or KLRD1;
CD3D, CD3E, CD2, CD3G, CD6, TRAT1, CD28, or LCK; and
FAP, FN1, MMP2, BGN, LOXL2, PDPN, PDGFRB,
COL4A1, COL4A2, COL5A1, COL8A1
KLRC3, KLRK1, KLRC2, or KLRD1;
CTLA4, BTLA, LAG3, HAVCR2, PDCD1, or TIGIT; and
CD274, PDL2, IDO1, PVR
KLRC3, KLRK1, KLRC2, or KLRD1;
CTLA4, BTLA, LAG3, HAVCR2, PDCD1, or TIGIT; and
CD4, IL2RA, CD69
KLRC3, KLRK1, KLRC2, or KLRD1;
CTLA4, BTLA, LAG3, HAVCR2, PDCD1, or TIGIT; and
TAPBP, TAP1, TAP2, PSMB9, PSMB8
KLRC3, KLRK1, KLRC2, or KLRD1;
CTLA4, BTLA, LAG3, HAVCR2, PDCD1, or TIGIT; and TABLE 3-continued Combinations of three gene signature sets CD40, CD80, CD86, CD70, GITRL
KLRC3, KLRK1, KLRC2, or KLRD1;
CTLA4, BTLA, LAG3, HAVCR2, PDCD1, or TIGIT; and
CD27, CD28, ICOS, TNFRSF4, TNFRSF14, TNFRSF18,
TNFRSF14, TNFSF14, CD226
KLRC3, KLRK1, KLRC2, or KLRD1;
CTLA4, BTLA, LAG3, HAVCR2, PDCD1, or TIGIT; and
GNLY, KLRK1, KLRB1, GZMH, GZMA, KLRD1, NKG7
KLRC3, KLRK1, KLRC2, or KLRD1;
CTLA4, BTLA, LAG3, HAVCR2, PDCD1, or TIGIT; and
FAP, FN1, MMP2, BGN, LOXL2, PDPN, PDGFRB,
COL4A1, COL4A2, COL5A1, COL8A1
KLRC3, KLRK1, KLRC2, or KLRD1;
CD274, PDL2, IDO1, or PVR; and
CD4, IL2RA, CD69
KLRC3, KLRK1, KLRC2, or KLRD1;
CD274, PDL2, IDO1, or PVR; and
TAPBP, TAP1, TAP2, PSMB9, PSMB8
KLRC3, KLRK1, KLRC2, or KLRD1;
CD274, PDL2, IDO1, or PVR; and
CD40, CD80, CD86, CD70, GITRL
KLRC3, KLRK1, KLRC2, or KLRD1;
CD274, PDL2, IDO1, or PVR; and
CD27, CD28, ICOS, TNFRSF4, TNFRSF14, TNFRSF18,
TNFRSF14, TNFSF14, CD226
KLRC3, KLRK1, KLRC2, or KLRD1;
CD274, PDL2, IDO1, or PVR; and
GNLY, KLRK1, KLRB1, GZMH, GZMA, KLRD1, NKG7
KLRC3, KLRK1, KLRC2, or KLRD1;
CD274, PDL2, IDO1, or PVR; and
FAP, FN1, MMP2, BGN, LOXL2, PDPN, PDGFRB,
COL4A1, COL4A2, COL5A1, COL8A1
KLRC3, KLRK1, KLRC2, or KLRD1;
CD4, IL2RA, or CD69; and
TAPBP, TAP1, TAP2, PSMB9, PSMB8
KLRC3, KLRK1, KLRC2, or KLRD1;
CD4, IL2RA, or CD69; and
CD40, CD80, CD86, CD70, GITRL
KLRC3, KLRK1, KLRC2, or KLRD1;
CD4, IL2RA, or CD69; and
CD27, CD28, ICOS, TNFRSF4, TNFRSF14, TNFRSF18,
TNFRSF14, TNFSF14, CD226
KLRC3, KLRK1, KLRC2, or KLRD1;
CD4, IL2RA, or CD69; and
GNLY, KLRK1, KLRB1, GZMH, GZMA, KLRD1, NKG7
KLRC3, KLRK1, KLRC2, or KLRD1;
CD4, IL2RA, or CD69; and
FAP, FN1, MMP2, BGN, LOXL2, PDPN, PDGFRB,
COL4A1, COL4A2, COL5A1, COL8A1
KLRC3, KLRK1, KLRC2, or KLRD1;
TAPBP, TAP1, TAP2, PSMB9, or PSMB8; and
CD40, CD80, CD86, CD70, GITRL
KLRC3, KLRK1, KLRC2, or KLRD1;
TAPBP, TAP1, TAP2, PSMB9, or PSMB8; and
CD27, CD28, ICOS, TNFRSF4, TNFRSF14, TNFRSF18,
TNFRSF14, TNFSF14, CD226
KLRC3, KLRK1, KLRC2, or KLRD1;
TAPBP, TAP1, TAP2, PSMB9, or PSMB8; and
GNLY, KLRK1, KLRB1, GZMH, GZMA, KLRD1, NKG7
KLRC3, KLRK1, KLRC2, or KLRD1;
TAPBP, TAP1, TAP2, PSMB9, or PSMB8; and
FAP, FN1, MMP2, BGN, LOXL2, PDPN, PDGFRB,
COL4A1, COL4A2, COL5A1, COL8A1
KLRC3, KLRK1, KLRC2, or KLRD1;
CD40, CD80, CD86, CD70, or GITRL; and
CD27, CD28, ICOS, TNFRSF4, TNFRSF14, TNFRSF18,
TNFRSF14, TNFSF14, CD226
KLRC3, KLRK1, KLRC2, or KLRD1;
CD40, CD80, CD86, CD70, or GITRL; and
GNLY, KLRK1, KLRB1, GZMH, GZMA, KLRD1, NKG7
KLRC3, KLRK1, KLRC2, or KLRD1;
CD40, CD80, CD86, CD70, or GITRL; and
FAP, FN1, MMP2, BGN, LOXL2, PDPN, PDGFRB,
COL4A1, COL4A2, COL5A1, COL8A1
KLRC3, KLRK1, KLRC2, or KLRD1;
CD27, CD28, ICOS, TNFRSF4, TNFRSF14, TNFRSF18,
TNFRSF14, TNFSF14, or CD226; and
GNLY, KLRK1, KLRB1, GZMH, GZMA, KLRD1, NKG7

TABLE 3-continued

| Combinations of three gene signature sets |
|---|
| KLRC3, KLRK1, KLRC2, or KLRD1; |
| CD27, CD28, ICOS, TNFRSF4, TNFRSF14, TNFRSF18, TNFRSF14, TNFSF14, or CD226; and |
| FAP, FN1, MMP2, BGN, LOXL2, PDPN, PDGFRB, COL4A1, COL4A2, COL5A1, COL8A1 |
| KLRC3, KLRK1, KLRC2, or KLRD1; |
| GNLY, KLRK1, KLRB1, GZMH, GZMA, KLRD1, or NKG7; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| CD3D, CD3E, CD2, CD3G, CD6, TRAT1, CD28, LCK |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| CTLA4, BTLA, LAG3, HAVCR2, PDCD1, TIGIT |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| CD274, PDL2, IDO1, PVR |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| CD4, IL2RA, CD69 |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| TAPBP, TAP1, TAP2, PSMB9, PSMB8 |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| CD40, CD80, CD86, CD70, GITRL |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| GNLY, KLRK1, KLRB1, GZMH, GZMA, KLRD1, NKG7 |
| CD68, CD163, ITGAM, ITGAX, or CD14; |
| LAPTM5, LAIR1, CD4, CSF1R, CD163, ADAP2, CD68, MRC1, CD45RO, SLA, MSR1, FPR3, FCGR2A, or FCGR3A; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| CD3D, CD3E, CD2, CD3G, CD6, TRAT1, CD28, or LCK; and |
| CTLA4, BTLA, LAG3, HAVCR2, PDCD1, TIGIT |
| CD68, CD163, ITGAM, ITGAX, or CD14; |
| CD3D, CD3E, CD2, CD3G, CD6, TRAT1, CD28, or LCK; and |
| CD274, PDL2, IDO1, PVR |
| CD68, CD163, ITGAM, ITGAX, or CD14; |
| CD3D, CD3E, CD2, CD3G, CD6, TRAT1, CD28, or LCK; and |
| CD4, IL2RA, CD69 |
| CD68, CD163, ITGAM, ITGAX, or CD14; |
| CD3D, CD3E, CD2, CD3G, CD6, TRAT1, CD28, or LCK; and |
| TAPBP, TAP1, TAP2, PSMB9, PSMB8 |
| CD68, CD163, ITGAM, ITGAX, or CD14; |
| CD3D, CD3E, CD2, CD3G, CD6, TRAT1, CD28, or LCK; and |
| CD40, CD80, CD86, CD70, GITRL |
| CD68, CD163, ITGAM, ITGAX, or CD14; |
| CD3D, CD3E, CD2, CD3G, CD6, TRAT1, CD28, or LCK; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| CD3D, CD3E, CD2, CD3G, CD6, TRAT1, CD28, or LCK; and |
| GNLY, KLRK1, KLRB1, GZMH, GZMA, KLRD1, NKG7 |
| CD68, CD163, ITGAM, ITGAX, or CD14; |
| CD3D, CD3E, CD2, CD3G, CD6, TRAT1, CD28, or LCK; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| CTLA4, BTLA, LAG3, HAVCR2, PDCD1, or TIGIT; and |
| CD274, PDL2, IDO1, PVR |
| CD68, CD163, ITGAM, ITGAX, or CD14; |
| CTLA4, BTLA, LAG3, HAVCR2, PDCD1, or TIGIT; and |
| CD4, IL2RA, CD69 |
| CD68, CD163, ITGAM, ITGAX, or CD14; |
| CTLA4, BTLA, LAG3, HAVCR2, PDCD1, or TIGIT; and |
| TAPBP, TAP1, TAP2, PSMB9, PSMB8 |
| CD68, CD163, ITGAM, ITGAX, or CD14; |
| CTLA4, BTLA, LAG3, HAVCR2, PDCD1, or TIGIT; and |
| CD40, CD80, CD86, CD70, GITRL |
| CD68, CD163, ITGAM, ITGAX, or CD14; |
| CTLA4, BTLA, LAG3, HAVCR2, PDCD1, or TIGIT; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| CTLA4, BTLA, LAG3, HAVCR2, PDCD1, or TIGIT; and |
| GNLY, KLRK1, KLRB1, GZMH, GZMA, KLRD1, NKG7 |
| CD68, CD163, ITGAM, ITGAX, or CD14; |
| CTLA4, BTLA, LAG3, HAVCR2, PDCD1, or TIGIT; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| CD274, PDL2, IDO1, or PVR; and |
| CD4, IL2RA, CD69 |
| CD68, CD163, ITGAM, ITGAX, or CD14; |
| CD274, PDL2, IDO1, or PVR; and |
| TAPBP, TAP1, TAP2, PSMB9, PSMB8 |
| CD68, CD163, ITGAM, ITGAX, or CD14; |
| CD274, PDL2, IDO1, or PVR; and |
| CD40, CD80, CD86, CD70, GITRL |
| CD68, CD163, ITGAM, ITGAX, or CD14; |
| CD274, PDL2, IDO1, or PVR; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| CD274, PDL2, IDO1, or PVR; and |
| GNLY, KLRK1, KLRB1, GZMH, GZMA, KLRD1, NKG7 |
| CD68, CD163, ITGAM, ITGAX, or CD14; |
| CD274, PDL2, IDO1, or PVR; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| CD4, IL2RA, or CD69; and |
| TAPBP, TAP1, TAP2, PSMB9, PSMB8 |
| CD68, CD163, ITGAM, ITGAX, or CD14; |
| CD4, IL2RA, or CD69; and |
| CD40, CD80, CD86, CD70, GITRL |
| CD68, CD163, ITGAM, ITGAX, or CD14; |
| CD4, IL2RA, or CD69; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| CD4, IL2RA, or CD69; and |
| GNLY, KLRK1, KLRB1, GZMH, GZMA, KLRD1, NKG7 |
| CD68, CD163, ITGAM, ITGAX, or CD14; |
| CD4, IL2RA, or CD69; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| TAPBP, TAP1, TAP2, PSMB9, or PSMB8; and |
| CD40, CD80, CD86, CD70, GITRL |
| CD68, CD163, ITGAM, ITGAX, or CD14; |
| TAPBP, TAP1, TAP2, PSMB9, or PSMB8; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| TAPBP, TAP1, TAP2, PSMB9, or PSMB8; and |
| GNLY, KLRK1, KLRB1, GZMH, GZMA, KLRD1, NKG7 |
| CD68, CD163, ITGAM, ITGAX, or CD14; |
| TAPBP, TAP1, TAP2, PSMB9, or PSMB8; and |
| FAP, FN1, MMP2, BGN, LOXL2, PDPN, PDGFRB, COL4A1, COL4A2, COL5A1, COL8A1 |
| CD68, CD163, ITGAM, ITGAX, or CD14; |
| CD40, CD80, CD86, CD70, or GITRL; and |
| CD27, CD28, ICOS, TNFRSF4, TNFRSF14, TNFRSF18, TNFRSF14, TNFSF14, CD226 |
| CD68, CD163, ITGAM, ITGAX, or CD14; |
| CD40, CD80, CD86, CD70, or GITRL; and |
| GNLY, KLRK1, KLRB1, GZMH, GZMA, KLRD1, NKG7 |
| CD68, CD163, ITGAM, ITGAX, or CD14; |
| CD40, CD80, CD86, CD70, or GITRL; and |

TABLE 3-continued

Combinations of three gene signature sets

FAP, FN1, MMP2, BGN, LOXL2, PDPN, PDGFRB,
COL4A1, COL4A2, COL5A1, COL8A1
CD68, CD163, ITGAM, ITGAX, or CD14;
CD27, CD28, ICOS, TNFRSF4, TNFRSF14, TNFRSF18,
TNFRSF14, TNFSF14, or CD226; and
GNLY, KLRK1, KLRB1, GZMH, GZMA, KLRD1, NKG7
CD68, CD163, ITGAM, ITGAX, or CD14;
CD27, CD28, ICOS, TNFRSF4, TNFRSF14, TNFRSF18,
TNFRSF14, TNFSF14, or CD226; and
FAP, FN1, MMP2, BGN, LOXL2, PDPN, PDGFRB,
COL4A1, COL4A2, COL5A1, COL8A1
CD68, CD163, ITGAM, ITGAX, or CD14;
GNLY, KLRK1, KLRB1, GZMH, GZMA, KLRD1, or NKG7; and
FAP, FN1, MMP2, BGN, LOXL2, PDPN, PDGFRB,
COL4A1, COL4A2, COL5A1, COL8A1
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
CTLA4, BTLA, LAG3, HAVCR2, PDCD1, TIGIT
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
CD274, PDL2, IDO1, PVR
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
CD4, IL2RA, CD69
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
TAPBP, TAP1, TAP2, PSMB9, PSMB8
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
CD40, CD80, CD86, CD70, GITRL
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
CD27, CD28, ICOS, TNFRSF4, TNFRSF14, TNFRSF18,
TNFRSF14, TNFSF14, CD226
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
GNLY, KLRK1, KLRB1, GZMH, GZMA, KLRD1, NKG7
LAPTM5, LAIR1, CD4, CSF1R, CD163, ADAP2, CD68, MRC1,
CD45RO, SLA, MSR1, FPR3, FCGR2A, or FCGR3A;
CD3D, CD3E, CD2, CD3G, CD6, TRAT1, CD28, or LCK; and
FAP, FN1, MMP2, BGN, LOXL2, PDPN, PDGFRB,
COL4A1, COL4A2, COL5A1, COL8A1
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
CD274, PDL2, IDO1, PVR
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
CD4, IL2RA, CD69
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
TAPBP, TAP1, TAP2, PSMB9, PSMB8
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
CD40, CD80, CD86, CD70, GITRL
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
CD27, CD28, ICOS, TNFRSF4, TNFRSF14, TNFRSF18,
TNFRSF14, TNFSF14, CD226
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
GNLY, KLRK1, KLRB1, GZMH, GZMA, KLRD1, NKG7
LAPTM5, LAIR1, CD4, CSF1R, CD163, ADAP2, CD68, MRC1,
CD45RO, SLA, MSR1, FPR3, FCGR2A, or FCGR3A;
CTLA4, BTLA, LAG3, HAVCR2, PDCD1, or TIGIT; and
FAP, FN1, MMP2, BGN, LOXL2, PDPN, PDGFRB,
COL4A1, COL4A2, COL5A1, COL8A1
LAPTM5, LAIR1, CD4, CSF1R, CD163, ADAP2, CD68, MRC1,
CD45RO, SLA, MSR1, FPR3, FCGR2A, or FCGR3A;
CD274, PDL2, IDO1, or PVR; and
CD4, IL2RA, CD69
LAPTM5, LAIR1, CD4, CSF1R, CD163, ADAP2, CD68, MRC1,
CD45RO, SLA, MSR1, FPR3, FCGR2A, or FCGR3A;
CD274, PDL2, IDO1, or PVR; and
TAPBP, TAP1, TAP2, PSMB9, PSMB8
LAPTM5, LAIR1, CD4, CSF1R, CD163, ADAP2, CD68, MRC1,
CD45RO, SLA, MSR1, FPR3, FCGR2A, or FCGR3A;
CD274, PDL2, IDO1, or PVR; and
CD40, CD80, CD86, CD70, GITRL
LAPTM5, LAIR1, CD4, CSF1R, CD163, ADAP2, CD68, MRC1,
CD45RO, SLA, MSR1, FPR3, FCGR2A, or FCGR3A;
CD274, PDL2, IDO1, or PVR; and
CD27, CD28, ICOS, TNFRSF4, TNFRSF14, TNFRSF18,
TNFRSF14, TNFSF14, CD226
LAPTM5, LAIR1, CD4, CSF1R, CD163, ADAP2, CD68, MRC1,
CD45RO, SLA, MSR1, FPR3, FCGR2A, or FCGR3A;
CD274, PDL2, IDO1, or PVR; and
GNLY, KLRK1, KLRB1, GZMH, GZMA, KLRD1, NKG7
LAPTM5, LAIR1, CD4, CSF1R, CD163, ADAP2, CD68, MRC1,
CD45RO, SLA, MSR1, FPR3, FCGR2A, or FCGR3A;
CD274, PDL2, IDO1, or PVR; and
FAP, FN1, MMP2, BGN, LOXL2, PDPN, PDGFRB,
COL4A1, COL4A2, COL5A1, COL8A1
LAPTM5, LAIR1, CD4, CSF1R, CD163, ADAP2, CD68, MRC1,
CD45RO, SLA, MSR1, FPR3, FCGR2A, or FCGR3A;
CD4, IL2RA, or CD69; and
TAPBP, TAP1, TAP2, PSMB9, PSMB8
LAPTM5, LAIR1, CD4, CSF1R, CD163, ADAP2, CD68, MRC1,
CD45RO, SLA, MSR1, FPR3, FCGR2A, or FCGR3A;
CD4, IL2RA, or CD69; and
CD40, CD80, CD86, CD70, GITRL
LAPTM5, LAIR1, CD4, CSF1R, CD163, ADAP2, CD68, MRC1,
CD45RO, SLA, MSR1, FPR3, FCGR2A, or FCGR3A;
CD4, IL2RA, or CD69; and
CD27, CD28, ICOS, TNFRSF4, TNFRSF14, TNFRSF18,
TNFRSF14, TNFSF14, CD226
LAPTM5, LAIR1, CD4, CSF1R, CD163, ADAP2, CD68, MRC1,
CD45RO, SLA, MSR1, FPR3, FCGR2A, or FCGR3A;
CD4, IL2RA, or CD69; and
GNLY, KLRK1, KLRB1, GZMH, GZMA, KLRD1, NKG7
LAPTM5, LAIR1, CD4, CSF1R, CD163, ADAP2, CD68, MRC1,
CD45RO, SLA, MSR1, FPR3, FCGR2A, or FCGR3A;
CD4, IL2RA, or CD69; and
FAP, FN1, MMP2, BGN, LOXL2, PDPN, PDGFRB,
COL4A1, COL4A2, COL5A1, COL8A1
LAPTM5, LAIR1, CD4, CSF1R, CD163, ADAP2, CD68, MRC1,
CD45RO, SLA, MSR1, FPR3, FCGR2A, or FCGR3A;
TAPBP, TAP1, TAP2, PSMB9, or PSMB8; and
CD40, CD80, CD86, CD70, GITRL
LAPTM5, LAIR1, CD4, CSF1R, CD163, ADAP2, CD68, MRC1,
CD45RO, SLA, MSR1, FPR3, FCGR2A, or FCGR3A;
TAPBP, TAP1, TAP2, PSMB9, or PSMB8; and
CD27, CD28, ICOS, TNFRSF4, TNFRSF14, TNFRSF18,
TNFRSF14, TNFSF14, CD226
LAPTM5, LAIR1, CD4, CSF1R, CD163, ADAP2, CD68, MRC1,
CD45RO, SLA, MSR1, FPR3, FCGR2A, or FCGR3A;
TAPBP, TAP1, TAP2, PSMB9, or PSMB8; and
GNLY, KLRK1, KLRB1, GZMH, GZMA, KLRD1, NKG7
LAPTM5, LAIR1, CD4, CSF1R, CD163, ADAP2, CD68, MRC1,
CD45RO, SLA, MSR1, FPR3, FCGR2A, or FCGR3A;
TAPBP, TAP1, TAP2, PSMB9, or PSMB8; and
FAP, FN1, MMP2, BGN, LOXL2, PDPN, PDGFRB,
COL4A1, COL4A2, COL5A1, COL8A1
LAPTM5, LAIR1, CD4, CSF1R, CD163, ADAP2, CD68, MRC1,
CD45RO, SLA, MSR1, FPR3, FCGR2A, or FCGR3A;
CD40, CD80, CD86, CD70, or GITRL; and
CD27, CD28, ICOS, TNFRSF4, TNFRSF14, TNFRSF18,
TNFRSF14, TNFSF14, CD226
LAPTM5, LAIR1, CD4, CSF1R, CD163, ADAP2, CD68, MRC1,
CD45RO, SLA, MSR1, FPR3, FCGR2A, or FCGR3A;
CD40, CD80, CD86, CD70, or GITRL; and
GNLY, KLRK1, KLRB1, GZMH, GZMA, KLRD1, NKG7
LAPTM5, LAIR1, CD4, CSF1R, CD163, ADAP2, CD68, MRC1,
CD45RO, SLA, MSR1, FPR3, FCGR2A, or FCGR3A;

TABLE 3-continued

Combinations of three gene signature sets

CD40, CD80, CD86, CD70, or GITRL; and
FAP, FN1, MMP2, BGN, LOXL2, PDPN, PDGFRB, COL4A1, COL4A2, COL5A1, COL8A1
LAPTM5, LAIR1, CD4, CSF1R, CD163, ADAP2, CD68, MRC1, CD45RO, SLA, MSR1, FPR3, FCGR2A, or FCGR3A;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
LAPTM5, LAIR1, CD4, CSF1R, CD163, ADAP2, CD68, MRC1, CD45RO, SLA, MSR1, FPR3, FCGR2A, or FCGR3A;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
LAPTM5, LAIR1, CD4, CSF1R, CD163, ADAP2, CD68, MRC1, CD45RO, SLA, MSR1, FPR3, FCGR2A, or FCGR3A;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
CTLA4, BTLA, LAG3, HAVCR2, PDCD1, or TIGIT; and
CD274, PDL2, IDO1, PVR
CD3D, CD3E, CD2, CD3G, CD6, TRAT1, CD28, or LCK;
CTLA4, BTLA, LAG3, HAVCR2, PDCD1, or TIGIT; and
CD4, IL2RA, CD69
CD3D, CD3E, CD2, CD3G, CD6, TRAT1, CD28, or LCK;
CTLA4, BTLA, LAG3, HAVCR2, PDCD1, or TIGIT; and
TAPBP, TAP1, TAP2, PSMB9, PSMB8
CD3D, CD3E, CD2, CD3G, CD6, TRAT1, CD28, or LCK;
CTLA4, BTLA, LAG3, HAVCR2, PDCD1, or TIGIT; and
CD40, CD80, CD86, CD70, GITRL
CD3D, CD3E, CD2, CD3G, CD6, TRAT1, CD28, or LCK;
CTLA4, BTLA, LAG3, HAVCR2, PDCD1, or TIGIT; and
CD27, CD28, ICOS, TNFRSF4, TNFRSF14, TNFRSF18, TNFRSF14, TNFSF14, CD226
CD3D, CD3E, CD2, CD3G, CD6, TRAT1, CD28, or LCK;
CTLA4, BTLA, LAG3, HAVCR2, PDCD1, or TIGIT; and
GNLY, KLRK1, KLRB1, GZMH, GZMA, KLRD1, NKG7
CD3D, CD3E, CD2, CD3G, CD6, TRAT1, CD28, or LCK;
CTLA4, BTLA, LAG3, HAVCR2, PDCD1, or TIGIT; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
CD274, PDL2, IDO1, or PVR; and
CD4, IL2RA, CD69
CD3D, CD3E, CD2, CD3G, CD6, TRAT1, CD28, or LCK;
CD274, PDL2, IDO1, or PVR; and
TAPBP, TAP1, TAP2, PSMB9, PSMB8
CD3D, CD3E, CD2, CD3G, CD6, TRAT1, CD28, or LCK;
CD274, PDL2, IDO1, or PVR; and
CD40, CD80, CD86, CD70, GITRL
CD3D, CD3E, CD2, CD3G, CD6, TRAT1, CD28, or LCK;
CD274, PDL2, IDO1, or PVR; and
CD27, CD28, ICOS, TNFRSF4, TNFRSF14, TNFRSF18, TNFRSF14, TNFSF14, CD226
CD3D, CD3E, CD2, CD3G, CD6, TRAT1, CD28, or LCK;
CD274, PDL2, IDO1, or PVR; and
GNLY, KLRK1, KLRB1, GZMH, GZMA, KLRD1, NKG7
CD3D, CD3E, CD2, CD3G, CD6, TRAT1, CD28, or LCK;
CD274, PDL2, IDO1, or PVR; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
CD4, IL2RA, or CD69; and
TAPBP, TAP1, TAP2, PSMB9, PSMB8
CD3D, CD3E, CD2, CD3G, CD6, TRAT1, CD28, or LCK;
CD4, IL2RA, or CD69; and
CD40, CD80, CD86, CD70, GITRL
CD3D, CD3E, CD2, CD3G, CD6, TRAT1, CD28, or LCK;
CD4, IL2RA, or CD69; and
CD27, CD28, ICOS, TNFRSF4, TNFRSF14, TNFRSF18, TNFRSF14, TNFSF14, CD226
CD3D, CD3E, CD2, CD3G, CD6, TRAT1, CD28, or LCK;
CD4, IL2RA, or CD69; and
GNLY, KLRK1, KLRB1, GZMH, GZMA, KLRD1, NKG7
CD3D, CD3E, CD2, CD3G, CD6, TRAT1, CD28, or LCK;
CD4, IL2RA, or CD69; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
TAPBP, TAP1, TAP2, PSMB9, or PSMB8; and
CD40, CD80, CD86, CD70, GITRL
CD3D, CD3E, CD2, CD3G, CD6, TRAT1, CD28, or LCK;
TAPBP, TAP1, TAP2, PSMB9, or PSMB8; and
CD27, CD28, ICOS, TNFRSF4, TNFRSF14, TNFRSF18, TNFRSF14, TNFSF14, CD226
CD3D, CD3E, CD2, CD3G, CD6, TRAT1, CD28, or LCK;
TAPBP, TAP1, TAP2, PSMB9, or PSMB8; and
GNLY, KLRK1, KLRB1, GZMH, GZMA, KLRD1, NKG7
CD3D, CD3E, CD2, CD3G, CD6, TRAT1, CD28, or LCK;
TAPBP, TAP1, TAP2, PSMB9, or PSMB8; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
CD40, CD80, CD86, CD70, or GITRL; and
CD27, CD28, ICOS, TNFRSF4, TNFRSF14, TNFRSF18, TNFRSF14, TNFSF14, CD226
CD3D, CD3E, CD2, CD3G, CD6, TRAT1, CD28, or LCK;
CD40, CD80, CD86, CD70, or GITRL; and
GNLY, KLRK1, KLRB1, GZMH, GZMA, KLRD1, NKG7
CD3D, CD3E, CD2, CD3G, CD6, TRAT1, CD28, or LCK;
CD40, CD80, CD86, CD70, or GITRL; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
CD3D, CD3E, CD2, CD3G, CD6, TRAT1, CD28, or LCK;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
CD3D, CD3E, CD2, CD3G, CD6, TRAT1, CD28, or LCK;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT;
CD274, PDL2, IDO1, or PVR; and
CD4, IL2RA, CD69
CTLA4, BTLA, LAG3, HAVCR2, PDCD1, or TIGIT;
CD274, PDL2, IDO1, or PVR; and
TAPBP, TAP1, TAP2, PSMB9, PSMB8
CTLA4, BTLA, LAG3, HAVCR2, PDCD1, or TIGIT;
CD274, PDL2, IDO1, or PVR; and
CD40, CD80, CD86, CD70, GITRL
CTLA4, BTLA, LAG3, HAVCR2, PDCD1, or TIGIT;
CD274, PDL2, IDO1, or PVR; and
CD27, CD28, ICOS, TNFRSF4, TNFRSF14, TNFRSF18, TNFRSF14, TNFSF14, CD226
CTLA4, BTLA, LAG3, HAVCR2, PDCD1, or TIGIT;
CD274, PDL2, IDO1, or PVR; and
GNLY, KLRK1, KLRB1, GZMH, GZMA, KLRD1, NKG7
CTLA4, BTLA, LAG3, HAVCR2, PDCD1, or TIGIT;
CD274, PDL2, IDO1, or PVR; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT;
CD4, IL2RA, or CD69; and
TAPBP, TAP1, TAP2, PSMB9, PSMB8
CTLA4, BTLA, LAG3, HAVCR2, PDCD1, or TIGIT;
CD4, IL2RA, or CD69; and
CD40, CD80, CD86, CD70, GITRL
CTLA4, BTLA, LAG3, HAVCR2, PDCD1, or TIGIT;
CD4, IL2RA, or CD69; and
CD27, CD28, ICOS, TNFRSF4, TNFRSF14, TNFRSF18, TNFRSF14, TNFSF14, CD226
CTLA4, BTLA, LAG3, HAVCR2, PDCD1, or TIGIT;
CD4, IL2RA, or CD69; and
GNLY, KLRK1, KLRB1, GZMH, GZMA, KLRD1, NKG7
CTLA4, BTLA, LAG3, HAVCR2, PDCD1, or TIGIT;
CD4, IL2RA, or CD69; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT;
TAPBP, TAP1, TAP2, PSMB9, or PSMB8; and

TABLE 3-continued

Combinations of three gene signature sets

CD40, CD80, CD86, CD70, GITRL
CTLA4, BTLA, LAG3, HAVCR2, PDCD1, or TIGIT;
TAPBP, TAP1, TAP2, PSMB9, or PSMB8; and
CD27, CD28, ICOS, TNFRSF4, TNFRSF14, TNFRSF18, TNFRSF14, TNFSF14, CD226
CTLA4, BTLA, LAG3, HAVCR2, PDCD1, or TIGIT;
TAPBP, TAP1, TAP2, PSMB9, or PSMB8; and
GNLY, KLRK1, KLRB1, GZMH, GZMA, KLRD1, NKG7
CTLA4, BTLA, LAG3, HAVCR2, PDCD1, or TIGIT;
TAPBP, TAP1, TAP2, PSMB9, or PSMB8; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT;
CD40, CD80, CD86, CD70, or GITRL; and
CD27, CD28, ICOS, TNFRSF4, TNFRSF14, TNFRSF18, TNFRSF14, TNFSF14, CD226
CTLA4, BTLA, LAG3, HAVCR2, PDCD1, or TIGIT;
CD40, CD80, CD86, CD70, or GITRL; and
GNLY, KLRK1, KLRB1, GZMH, GZMA, KLRD1, NKG7
CTLA4, BTLA, LAG3, HAVCR2, PDCD1, or TIGIT;
CD40, CD80, CD86, CD70, or GITRL; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
CTLA4, BTLA, LAG3, HAVCR2, PDCD1, or TIGIT;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
CTLA4, BTLA, LAG3, HAVCR2, PDCD1, or TIGIT;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
CD274, PDL2, IDO1, or PVR;
CD4, IL2RA, or CD69; and
TAPBP, TAP1, TAP2, PSMB9, PSMB8
CD274, PDL2, IDO1, or PVR;
CD4, IL2RA, or CD69; and
CD40, CD80, CD86, CD70, GITRL
CD274, PDL2, IDO1, or PVR;
CD4, IL2RA, or CD69; and
CD27, CD28, ICOS, TNFRSF4, TNFRSF14, TNFRSF18, TNFRSF14, TNFSF14, CD226
CD274, PDL2, IDO1, or PVR;
CD4, IL2RA, or CD69; and
GNLY, KLRK1, KLRB1, GZMH, GZMA, KLRD1, NKG7
CD274, PDL2, IDO1, or PVR;
CD4, IL2RA, or CD69; and
FAP, FN1, MMP2, BGN, LOXL2, PDPN, PDGFRB, COL4A1, COL4A2, COL5A1, COL8A1
CD274, PDL2, IDO1, or PVR;
TAPBP, TAP1, TAP2, PSMB9, or PSMB8; and
CD40, CD80, CD86, CD70, GITRL
CD274, PDL2, IDO1, or PVR;
TAPBP, TAP1, TAP2, PSMB9, or PSMB8; and
CD27, CD28, ICOS, TNFRSF4, TNFRSF14, TNFRSF18, TNFRSF14, TNFSF14, CD226
CD274, PDL2, IDO1, or PVR;
TAPBP, TAP1, TAP2, PSMB9, or PSMB8; and
GNLY, KLRK1, KLRB1, GZMH, GZMA, KLRD1, NKG7
CD274, PDL2, IDO1, or PVR;
TAPBP, TAP1, TAP2, PSMB9, or PSMB8; and
FAP, FN1, MMP2, BGN, LOXL2, PDPN, PDGFRB, COL4A1, COL4A2, COL5A1, COL8A1
CD274, PDL2, IDO1, or PVR;
CD40, CD80, CD86, CD70, or GITRL; and
CD27, CD28, ICOS, TNFRSF4, TNFRSF14, TNFRSF18, TNFRSF14, TNFSF14, CD226
CD274, PDL2, IDO1, or PVR;
CD40, CD80, CD86, CD70, or GITRL; and
GNLY, KLRK1, KLRB1, GZMH, GZMA, KLRD1, NKG7
CD274, PDL2, IDO1, or PVR;
CD40, CD80, CD86, CD70, or GITRL; and
FAP, FN1, MMP2, BGN, LOXL2, PDPN, PDGFRB, COL4A1, COL4A2, COL5A1, COL8A1

TABLE 3-continued

Combinations of three gene signature sets

CD274, PDL2, IDO1, or PVR;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
CD274, PDL2, IDO1, or PVR;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
CD274, PDL2, IDO1, or PVR;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
CD4, IL2RA, or CD69;
TAPBP, TAP1, TAP2, PSMB9, or PSMB8; and
CD40, CD80, CD86, CD70, GITRL
CD4, IL2RA, or CD69;
TAPBP, TAP1, TAP2, PSMB9, or PSMB8; and
CD27, CD28, ICOS, TNFRSF4, TNFRSF14, TNFRSF18, TNFRSF14, TNFSF14, CD226
CD4, IL2RA, or CD69;
TAPBP, TAP1, TAP2, PSMB9, or PSMB8; and
GNLY, KLRK1, KLRB1, GZMH, GZMA, KLRD1, NKG7
CD4, IL2RA, or CD69;
TAPBP, TAP1, TAP2, PSMB9, or PSMB8; and
FAP, FN1, MMP2, BGN, LOXL2, PDPN, PDGFRB, COL4A1, COL4A2, COL5A1, COL8A1
CD4, IL2RA, or CD69;
CD40, CD80, CD86, CD70, or GITRL; and
CD27, CD28, ICOS, TNFRSF4, TNFRSF14, TNFRSF18, TNFRSF14, TNFSF14, CD226
CD4, IL2RA, or CD69;
CD40, CD80, CD86, CD70, or GITRL; and
GNLY, KLRK1, KLRB1, GZMH, GZMA, KLRD1, NKG7
CD4, IL2RA, or CD69;
CD40, CD80, CD86, CD70, or GITRL; and
FAP, FN1, MMP2, BGN, LOXL2, PDPN, PDGFRB, COL4A1, COL4A2, COL5A1, COL8A1
CD4, IL2RA, or CD69;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
CD4, IL2RA, or CD69;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
CD4, IL2RA, or CD69;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
TAPBP, TAP1, TAP2, PSMB9, or PSMB8;
CD40, CD80, CD86, CD70, or GITRL; and
CD27, CD28, ICOS, TNFRSF4, TNFRSF14, TNFRSF18, TNFRSF14, TNFSF14, CD226
TAPBP, TAP1, TAP2, PSMB9, or PSMB8;
CD40, CD80, CD86, CD70, or GITRL; and
GNLY, KLRK1, KLRB1, GZMH, GZMA, KLRD1, NKG7
TAPBP, TAP1, TAP2, PSMB9, or PSMB8;
CD40, CD80, CD86, CD70, or GITRL; and
FAP, FN1, MMP2, BGN, LOXL2, PDPN, PDGFRB, COL4A1, COL4A2, COL5A1, COL8A1
TAPBP, TAP1, TAP2, PSMB9, or PSMB8;
CD27, CD28, ICOS, TNFRSF4, TNFRSF14, TNFRSF18, TNFRSF14, TNFSF14, or CD226; and
GNLY, KLRK1, KLRB1, GZMH, GZMA, KLRD1, NKG7
TAPBP, TAP1, TAP2, PSMB9, or PSMB8;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
TAPBP, TAP1, TAP2, PSMB9, or PSMB8;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
CD40, CD80, CD86, CD70, or GITRL;
CD27, CD28, ICOS, TNFRSF4, TNFRSF14, TNFRSF18, TNFRSF14, TNFSF14, or CD226; and

TABLE 3-continued

Combinations of three gene signature sets

GNLY, KLRK1, KLRB1, GZMH, GZMA, KLRD1, NKG7
CD40, CD80, CD86, CD70, or GITRL;
CD27, CD28, ICOS, TNFRSF4, TNFRSF14, TNFRSF18, TNFRSF14, TNFSF14, or CD226; and
FAP, FN1, MMP2, BGN, LOXL2, PDPN, PDGFRB, COL4A1, COL4A2, COL5A1, COL8A1
CD40, CD80, CD86, CD70, or GITRL;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1
CD27, CD28, ICOS, TNFRSF4, TNFRSF14, TNFRSF18, TNFRSF14, TNFSF14, or CD226;
GNLY, KLRK1, KLRB1, GZMH, GZMA, KLRD1, or NKG7; and
FAP, FN1, MMP2, BGN, LOXL2, PDPN, PDGFRB, COL4A1, COL4A2, COL5A1, COL8A1

In another embodiment, the expression levels of one or more of the genes in an immune cell gene signature in four particular gene signature sets are determined. For example, combinations of four particular gene signature sets are set forth in Table 4 below.

TABLE 4

Combinations of four gene signature sets

CD8A, GZMA, GZMB, IFNγ, EOMES, or PRF1;
FOXP3;
MS4A1 or CD48; and
NCAM1 or NKP46.
CD8A, GZMA, GZMB, IFNγ, EOMES, or PRF1;
FOXP3;
MS4A1 or CD48; and
ITGAM, ITGAX, CD1C, or CLEC4C.
CD8A, GZMA, GZMB, IFNγ, EOMES, or PRF1;
FOXP3;
MS4A1 or CD48; and
IL17A or IL17F.
CD8A, GZMA, GZMB, IFNγ, EOMES, or PRF1;
FOXP3;
MS4A1 or CD48; and
CCL2, IL1B, IL8, IL6, or PTGS2.
CD8A, GZMA, GZMB, IFNγ, EOMES, or PRF1;
FOXP3;
MS4A1 or CD48; and
CTLA4, BTLA, LAG3, HAVCR2, or PDCD1.
CD8A, GZMA, GZMB, IFNγ, EOMES, or PRF1;
FOXP3;
MS4A1 or CD48; and
CD276, PDL1, PDL2, or IDO1.
CD8A, GZMA, GZMB, IFNγ, EOMES, or PRF1;
FOXP3;
NCAM1 or NKP46; and
ITGAM, ITGAX, CD1C, or CLEC4C.
CD8A, GZMA, GZMB, IFNγ, EOMES, or PRF1;
FOXP3;
NCAM1 or NKP46; and
IL17A or IL17F.
CD8A, GZMA, GZMB, IFNγ, EOMES, or PRF1;
FOXP3;
NCAM1 or NKP46; and
CCL2, IL1B, IL8, IL6, or PTGS2.
CD8A, GZMA, GZMB, IFNγ, EOMES, or PRF1;
FOXP3;
NCAM1 or NKP46; and
CTLA4, BTLA, LAG3, HAVCR2, or PDCD1.
CD8A, GZMA, GZMB, IFNγ, EOMES, or PRF1;
FOXP3;
NCAM1 or NKP46; and
CD276, PDL1, PDL2, or IDO1.
CD8A, GZMA, GZMB, IFNγ, EOMES, or PRF1;
FOXP3;
ITGAM, ITGAX, CD1C, CLEC4C, and
IL17A or IL17F.
CD8A, GZMA, GZMB, IFNγ, EOMES, or PRF1;

TABLE 4-continued

Combinations of four gene signature sets

FOXP3;
ITGAM, ITGAX, CD1C, CLEC4C, and
CCL2, IL1B, IL8, IL6, or PTGS2.
CD8A, GZMA, GZMB, IFNγ, EOMES, or PRF1;
FOXP3;
ITGAM, ITGAX, CD1C, CLEC4C, and
CTLA4, BTLA, LAG3, HAVCR2, or PDCD1.
CD8A, GZMA, GZMB, IFNγ, EOMES, or PRF1;
FOXP3;
ITGAM, ITGAX, CD1C, CLEC4C, and
CD276, PDL1, PDL2, or IDO1.
CD8A, GZMA, GZMB, IFNγ, EOMES, or PRF1;
FOXP3;
IL17A or IL17F; and
CCL2, IL1B, IL8, IL6, or PTGS2.
CD8A, GZMA, GZMB, IFNγ, EOMES, or PRF1;
FOXP3;
IL17A or IL17F; and
CTLA4, BTLA, LAG3, HAVCR2, or PDCD1.
CD8A, GZMA, GZMB, IFNγ, EOMES, or PRF1;
FOXP3;
IL17A or IL17F; and
CD276, PDL1, PDL2, or IDO1.
CD8A, GZMA, GZMB, IFNγ, EOMES, or PRF1;
FOXP3;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46; and
ITGAM, ITGAX, CD1C, or CLEC4C.
CD8A, GZMA, GZMB, IFNγ, EOMES, or PRF1;
MS4A1 or CD48;
NCAM1 or NKP46; and
IL17A or IL17F.
CD8A, GZMA, GZMB, IFNγ, EOMES, or PRF1;
MS4A1 or CD48;
NCAM1 or NKP46; and
CCL2, IL1B, IL8, IL6, or PTGS2.
CD8A, GZMA, GZMB, IFNγ, EOMES, or PRF1;
MS4A1 or CD48;
NCAM1 or NKP46; and
CTLA4, BTLA, LAG3, HAVCR2, or PDCD1.
CD8A, GZMA, GZMB, IFNγ, EOMES, or PRF1;
MS4A1 or CD48;
NCAM1 or NKP46; and
CD276, PDL1, PDL2, or IDO1.
CD8A, GZMA, GZMB, IFNγ, EOMES, or PRF1;
MS4A1 or CD48;
ITGAM, ITGAX, CD1C, CLEC4C, and
IL17A or IL17F.
CD8A, GZMA, GZMB, IFNγ, EOMES, or PRF1;
MS4A1 or CD48;
ITGAM, ITGAX, CD1C, CLEC4C, and
CCL2, IL1B, IL8, IL6, or PTGS2.
CD8A, GZMA, GZMB, IFNγ, EOMES, or PRF1;
MS4A1 or CD48;
ITGAM, ITGAX, CD1C, CLEC4C, and
CTLA4, BTLA, LAG3, HAVCR2, or PDCD1.
CD8A, GZMA, GZMB, IFNγ, EOMES, or PRF1;
MS4A1 or CD48;
ITGAM, ITGAX, CD1C, CLEC4C, and
CD276, PDL1, PDL2, or IDO1.
CD8A, GZMA, GZMB, IFNγ, EOMES, or PRF1;
MS4A1 or CD48;
IL17A or IL17F; and
CCL2, IL1B, IL8, IL6, or PTGS2.
CD8A, GZMA, GZMB, IFNγ, EOMES, or PRF1;
MS4A1 or CD48;
IL17A or IL17F; and

TABLE 4-continued

Combinations of four gene signature sets

CTLA4, BTLA, LAG3, HAVCR2, or PDCD1.
CD8A, GZMA, GZMB, IFNγ, EOMES, or PRF1;
MS4A1 or CD48;
IL17A or IL17F; and
CD276, PDL1, PDL2, or IDO1.
CD8A, GZMA, GZMB, IFNγ, EOMES, or PRF1;
MS4A1 or CD48;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
ITGAM, ITGAX, CD1C, CLEC4C, and
IL17A or IL17F.
CD8A, GZMA, GZMB, IFNγ, EOMES, or PRF1;
NCAM1 or NKP46;
ITGAM, ITGAX, CD1C, CLEC4C, and
CCL2, IL1B, IL8, IL6, or PTGS2.
CD8A, GZMA, GZMB, IFNγ, EOMES, or PRF1;
NCAM1 or NKP46;
ITGAM, ITGAX, CD1C, CLEC4C, and
CTLA4, BTLA, LAG3, HAVCR2, or PDCD1.
CD8A, GZMA, GZMB, IFNγ, EOMES, or PRF1;
NCAM1 or NKP46;
ITGAM, ITGAX, CD1C, CLEC4C, and
CD276, PDL1, PDL2, or IDO1.
CD8A, GZMA, GZMB, IFNγ, EOMES, or PRF1;
NCAM1 or NKP46;
IL17A or IL17F; and
CCL2, IL1B, IL8, IL6, or PTGS2.
CD8A, GZMA, GZMB, IFNγ, EOMES, or PRF1;
NCAM1 or NKP46;
IL17A or IL17F; and
CTLA4, BTLA, LAG3, HAVCR2, or PDCD1.
CD8A, GZMA, GZMB, IFNγ, EOMES, or PRF1;
NCAM1 or NKP46;
IL17A or IL17F; and
CD276, PDL1, PDL2, or IDO1.
CD8A, GZMA, GZMB, IFNγ, EOMES, or PRF1;
NCAM1 or NKP46;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
NCAM1 or NKP46;
CCL2, IL1B, IL8, IL6, or PTGS2; and
CD276, PDL1, PDL2, or IDO1.
CD8A, GZMA, GZMB, IFNγ, EOMES, or PRF1;
NCAM1 or NKP46;
CTLA4, BTLA, LAG3, HAVCR2, or PDCD1; and
CD276, PDL1, PDL2, or IDO1.
CD8A, GZMA, GZMB, IFNγ, EOMES, or PRF1;
ITGAM, ITGAX, CD1C, CLEC4C,
IL17A or IL17F; and
CCL2, IL1B, IL8, IL6, or PTGS2.
CD8A, GZMA, GZMB, IFNγ, EOMES, or PRF1;
ITGAM, ITGAX, CD1C, CLEC4C,
IL17A or IL17F; and
CTLA4, BTLA, LAG3, HAVCR2, or PDCD1.
CD8A, GZMA, GZMB, IFNγ, EOMES, or PRF1;
ITGAM, ITGAX, CD1C, CLEC4C,
IL17A or IL17F; and
CD276, PDL1, PDL2, or IDO1.
CD8A, GZMA, GZMB, IFNγ, EOMES, or PRF1;
ITGAM, ITGAX, CD1C, CLEC4C,
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
ITGAM, ITGAX, CD1C, CLEC4C,
CCL2, IL1B, IL8, IL6, or PTGS2; and
CD276, PDL1, PDL2, or IDO1.
CD8A, GZMA, GZMB, IFNγ, EOMES, or PRF1;
ITGAM, ITGAX, CD1C, CLEC4C,
CTLA4, BTLA, LAG3, HAVCR2, or PDCD1; and
CD276, PDL1, PDL2, or IDO1.
CD8A, GZMA, GZMB, IFNγ, EOMES, or PRF1;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
NCAM1 or NKP46; and
ITGAM, ITGAX, CD1C, or CLEC4C.
FOXP3;
MS4A1 or CD48;
NCAM1 or NKP46; and
IL17A or IL17F.
FOXP3;
MS4A1 or CD48;
NCAM1 or NKP46; and
CCL2, IL1B, IL8, IL6, or PTGS2.
FOXP3;
MS4A1 or CD48;
NCAM1 or NKP46; and
CTLA4, BTLA, LAG3, HAVCR2, or PDCD1.
FOXP3;
MS4A1 or CD48;
NCAM1 or NKP46; and
CD276, PDL1, PDL2, or IDO1.
FOXP3;
MS4A1 or CD48;
ITGAM, ITGAX, CD1C, CLEC4C, and
IL17A or IL17F.
FOXP3;
MS4A1 or CD48;
ITGAM, ITGAX, CD1C, CLEC4C; and
CCL2, IL1B, IL8, IL6, or PTGS2.
FOXP3;
MS4A1 or CD48;
ITGAM, ITGAX, CD1C, CLEC4C; and
CTLA4, BTLA, LAG3, HAVCR2, or PDCD1.
FOXP3;
MS4A1 or CD48;
ITGAM, ITGAX, CD1C, CLEC4C; and
CD276, PDL1, PDL2, or IDO1.
FOXP3;
MS4A1 or CD48;
IL17A or IL17F; and
CCL2, IL1B, IL8, IL6, or PTGS2.
FOXP3;
MS4A1 or CD48;
IL17A or IL17F; and
CTLA4, BTLA, LAG3, HAVCR2, or PDCD1.
FOXP3;
MS4A1 or CD48;
IL17A or IL17F; and
CD276, PDL1, PDL2, or IDO1.
FOXP3;
MS4A1 or CD48;
CCL2, IL1B, IL8, IL6, or PTGS2; and
CTLA4, BTLA, LAG3, HAVCR2, or PDCD1.
FOXP3;
MS4A1 or CD48;
CCL2, IL1B, IL8, IL6, or PTGS2; and
CD276, PDL1, PDL2, or IDO1.
FOXP3;
MS4A1 or CD48;
CTLA4, BTLA, LAG3, HAVCR2, or PDCD1; and

TABLE 4-continued

Combinations of four gene signature sets

CD276, PDL1, PDL2, or IDO1.
FOXP3;
NCAM1 or NKP46;
ITGAM, ITGAX, CD1C, CLEC4C; and
IL17A or IL17F.
FOXP3;
NCAM1 or NKP46;
ITGAM, ITGAX, CD1C, CLEC4C; and
CCL2, IL1B, IL8, IL6, or PTGS2.
FOXP3;
NCAM1 or NKP46;
ITGAM, ITGAX, CD1C, CLEC4C; and
CTLA4, BTLA, LAG3, HAVCR2, or PDCD1.
FOXP3;
NCAM1 or NKP46;
ITGAM, ITGAX, CD1C, CLEC4C; and
CD276, PDL1, PDL2, or IDO1.
FOXP3;
NCAM1 or NKP46;
IL17A or IL17F; and
CCL2, IL1B, IL8, IL6, or PTGS2.
FOXP3;
NCAM1 or NKP46;
IL17A or IL17F; and
CTLA4, BTLA, LAG3, HAVCR2, or PDCD1.
FOXP3;
NCAM1 or NKP46;
IL17A or IL17F; and
CD276, PDL1, PDL2, or IDO1.
FOXP3;
NCAM1 or NKP46;
CCL2, IL1B, IL8, IL6, or PTGS2; and
CTLA4, BTLA, LAG3, HAVCR2, or PDCD1.
FOXP3;
NCAM1 or NKP46;
CCL2, IL1B, IL8, IL6, or PTGS2; and
CD276, PDL1, PDL2, or IDO1.
FOXP3;
NCAM1 or NKP46;
CTLA4, BTLA, LAG3, HAVCR2, or PDCD1; and
CD276, PDL1, PDL2, or IDO1.
FOXP3;
ITGAM, ITGAX, CD1C, CLEC4C;
IL17A or IL17F; and
CCL2, IL1B, IL8, IL6, or PTGS2.
FOXP3;
ITGAM, ITGAX, CD1C, CLEC4C;
IL17A or IL17F; and
CTLA4, BTLA, LAG3, HAVCR2, or PDCD1.
FOXP3;
ITGAM, ITGAX, CD1C, CLEC4C;
IL17A or IL17F; and
CD276, PDL1, PDL2, or IDO1.
FOXP3;
ITGAM, ITGAX, CD1C, CLEC4C;
CCL2, IL1B, IL8, IL6, or PTGS2; and
CTLA4, BTLA, LAG3, HAVCR2, or PDCD1.
FOXP3;
ITGAM, ITGAX, CD1C, CLEC4C;
CCL2, IL1B, IL8, IL6, or PTGS2; and
CD276, PDL1, PDL2, or IDO1.
FOXP3;
ITGAM, ITGAX, CD1C, CLEC4C;
CTLA4, BTLA, LAG3, HAVCR2, or PDCD1; and
CD276, PDL1, PDL2, or IDO1.
FOXP3;
IL17A or IL17F;
CCL2, IL1B, IL8, IL6, or PTGS2; and
CTLA4, BTLA, LAG3, HAVCR2, or PDCD1.
FOXP3;
IL17A or IL17F;
ITGAM, ITGAX, CD1C, CLEC4C; and
CD276, PDL1, PDL2, or IDO1.
FOXP3;
IL17A or IL17F;
CTLA4, BTLA, LAG3, HAVCR2, or PDCD1; and
CD276, PDL1, PDL2, or IDO1.
FOXP3;

CCL2, IL1B, IL8, IL6, or PTGS2;
CTLA4, BTLA, LAG3, HAVCR2, or PDCD1; and
CD276, PDL1, PDL2, or IDO1.
MS4A1 or CD48;
NCAM1 or NKP46;
ITGAM, ITGAX, CD1C, or CLEC4C; and
IL17A or IL17F.
MS4A1 or CD48;
NCAM1 or NKP46;
ITGAM, ITGAX, CD1C, or CLEC4C; and
CCL2, IL1B, IL8, IL6, or PTGS2.
MS4A1 or CD48;
NCAM1 or NKP46;
ITGAM, ITGAX, CD1C, or CLEC4C; and
CTLA4, BTLA, LAG3, HAVCR2, or PDCD1.
MS4A1 or CD48;
NCAM1 or NKP46;
ITGAM, ITGAX, CD1C, or CLEC4C; and
CD276, PDL1, PDL2, or IDO1.
MS4A1 or CD48;
NCAM1 or NKP46;
IL17A or IL17F; and
CCL2, IL1B, IL8, IL6, or PTGS2.
MS4A1 or CD48;
NCAM1 or NKP46;
IL17A or IL17F; and
CTLA4, BTLA, LAG3, HAVCR2, or PDCD1.
MS4A1 or CD48;
NCAM1 or NKP46;
IL17A or IL17F; and
CD276, PDL1, PDL2, or IDO1.
MS4A1 or CD48;
NCAM1 or NKP46;
CCL2, IL1B, IL8, IL6, or PTGS2; and
CTLA4, BTLA, LAG3, HAVCR2, or PDCD1.
MS4A1 or CD48;
NCAM1 or NKP46;
CCL2, IL1B, IL8, IL6, or PTGS2; and
CD276, PDL1, PDL2, or IDO1.
MS4A1 or CD48;
NCAM1 or NKP46;
CTLA4, BTLA, LAG3, HAVCR2, or PDCD1; and
CD276, PDL1, PDL2, or IDO1.
MS4A1 or CD48;
ITGAM, ITGAX, CD1C, or CLEC4C;
IL17A or IL17F; and
CCL2, IL1B, IL8, IL6, or PTGS2.
MS4A1 or CD48;
ITGAM, ITGAX, CD1C, or CLEC4C;
IL17A or IL17F; and
CTLA4, BTLA, LAG3, HAVCR2, or PDCD1.
MS4A1 or CD48;
ITGAM, ITGAX, CD1C, or CLEC4C;
IL17A or IL17F; and
CD276, PDL1, PDL2, or IDO1.
MS4A1 or CD48;
ITGAM, ITGAX, CD1C, or CLEC4C;
CCL2, IL1B, IL8, IL6, or PTGS2; and
CTLA4, BTLA, LAG3, HAVCR2, or PDCD1.
MS4A1 or CD48;
ITGAM, ITGAX, CD1C, or CLEC4C;
CCL2, IL1B, IL8, IL6, or PTGS2; and
CD276, PDL1, PDL2, or IDO1.
MS4A1 or CD48;
ITGAM, ITGAX, CD1C, or CLEC4C;
CTLA4, BTLA, LAG3, HAVCR2, or PDCD1; and
CD276, PDL1, PDL2, or IDO1.
MS4A1 or CD48;
IL17F;
CCL2, IL1B, IL8, IL6, or PTGS2; and
CTLA4, BTLA, LAG3, HAVCR2, or PDCD1.
MS4A1 or CD48;
IL17A or IL17F;
CCL2, IL1B, IL8, IL6, or PTGS2; and
CD276, PDL1, PDL2, or IDO1.
MS4A1 or CD48;
IL17A or IL17F;
CTLA4, BTLA, LAG3, HAVCR2, or PDCD1; and

TABLE 4-continued

Combinations of four gene signature sets

CD276, PDL1, PDL2, or IDO1.
MS4A1 or CD48;
CCL2, IL1B, IL8, IL6, or PTGS2;
CTLA4, BTLA, LAG3, HAVCR2, or PDCD1; and
CD276, PDL1, PDL2, or IDO1.
NCAM1 or NKP46;
ITGAM, ITGAX, CD1C, or CLEC4C;
IL17A or IL17F; and
CCL2, IL1B, IL8, IL6, or PTGS2.
NCAM1 or NKP46;
ITGAM, ITGAX, CD1C, or CLEC4C;
IL17A or IL17F; and
CTLA4, BTLA, LAG3, HAVCR2, or PDCD1.
NCAM1 or NKP46;
ITGAM, ITGAX, CD1C, or CLEC4C;
IL17A or IL17F; and
CD276, PDL1, PDL2, or IDO1.
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
NCAM1 or NKP46;
ITGAM, ITGAX, CD1C, or CLEC4C;
CCL2, IL1B, IL8, IL6, or PTGS2; and
CD276, PDL1, PDL2, or IDO1.
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
NCAM1 or NKP46;
IL17A or IL17F;
CCL2, IL1B, IL8, IL6, or PTGS2; and
CTLA4, BTLA, LAG3, HAVCR2, or PDCD1.
NCAM1 or NKP46;
IL17A or IL17F;
CCL2, IL1B, IL8, IL6, or PTGS2; and
CD276, PDL1, PDL2, or IDO1.
NCAM1 or NKP46;
IL17A or IL17F;
CTLA4, BTLA, LAG3, HAVCR2, or PDCD1; and
CD276, PDL1, PDL2, or IDO1.
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
ITGAM, ITGAX, CD1C, or CLEC4C;
IL17A or IL17F;
CCL2, IL1B, IL8, IL6, or PTGS2; and
CD276, PDL1, PDL2, or IDO1.
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48; and
CX3CL1, CXCL9, CXCL10, CXCR3, CCL21, or CCL22.
CD8A, GZMA, GZMB, IFNγ, EOMES, or PRF1;
FOXP3;
NCAM1 or NKP46; and
CX3CL1, CXCL9, CXCL10, CXCR3, CCL21, or CCL22.
CD8A, GZMA, GZMB, IFNγ, EOMES, or PRF1;
FOXP3;
ITGAM, ITGAX, CD1C, or CLEC4C; and
CX3CL1, CXCL9, CXCL10, CXCR3, CCL21, or CCL22.
CD8A, GZMA, GZMB, IFNγ, EOMES, or PRF1;
FOXP3;
IL17A or IL17F; and
CX3CL1, CXCL9, CXCL10, CXCR3, CCL21, or CCL22.
CD8A, GZMA, GZMB, IFNγ, EOMES, or PRF1;
FOXP3;
CCL2, IL1B, IL8, IL6, or PTGS2; and
CX3CL1, CXCL9, CXCL10, CXCR3, CCL21, or CCL22.
CD8A, GZMA, GZMB, IFNγ, EOMES, or PRF1;
FOXP3;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
FOXP3;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
MS4A1 or CD48;
NCAM1 or NKP46; and
CX3CL1, CXCL9, CXCL10, CXCR3, CCL21, or CCL22.
CD8A, GZMA, GZMB, IFNγ, EOMES, or PRF1;
MS4A1 or CD48;
ITGAM, ITGAX, CD1C, or CLEC4C; and
CX3CL1, CXCL9, CXCL10, CXCR3, CCL21, or CCL22.
CD8A, GZMA, GZMB, IFNγ, EOMES, or PRF1;
MS4A1 or CD48;
IL17A or IL17F; and
CX3CL1, CXCL9, CXCL10, CXCR3, CCL21, or CCL22.
CD8A, GZMA, GZMB, IFNγ, EOMES, or PRF1;
MS4A1 or CD48;
CCL2, IL1B, IL8, IL6, or PTGS2; and
CX3CL1, CXCL9, CXCL10, CXCR3, CCL21, or CCL22.
CD8A, GZMA, GZMB, IFNγ, EOMES, or PRF1;
MS4A1 or CD48;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
MS4A1 or CD48;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
NCAM1 or NKP46;
ITGAM, ITGAX, CD1C, or CLEC4C; and
CX3CL1, CXCL9, CXCL10, CXCR3, CCL21, or CCL22.
CD8A, GZMA, GZMB, IFNγ, EOMES, or PRF1;
NCAM1 or NKP46;
IL17A or IL17F; and
CX3CL1, CXCL9, CXCL10, CXCR3, CCL21, or CCL22.
CD8A, GZMA, GZMB, IFNγ, EOMES, or PRF1;
NCAM1 or NKP46;
CCL2, IL1B, IL8, IL6, or PTGS2; and
CX3CL1, CXCL9, CXCL10, CXCR3, CCL21, or CCL22.
CD8A, GZMA, GZMB, IFNγ, EOMES, or PRF1;
NCAM1 or NKP46;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
NCAM1 or NKP46;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
ITGAM, ITGAX, CD1C, or CLEC4C;
IL17A or IL17F; and
CX3CL1, CXCL9, CXCL10, CXCR3, CCL21, or CCL22.
CD8A, GZMA, GZMB, IFNγ, EOMES, or PRF1;
ITGAM, ITGAX, CD1C, or CLEC4C;
CCL2, IL1B, IL8, IL6, or PTGS2; and
CX3CL1, CXCL9, CXCL10, CXCR3, CCL21, or CCL22.
CD8A, GZMA, GZMB, IFNγ, EOMES, or PRF1;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
ITGAM, ITGAX, CD1C, or CLEC4C;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
IL17A or IL17F;
CCL2, IL1B, IL8, IL6, or PTGS2; and

TABLE 4-continued

Combinations of four gene signature sets

CX3CL1, CXCL9, CXCL10, CXCR3, CCL21, or CCL22.
CD8A, GZMA, GZMB, IFNγ, EOMES, or PRF1;
IL17A or IL17F;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
IL17A or IL17F;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
CCL2, IL1B, IL8, IL6, or PTGS2;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
FOXP3;
MS4A1 or CD48;
NCAM1 or NKP46; and
CX3CL1, CXCL9, CXCL10, CXCR3, CCL21, or CCL22.
FOXP3;
MS4A1 or CD48;
ITGAM, ITGAX, CD1C, or CLEC4C; and
CX3CL1, CXCL9, CXCL10, CXCR3, CCL21, or CCL22.
FOXP3;
MS4A1 or CD48;
IL17A or IL17F; and
CX3CL1, CXCL9, CXCL10, CXCR3, CCL21, or CCL22.
FOXP3;
MS4A1 or CD48;
CCL2, IL1B, IL8, IL6, or PTGS2; and
CX3CL1, CXCL9, CXCL10, CXCR3, CCL21, or CCL22.
FOXP3;
MS4A1 or CD48;
CTLA4, BTLA, LAG3, HAVCR2, or PDCD1; and
CX3CL1, CXCL9, CXCL10, CXCR3, CCL21, or CCL22.
FOXP3;
MS4A1 or CD48;
CD276, PDL1, PDL2, or IDO1; and
CX3CL1, CXCL9, CXCL10, CXCR3, CCL21, or CCL22.
FOXP3;
NCAM1 or NKP46;
ITGAM, ITGAX, CD1C, or CLEC4C; and
CX3CL1, CXCL9, CXCL10, CXCR3, CCL21, or CCL22.
FOXP3;
NCAM1 or NKP46;
IL17A or IL17F; and
CX3CL1, CXCL9, CXCL10, CXCR3, CCL21, or CCL22.
FOXP3;
NCAM1 or NKP46;
CCL2, IL1B, IL8, IL6, or PTGS2; and
CX3CL1, CXCL9, CXCL10, CXCR3, CCL21, or CCL22.
FOXP3;
NCAM1 or NKP46;
CTLA4, BTLA, LAG3, HAVCR2, or PDCD1; and
CX3CL1, CXCL9, CXCL10, CXCR3, CCL21, or CCL22.
FOXP3;
NCAM1 or NKP46;
CD276, PDL1, PDL2, or IDO1; and
CX3CL1, CXCL9, CXCL10, CXCR3, CCL21, or CCL22.
FOXP3;
ITGAM, ITGAX, CD1C, or CLEC4C;
IL17A or IL17F; and
CX3CL1, CXCL9, CXCL10, CXCR3, CCL21, or CCL22.
FOXP3;
ITGAM, ITGAX, CD1C, or CLEC4C;
CCL2, IL1B, IL8, IL6, or PTGS2; and
CX3CL1, CXCL9, CXCL10, CXCR3, CCL21, or CCL22.
FOXP3;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, or CCL22.
FOXP3;
ITGAM, ITGAX, CD1C, or CLEC4C;
CD276, PDL1, PDL2, or IDO1; and
CX3CL1, CXCL9, CXCL10, CXCR3, CCL21, or CCL22.
FOXP3;
IL17A or IL17F;
CCL2, IL1B, IL8, IL6, or PTGS2; and
CX3CL1, CXCL9, CXCL10, CXCR3, CCL21, or CCL22.
FOXP3;
IL17A or IL17F;
CTLA4, BTLA, LAG3, HAVCR2, or PDCD1; and
CX3CL1, CXCL9, CXCL10, CXCR3, CCL21, or CCL22.
FOXP3;
IL17A or IL17F;
CD276, PDL1, PDL2, or IDO1; and
CX3CL1, CXCL9, CXCL10, CXCR3, CCL21, or CCL22.
FOXP3;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
FOXP3;
CCL2, IL1B, IL8, IL6, or PTGS2;
CD276, PDL1, PDL2, or IDO1; and
CX3CL1, CXCL9, CXCL10, CXCR3, CCL21, or CCL22.
FOXP3;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
MS4A1 or CD48;
NCAM1 or NKP46;
ITGAM, ITGAX, CD1C, or CLEC4C; and
CX3CL1, CXCL9, CXCL10, CXCR3, CCL21, or CCL22.
MS4A1 or CD48;
NCAM1 or NKP46;
IL17A or IL17F; and
CX3CL1, CXCL9, CXCL10, CXCR3, CCL21, or CCL22.
MS4A1 or CD48;
NCAM1 or NKP46;
CCL2, IL1B, IL8, IL6, or PTGS2; and
CX3CL1, CXCL9, CXCL10, CXCR3, CCL21, or CCL22.
MS4A1 or CD48;
NCAM1 or NKP46;
CTLA4, BTLA, LAG3, HAVCR2, or PDCD1; and
CX3CL1, CXCL9, CXCL10, CXCR3, CCL21, or CCL22.
MS4A1 or CD48;
NCAM1 or NKP46;
CD276, PDL1, PDL2, or IDO1; and
CX3CL1, CXCL9, CXCL10, CXCR3, CCL21, or CCL22.
MS4A1 or CD48;
ITGAM, ITGAX, CD1C, or CLEC4C;
IL17A or IL17F; and
CX3CL1, CXCL9, CXCL10, CXCR3, CCL21, or CCL22.
MS4A1 or CD48;
ITGAM, ITGAX, CD1C, or CLEC4C;
CCL2, IL1B, IL8, IL6, or PTGS2; and
CX3CL1, CXCL9, CXCL10, CXCR3, CCL21, or CCL22.
MS4A1 or CD48;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, or CCL22.
MS4A1 or CD48;
ITGAM, ITGAX, CD1C, or CLEC4C;
CD276, PDL1, PDL2, or IDO1; and
CX3CL1, CXCL9, CXCL10, CXCR3, CCL21, or CCL22.
MS4A1 or CD48;
IL17A or IL17F;
CCL2, IL1B, IL8, IL6, or PTGS2; and
CX3CL1, CXCL9, CXCL10, CXCR3, CCL21, or CCL22.
MS4A1 or CD48;
IL17A or IL17F;
CTLA4, BTLA, LAG3, HAVCR2, or PDCD1; and
CX3CL1, CXCL9, CXCL10, CXCR3, CCL21, or CCL22.
MS4A1 or CD48;
IL17A or IL17F;
CD276, PDL1, PDL2, or IDO1; and
CX3CL1, CXCL9, CXCL10, CXCR3, CCL21, or CCL22.
MS4A1 or CD48;
CCL2, IL1B, IL8, IL6, or PTGS2;
CTLA4, BTLA, LAG3, HAVCR2, or PDCD1; and

TABLE 4-continued

Combinations of four gene signature sets

CX3CL1, CXCL9, CXCL10, CXCR3, CCL21, or CCL22.
MS4A1 or CD48;
CCL2, IL1B, IL8, IL6, or PTGS2;
CD276, PDL1, PDL2, or IDO1; and
CX3CL1, CXCL9, CXCL10, CXCR3, CCL21, or CCL22.
MS4A1 or CD48;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
NCAM1 or NKP46;
ITGAM, ITGAX, CD1C, or CLEC4C;
IL17A or IL17F; and
CX3CL1, CXCL9, CXCL10, CXCR3, CCL21, or CCL22.
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, or CCL22.
NCAM1 or NKP46;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, or CCL22.
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, or CCL22.
NCAM1 or NKP46;
IL17A or IL17F;
CCL2, IL1B, IL8, IL6, or PTGS2; and
CX3CL1, CXCL9, CXCL10, CXCR3, CCL21, or CCL22.
NCAM1 or NKP46;
IL17A or IL17F;
CTLA4, BTLA, LAG3, HAVCR2, or PDCD1; and
CX3CL1, CXCL9, CXCL10, CXCR3, CCL21, or CCL22.
NCAM1 or NKP46;
IL17A or IL17F;
CD276, PDL1, PDL2, or IDO1; and
CX3CL1, CXCL9, CXCL10, CXCR3, CCL21, or CCL22.
NCAM1 or NKP46;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, or CCL22.
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, or CCL22.
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, or CCL22.
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, or CCL22.
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, or CCL22.
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.

In some embodiments, a combination of four particular gene signature sets includes, or consists of, a combination including one or more of the following gene signature sets: B cell Signature 2 (CD79A, MS4A1, CD19, STAP1, KIAA0125, POU2AF1, FCRL5); NK cell Signature 2 (KLRC3, KLRK1, KLRC2, KLRD1); Macrophage (CD68, CD163, ITGAM, ITGAX, CD14); M2 Macrophage (LAPTM5, LAIR1, CD4, CSF1R, CD163, ADAP2, CD68, MRC1, CD45RO, SLA, MSR1, FPR3, FCGR2A, FCGR3A); T cell (CD3D, CD3E, CD2, CD3G, CD6, TRAT1, CD28, LCK); IB T cell Signature 2 (CTLA4, BTLA, LAG3, HAVCR2, PDCD1, TIGIT); IB APC Signature 2 (CD274, PDL2, IDO1, PVR); Activated CD4 T cell (CD4, IL2RA, CD69); Antigen processing (TAPBP, TAP1, TAP2, PSMB9, PSMB8); Costimulatory ligand (CD40, CD80, CD86, CD70, GITRL); Costimulatory receptor (CD27, CD28, ICOS, TNFRSF4, TNFRSF14, TNFRSF18, TNFSF14, CD226); Cytolytic (GNLY, KLRK1, KLRB1, GZMH, GZMA, KLRD1, NKG7); and/or Active fibroblast (FAP, FN1, MMP2, BGN, LOXL2, PDPN, PDGFRB, COL4A1, COL4A2, COL5A1, COL8A1).

In another embodiment, the expression levels of one or more of the genes in an immune cell gene signature in five particular gene signature sets are determined. For example, combinations of five particular gene signature sets are set forth in Table 5 below.

TABLE 5

Combinations of five gene signature sets

CD8A, GZMA, GZMB, IFNγ, EOMES, or PRF1;
FOXP3;
MS4A1 or CD48;
NCAM1 or NKP46; and
ITGAM, ITGAX, CD1C, or CLEC4C.
CD8A, GZMA, GZMB, IFNγ, EOMES, or PRF1;
FOXP3;
MS4A1 or CD48;
NCAM1 or NKP46; and
IL17A or IL17F.
CD8A, GZMA, GZMB, IFNγ, EOMES, or PRF1;
FOXP3;
MS4A1 or CD48;
NCAM1 or NKP46; and
CCL2, IL1B, IL8, IL6, or PTGS2.
CD8A, GZMA, GZMB, IFNγ, EOMES, or PRF1;
FOXP3;
MS4A1 or CD48;
NCAM1 or NKP46; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C; and
IL17A or IL17F.
CD8A, GZMA, GZMB, IFNγ, EOMES, or PRF1;
FOXP3;
MS4A1 or CD48;
ITGAM, ITGAX, CD1C, or CLEC4C; and
CCL2, IL1B, IL8, IL6, or PTGS2.
CD8A, GZMA, GZMB, IFNγ, EOMES, or PRF1;
FOXP3;
MS4A1 or CD48;
ITGAM, ITGAX, CD1C, or CLEC4C; and
CTLA4, BTLA, LAG3, HAVCR2, or PDCD1.
CD8A, GZMA, GZMB, IFNγ, EOMES, or PRF1;
FOXP3;
MS4A1 or CD48;
ITGAM, ITGAX, CD1C, or CLEC4C; and
CD276, PDL1, PDL2, or IDO1.
CD8A, GZMA, GZMB, IFNγ, EOMES, or PRF1;
FOXP3;
MS4A1 or CD48;

TABLE 5-continued

| Combinations of five gene signature sets |
|---|
| IL17A or IL17F; and |
| CCL2, IL1B, IL8, IL6, or PTGS2. |
| CD8A, GZMA, GZMB, IFNγ, EOMES, or PRF1; |
| FOXP3; |
| MS4A1 or CD48; |
| IL17A or IL17F; and |
| CTLA4, BTLA, LAG3, HAVCR2, or PDCD1. |
| CD8A, GZMA, GZMB, IFNγ, EOMES, or PRF1; |
| FOXP3; |
| MS4A1 or CD48; |
| IL17A or IL17F; and |
| CD276, PDL1, PDL2, or IDO1. |
| CD8A, GZMA, GZMB, IFNγ, EOMES, or PRF1; |
| FOXP3; |
| MS4A1 or CD48; |
| CCL2, IL1B, IL8, IL6, or PTGS2; and |
| CTLA4, BTLA, LAG3, HAVCR2, or PDCD1. |
| CD8A, GZMA, GZMB, IFNγ, EOMES, or PRF1; |
| FOXP3; |
| MS4A1 or CD48; |
| CCL2, IL1B, IL8, IL6, or PTGS2; and |
| CD276, PDL1, PDL2, or IDO1. |
| CD8A, GZMA, GZMB, IFNγ, EOMES, or PRF1; |
| FOXP3; |
| MS4A1 or CD48; |
| CTLA4, BTLA, LAG3, HAVCR2, or PDCD1; and |
| CD276, PDL1, PDL2, or IDO1. |
| CD8A, GZMA, GZMB, IFNγ, EOMES, or PRF1; |
| FOXP3; |
| NCAM1 or NKP46; |
| ITGAM, ITGAX, CD1C, or CLEC4C; and |
| IL17A or IL17F. |
| CD8A, GZMA, GZMB, IFNγ, EOMES, or PRF1; |
| FOXP3; |
| NCAM1 or NKP46; |
| ITGAM, ITGAX, CD1C, or CLEC4C; and |
| CCL2, IL1B, IL8, IL6, or PTGS2. |
| CD8A, GZMA, GZMB, IFNγ, EOMES, or PRF1; |
| FOXP3; |
| NCAM1 or NKP46; |
| ITGAM, ITGAX, CD1C, or CLEC4C; and |
| CTLA4, BTLA, LAG3, HAVCR2, or PDCD1. |
| CD8A, GZMA, GZMB, IFNγ, EOMES, or PRF1; |
| FOXP3; |
| NCAM1 or NKP46; |
| ITGAM, ITGAX, CD1C, or CLEC4C; and |
| CD276, PDL1, PDL2, or IDO1. |
| CD8A, GZMA, GZMB, IFNγ, EOMES, or PRF1; |
| FOXP3; |
| NCAM1 or NKP46; |
| IL17A or IL17F; and |
| CCL2, IL1B, IL8, IL6, or PTGS2. |
| CD8A, GZMA, GZMB, IFNγ, EOMES, or PRF1; |
| FOXP3; |
| NCAM1 or NKP46; |
| IL17A or IL17F; and |
| CTLA4, BTLA, LAG3, HAVCR2, or PDCD1. |
| CD8A, GZMA, GZMB, IFNγ, EOMES, or PRF1; |
| FOXP3; |
| NCAM1 or NKP46; |
| IL17A or IL17F; and |
| CD276, PDL1, PDL2, or IDO1. |
| CD8A, GZMA, GZMB, IFNγ, EOMES, or PRF1; |
| FOXP3; |
| NCAM1 or NKP46; |
| CCL2, IL1B, IL8, IL6, or PTGS2; and |
| CTLA4, BTLA, LAG3, HAVCR2, or PDCD1. |
| CD8A, GZMA, GZMB, IFNγ, EOMES, or PRF1; |
| FOXP3; |
| NCAM1 or NKP46; |
| CCL2, IL1B, IL8, IL6, or PTGS2; and |
| CD276, PDL1, PDL2, or IDO1. |
| CD8A, GZMA, GZMB, IFNγ, EOMES, or PRF1; |
| FOXP3; |
| NCAM1 or NKP46; |
| CTLA4, BTLA, LAG3, HAVCR2, or PDCD1; and |
| CD276, PDL1, PDL2, or IDO1. |
| CD8A, GZMA, GZMB, IFNγ, EOMES, or PRF1; |
| FOXP3; |
| ITGAM, ITGAX, CD1C, or CLEC4C; |
| IL17A or IL17F; and |
| CCL2, IL1B, IL8, IL6, or PTGS2. |
| CD8A, GZMA, GZMB, IFNγ, EOMES, or PRF1; |
| FOXP3; |
| ITGAM, ITGAX, CD1C, or CLEC4C; |
| IL17A or IL17F; and |
| CTLA4, BTLA, LAG3, HAVCR2, or PDCD1. |
| CD8A, GZMA, GZMB, IFNγ, EOMES, or PRF1; |
| FOXP3; |
| ITGAM, ITGAX, CD1C, or CLEC4C; |
| IL17A or IL17F; and |
| CD276, PDL1, PDL2, or IDO1. |
| CD8A, GZMA, GZMB, IFNγ, EOMES, or PRF1; |
| FOXP3; |
| ITGAM, ITGAX, CD1C, or CLEC4C; |
| CCL2, IL1B, IL8, IL6, or PTGS2; and |
| CTLA4, BTLA, LAG3, HAVCR2, or PDCD1. |
| CD8A, GZMA, GZMB, IFNγ, EOMES, or PRF1; |
| FOXP3; |
| ITGAM, ITGAX, CD1C, or CLEC4C; |
| CCL2, IL1B, IL8, IL6, or PTGS2; and |
| CD276, PDL1, PDL2, or IDO1. |
| CD8A, GZMA, GZMB, IFNγ, EOMES, or PRF1; |
| FOXP3; |
| ITGAM, ITGAX, CD1C, or CLEC4C; |
| CTLA4, BTLA, LAG3, HAVCR2, or PDCD1; and |
| CD276, PDL1, PDL2, or IDO1. |
| CD8A, GZMA, GZMB, IFNγ, EOMES, or PRF1; |
| FOXP3; |
| IL17A or IL17F; |
| CCL2, IL1B, IL8, IL6, or PTGS2; and |
| CTLA4, BTLA, LAG3, HAVCR2, or PDCD1. |
| CD8A, GZMA, GZMB, IFNγ, EOMES, or PRF1; |
| FOXP3; |
| IL17A or IL17F; |
| CCL2, IL1B, IL8, IL6, or PTGS2; and |
| CD276, PDL1, PDL2, or IDO1. |
| CD8A, GZMA, GZMB, IFNγ, EOMES, or PRF1; |
| FOXP3; |
| IL17A or IL17F; |
| CTLA4, BTLA, LAG3, HAVCR2, or PDCD1; and |
| CD276, PDL1, PDL2, or IDO1. |
| CD8A, GZMA, GZMB, IFNγ, EOMES, or PRF1; |
| FOXP3; |
| CCL2, IL1B, IL8, IL6, or PTGS2; |
| CTLA4, BTLA, LAG3, HAVCR2, or PDCD1; and |
| CD276, PDL1, PDL2, or IDO1. |
| CD8A, GZMA, GZMB, IFNγ, EOMES, or PRF1; |
| MS4A1 or CD48; |
| NCAM1 or NKP46; |
| ITGAM, ITGAX, CD1C, or CLEC4C; and |
| IL17A or IL17F. |
| CD8A, GZMA, GZMB, IFNγ, EOMES, or PRF1; |
| MS4A1 or CD48; |
| NCAM1 or NKP46; |
| ITGAM, ITGAX, CD1C, or CLEC4C; and |
| CCL2, IL1B, IL8, IL6, or PTGS2. |
| CD8A, GZMA, GZMB, IFNγ, EOMES, or PRF1; |
| MS4A1 or CD48; |
| NCAM1 or NKP46; |
| ITGAM, ITGAX, CD1C, or CLEC4C; and |
| CTLA4, BTLA, LAG3, HAVCR2, or PDCD1. |
| CD8A, GZMA, GZMB, IFNγ, EOMES, or PRF1; |
| MS4A1 or CD48; |
| NCAM1 or NKP46; |
| ITGAM, ITGAX, CD1C, or CLEC4C; and |
| CD276, PDL1, PDL2, or IDO1. |
| CD8A, GZMA, GZMB, IFNγ, EOMES, or PRF1; |
| MS4A1 or CD48; |
| NCAM1 or NKP46; |
| IL17A or IL17F; and |

TABLE 5-continued

Combinations of five gene signature sets

CTLA4, BTLA, LAG3, HAVCR2, or PDCD1.
CD8A, GZMA, GZMB, IFNγ, EOMES, or PRF1;
MS4A1 or CD48;
NCAM1 or NKP46;
IL17A or IL17F; and
CD276, PDL1, PDL2, or IDO1.
CD8A, GZMA, GZMB, IFNγ, EOMES, or PRF1;
MS4A1 or CD48;
NCAM1 or NKP46;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
NCAM1 or NKP46;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
NCAM1 or NKP46;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
IL17A or IL17F; and
CCL2, IL1B, IL8, IL6, or PTGS2.
CD8A, GZMA, GZMB, IFNγ, EOMES, or PRF1;
MS4A1 or CD48;
ITGAM, ITGAX, CD1C, or CLEC4C;
IL17A or IL17F; and
CTLA4, BTLA, LAG3, HAVCR2, or PDCD1.
CD8A, GZMA, GZMB, IFNγ, EOMES, or PRF1;
MS4A1 or CD48;
ITGAM, ITGAX, CD1C, or CLEC4C;
IL17A or IL17F; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
IL17A or IL17F; and
CCL2, IL1B, IL8, IL6, or PTGS2.
CD8A, GZMA, GZMB, IFNγ, EOMES, or PRF1;
NCAM1 or NKP46;
ITGAM, ITGAX, CD1C, or CLEC4C;
IL17A or IL17F; and
CTLA4, BTLA, LAG3, HAVCR2, or PDCD1.
CD8A, GZMA, GZMB, IFNγ, EOMES, or PRF1;
NCAM1 or NKP46;
ITGAM, ITGAX, CD1C, or CLEC4C;
IL17A or IL17F; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
NCAM1 or NKP46;
ITGAM, ITGAX, CD1C, or CLEC4C;
CCL2, IL1B, IL8, IL6, or PTGS2; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
NCAM1 or NKP46;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
NCAM1 or NKP46;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
NCAM1 or NKP46;
ITGAM, ITGAX, CD1C, or CLEC4C; and
IL17A or IL17F.
FOXP3;
MS4A1 or CD48;
NCAM1 or NKP46;
ITGAM, ITGAX, CD1C, or CLEC4C; and
CCL2, IL1B, IL8, IL6, or PTGS2.

TABLE 5-continued

Combinations of five gene signature sets

FOXP3;
MS4A1 or CD48;
NCAM1 or NKP46;
ITGAM, ITGAX, CD1C, or CLEC4C; and
CTLA4, BTLA, LAG3, HAVCR2, or PDCD1.
FOXP3;
MS4A1 or CD48;
NCAM1 or NKP46;
ITGAM, ITGAX, CD1C, or CLEC4C; and
CD276, PDL1, PDL2, or IDO1.
FOXP3;
MS4A1 or CD48;
NCAM1 or NKP46;
IL17A or IL17F; and
CCL2, IL1B, IL8, IL6, or PTGS2.
FOXP3;
MS4A1 or CD48;
NCAM1 or NKP46;
IL17A or IL17F; and
CTLA4, BTLA, LAG3, HAVCR2, or PDCD1.
FOXP3;
MS4A1 or CD48;
NCAM1 or NKP46;
IL17A or IL17F; and
CD276, PDL1, PDL2, or IDO1.
FOXP3;
MS4A1 or CD48;
NCAM1 or NKP46;
CCL2, IL1B, IL8, IL6, or PTGS2; and
CTLA4, BTLA, LAG3, HAVCR2, or PDCD1.
FOXP3;
MS4A1 or CD48;
NCAM1 or NKP46;
CCL2, IL1B, IL8, IL6, or PTGS2; and
CD276, PDL1, PDL2, or IDO1.
FOXP3;
MS4A1 or CD48;
NCAM1 or NKP46;
CTLA4, BTLA, LAG3, HAVCR2, or PDCD1; and
CD276, PDL1, PDL2, or IDO1.
FOXP3;
MS4A1 or CD48;
ITGAM, ITGAX, CD1C, or CLEC4C;
IL17A or IL17F; and
CCL2, IL1B, IL8, IL6, or PTGS2.
FOXP3;
MS4A1 or CD48;
ITGAM, ITGAX, CD1C, or CLEC4C;
IL17A or IL17F; and
CTLA4, BTLA, LAG3, HAVCR2, or PDCD1.
FOXP3;
MS4A1 or CD48;
ITGAM, ITGAX, CD1C, or CLEC4C;
IL17A or IL17F; and
CD276, PDL1, PDL2, or IDO1.
FOXP3;
MS4A1 or CD48;
ITGAM, ITGAX, CD1C, or CLEC4C;
CCL2, IL1B, IL8, IL6, or PTGS2; and
CTLA4, BTLA, LAG3, HAVCR2, or PDCD1.
FOXP3;
MS4A1 or CD48;
ITGAM, ITGAX, CD1C, or CLEC4C;
CCL2, IL1B, IL8, IL6, or PTGS2; and
CD276, PDL1, PDL2, or IDO1.
FOXP3;
MS4A1 or CD48;
ITGAM, ITGAX, CD1C, or CLEC4C;
CTLA4, BTLA, LAG3, HAVCR2, or PDCD1; and
CD276, PDL1, PDL2, or IDO1.
FOXP3;
MS4A1 or CD48;
IL17A or IL17F;
CCL2, IL1B, IL8, IL6, or PTGS2; and
CTLA4, BTLA, LAG3, HAVCR2, or PDCD1.
FOXP3;
MS4A1 or CD48;
IL17A or IL17F;

TABLE 5-continued

Combinations of five gene signature sets

CCL2, IL1B, IL8, IL6, or PTGS2; and
CD276, PDL1, PDL2, or IDO1.
FOXP3;
MS4A1 or CD48;
IL17A or IL17F;
CTLA4, BTLA, LAG3, HAVCR2, or PDCD1; and
CD276, PDL1, PDL2, or IDO1.
FOXP3;
MS4A1 or CD48;
CCL2, IL1B, IL8, IL6, or PTGS2;
CTLA4, BTLA, LAG3, HAVCR2, or PDCD1; and
CD276, PDL1, PDL2, or IDO1.
FOXP3;
NCAM1 or NKP46;
ITGAM, ITGAX, CD1C, or CLEC4C;
IL17A or IL17F; and
CCL2, IL1B, IL8, IL6, or PTGS2.
FOXP3;
NCAM1 or NKP46;
ITGAM, ITGAX, CD1C, or CLEC4C;
IL17A or IL17F; and
CTLA4, BTLA, LAG3, HAVCR2, or PDCD1.
FOXP3;
NCAM1 or NKP46;
ITGAM, ITGAX, CD1C, or CLEC4C;
IL17A or IL17F; and
CD276, PDL1, PDL2, or IDO1.
FOXP3;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
FOXP3;
NCAM1 or NKP46;
ITGAM, ITGAX, CD1C, or CLEC4C;
CCL2, IL1B, IL8, IL6, or PTGS2; and
CD276, PDL1, PDL2, or IDO1.
FOXP3;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
FOXP3;
NCAM1 or NKP46;
IL17A or IL17F;
CCL2, IL1B, IL8, IL6, or PTGS2; and
CTLA4, BTLA, LAG3, HAVCR2, or PDCD1.
FOXP3;
NCAM1 or NKP46;
IL17A or IL17F;
CCL2, IL1B, IL8, IL6, or PTGS2; and
CD276, PDL1, PDL2, or IDO1.
FOXP3;
NCAM1 or NKP46;
IL17A or IL17F;
CTLA4, BTLA, LAG3, HAVCR2, or PDCD1; and
CD276, PDL1, PDL2, or IDO1.
FOXP3;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
FOXP3;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
FOXP3;
ITGAM, ITGAX, CD1C, or CLEC4C;
IL17A or IL17F;
CCL2, IL1B, IL8, IL6, or PTGS2; and
CD276, PDL1, PDL2, or IDO1.
FOXP3;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
FOXP3;

TABLE 5-continued

Combinations of five gene signature sets

ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
FOXP3;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
MS4A1 or CD48;
NCAM1 or NKP46;
ITGAM, ITGAX, CD1C, or CLEC4C;
IL17A or IL17F; and
CCL2, IL1B, IL8, IL6, or PTGS2.
MS4A1 or CD48;
NCAM1 or NKP46;
ITGAM, ITGAX, CD1C, or CLEC4C;
IL17A or IL17F; and
CTLA4, BTLA, LAG3, HAVCR2, or PDCD1.
MS4A1 or CD48;
NCAM1 or NKP46;
ITGAM, ITGAX, CD1C, or CLEC4C;
IL17A or IL17F; and
CD276, PDL1, PDL2, or IDO1.
MS4A1 or CD48;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
MS4A1 or CD48;
NCAM1 or NKP46;
ITGAM, ITGAX, CD1C, or CLEC4C;
CCL2, IL1B, IL8, IL6, or PTGS2; and
CD276, PDL1, PDL2, or IDO1.
MS4A1 or CD48;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
MS4A1 or CD48;
NCAM1 or NKP46;
IL17A or IL17F;
CCL2, IL1B, IL8, IL6, or PTGS2; and
CTLA4, BTLA, LAG3, HAVCR2, or PDCD1.
MS4A1 or CD48;
NCAM1 or NKP46;
IL17A or IL17F;
CCL2, IL1B, IL8, IL6, or PTGS2; and
CD276, PDL1, PDL2, or IDO1.
MS4A1 or CD48;
NCAM1 or NKP46;
IL17A or IL17F;
CTLA4, BTLA, LAG3, HAVCR2, or PDCD1; and
CD276, PDL1, PDL2, or IDO1.
MS4A1 or CD48;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
MS4A1 or CD48;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
MS4A1 or CD48;
ITGAM, ITGAX, CD1C, or CLEC4C;
IL17A or IL17F;
CCL2, IL1B, IL8, IL6, or PTGS2; and
CD276, PDL1, PDL2, or IDO1.
MS4A1 or CD48;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1 .
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1 .
MS4A1 or CD48;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1 .
CD8A, GZMA, GZMB, IFNγ, EOMES, or PRF1;
FOXP3;
MS4A1 or CD48;
NCAM1 or NKP46; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;

TABLE 5-continued

Combinations of five gene signature sets

ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C; and
CX3CL1, CXCL9, CXCL10, CXCR3, CCL21, CCL22.
CD8A, GZMA, GZMB; IFNγ, EOMES, or PRF1;
MS4A1 or CD48;
NCAM1 or NKP46;
IL17A or IL17F; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
CTLA4, BTLA, LAG3, HAVCR2, or PDCD1;

TABLE 5-continued

Combinations of five gene signature sets

CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C; and
CX3CL1, CXCL9, CXCL10, CXCR3, CCL21, CCL22.
FOXP3;
MS4A1 or CD48;
NCAM1 or NKP46;
IL17A or IL17F; and
CX3CL1, CXCL9, CXCL10, CXCR3, CCL21, CCL22.
FOXP3;
MS4A1 or CD48;
NCAM1 or NKP46;
CCL2, IL1B, IL8, IL6, or PTGS2; and
CX3CL1, CXCL9, CXCL10, CXCR3, CCL21, CCL22.
FOXP3;
MS4A1 or CD48;
NCAM1 or NKP46;
CTLA4, BTLA, LAG3, HAVCR2, or PDCD1; and
CX3CL1, CXCL9, CXCL10, CXCR3, CCL21, CCL22.
FOXP3;
MS4A1 or CD48;
NCAM1 or NKP46;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F; and
CX3CL1, CXCL9, CXCL10, CXCR3, CCL21, CCL22.
FOXP3;
MS4A1 or CD48;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
FOXP3;
MS4A1 or CD48;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
FOXP3;
MS4A1 or CD48;
ITGAM, ITGAX, CD1C, or CLEC4C;
CD276, PDL1, PDL2, or IDO1; and
CX3CL1, CXCL9, CXCL10, CXCR3, CCL21, CCL22.
FOXP3;
MS4A1 or CD48;
IL17A or IL17F;
CCL2, IL1B, IL8, IL6, or PTGS2; and
CX3CL1, CXCL9, CXCL10, CXCR3, CCL21, CCL22.
FOXP3;
MS4A1 or CD48;
IL17A or IL17F;
CTLA4, BTLA, LAG3, HAVCR2, or PDCD1; and
CX3CL1, CXCL9, CXCL10, CXCR3, CCL21, CCL22.
FOXP3;
MS4A1 or CD48;
IL17A or IL17F;
CD276, PDL1, PDL2, or IDO1; and
CX3CL1, CXCL9, CXCL10, CXCR3, CCL21, CCL22.
FOXP3;
MS4A1 or CD48;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
MS4A1 or CD48;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F; and
CX3CL1, CXCL9, CXCL10, CXCR3, CCL21, CCL22.
FOXP3;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
FOXP3;
NCAM1 or NKP46;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
FOXP3;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
FOXP3;
NCAM1 or NKP46;
IL17A or IL17F;
CCL2, IL1B, IL8, IL6, or PTGS2; and
CX3CL1, CXCL9, CXCL10, CXCR3, CCL21, CCL22.
FOXP3;
NCAM1 or NKP46;
IL17A or IL17F;
CTLA4, BTLA, LAG3, HAVCR2, or PDCD1; and

TABLE 5-continued

Combinations of five gene signature sets

CX3CL1, CXCL9, CXCL10, CXCR3, CCL21, CCL22.
FOXP3;
NCAM1 or NKP46;
IL17A or IL17F;
CD276, PDL1, PDL2, or IDO1; and
CX3CL1, CXCL9, CXCL10, CXCR3, CCL21, CCL22.
FOXP3;
NCAM1 or NKP46;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
FOXP3;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
FOXP3;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
IL17A or IL17F; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
MS4A1 or CD48;
NCAM1 or NKP46;
IL17A or IL17F;
CCL2, IL1B, IL8, IL6, or PTGS2; and
CX3CL1, CXCL9, CXCL10, CXCR3, CCL21, CCL22.
MS4A1 or CD48;
NCAM1 or NKP46;
IL17A or IL17F;
CTLA4, BTLA, LAG3, HAVCR2, or PDCD1; and
CX3CL1, CXCL9, CXCL10, CXCR3, CCL21, CCL22.
MS4A1 or CD48;
NCAM1 or NKP46;
IL17A or IL17F;
CD276, PDL1, PDL2, or IDO1; and
CX3CL1, CXCL9, CXCL10, CXCR3, CCL21, CCL22.
MS4A1 or CD48;
NCAM1 or NKP46;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
MS4A1 or CD48;
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, CCL22.
MS4A1 or CD48;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
MS4A1 or CD48;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
MS4A1 or CD48;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
MS4A1 or CD48;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
MS4A1 or CD48;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.

TABLE 5-continued

Combinations of five gene signature sets

MS4A1 or CD48;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
MS4A1 or CD48;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
NCAM1 or NKP46;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
NCAM1 or NKP46;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.

In some embodiments, a combination of five particular gene signature sets includes, or consists of, a combination including one or more of the following gene signature sets: B cell Signature 2 (CD79A, MS4A1, CD19, STAP1, KIAA0125, POU2AF1, FCRL5); NK cell Signature 2 (KLRC3, KLRK1, KLRC2, KLRD1); Macrophage (CD68, CD163, ITGAM, ITGAX, CD14); M2 Macrophage (LAPTM5, LAIR1, CD4, CSF1R, CD163, ADAP2, CD68, MRC1, CD45RO, SLA, MSR1, FPR3, FCGR2A, FCGR3A); T cell (CD3D, CD3E, CD2, CD3G, CD6, TRAT1, CD28, LCK); IB T cell Signature 2 (CTLA4, BTLA, LAG3, HAVCR2, PDCD1, TIGIT); IB APC Signature 2 (CD274, PDL2, IDO1, PVR); Activated CD4 T cell (CD4, IL2RA, CD69); Antigen processing (TAPBP, TAP1, TAP2, PSMB9, PSMB8); Costimulatory ligand (CD40, CD80, CD86, CD70, GITRL); Costimulatory receptor (CD27, CD28, ICOS, TNFRSF4, TNFRSF14, TNFRSF18, TNFSF14, CD226); Cytolytic (GNLY, KLRK1, KLRB1, GZMH, GZMA, KLRD1, NKG7); and/or Active fibroblast (FAP, FN1, MMP2, BGN, LOXL2, PDPN, PDGFRB, COL4A1, COL4A2, COL5A1, COL8A1).

In another embodiment, the expression levels of one or more of the genes in an immune cell gene signature in six particular gene signature sets are determined. For example, combinations of six particular gene signature sets are set forth in Table 6 below.

TABLE 6

Combinations of six gene signature sets

CD8A, GZMA, GZMB, IFNγ, EOMES, or PRF1;
FOXP3;
MS4A1 or CD48;
NCAM1 or NKP46;
ITGAM, ITGAX, CD1C, or CLEC4C; and
IL17A or IL17F.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C; and
CCL2, IL1B, IL8, IL6, or PTGS2.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C; and
CD276, PDL1, PDL2, or IDO1.
CD8A, GZMA, GZMB, IFNγ, EOMES, or PRF1;
FOXP3;

TABLE 6-continued

Combinations of six gene signature sets

MS4A1 or CD48;
NCAM1 or NKP46;
IL17A or IL17F; and
CCL2, IL1B, IL8, IL6, or PTGS2.
CD8A, GZMA, GZMB, IFNγ, EOMES, or PRF1;
FOXP3;
MS4A1 or CD48;
NCAM1 or NKP46;
IL17A or IL17F; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
IL17A or IL17F; and
CD276, PDL1, PDL2, or IDO1.
CD8A, GZMA, GZMB, IFNγ, EOMES, or PRF1;
FOXP3;
MS4A1 or CD48;
NCAM1 or NKP46;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
MS4A1 or CD48;
NCAM1 or NKP46;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
IL17A or IL17F; and
CCL2, IL1B, IL8, IL6, or PTGS2.
CD8A, GZMA, GZMB, IFNγ, EOMES, or PRF1;
FOXP3;
MS4A1 or CD48;
ITGAM, ITGAX, CD1C, or CLEC4C;
IL17A or IL17F; and
CTLA4, BTLA, LAG3, HAVCR2, or PDCD1.
CD8A, GZMA, GZMB, IFNγ, EOMES, or PRF1;
FOXP3;
MS4A1 or CD48;
ITGAM, ITGAX, CD1C, or CLEC4C;
IL17A or IL17F; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;

MS4A1 or CD48;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
MS4A1 or CD48;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F; and
CCL2, IL1B, IL8, IL6, or PTGS2.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F; and
CTLA4, BTLA, LAG3, HAVCR2, or PDCD1.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
NCAM1 or NKP46;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;

TABLE 6-continued

Combinations of six gene signature sets

ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F; and
CCL2, IL1B, IL8, IL6, or PTGS2.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F; and
CTLA4, BTLA, LAG3, HAVCR2, or PDCD1.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
NCAM1 or NKP46;
ITGAM, ITGAX, CD1C, or CLEC4C;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
NCAM1 or NKP46;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;

TABLE 6-continued

Combinations of six gene signature sets

NCAM1 or NKP46;
ITGAM, ITGAX, CD1C, or CLEC4C;
IL17A or IL17F; and
CCL2, IL1B, IL8, IL6, or PTGS2.
FOXP3;
MS4A1 or CD48;
NCAM1 or NKP46;
ITGAM, ITGAX, CD1C, or CLEC4C;
IL17A or IL17F; and
CTLA4, BTLA, LAG3, HAVCR2, or PDCD1.
FOXP3;
MS4A1 or CD48;
NCAM1 or NKP46;
ITGAM, ITGAX, CD1C, or CLEC4C;
IL17A or IL17F; and
CD276, PDL1, PDL2, or IDO1.
FOXP3;
MS4A1 or CD48;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
FOXP3;
MS4A1 or CD48;
NCAM1 or NKP46;
ITGAM, ITGAX, CD1C, or CLEC4C;
CCL2, IL1B, IL8, IL6, or PTGS2; and
CD276, PDL1, PDL2, or IDO1.
FOXP3;
MS4A1 or CD48;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
FOXP3;
MS4A1 or CD48;
NCAM1 or NKP46;
IL17A or IL17F;
CCL2, IL1B, IL8, IL6, or PTGS2; and
CTLA4, BTLA, LAG3, HAVCR2, or PDCD1.
FOXP3;
MS4A1 or CD48;
NCAM1 or NKP46;
IL17A or IL17F;
CCL2, IL1B, IL8, IL6, or PTGS2; and
CD276, PDL1, PDL2, or IDO1.
FOXP3;
MS4A1 or CD48;
NCAM1 or NKP46;
IL17A or IL17F;
CTLA4, BTLA, LAG3, HAVCR2, or PDCD1; and
CD276, PDL1, PDL2, or IDO1.
FOXP3;
MS4A1 or CD48;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
FOXP3;
MS4A1 or CD48;
ITGAM, ITGAX, CD1C, or CLEC4C;
IL17A or IL17F;
CCL2, IL1B, IL8, IL6, or PTGS2; and
CD276, PDL1, PDL2, or IDO1.
FOXP3;
MS4A1 or CD48;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
FOXP3;
MS4A1 or CD48;

TABLE 6-continued

Combinations of six gene signature sets

ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
FOXP3;
NCAM1 or NKP46;
ITGAM, ITGAX, CD1C, or CLEC4C;
IL17A or IL17F;
CCL2, IL1B, IL8, IL6, or PTGS2; and
CD276, PDL1, PDL2, or IDO1.
FOXP3;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
FOXP3;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
FOXP3;
NCAM1 or NKP46;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CD276, PDL1, PDL2, or IDO1.
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
IL17A or IL17F; and
CX3CL1, CXCL9, CXCL10, CXCR3, CCL21, CCL22.
CD8A, GZMA, GZMB, IFNγ, EOMES, or PRF1;
FOXP3;

TABLE 6-continued

Combinations of six gene signature sets

MS4A1 or CD48;
NCAM1 or NKP46;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
CCL2, IL1B, IL8, IL6, or PTGS2;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
MS4A1 or CD48;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;

TABLE 6-continued

Combinations of six gene signature sets

NCAM1 or NKP46;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46; ITGAM, ITGAX, CD1C, or CLEC4C;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
CCL2, IL1B, IL8, IL6, or PTGS2;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
IL17A or IL17F;
CTLA4, BTLA, LAG3, HAVCR2, or PDCD1; and CX3CL1,
CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;

TABLE 6-continued

Combinations of six gene signature sets

CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
FOXP3;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB; IFNγ, EOMES, or PRF1;
MS4A1 or CD48;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
IL17A or IL17F;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;

TABLE 6-continued

Combinations of six gene signature sets

IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
CCL2, IL1B, IL8, IL6, or PTGS2;

TABLE 6-continued

Combinations of six gene signature sets

CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;

TABLE 6-continued

Combinations of six gene signature sets

CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3; MS4A1 or CD48;
NCAM1 or NKP46;
ITGAM, ITGAX, CD1C, or CLEC4C;
IL17A or IL17F; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
CTLA4, BTLA, LAG3, HAVCR2, or PDCD1; and CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
IL17A or IL17F;
CCL2, IL1B, IL8, IL6, or PTGS2; and
CX3CL1, CXCL9, CXCL10, CXCR3, CCL21, CCL22.
FOXP3;
MS4A1 or CD48;
NCAM1 or NKP46;
IL17A or IL17F;
CTLA4, BTLA, LAG3, HAVCR2, or PDCD1; and CX3CL1, CXCL9, CXCL10, CXCR3, CCL21, CCL22.
FOXP3;
MS4A1 or CD48;
NCAM1 or NKP46;
IL17A or IL17F;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
FOXP3;
MS4A1 or CD48;
NCAM1 or NKP46;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F;

TABLE 6-continued

Combinations of six gene signature sets

CCL2, IL1B, IL8, IL6, or PTGS2; and
CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F;
CTLA4, BTLA, LAG3, HAVCR2, or PDCD1; and CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
FOXP3;
MS4A1 or CD48;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
FOXP3;
MS4A1 or CD48;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F;
CTLA4, BTLA, LAG3, HAVCR2, or PDCD1; and CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
CCL2, IL1B, IL8, IL6, or PTGS2;

CTLA4, BTLA, LAG3, HAVCR2, or PDCD1; and CX3CL1, CXCL9, CXCL10, CXCR3, CCL21, CCL22.
FOXP3;
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
FOXP3;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
FOXP3;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
IL17A or IL17F;

TABLE 6-continued

Combinations of six gene signature sets

CTLA4, BTLA, LAG3, HAVCR2, or PDCD1; and CX3CL1, CXCL9, CXCL10, CXCR3, CCL21, CCL22.
MS4A1 or CD48;
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
MS4A1 or CD48;
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
MS4A1 or CD48;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
MS4A1 or CD48;
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
ITGAM, ITGAX, CD1C, or CLEC4C;
L17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
MS4A1 or CD48;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
MS4A1 or CD48;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
IL17A or IL17F;
CCL2, IL1B, IL8, IL6, or PTGS2;
CTLA4, BTLA, LAG3, HAVCR2, or PDCD1;

TABLE 6-continued

Combinations of six gene signature sets

CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
NCAM1 or NKP46;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
NCAM1 or NKP46;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
ITGAM, ITGAX, CD1C or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.

In some embodiments, a combination of six particular gene signature sets includes, or consists of, a combination including one or more of the following gene signature sets: B cell Signature 2 (CD79A, MS4A1, CD19, STAP1, KIAA0125, POU2AF1, FCRL5); NK cell Signature 2 (KLRC3, KLRK1, KLRC2, KLRD1); Macrophage (CD68, CD163, ITGAM, ITGAX, CD14); M2 Macrophage (LAPTM5, LAIR1, CD4, CSF1R, CD163, ADAP2, CD68, MRC1, CD45RO, SLA, MSR1, FPR3, FCGR2A, FCGR3A); T cell (CD3D, CD3E, CD2, CD3G, CD6, TRAT1, CD28, LCK); IB T cell Signature 2 (CTLA4, BTLA, LAG3, HAVCR2, PDCD1, TIGIT); IB APC Signature 2 (CD274, PDL2, IDO1, PVR); Activated CD4 T cell (CD4, IL2RA, CD69); Antigen processing (TAPBP, TAP1, TAP2, PSMB9, PSMB8); Costimulatory ligand (CD40, CD80, CD86, CD70, GITRL); Costimulatory receptor (CD27, CD28, ICOS, TNFRSF4, TNFRSF14, TNFRSF18, TNFSF14, CD226); Cytolytic (GNLY, KLRK1, KLRB1, GZMH, GZMA, KLRD1, NKG7); and/or Active fibroblast (FAP, FN1, MMP2, BGN, LOXL2, PDPN, PDGFRB, COL4A1, COL4A2, COL5A1, COL8A1).

In another embodiment, the expression levels of one or more of the genes in an immune cell gene signature in seven particular gene signature sets are determined. For example, combinations of seven particular gene signature sets are set forth in Table 7 below.

TABLE 7

Combinations of seven gene signature sets

CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F; and
CCL2, IL1B, IL8, IL6, or PTGS2.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F; and
CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
MS4A1 or CD48;
NCAM1 or NKP46;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
MS4A1 or CD48;

TABLE 7-continued

Combinations of seven gene signature sets

NCAM1 or NKP46;
ITGAM, ITGAX, CD1C, or CLEC4C;
IL17A or IL17F;
CCL2, IL1B, IL8, IL6, or PTGS2; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CD276, PDL1, PDL2, or IDO1.
FOXP3;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
FOXP3;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;

TABLE 7-continued

Combinations of seven gene signature sets

CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3; NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.

TABLE 7-continued

Combinations of seven gene signature sets

CD8A, GZMA, GZMB, IFNγ, EOMES, or PRF1;
FOXP3;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;

TABLE 7-continued

Combinations of seven gene signature sets

ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
NCAM1 or NKP46;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
IL17A or IL17F;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
MS4A1 or CD48;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
NCAM1 or NKP46;
IL17A or IL17F;
CCL2, IL1B, IL8, IL6, or PTGS2;

TABLE 7-continued

Combinations of seven gene signature sets

CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and CX3CL1, CXCL9, CXCL10, CXCR3, CCL21, CCL22.
MS4A1 or CD48;
NCAM1 or NKP46;
ITGAM, ITGAX, CD1C, or CLEC4C;
IL17A or IL17F; CCL2, IL1B, IL8, IL6, or PTGS2;
CD276, PDL1, PDL2, or IDO1; and
CX3CL1, CXCL9, CXCL10, CXCR3, CCL21, CCL22.

In some embodiments, a combination of seven particular gene signature sets includes, or consists of, a combination including one or more of the following gene signature sets: B cell Signature 2 (CD79A, MS4A1, CD19, STAP1, KIAA0125, POU2AF1, FCRL5); NK cell Signature 2 (KLRC3, KLRK1, KLRC2, KLRD1); Macrophage (CD68, CD163, ITGAM, ITGAX, CD14); M2 Macrophage (LAPTM5, LAIR1, CD4, CSF1R, CD163, ADAP2, CD68, MRC1, CD45RO, SLA, MSR1, FPR3, FCGR2A, FCGR3A); T cell (CD3D, CD3E, CD2, CD3G, CD6, TRAT1, CD28, LCK); IB T cell Signature 2 (CTLA4, BTLA, LAG3, HAVCR2, PDCD1, TIGIT); IB APC Signature 2 (CD274, PDL2, IDO1, PVR); Activated CD4 T cell (CD4, IL2RA, CD69); Antigen processing (TAPBP, TAP1, TAP2, PSMB9, PSMB8); Costimulatory ligand (CD40, CD80, CD86, CD70, GITRL); Costimulatory receptor (CD27, CD28, ICOS, TNFRSF4, TNFRSF14, TNFRSF18, TNFSF14, CD226); Cytolytic (GNLY, KLRK1, KLRB1, GZMH, GZMA, KLRD1, NKG7); and/or Active fibroblast (FAP, FN1, MMP2, BGN, LOXL2, PDPN, PDGFRB, COL4A1, COL4A2, COL5A1, COL8A1).

In another embodiment, the expression levels of one or more of the genes in an immune cell gene signature in eight particular gene signature sets are determined. For example, combinations of eight particular gene signature sets are set forth in Table 8 below.

TABLE 8

Combinations of eight gene signature sets

CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CTLA4, BTLA, LAG3, HAVCR2, or PDCD1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and

TABLE 8-continued

Combinations of eight gene signature sets

CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;

TABLE 8-continued

Combinations of eight gene signature sets

IL17A or IL17F;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
NCAM1 or NKP46;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
MS4A1 or CD48;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
NCAM1 or NKP46;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
FOXP3;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
CD8A, GZMA, GZMB; IFNγ, EOMES, or PRF1;

TABLE 8-continued

Combinations of eight gene signature sets

MS4A1 or CD48;
NCAM1 or NKP46;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
CD8A, GZMA, GZMB, IFNγ, EOMES, or PRF1;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, or CCL22.
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
FOXP3;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
FOXP3;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
FOXP3;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
FOXP3;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, or CCL22.

In some embodiments, a combination of eight particular gene signature sets includes, or consists of, a combination including one or more of the following gene signature sets: B cell Signature 2 (CD79A, MS4A1, CD19, STAP1, KIAA0125, POU2AF1, FCRL5); NK cell Signature 2 (KLRC3, KLRK1, KLRC2, KLRD1); Macrophage (CD68, CD163, ITGAM, ITGAX, CD14); M2 Macrophage (LAPTM5, LAIR1, CD4, CSF1R, CD163, ADAP2, CD68, MRC1, CD45RO, SLA, MSR1, FPR3, FCGR2A, FCGR3A); T cell (CD3D, CD3E, CD2, CD3G, CD6, TRAT1, CD28, LCK); IB T cell Signature 2 (CTLA4, BTLA, LAG3, HAVCR2, PDCD1, TIGIT); IB APC Signature 2 (CD274, PDL2, IDO1, PVR); Activated CD4 T cell (CD4, IL2RA, CD69); Antigen processing (TAPBP, TAP1, TAP2, PSMB9, PSMB8); Costimulatory ligand (CD40, CD80, CD86, CD70, GITRL); Costimulatory receptor (CD27, CD28, ICOS, TNFRSF4, TNFRSF14, TNFRSF18, TNFSF14, CD226); Cytolytic (GNLY, KLRK1, KLRB1, GZMH, GZMA, KLRD1, NKG7); and/or Active fibroblast (FAP, FN1, MMP2, BGN, LOXL2, PDPN, PDGFRB, COL4A1, COL4A2, COL5A1, COL8A1).

In some embodiment, the expression levels of one or more of the genes in the immune cell gene signature in nine gene signature sets are determined. For example, combinations of nine particular gene signature sets are set forth in Table 9 below.

TABLE 9

Combinations of nine gene signature sets

CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;

TABLE 9-continued

Combinations of nine gene signature sets

IL17A or IL17F;
CCL2, IL1B, IL8, IL6, or PTGS2;
CTLA4, BTLA, LAG3, HAVCR2, or PDCD1; and
CD276, PDL1, PDL2, or IDO1.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
IL17A or IL17F;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
ITGAM, ITGAX, CD1C, or CLEC4C;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
NCAM1 or NKP46;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
MS4A1 or CD48;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
FOXP3;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
CD8A, GZMA, GZMB, IFNγ, EOMES, or PRF1;
MS4A1 or CD48;
NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.
FOXP3;
MS4A1 or CD48;

TABLE 9-continued

Combinations of nine gene signature sets

NCAM1 or NKP46;
ITGAM, ITGAX, CD1C, or CLEC4C;
IL17A or IL17F;
CCL2, IL1B, IL8, IL6, or PTGS2;
CTLA4, BTLA, LAG3, HAVCR2, or PDCD1;
CD276, PDL1, PDL2, or IDO1; and
CX3CL1, CXCL9, CXCL10, CXCR3, CCL21, CCL22.

In some embodiments, a combination of nine particular gene signature sets includes, or consists of, a combination including one or more of the following gene signature sets: B cell Signature 2 (CD79A, MS4A1, CD19, STAP1, KIAA0125, POU2AF1, FCRL5); NK cell Signature 2 (KLRC3, KLRK1, KLRC2, KLRD1); Macrophage (CD68, CD163, ITGAM, ITGAX, CD14); M2 Macrophage (LAPTM5, LAIR1, CD4, CSF1R, CD163, ADAP2, CD68, MRC1, CD45RO, SLA, MSR1, FPR3, FCGR2A, FCGR3A); T cell (CD3D, CD3E, CD2, CD3G, CD6, TRAT1, CD28, LCK); IB T cell Signature 2 (CTLA4, BTLA, LAG3, HAVCR2, PDCD1, TIGIT); IB APC Signature 2 (CD274, PDL2, IDO1, PVR); Activated CD4 T cell (CD4, IL2RA, CD69); Antigen processing (TAPBP, TAP1, TAP2, PSMB9, PSMB8); Costimulatory ligand (CD40, CD80, CD86, CD70, GITRL); Costimulatory receptor (CD27, CD28, ICOS, TNFRSF4, TNFRSF14, TNFRSF18, TNFSF14, CD226); Cytolytic (GNLY, KLRK1, KLRB1, GZMH, GZMA, KLRD1, NKG7); and/or Active fibroblast (FAP, FN1, MMP2, BGN, LOXL2, PDPN, PDGFRB, COL4A1, COL4A2, COL5A1, COL8A1).

In other embodiments, the expression level of one or more of the genes in an immune cell gene signature in any 10, 11, 12, 13, 14, 15, 16, 17, 18, 19, 20, 21, or 22 particular gene signature sets set forth in Table 1 are determined.

In some embodiments, the expression levels of one or more of the genes in an immune cell gene signature in all 23 gene signature sets are determined. For example:
CD8A, GZMA, GZMB, IFNγ, EOMES, or PRF1;
FOXP3;
MS4A1 or CD48;
CD79A, MS4A1, CD19, STAP1, KIAA0125, POU2AF1, or FCRL5;
NCAM1 or NKP46;
KLRC3, KLRK1, KLRC2, or KLRD1;
ITGAM, ITGAX, CD1C, or CLEC4C;
CD68, CD163, ITGAM, ITGAX, or CD14;
LAPTM5, LAIR1, CD4, CSF1R, CD163, ADAP2, CD68, MRC1, CD45RO, SLA, MSR1, FPR3, FCGR2A, or FCGR3A;
IL17A or IL17F;
CCL2, IL1B, IL8, IL6, or PTGS2;
CD3D, CD3E, CD2, CD3G, CD6, TRAT1, CD28, or LCK;
CTLA4, BTLA, LAG3, HAVCR2, or PDCD1;
CTLA4, BTLA, LAG3, HAVCR2, PDCD1, or TIGIT;
CD276, PDL1, PDL2, or IDO1;
CD274, PDL2, IDO1, or PVR;
CX3CL1, CXCL9, CXCL10, CXCR3, CCL21, or CCL22;
CD4, IL2RA, or CD69;
TAPBP, TAP1, TAP2, PSMB9, or PSMB8;
CD40, CD80, CD86, CD70, or GITRL;
CD27, CD28, ICOS, TNFRSF4, TNFRSF14, TNFRSF18, TNFSF14, or CD226;

GNLY, KLRK1, KLRB1, GZMH, GZMA, KLRD1, or NKG7; and

FAP, FN1, MMP2, BGN, LOXL2, PDPN, PDGFRB, COL4A1, COL4A2, COL5A1, COL8A1 is determined. In some embodiments, one or more of the genes in Table 14 is further included as an immune cell signature gene in one of the gene sets described herein (e.g., $T_{eff}$, B cell, NK cell, $T_{reg}$, myeloid, T cell chemotaxis, etc.). In other embodiments, one or more of the genes in Table 14 is further included as an immune cell signature gene in a further identified gene set (e.g., Th1, Th2, mast cells, antigen presenting cells (APC), etc.).

Optionally, the methods include determining the ratio of expression levels of one or more immune cell gene signatures between gene sets to further identify a cancer patient for treatment with an immunotherapy or who may have the likelihood of benefiting from a particular immunotherapy. For example, the ratio of expression levels of one or more immune cell gene signatures in the $T_{eff}$ gene set (e.g., one or more of CD8A, GZMA, GZMB, IFNγ, EOMES, or PRF1) may be compared to the expression levels of one or more immune cell gene signatures in any of the $T_{reg}$ gene set (e.g., FOXP3), an IB APC gene signature set (e.g., one or more of CD276, PDL1, PDL2, or IDO1), and/or an IB T cell gene signature set (e.g., one or more of CTLA4, BTLA, LAG3, HAVCR2, or PDCD1) to determine whether the patient should be treated with an immunotherapy or would have a likelihood of benefiting from particular immunotherapy. In other embodiments, the methods include determining the ratio of the presence of the immune cell subtype (e.g., $T_{eff}$ to $T_{reg}$, $T_{eff}$ to B cells, $T_{eff}$ to NK cells, $T_{eff}$ to IB T cell, $T_{eff}$ to IB APC, $T_{eff}$ to inflammatory cells) in a sample from a patient with cancer (e.g., bladder cancer, breast cancer, colorectal cancer, gastric cancer, liver cancer, melanoma, lung cancer (e.g., non-small cell lung carcinoma), ovarian cancer, or renal cell carcinoma).

The expression level of an immune cell gene signature may be assessed by any method known in the art suitable for determination of specific protein levels in a patient sample, and is preferably determined by an immunohistochemical ("IHC") method employing antibodies specific for an immune cell gene signature. Such methods are well known and routinely implemented in the art, and corresponding commercial antibodies and/or kits are readily available. Preferably, the expression levels of the marker/indicator proteins of the invention are assessed using the reagents and/or protocol recommendations of the antibody or kit manufacturer. The skilled person will also be aware of further means for determining the expression level of an immune cell gene signature by IHC methods. Therefore, the expression level of one or more of the markers/indicators of the invention can be routinely and reproducibly determined by a person skilled in the art without undue burden. However, to ensure accurate and reproducible results, the invention also encompasses the testing of patient samples in a specialized laboratory that can ensure the validation of testing procedures.

Preferably, the expression level of an immune cell gene signature is assessed in a biological sample that contains or is suspected to contain cancer cells. The sample may be, for example, a tissue resection, a tissue biopsy, or a metastatic lesion obtained from a patient suffering from, suspected to suffer from, or diagnosed with cancer (e.g., bladder cancer, breast cancer, colorectal cancer, gastric cancer, liver cancer, melanoma, lung cancer (e.g., non-small cell lung carcinoma), ovarian cancer, or renal cell carcinoma). Preferably, the sample is a sample of a tissue, a resection or biopsy of a tumor, a known or suspected metastatic cancer lesion or section, or a blood sample, e.g., a peripheral blood sample, known or suspected to comprise circulating cancer cells. The sample may comprise both cancer cells, i.e., tumor cells, and non-cancerous cells, and, in certain embodiments, comprises both cancerous and non-cancerous cells. In aspects of the invention comprising the determination of gene expression in stroma components, the sample comprises both cancer/tumor cells and non-cancerous cells that are, e.g., associated with the cancer/tumor cells (e.g., tumor associated fibroblasts, endothelial cells, pericytes, the extra-cellular matrix, and/or various classes of leukocytes). In other aspects, the skilled artisan, e.g., a pathologist, can readily discern cancer cells from non-cancerous (e.g., stromal cells, endothelial cells, etc.). Methods of obtaining biological samples including tissue resections, biopsies, and body fluids, e.g., blood samples comprising cancer/tumor cells, are well known in the art. In some embodiments, the sample obtained from the patient is collected prior to beginning any immunotherapy or other treatment regimen or therapy, e.g., chemotherapy or radiation therapy for the treatment of cancer or the management or amelioration of a symptom thereof. Therefore, in some embodiments, the sample is collected before the administration of immunotherapeutic agents or other agents, or the start of immunotherapy or other treatment regimen.

In addition to the methods described above, the invention also encompasses further immunohistochemical methods for assessing the expression level of one or more immune cell gene signatures, such as by Western blotting and ELISA-based detection. As is understood in the art, the expression level of the marker/indicator proteins of the invention may also be assessed at the mRNA level by any suitable method known in the art, such as Northern blotting, real time PCR, and RT PCR. Immunohistochemical- and mRNA-based detection methods and systems are well known in the art and can be deduced from standard textbooks, such as Lottspeich (Bioanalytik, Spektrum Akademisher Verlag, 1998) or Sambrook and Russell (Molecular Cloning: A Laboratory Manual, CSH Press, Cold Spring Harbor, N.Y., U.S.A., 2001). The described methods are of particular use for determining the expression levels of an immune cell gene signature in a patient or group of patients relative to control levels established in a population diagnosed with advanced stages of a cancer (e.g., bladder cancer, breast cancer, colorectal cancer, gastric cancer, liver cancer, melanoma, lung cancer (e.g., non-small cell lung carcinoma), ovarian cancer, or renal cell carcinoma).

For use in the detection methods described herein, the skilled person has the ability to label the polypeptides or oligonucleotides encompassed by the present invention. As routinely practiced in the art, hybridization probes for use in detecting mRNA levels and/or antibodies or antibody fragments for use in IHC methods can be labeled and visualized according to standard methods known in the art. Non-limiting examples of commonly used systems include the use of radiolabels, enzyme labels, fluorescent tags, biotin-avidin complexes, chemiluminescence, and the like.

The expression level of one or more of an immune cell gene signature can also be determined on the protein level by taking advantage of immunoagglutination, immunoprecipitation (e.g., immunodiffusion, immunoelectrophoresis, immune fixation), western blotting techniques (e.g., in situ immuno histochemistry, in situ immuno cytochemistry, affinity chromatography, enzyme immunoassays), and the like. Amounts of purified polypeptide may also be determined by physical methods, e.g., photometry. Methods of quantifying a particular polypeptide in a mixture usually rely on specific binding, e.g., of antibodies.

As mentioned above, the expression level of the marker/indicator proteins according to the present invention may also be reflected in increased or decreased expression of the corresponding gene(s) encoding the immune cell gene signature. Therefore, a quantitative assessment of the gene product prior to translation (e.g. spliced, unspliced or partially spliced mRNA) can be performed in order to evaluate the expression of the corresponding gene(s). The person skilled in the art is aware of standard methods to be used in this context or may deduce these methods from standard textbooks (e.g. Sambrook, 2001). For example, quantitative data on the respective concentration/amounts of mRNA encoding one or more of an immune cell gene signature as described herein can be obtained by Northern Blot, Real Time PCR, and the like.

IV. Methods of Treatment

The invention further provides methods for administering an activating or suppressing immunotherapy to patients with a cancer (e.g., bladder cancer, breast cancer, colorectal cancer, gastric cancer, liver cancer, melanoma, lung cancer (e.g., non-small cell lung carcinoma), ovarian cancer, or renal cell carcinoma that is chemotherapy-resistant, chemotherapy-sensitive, refractory, primary, advanced, or recurrent), if the patient is determined to have a change in the level of expression of one or more immune cell gene signatures in any of the gene sets. In one embodiment, the patient is administered an activating immunotherapy if there is an increase in expression level of one or more immune cell gene signatures in the $T_{eff}$ gene set (i.e., one or more of CD8A, GZMA, GZMB, IFNγ, EOMES, or PRF1) or a decrease in expression level of one or more immune cell gene signatures in the $T_{reg}$ gene set. In other embodiments, the patient is administered a suppressing immunotherapy if there is an increase in expression level of one or more immune cell gene signatures in the $T_{reg}$ gene set (i.e., FOXP3) or a decrease in expression level of one or more immune cell gene signatures in the $T_{eff}$ gene set (i.e., one or more of CD8A, GZMA, GZMB, IFNγ, EOMES, or PRF1). In other embodiments, in addition to determining the expression levels of one or more immune cell gene signatures in the $T_{eff}$ and/or $T_{reg}$ gene sets, expression levels of one or more immune cell gene signatures in combinations of any one of the gene sets as set forth in Tables 2-8 can be determined prior to administering a particular immunotherapy regimen to the patient (e.g., an activating immunotherapy regimen or a suppressing immunotherapy regimen).

In some embodiments, the activating immunotherapy includes a CD28, OX40, GITR, CD137, CD27, ICOS, HVEM, NKG2D, MICA, or 2B4 agonist. In particular embodiments, the agonist (e.g., a CD28, OX40, GITR, CD137, CD27, ICOS, HVEM, NKG2D, MICA, or 2B4 agonist) increases, enhances, or stimulates an immune response or function in a patient having cancer. In some embodiments, the agonist modulates the expression and/or activity of a ligand (e.g., a T cell receptor ligand), and/or increases or stimulates the interaction of the ligand with its immune receptor, and/or increases or stimulates the intracellular signaling mediated by ligand binding to the immune receptor. In other embodiments, the suppressing immunotherapy includes a CTLA-4, PD-1 axis, TIM-3, BTLA, VISTA, LAG-3, B7H4, CD96, TIGIT, or CD226 antagonist. In particular embodiments, the antagonist (e.g., a CTLA-4, PD-1 axis, TIM-3, BTLA, VISTA, LAG-3, B7H4, CD96, TIGIT, or CD226 antagonist) is an agent that inhibits and/or blocks the interaction of a ligand (e.g., a T cell receptor ligand) with its immune receptor or is an antagonist of ligand and/or receptor expression and/or activity, or is an agent that blocks the intracellular signaling mediated by a ligand (e.g., a T cell receptor ligand) with its immune receptor.

In some embodiments, the methods of the invention may further comprise administering the activating immunotherapy (e.g., a CD28, OX40, GITR, CD137, CD27, ICOS, HVEM, NKG2D, MICA, or 2B4 agonist) or the suppressing immunotherapy (e.g., a CTLA-4, PD-1 axis, TIM-3, BTLA, VISTA, LAG-3, B7H4, CD96, TIGIT, or CD226 antagonist) with an additional therapy. The additional therapy may be radiation therapy, surgery, chemotherapy, gene therapy, DNA therapy, viral therapy, RNA therapy, bone marrow transplantation, nanotherapy, monoclonal antibody therapy, or a combination of the foregoing. The additional therapy may be in the form of an adjuvant or neoadjuvant therapy. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy may be one or more of the chemotherapeutic agents described hereinabove. For example, these methods involve the co-administration of the activating immunotherapy (e.g., a CD28, OX40, GITR, CD137, CD27, ICOS, HVEM, NKG2D, MICA, or 2B4 agonist) or the suppressing immunotherapy (e.g., a CTLA-4, PD-1 axis, TIM-3, BTLA, VISTA, LAG-3, B7H4, CD96, TIGIT, or CD226 antagonist) with one or more additional chemotherapeutic agents (e.g., carboplatin and/or paclitaxel), as described further below. Immunotherapy optionally in combination with one or more chemotherapeutic agents (e.g., carboplatin and/or paclitaxel) preferably extends and/or improves survival, including progression free survival (PFS) and/or overall survival (OS). In one embodiment, immunotherapy extends survival at least about 20% more than survival achieved by administering an approved anti-tumor agent, or standard of care, for the cancer being treated.

For the prevention or treatment of cancer (e.g., bladder cancer, breast cancer, colorectal cancer, gastric cancer, liver cancer, melanoma, lung cancer (e.g., non-small cell lung carcinoma), ovarian cancer, or renal cell carcinoma), the dose of the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) will depend on the type of cancer to be treated, as defined above, the severity and course of the cancer, whether the antibody is administered for preventive or therapeutic purposes, previous therapy, the patient's clinical history and response to the drug, and the discretion of the attending physician.

In one embodiment, a fixed dose of the agonist or antagonist is administered. The fixed dose may suitably be administered to the patient at one time or over a series of treatments. Where a fixed dose is administered, preferably it is in the range from about 20 mg to about 2000 mg. For example, the fixed dose may be approximately 420 mg, approximately 525 mg, approximately 840 mg, or approximately 1050 mg of the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist). Where a series of doses are administered, these may, for example, be administered approximately every week, approximately every 2 weeks, approximately every 3 weeks, or approximately every 4 weeks, but preferably approximately every 3 weeks. The fixed doses may, for example, continue to be administered until disease progression, adverse event, or other time as determined by the physician. For example, from about two, three, or four, up to about 17 or more fixed doses may be administered.

In one embodiment, one or more loading dose(s) of the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) are administered, followed by one or more maintenance dose(s). In another embodiment, a plurality of the same dose is administered to the patient.

While the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) may be administered as a single anti-tumor agent, the patient is optionally treated with a combination of agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) and one or more (additional) chemotherapeutic agent(s). Exemplary chemotherapeutic agents herein include: gemcitabine, carboplatin, oxaliplatin, irinotecan, fluoropyrimidine (e.g., 5-FU), paclitaxel (e.g., nab-paclitaxel), docetaxel, topotecan, capecitabine, temozolomide, interferon-alpha, and/or liposomal doxorubicin (e.g., pegylated liposomal doxorubicin). The combined administration includes co-administration or concurrent administration, using separate formulations or a single pharmaceutical formulation, and consecutive administration in either order, wherein preferably there is a time period while both (or all) active agents simultaneously exert their biological activities. Thus, the chemotherapeutic agent may be administered prior to, or following, administration of the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist). In this embodiment, the timing between at least one administration of the chemotherapeutic agent and at least one administration of the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) is preferably approximately 1 month or less (3 weeks, 2, weeks, 1 week, 6 days, 5, days, 4 days, 3 days, 2 days, 1 day). Alternatively, the chemotherapeutic agent and the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) are administered concurrently to the patient, in a single formulation or separate formulations. Treatment with the combination of the chemotherapeutic agent (e.g., carboplatin and/or paclitaxel) and the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) may result in a synergistic, or greater than additive, therapeutic benefit to the patient.

Particularly desired chemotherapeutic agents for combining with the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist), e.g. for therapy of ovarian cancer, include: a chemotherapeutic agent such as a platinum compound (e.g., carboplatin), a taxol such as paclitaxel or docetaxel, topotecan, or liposomal doxorubicin.

Particularly desired chemotherapeutic agents for combining with the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist), e.g., for therapy of breast cancer, include: chemotherapeutic agents such as capecitabine, and a taxol such as paclitaxel (e.g., nab-paclitaxel) or docetaxel.

Particularly desired chemotherapeutic agents for combining with the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist), e.g., for therapy of colorectal cancer, include: chemotherapeutic agents such as a fluoropyrimidine (e.g., 5-FU), paclitaxel, cisplatin, topotecan, irinotecan, fluoropyrimidine-oxaliplatin, fluoropyrimidine-irinotecan, FOLFOX4 (5-FU, lecovorin, oxaliplatin), and IFL (ironotecan, 5-FU, leucovorin).

Particularly desired chemotherapeutic agents for combining with the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist), e.g., for therapy of renal cell carcinoma, include: chemotherapeutic agents such as interferon-alpha2a.

A chemotherapeutic agent, if administered, is usually administered at dosages known therefore, or optionally lowered due to combined action of the drugs or negative side effects attributable to administration of the chemotherapeutic agent. Preparation and dosing schedules for such chemotherapeutic agents may be used according to manufacturers' instructions or as determined empirically by the skilled practitioner. Where the chemotherapeutic agent is paclitaxel, preferably, it is administered at a dose between about 130 mg/m$^2$ to 200 mg/m$^2$ (for example approximately 175 mg/m$^2$), for instance, over 3 hours, once every 3 weeks. Where the chemotherapeutic agent is carboplatin, preferably it is administered by calculating the dose of carboplatin using the Calvert formula which is based on a patient's preexisting renal function or renal function and desired platelet nadir. Renal excretion is the major route of elimination for carboplatin. The use of this dosing formula, as compared to empirical dose calculation based on body surface area, allows compensation for patient variations in pretreatment renal function that might otherwise result in either underdosing (in patients with above average renal function) or overdosing (in patients with impaired renal function). The target AUC of 4-6 mg/mL/min using single agent carboplatin appears to provide the most appropriate dose range in previously treated patients.

Aside from the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) and chemotherapeutic agent, other therapeutic regimens may be combined therewith.

For example, a second (third, fourth, etc.) chemotherapeutic agent(s) may be administered, wherein the second chemotherapeutic agent is an antimetabolite chemotherapeutic agent, or a chemotherapeutic agent that is not an antimetabolite. For example, the second chemotherapeutic agent may be a taxane (such as paclitaxel or docetaxel), capecitabine, or platinum-based chemotherapeutic agent (such as carboplatin, cisplatin, or oxaliplatin), anthracycline (such as doxorubicin, including, liposomal doxorubicin), topotecan, pemetrexed, vinca alkaloid (such as vinorelbine), and TLK 286. "Cocktails" of different chemotherapeutic agents may be administered.

Other therapeutic agents that may be combined with the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist), and/or chemotherapeutic agent include any one or more of: a HER inhibitor, HER dimerization inhibitor (for example, a growth inhibitory HER2 antibody such as trastuzumab, or a HER2 antibody which induces apoptosis of a HER2-overexpressing cell, such as 7C2, 7F3 or humanized variants thereof); an antibody directed against a different tumor associated antigen, such as EGFR, HER3, HE R4; anti-hormonal compound, e.g., an anti-estrogen compound such as tamoxifen, or an aromatase inhibitor; a cardioprotectant (to prevent or reduce any myocardial dysfunction associated with the therapy); a cytokine; an EGFR-targeted drug (such as TARCEVA® IRESSA® or cetuximab); a tyrosine kinase inhibitor; a COX inhibitor (for instance a COX-1 or COX-2 inhibitor); non-steroidal anti-inflammatory drug, celecoxib (CELEBREX®); farnesyl transferase inhibitor (for example, Tipifarnib/ZARNESTRA® R115777 available from Johnson and Johnson or Lonafarnib SCH66336 available from Schering-Plough); antibody that binds oncofetal protein CA 125 such as Oregovomab (MoAb B43.13); HER2 vaccine (such as HER2AutoVac vaccine from Pharmexia, or APC8024 protein vaccine from Dendreon, or HER2 peptide vaccine from GSK/Corixa); another HER targeting therapy (e.g. trastuzumab, cetuximab, ABX-EGF, EMD7200, gefitinib, erlotinib, CP724714, C11033, GW572016, IMC-11F8, TAK165, etc); Raf and/or ras inhibitor (see, for example, WO 2003/86467); doxorubicin HCl liposome injection (DOXIL®); topoisomerase 1 inhibitor such as topotecan; taxane; HER2 and EGFR dual tyrosine kinase inhibitor such as lapatinib/GW572016; TLK286 (TELCYTA®); EMD-7200; a medicament that treats nausea such as a serotonin antagonist, steroid, or benzodiazepine; a medicament that prevents or treats skin rash or standard acne therapies, including topical or oral antibiotic; a medicament that treats or prevents diarrhea; a body temperature-reducing medicament such as acetaminophen, diphenhydramine, or meperidine; hematopoietic growth factor, etc.

Suitable dosages for any of the above-noted co-administered agents are those presently used and may be lowered due to the combined action (synergy) of the agent and the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist). In addition to the above therapeutic regimes, the patient may be subjected to surgical removal of tumors and/or cancer cells, and/or radiation therapy.

Where the agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) is an antibody, preferably the administered antibody is a naked antibody. The agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) administered may be conjugated with a cytotoxic agent. Preferably, the conjugate and/or antigen to which it is bound is/are internalized by the cell, resulting in increased therapeutic efficacy of the conjugate in killing the cancer cell to which it binds. In a preferred embodiment, the cytotoxic agent targets or interferes with nucleic acid in the cancer cell. Examples of such cytotoxic agents include maytansinoids, calicheamicins, ribonucleases, and DNA endonucleases.

The agonist (e.g., a CD28, OX40, GITR, CD137, CD27, ICOS, HVEM, NKG2D, MICA, or 2B4 agonist) or antagonist (e.g., a CTLA-4, PD-1 axis, TIM-3, BTLA, VISTA, LAG-3, B7H4, CD96, TIGIT, or CD226 antagonist) can be administered by gene therapy. See, for example, WO 96/07321 published Mar. 14, 1996 concerning the use of gene therapy to generate intracellular antibodies. There are two major approaches to getting the nucleic acid (optionally contained in a vector) into the patient's cells; in vivo and ex vivo. For in vivo delivery the nucleic acid is injected directly into the patient, usually at the site where the antibody is required. For ex vivo treatment, the patient's cells are removed, the nucleic acid is introduced into these isolated cells and the modified cells are administered to the patient either directly or, for example, encapsulated within porous membranes which are implanted into the patient (see, e.g. U.S. Pat. Nos. 4,892,538 and 5,283,187). There are a variety of techniques available for introducing nucleic acids into viable cells. The techniques vary depending upon whether the nucleic acid is transferred into cultured cells in vitro or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus. The currently preferred in vivo nucleic acid transfer techniques include transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g. capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., *J. Biol. Chem.* 262:44294432 (1987); and Wagner et al., *Proc. Natl. Acad. Sci. USA* 87:3410-3414 (1990). For review of the currently known gene marking and gene therapy protocols see Anderson et al., *Science* 256:808-813 (1992). See also WO 93/25673 and the references cited therein.

EXAMPLES

Materials and Experimental Methods
Statistical Analysis

Statistical analysis was performed using the R statistical software. FLUIDIGM™ and Nanostring data were normalized using the housekeeping gene approach. Specifically, median gene expression of the five housekeeping genes (SP2, GUSB, TMEM55B, VPS33B, and SDHA) was estimated and subtracted from each sample. Gene set expression was represented by the median expression of the member genes. To evaluate between-indication and within-indication variability for each gene signature, linear mixed effects models were used with indications as the random effect. ICC (intraclass correlation), the ratio of the between-indication variance to the total variance, was computed for each gene signature. Differential expression analysis between the clinical response groups was carried out using Wilcoxon rank sum tests. P values were not adjusted for multiple corrections. Differential expression between primary and metastatic CRC pairs was assessed using Wilcoxon signed rank tests, and the derived p-values were adjusted for multiple testing errors using the Bonferroni method.

Example 1: A High Degree of Correlation was Observed for Immune Cell Signature Genes within a Given Gene Signature Set To assess the characteristics of the immune landscape in the tumor microenvironment of different tumors, PCR based gene expression signatures were employed to analyze the distribution of immune cell subsets across seven cancer types including urothelial bladder cancer (UBC), breast cancer (BC), non-small cell lung cancer (NSCLC), melanoma, renal cell cancers (RCC), ovarian cancer (OvCa), gastric cancer, liver cancer, and colorectal cancer (CRC). Table 1 depicts the immune gene signatures generated based on exclusive expression of genes in immune cell subsets including effector CD8 T cells (Ten), regulatory T cells ($T_{reg}$), T cells (all), activated CD4 T cells, T cell chemotaxis, myeloid cells, macrophages (all), M2 macrophages, B cells, Th17 cells, NK cells, and innate inflammatory signatures. Expression of immune blockers present in T cells (IB T cells) and antigen presenting cells or tumor cells (IB APC/tumors) were also analyzed (Table 1). Table 1 also depicts the immune gene signature sets of antigen processing, costimulatory ligands, costimulatory receptors, cytolytic, angiogenesis, and active fibroblast signatures. The gene signature sets were analyzed using a 90-gene FLUIDIGM™ panel or an 800-gene custom Nanostring panel, as indicated in Table 1, using RNA extracted from archival FFPE tumor specimens. In general, a high degree of correlation was observed for genes within a given gene set by METHODOLOGY (FIGS. 1-11): $T_{eff}$, 0.72; B cell, 0.8; Myeloid, 0.54; Inflammatory, 0.59; T cell IB, 0.49; IB APC/tumors, 0.5. The only exception was IL17 signatures (R=0.3).

Figure 12A:
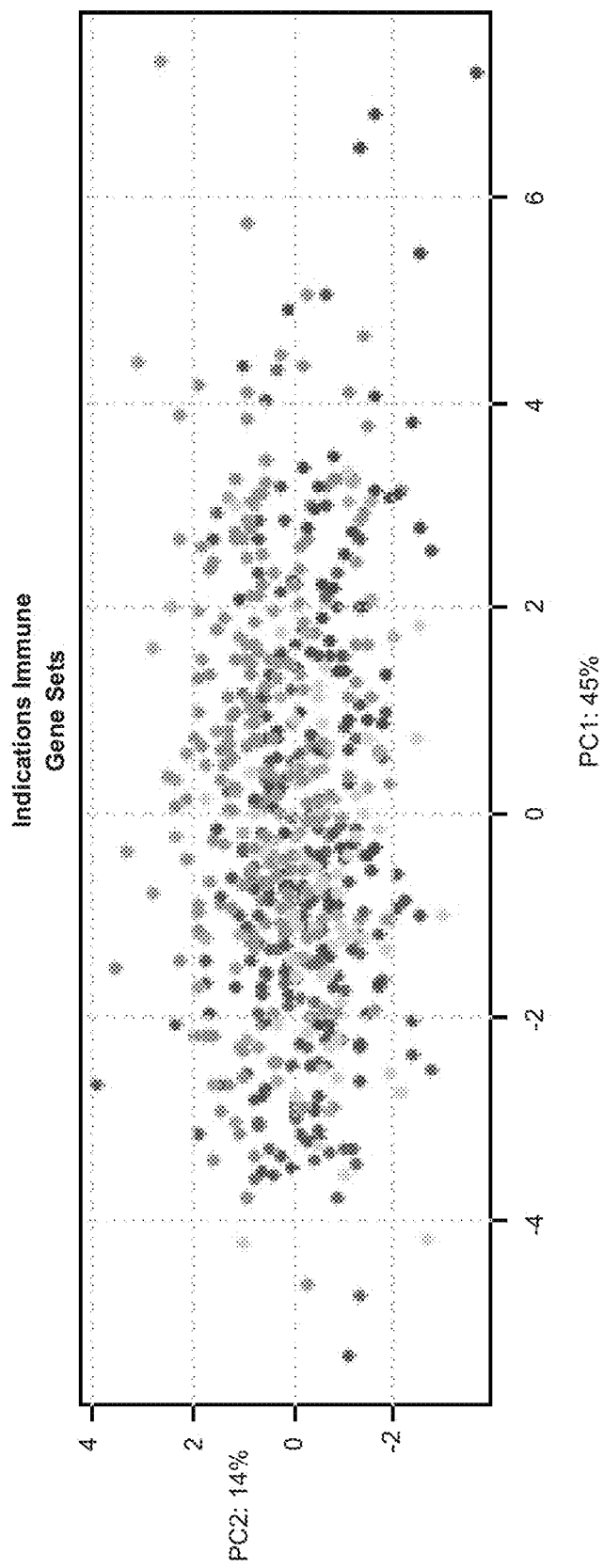
FIGS. 12A-12C are plots of Principal Component Analysis of nine gene sets across cancer indications.
Figure 12B:
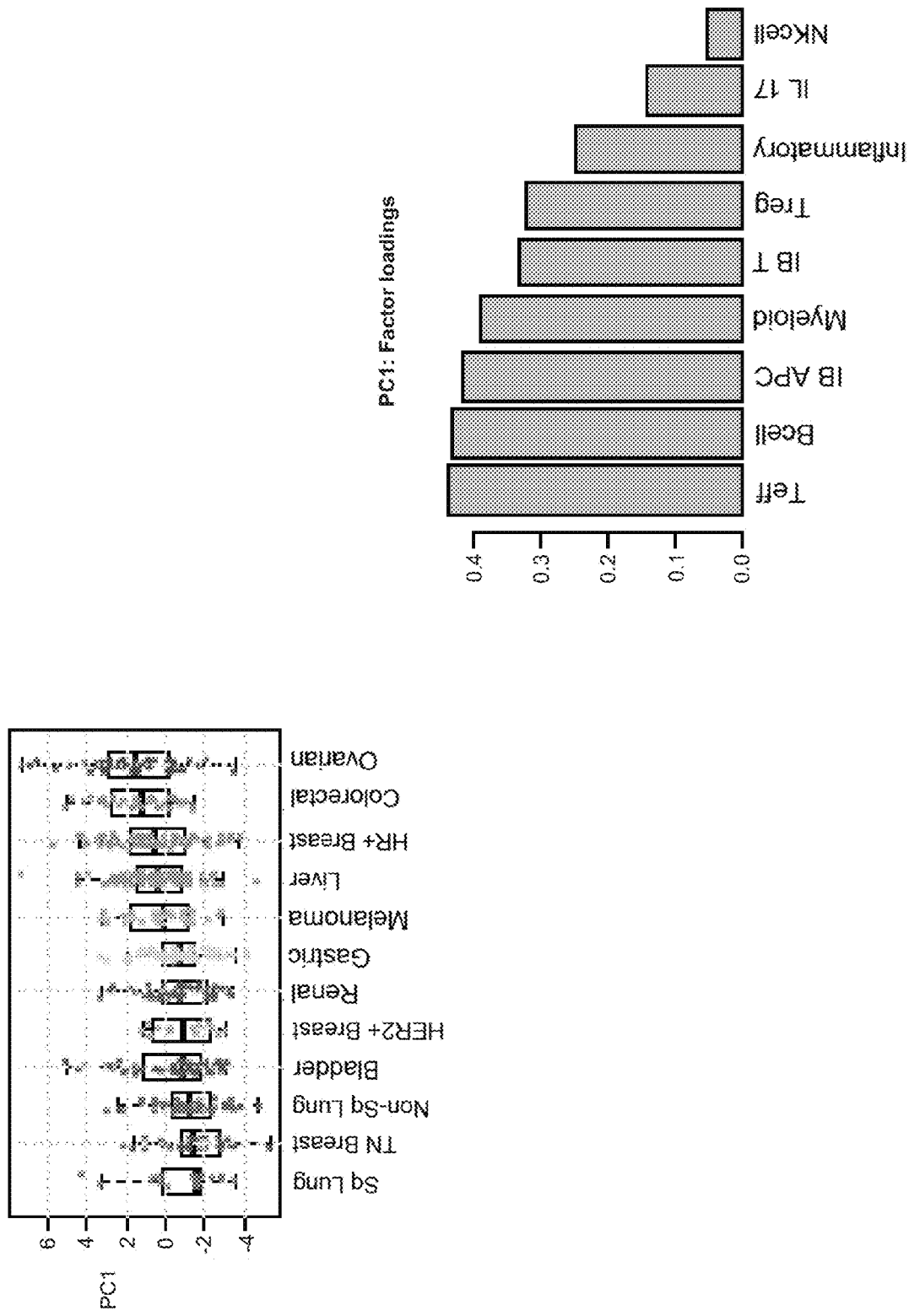
Figure 12C:
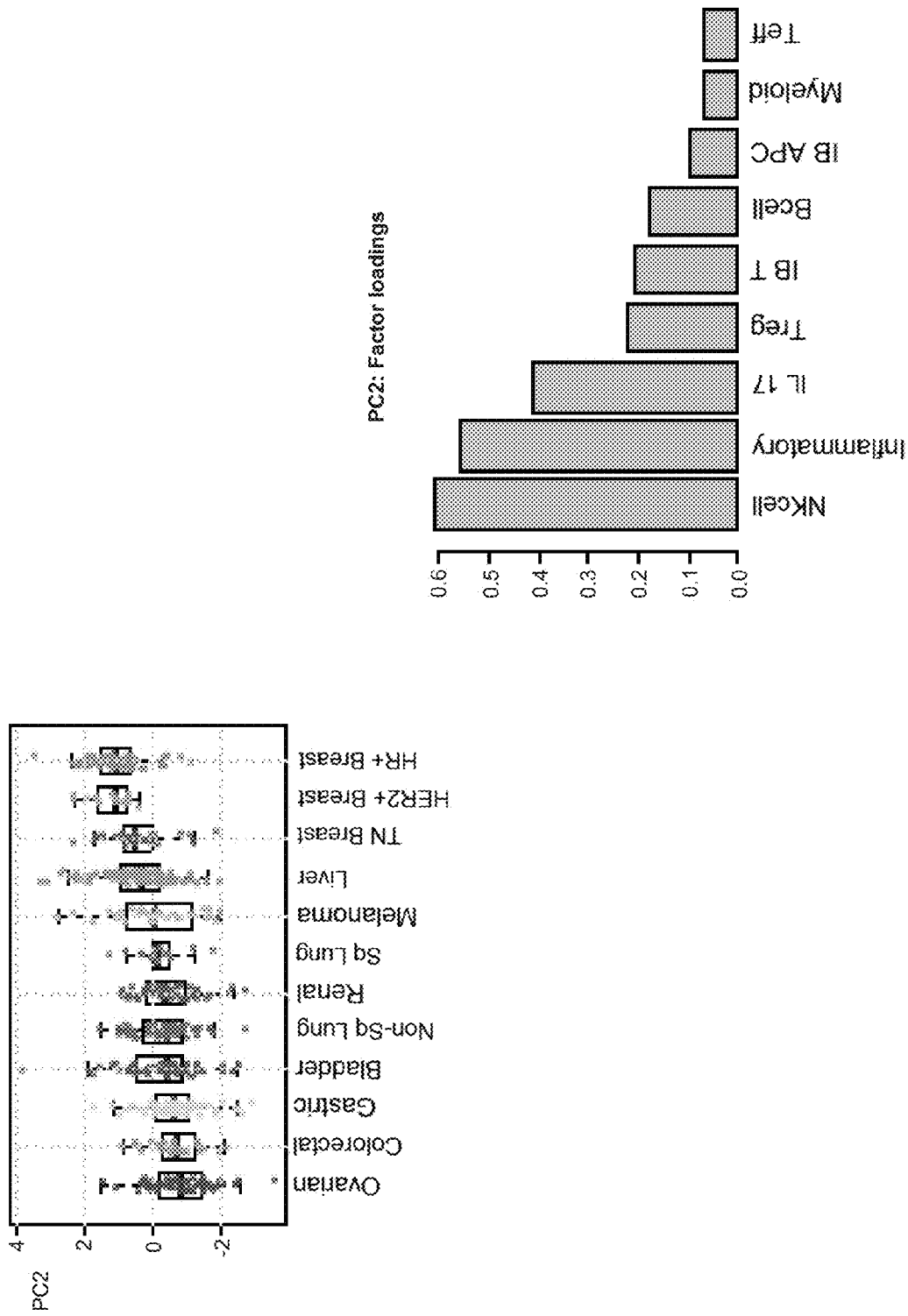

Principal component analysis was applied to decompose the variance for the nine gene signatures. The first two principal components accounted for the majority of the variability (45% and 14% for the first and second components, respectively; FIG. 12A). Inspection of the factor loading of the first component revealed that the first principal component was related to Tefn, B cell, and IB APC/tumors signatures (FIGS. 12B and 12C).

Principal component analysis further suggested that immune landscapes varied between tumor types. To examine whether this between-indication heterogeneity dominates the total variability, linear mixed effects models were used with indications as the random effect to decompose within- and between-indication variability. Intraclass correlation (ICC) was calculated for each gene signature. The ICC is calculated as the ratio of the between-indication variance to the total variance and has a value between 0 and 1. As shown in Table 10, ICCs ranged from 0.11 to 0.29, indicating that there was a substantial amount of within-indication heterogeneity for all gene signatures considered despite clear mean differences between indications.

TABLE 10

| Signature | Between-Indication Variance | Total Variance | ICC |
|---|---|---|---|
| Teff | 0.65 | 2.61 | 0.2 |
| Treg | 0.84 | 2.47 | 0.25 |
| Bcell | 1.02 | 3.32 | 0.24 |
| NKcell | 1.06 | 4.18 | 0.2 |
| Myeloid | 0.32 | 1.57 | 0.17 |
| IL17 | 3.23 | 11.45 | 0.22 |
| Inflammatory | 1.02 | 2.51 | 0.29 |
| IB,T | 0.58 | 4.91 | 0.11 |
| IB,APC | 0.53 | 1.89 | 0.22 |

Example 2: $T_{eff}$ Signature Genes Represent CD8 T Cell Infiltration

Figure 13:
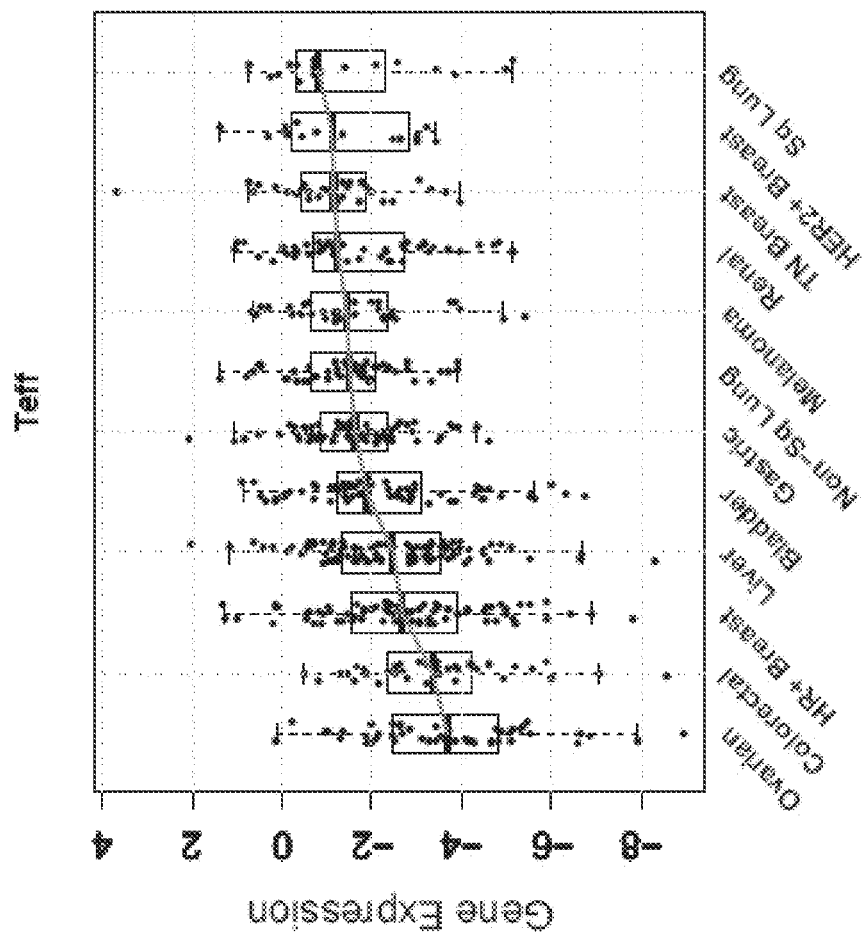
FIG. 13 is a plot of gene expression levels of T effector signature genes across indications.

The expression profile of the signature genes within the $T_{eff}$ gene set (see, Table 1 above) across cancer types was determined. A survey of the $T_{eff}$ signature across cancer types showed differences in median expression not just between cancers but also between subtypes within a given indication. While most indications exhibited comparable expression of Ten genes, NSCLC, melanoma, RCC, and Her2$^+$ or TN BC had the highest levels of $T_{eff}$, while CRC and OvCa had the lowest, followed by hormone receptor positive (HR+) BC (FIG. 13). Within a cancer type, a wide range of expression patterns was observed suggesting that subpopulations within CRC or OvCa may have $T_{eff}$ expression levels similar to cancer types like melanoma or RCC.

Figure 30:
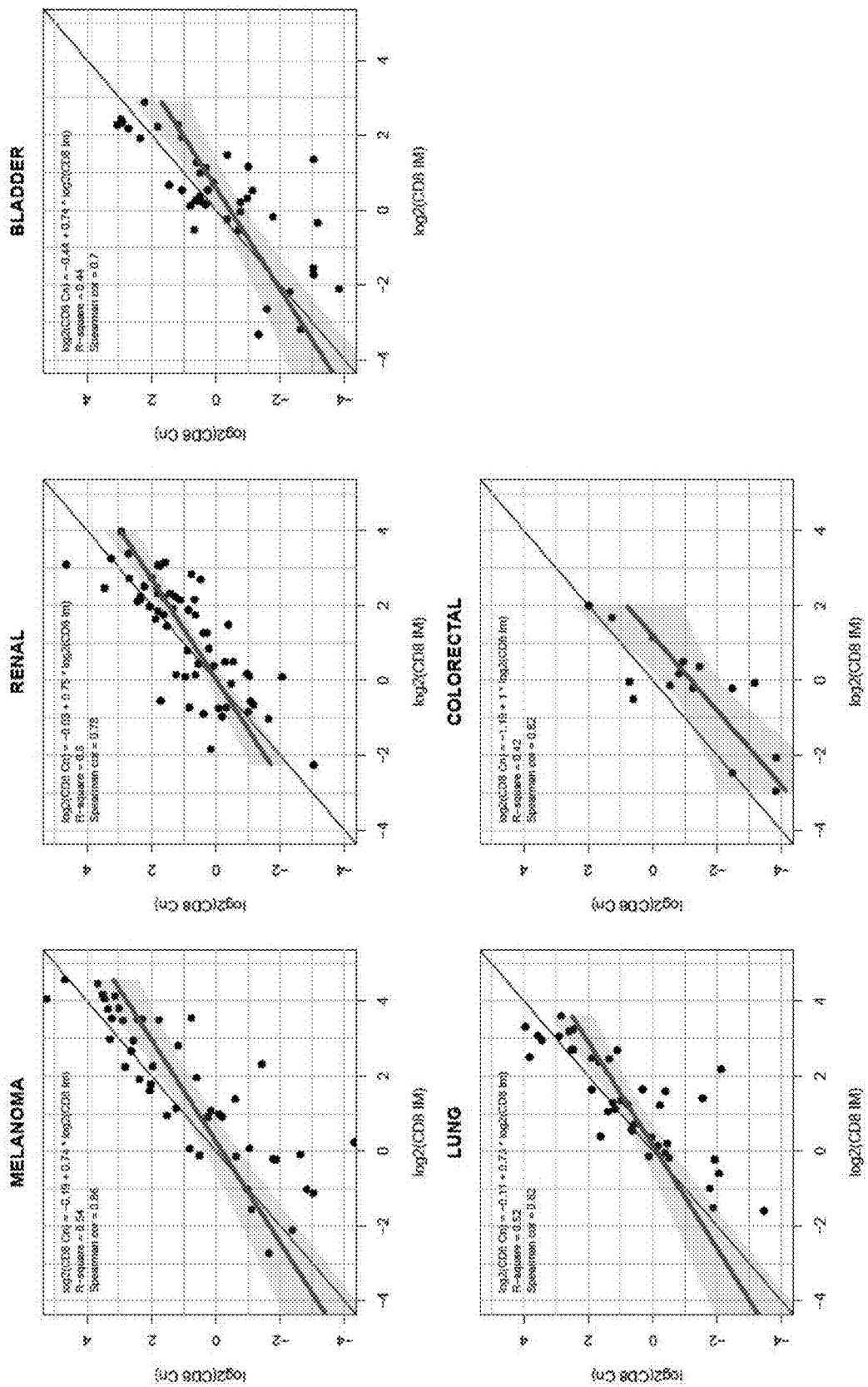
FIG. 30 shows Scatterplots of CD8 IHC by regions and by indications. Blue lines are least square regression lines. Shaded areas indicate 95% confidence intervals.

To determine if the $T_{eff}$ gene set represented the presence of CD8 T cells, digital pathology was conducted for CD8 IHC to enumerate the number of CD8 T cells in the tumor center (CN) and the invasive margin (IM) (FIG. 30).

CD8 IHC were evaluated in three regions, tumor peripheral, invasive margin (IM) and center (Cn).

Figure 29:
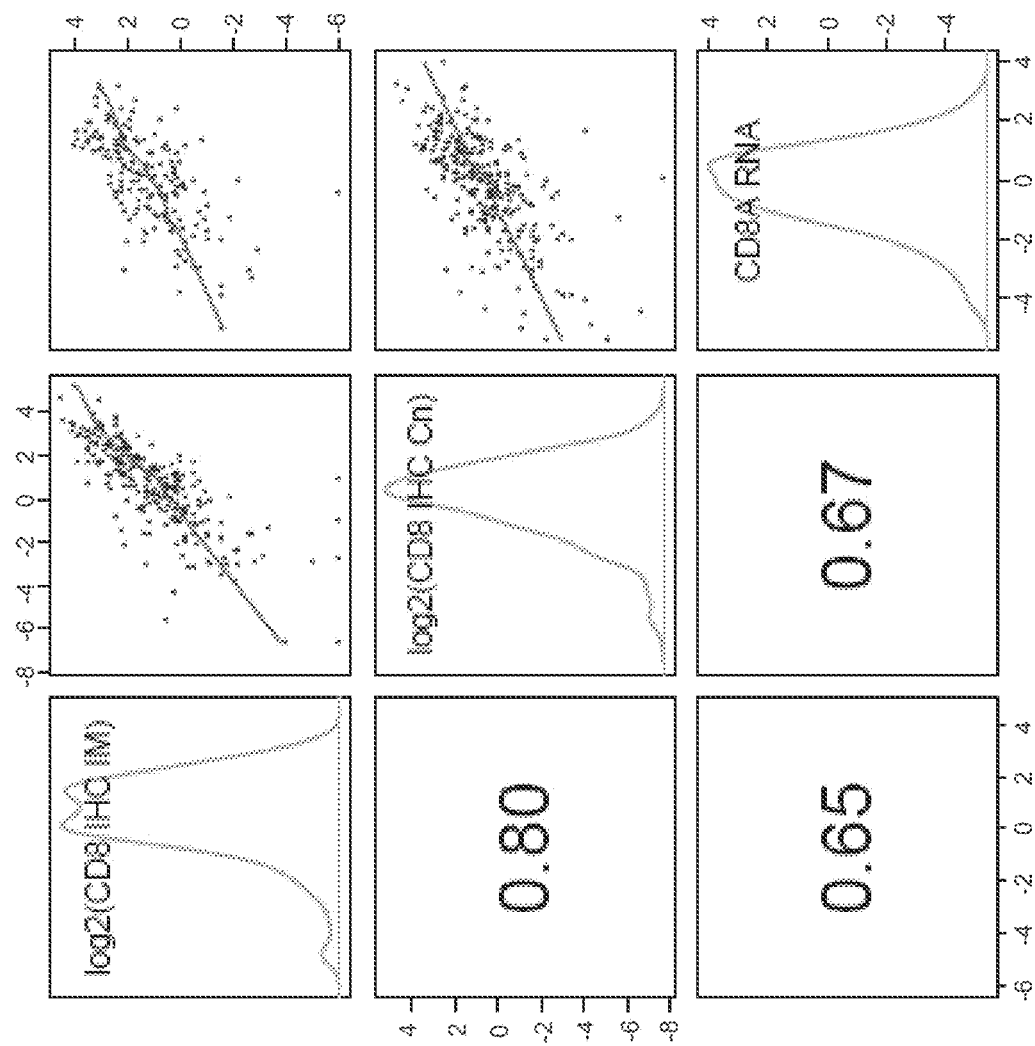
FIG. 29 is a Scattermatrix plot of CD8 IHC by regions and CD8 RNA levels. log 2 transformation was performed to normalize the distribution.

The relationship between IM and Cn CD8 IHC, as well as between CD8 IHC and RNA, was assessed using scatter-matrix plot. Raw values of CD8 IHC readings are right skewed; therefore, log 2-transformation was performed to normalize the distribution. CD8 IHC values that were zero were imputed to be half of the minimum non-zero value for log 2 transformation. A high degree of correlation was observed between CD8 IHC and CD8 RNA transcripts across indications (FIG. 29). A high degree of correlation was observed between IM and CN CD8 IHC readings, with a Spearman correlation coefficient equaling 0.76 for the log 2 transformed values. CD8 RNA was found to be highly correlated with center/IM CD8 IHC positivity, with a Spearman correlation coefficient approximately 0.66 (samples from the same patients were not consolidated for the analyses in this section). When breaking down by indication, high correlation between IM and Cn CD8 IHC positivity persists, with Spearman correlation ranging from 0.69 to 0.82.

Figure 31:
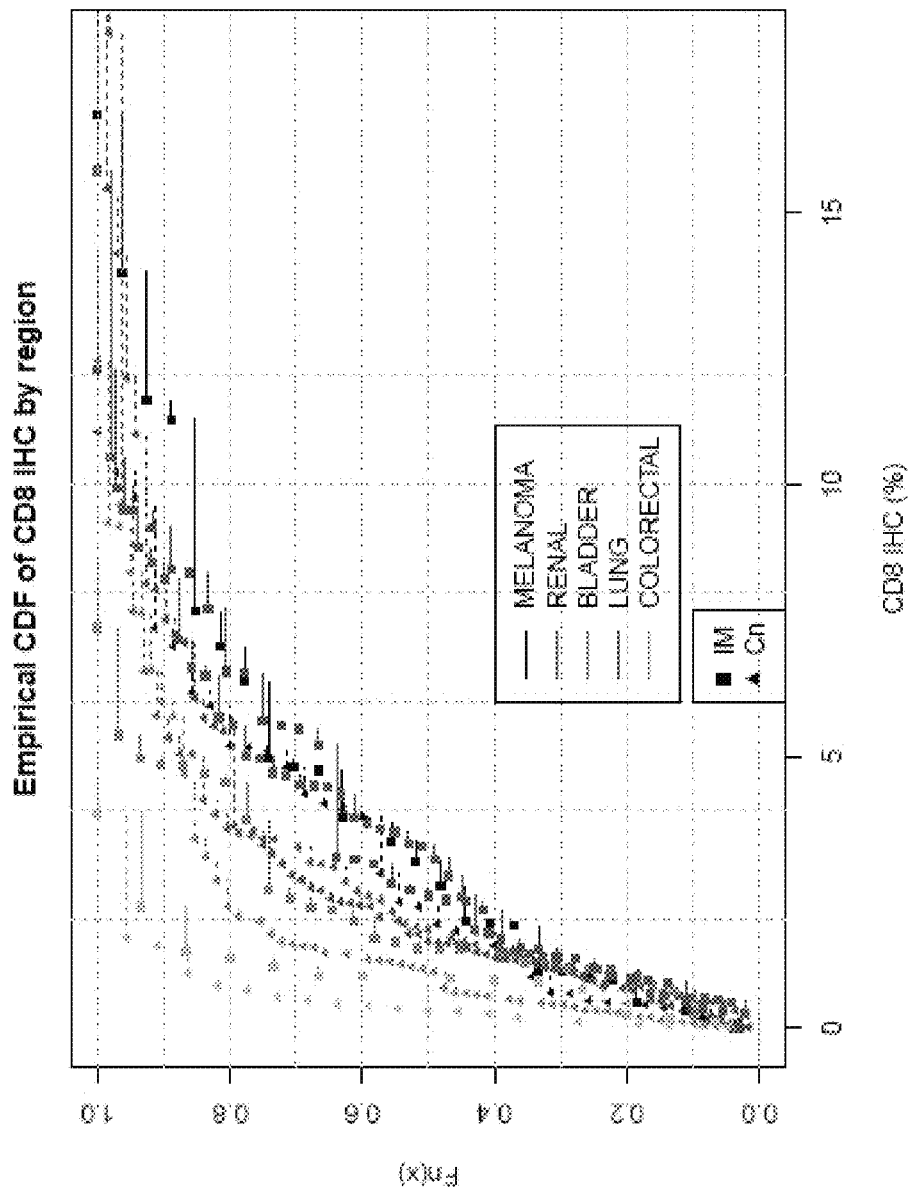
FIG. 31 is a plot showing the empirical distribution function (or Empirical CDF, a cumulative distribution function associated with the empirical measure of a sample) of CD8 IHC by regions. The Y axis is the fraction of samples ≤ that of the associated CD8 IHC percentage indicated by the X axis.

In addition, a marked correlation was observed between IM and CN prevalence of CD8 T cells across indications (FIG. 30). A summary of CD8 positivity by invasive margin (IM) and tumor center (CN) within each indication is presented in Table 11. The empirical cumulative distributions were plotted for both IM and CN in FIG. 31 to detect distributional differences between these two regions and between indications. Among the five indications, melanoma tumors on average had the highest CD8 T cell presence and the largest dynamic range. CRC and bladder tumors, on average, had the lowest CD8 T cell infiltrates and also, the smallest dynamic range. These results were highly correlated with the rank order of the Teffsignatures.

In addition, CD8 T cells were significantly more abundant at invasive margin than at tumor center for melanoma and RCC tumors.

TABLE 11

|  | N | IM. Median | IM. 25th%-75th% | Cn. Median | Cn. 25th%-75th% |
|---|---|---|---|---|---|
| MELANOMA | 35 | 3.07 | (0.98-5.66) | 2.22 | (0.57-5.13) |
| RENAL | 56 | 3.36 | (1.11-4.97) | 1.835 | (0.925-3.503) |
| BLADDER | 61 | 1.47 | (1.09-3.19) | 1.08 | (0.33-1.96) |
| LUNG | 68 | 2.495 | (1.245-5.87) | 1.66 | (0.9275-3.432) |
| COLORECTAL | 22 | 0.96 | (0.785-1.21) | 0.34 | (0.1275-0.6575) |

Figure 15:
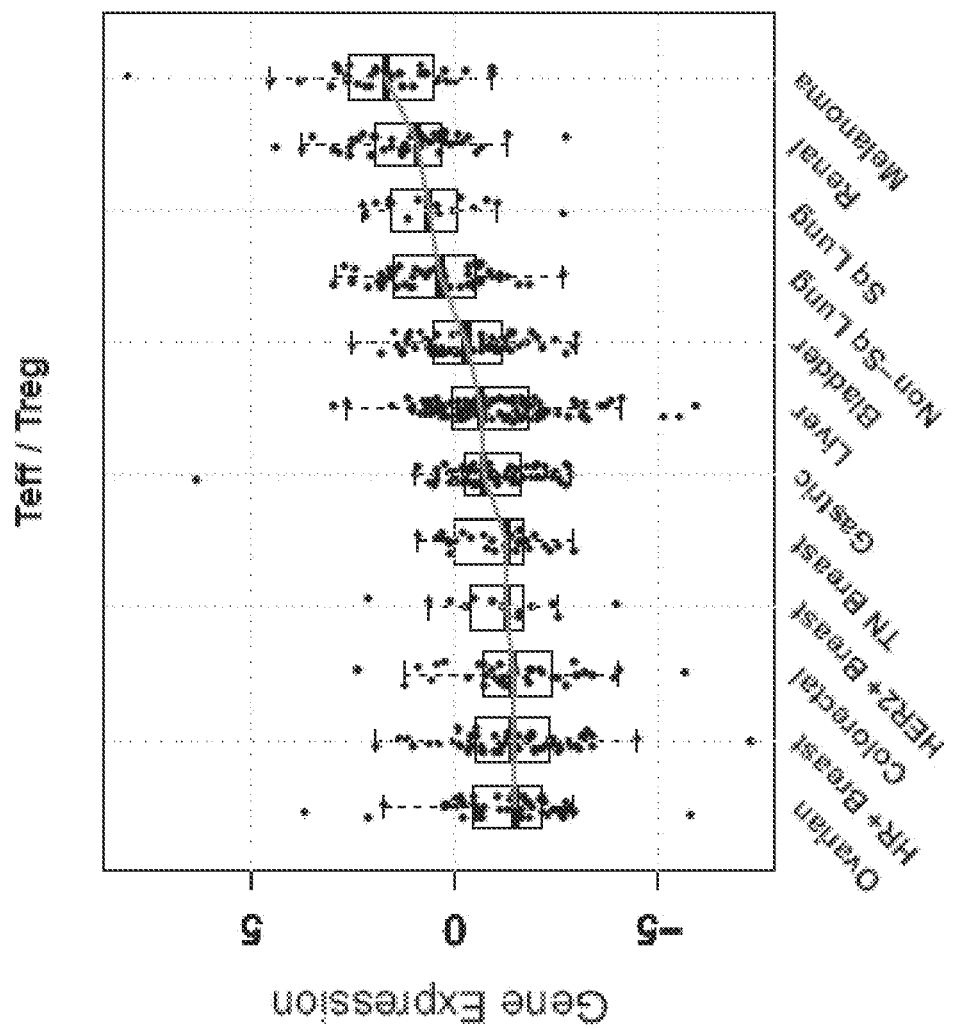
FIG. 15 is a plot of gene expression ratios of T effector vs. T regulatory signature genes across indications.

The cancer types that contain a CD8 T cell infiltrate most likely represented tumors that prevent anti-tumor immunity by overexpressing immunosuppressive cells relative to activated T cells. While the general prevalence of Ten signatures reflected the abundance of tumor infiltrating lymphocytes across indications, the ratio of $T_{eff}$ signatures to $T_{reg}$ ranked the cancer types in a manner similar to the ones most likely to respond to immunotherapies. NSCLC, RCC, and melanoma had the highest ratio of $T_{eff}:T_{reg}$ reflecting "immunogenic" tumor types. Indications known to have poor responses to immunotherapies like CRC and OvCa were the cancer types with the lowest ratio of $T_{eff}:T_{reg}$ (FIG. 15). While TN and Her2+ breast cancers exhibited a higher median expression of $T_{eff}$ signatures, their tumor microenvironment was also shown to be rich in $T_{reg}$ and this is reflected by the low relative ratio of $T_{eff}$ to $T_{reg}$ signatures. Thus, therapies targeting T regulatory cells, such as anti-OX40 (abundantly expressed in $T_{reg}$) in combination with checkpoint inhibitors, provide useful therapies for triggering an effective anti-tumor immune response.

Example 3: $T_{reg}$ Signature Genes are Abundant in Breast Cancer

Figure 14:
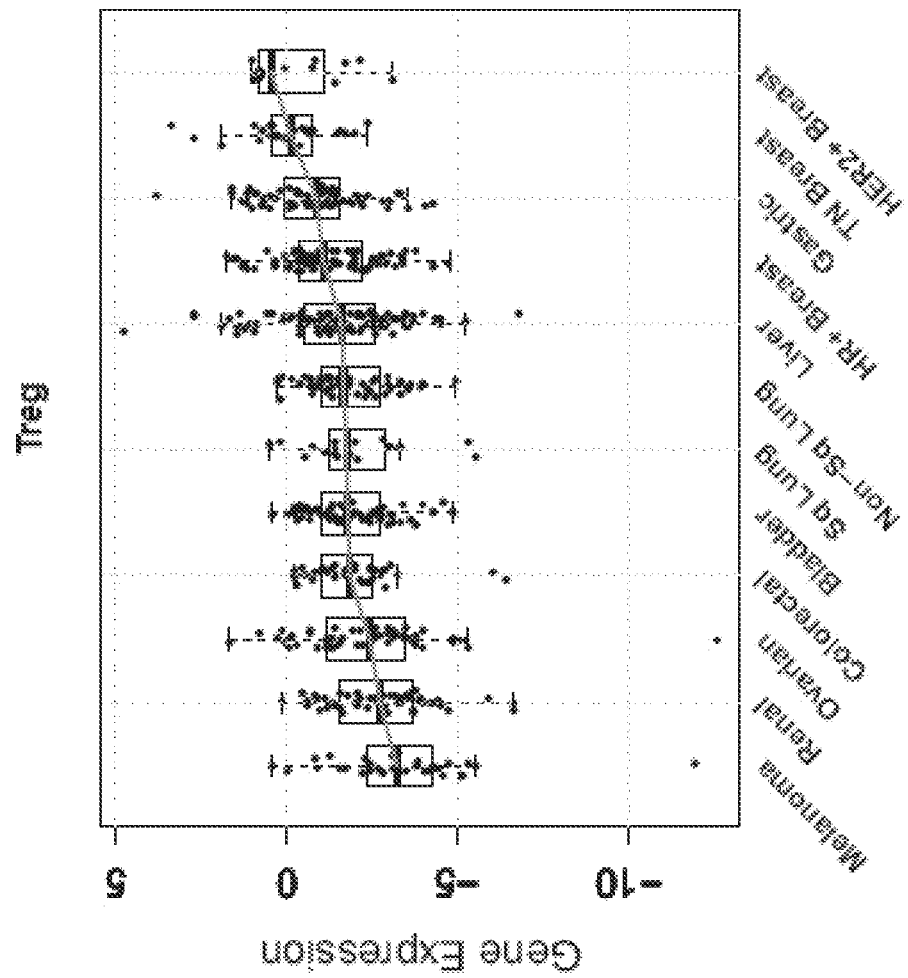
FIG. 14 is a plot of gene expression levels of T regulatory signature genes across indications.

Tumors recruit immunosuppressive cells to inhibit anti-tumoral $T_{eff}$ responses. Regulatory T cells ($T_{reg}$), characterized by Foxp3 expression, antagonize $T_{eff}$ action. To test the potential of in-situ immunosuppression, prevalence of Foxp3 was evaluated among tumor indications. Presence of $T_{reg}$ was highest among BC subtypes (Her2+ similar to triple negative (TN), both higher than hormone receptor positive (HR+)) followed by NSCLC, UBC, CRC, OvCa, RCC, and melanoma, with significantly reduced counts (FIG. 14). Effective $T_{reg}$-dependent immunosuppression requires a certain proportion of $T_{eff}:T_{reg}$, thus the proportion of Ten to $T_{reg}$ was assessed. $T_{eff}:T_{reg}$ ratio was highest in melanoma, followed by RCC, NSCLC, and UBC (FIG. 15). Despite differences in independent $T_{eff}$ and $T_{reg}$ values, BC (HR+, Her2+ and TN), CRC, and ovarian had similarly reduced $T_{eff}:T_{reg}$ ratios (FIG. 15). These results suggest that tumors with low $T_{eff}:T_{reg}$ may benefit from therapies targeting $T_{reg}$.

Figure 16:
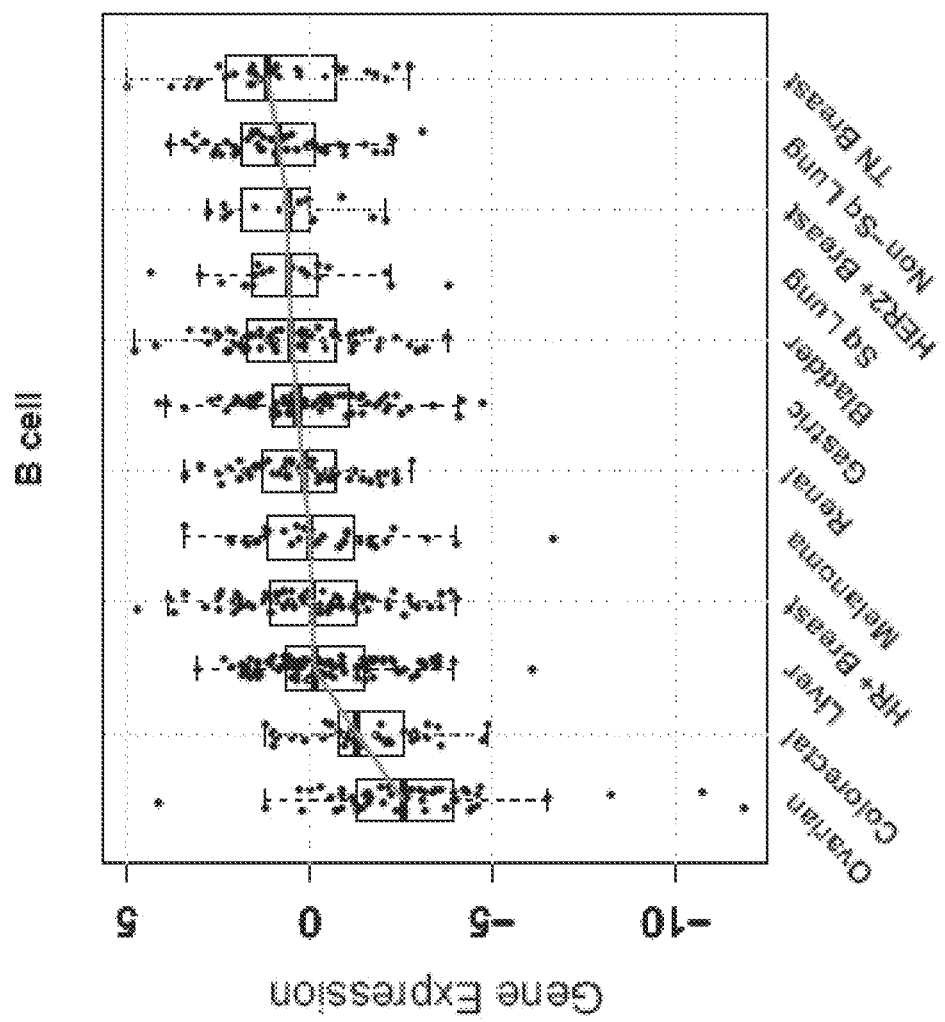
FIG. 16 is a plot of gene expression levels of B cell signature genes across indications.
Figure 17:
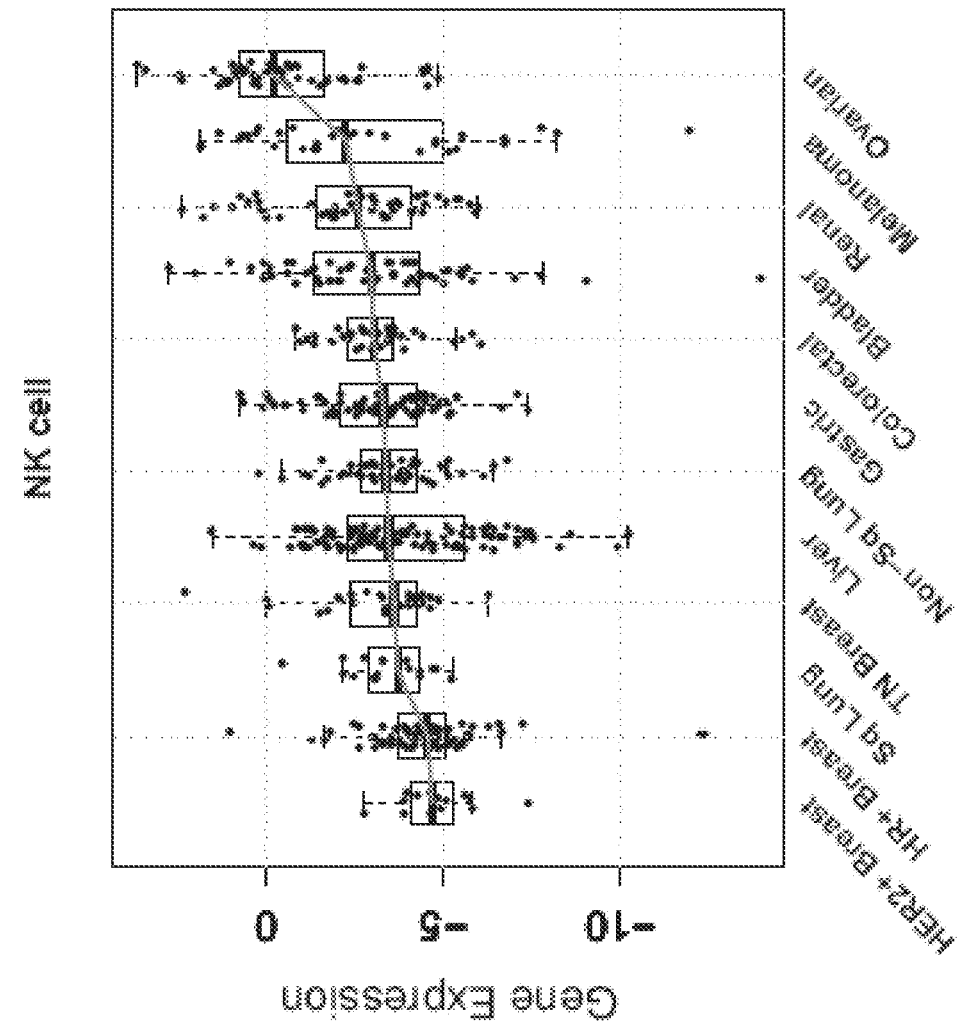
FIG. 17 is a plot of gene expression levels of NK cell signature genes across indications.
Figure 18:
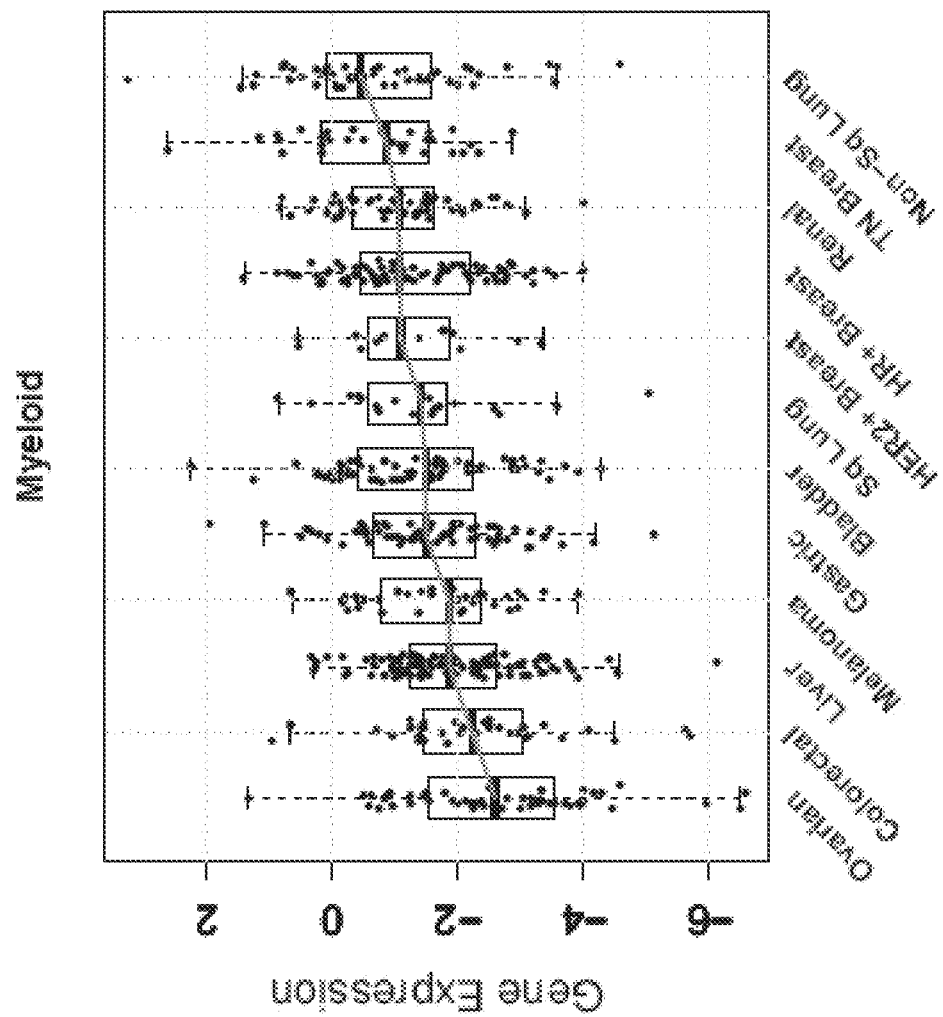
FIG. 18 is a plot of gene expression levels of myeloid signature genes across indications.

Example 4: B Cell, NK Cell, and Myeloid Cell Signature Genes Vary Across Cancer Indications In preclinical models, B cells were shown to promote intratumoral immunosuppression by recruiting and enabling anti-inflammatory macrophages. On the other hand, NK cells were shown to recognize stress molecules expressed by tumors and direct tumor rejection. The presence of B cells followed a distribution similar to Ten across indications (FIG. 16), while NK cells were highest in OvCa, followed by all the other indications (FIG. 17). Myeloid signature, which encompasses both macrophages and dendritic cells, was similar among indications, except for reduced levels in CRC and OvCa (FIG. 18), likely representing a low immune infiltrate in these indications. A further distinction was that the median expression of myeloid gene set was higher in non squamous NSCLC compared to squamous NSCLC.

Example 5: Th17 Signature Genes are Distinct in Each Tumor Type

Figure 2A:
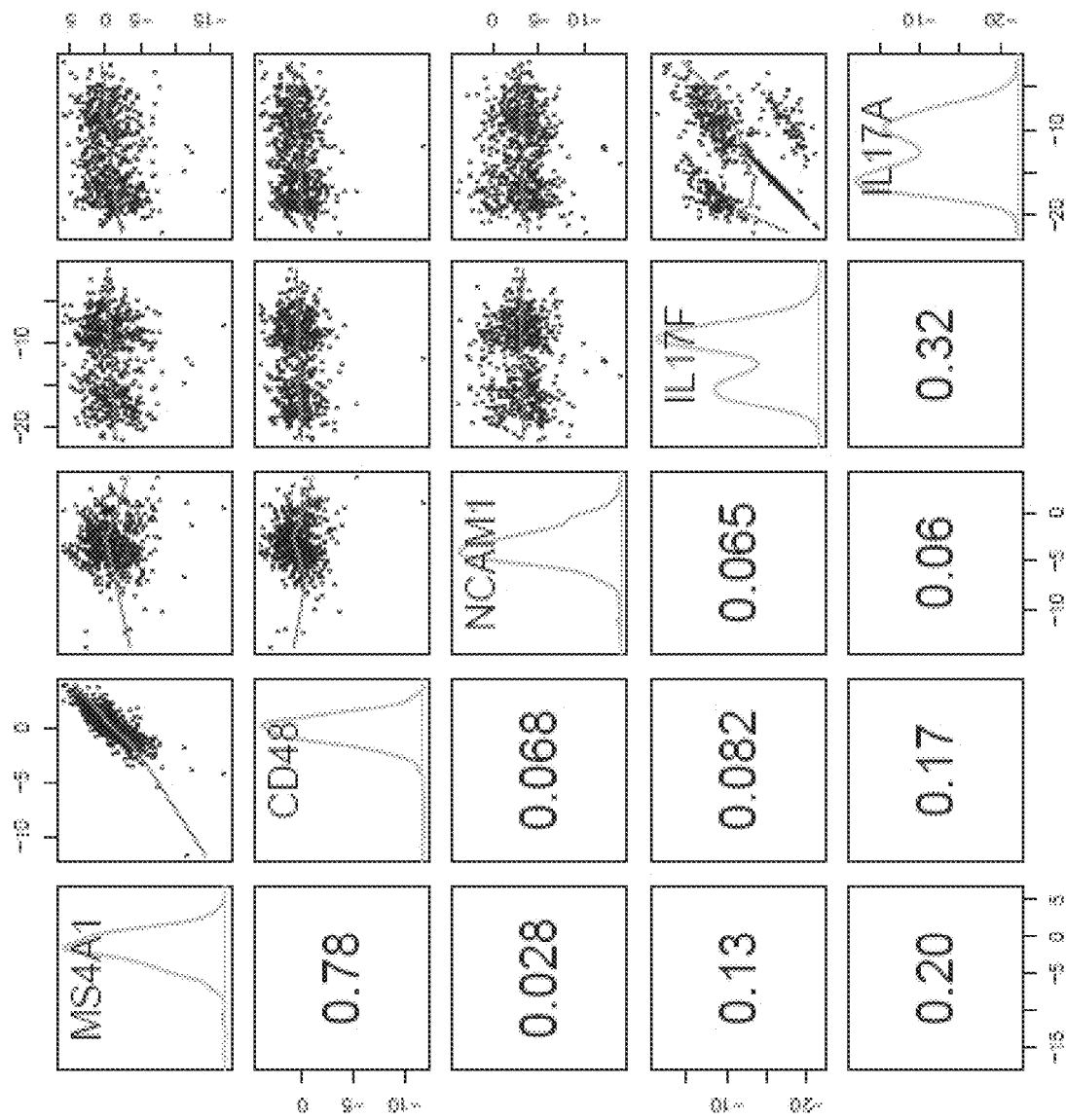
FIG. 2A is a Scattermatrix plot of B cell Signature 1, NK cell Signature 1, and IL17 signature genes.
Figure 2B:
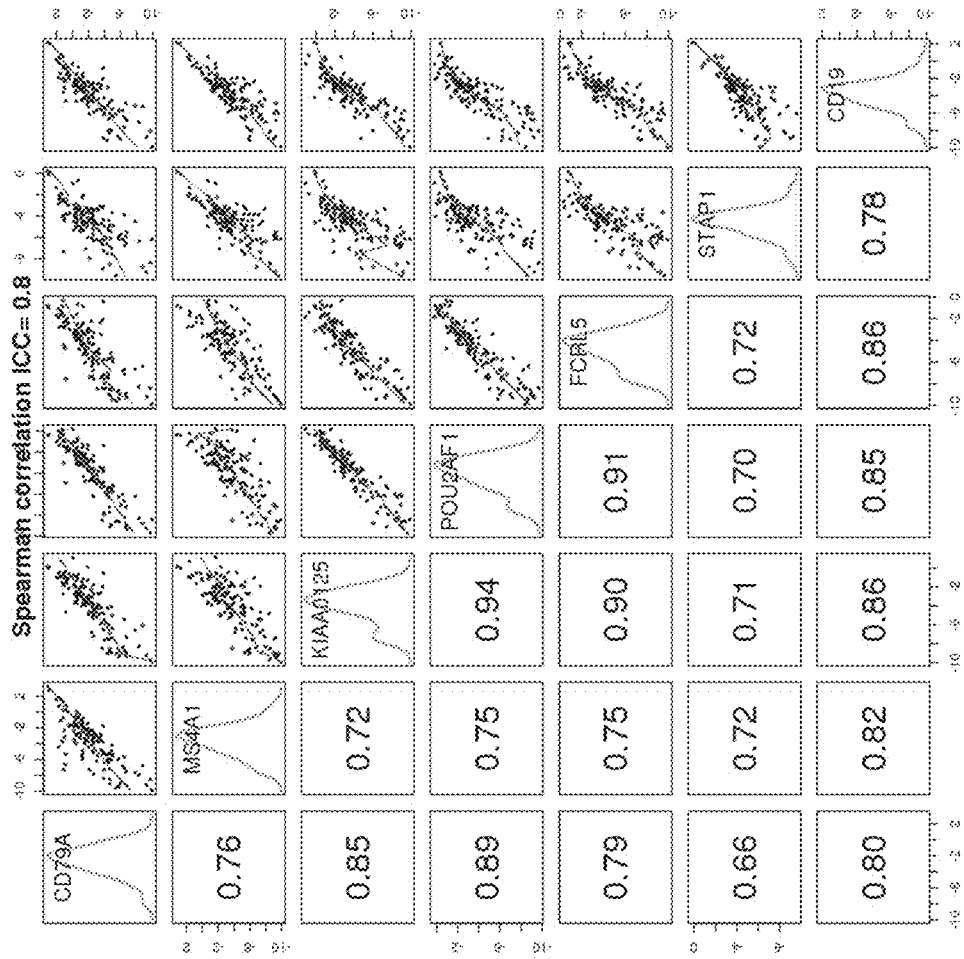
FIG. 2B is Scattermatrix plot of B cell Signature 2 genes.
Figure 2C:
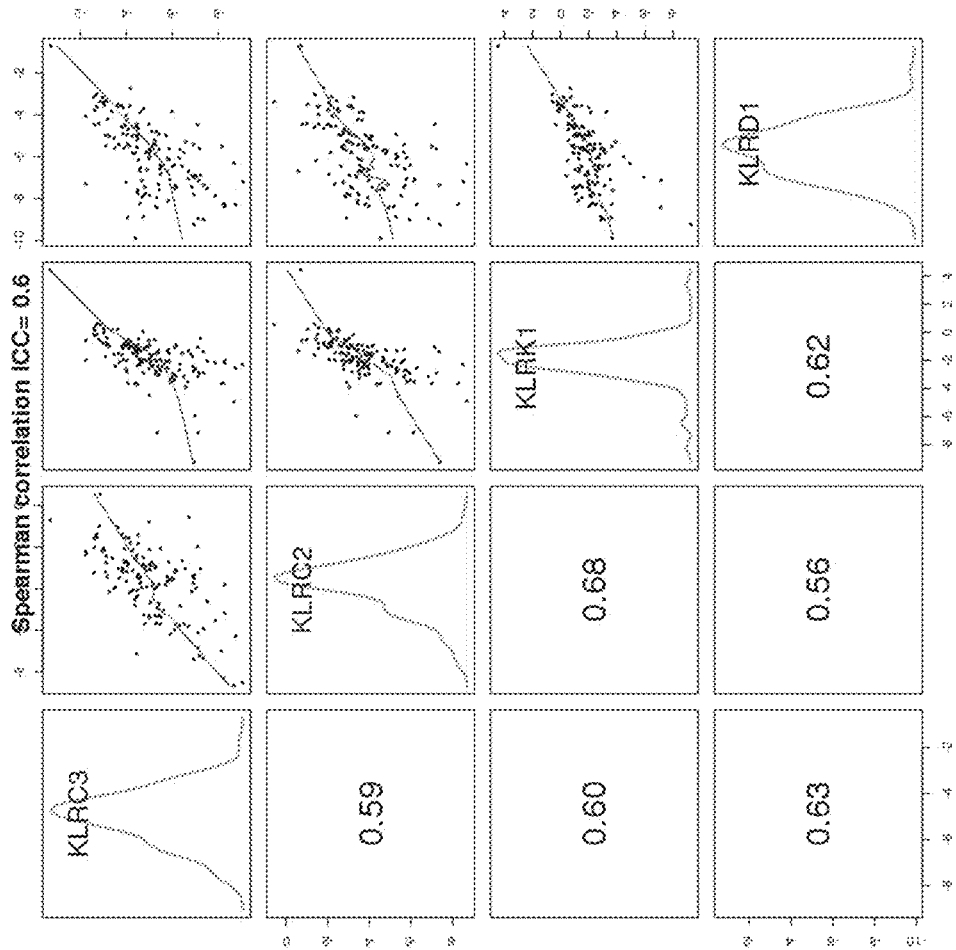
FIG. 2C is Scattermatrix plot of NK cell Signature 2 genes.
Figure 3A:
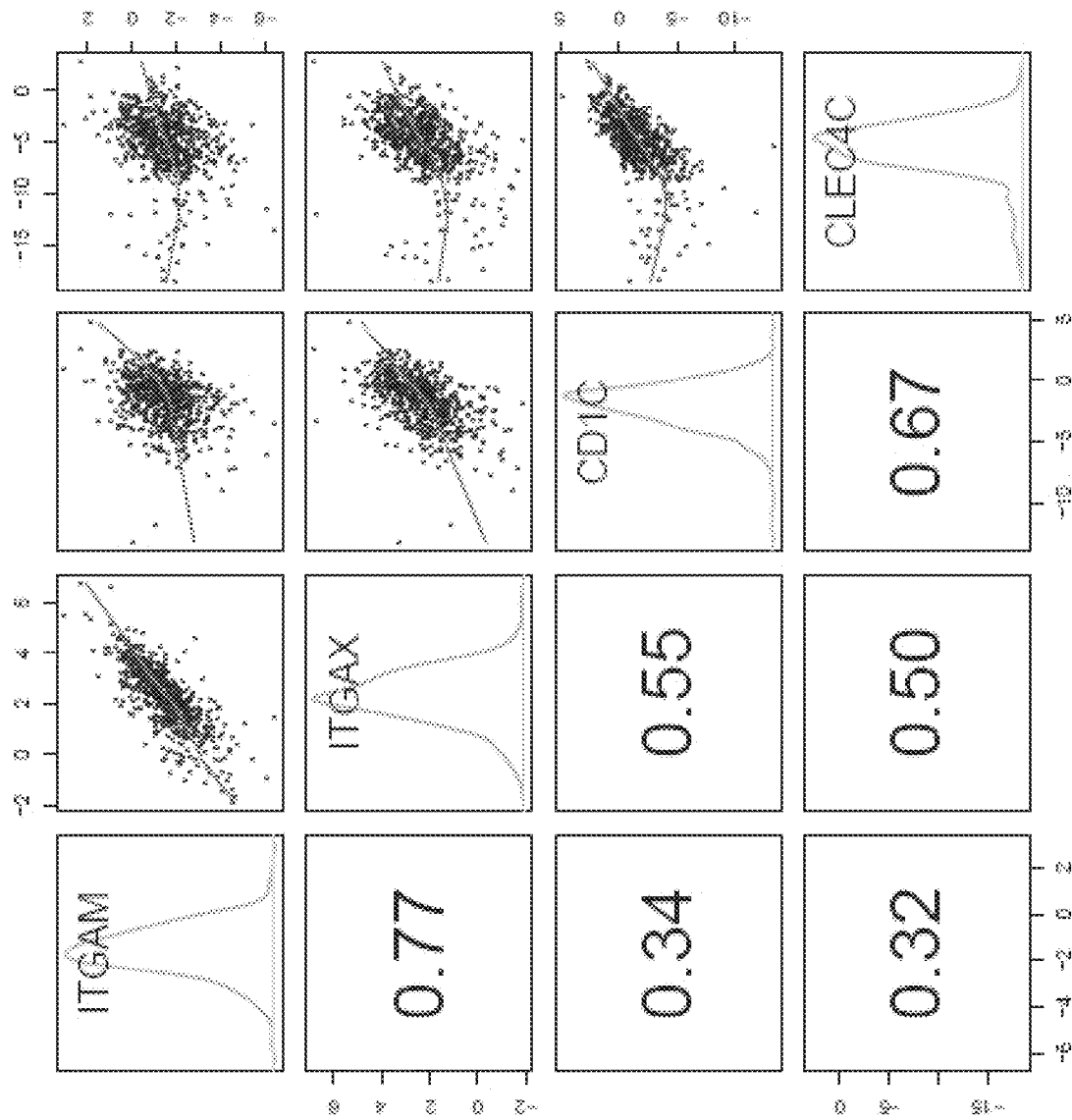
FIG. 3A is a Scattermatrix plot of myeloid signature genes.
Figure 3B:
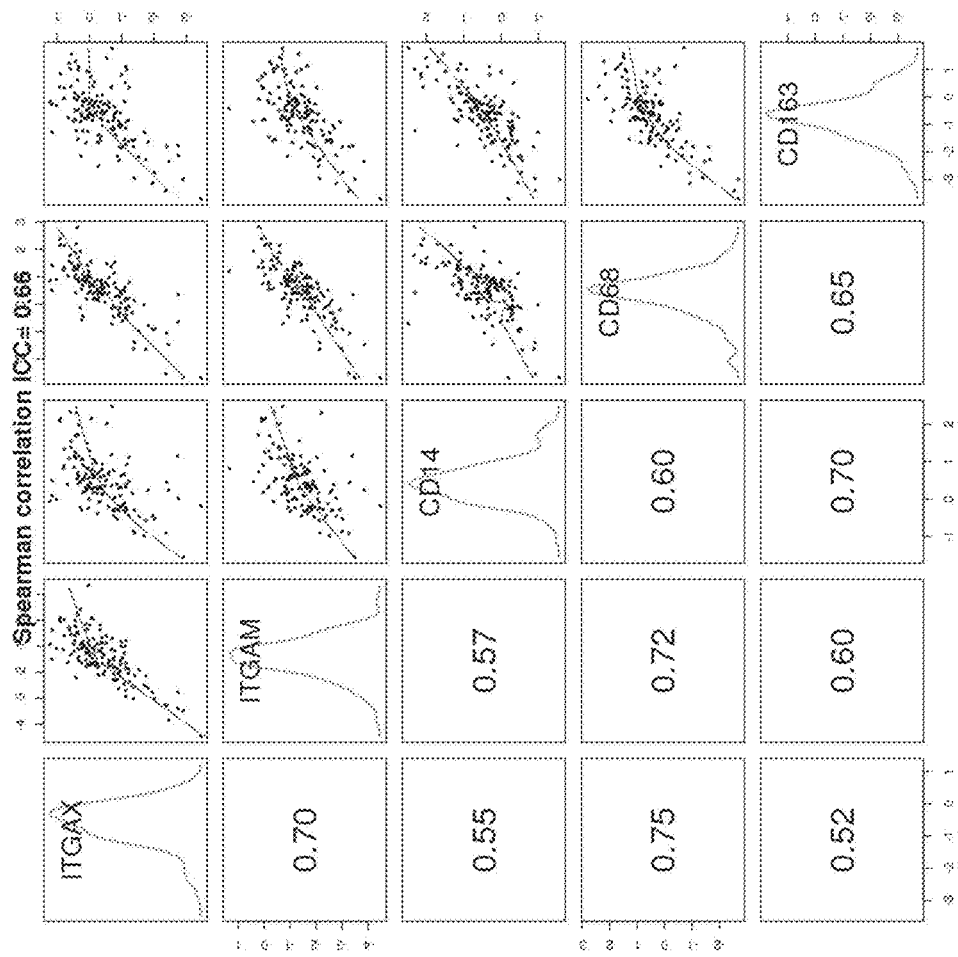
FIG. 3B is a Scattermatrix plot of macrophage signature genes.
Figure 3C:
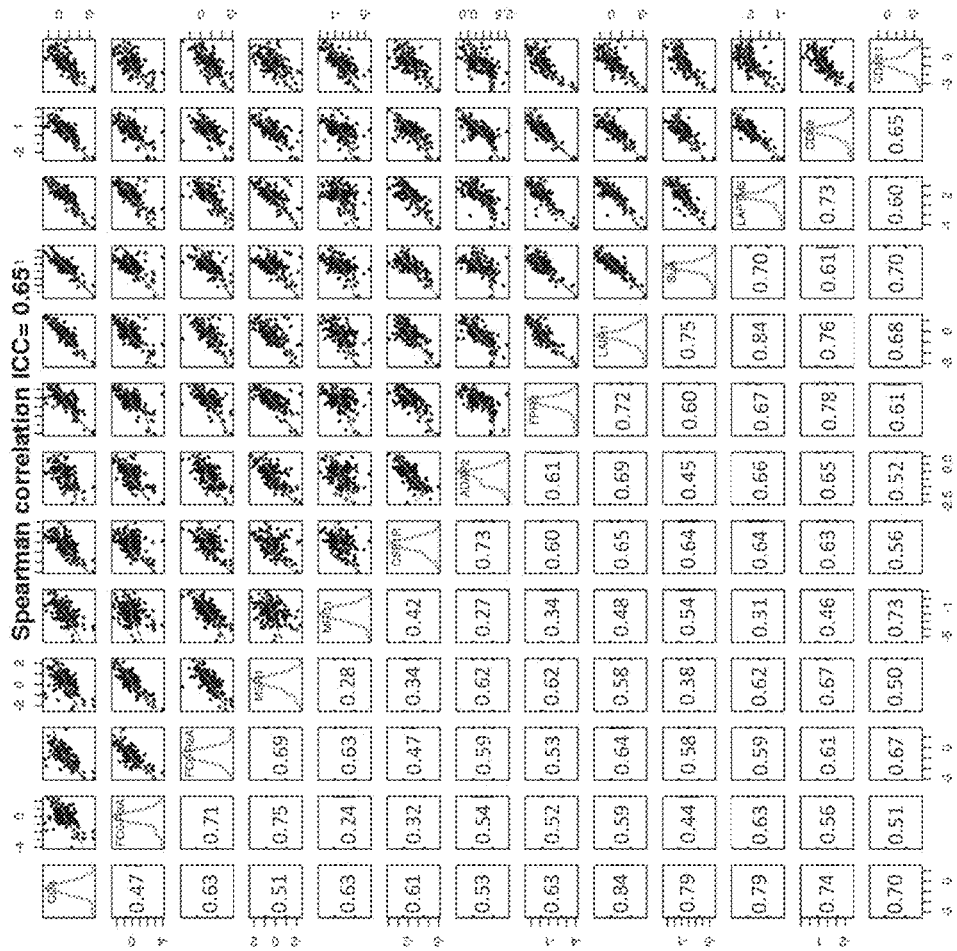
FIG. 3C is a Scattermatrix plot of M2 macrophage signature genes.
Figure 4:
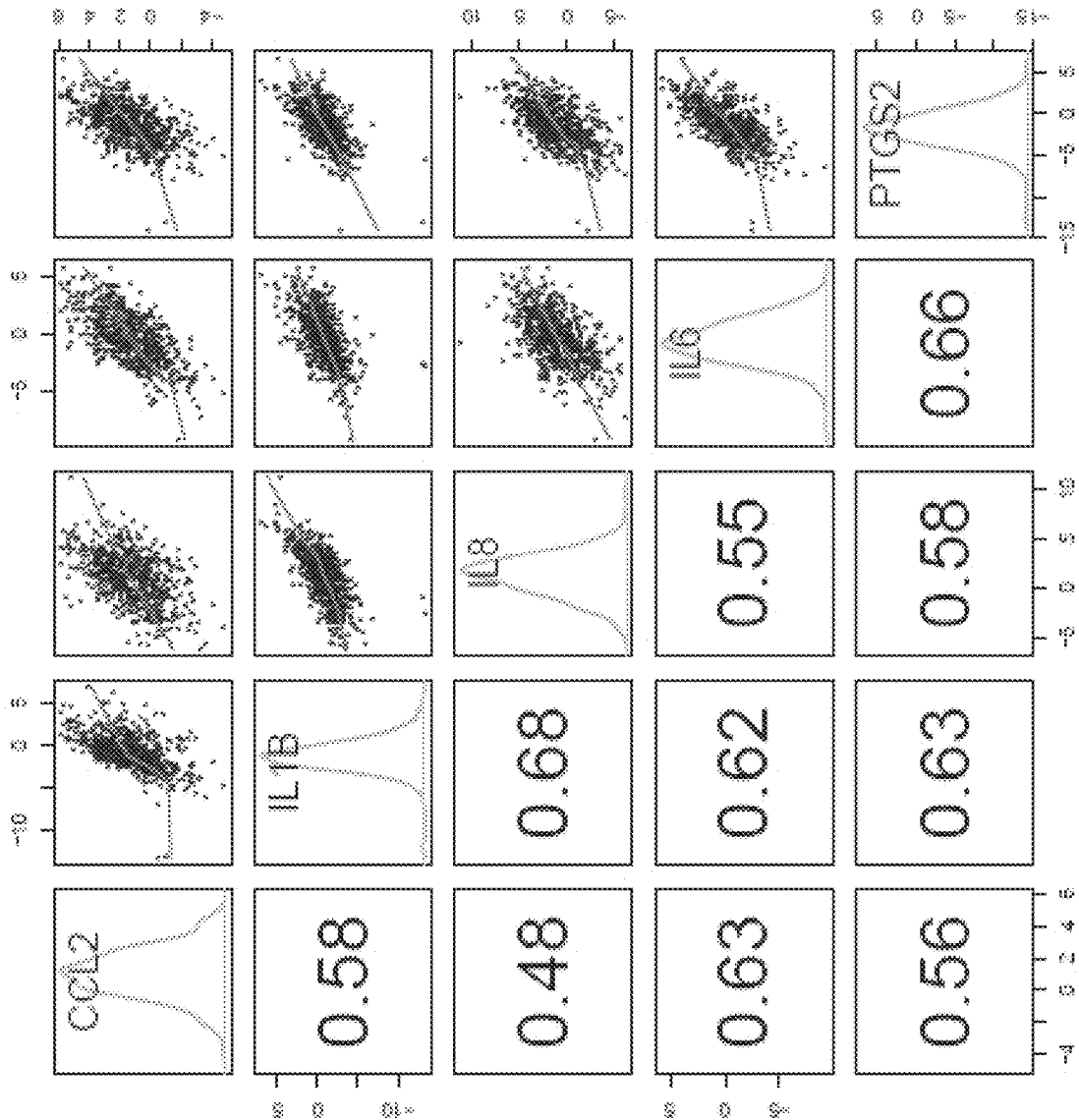
FIG. 4 is a Scattermatrix plot of inflammatory signature genes.
Figure 5A:
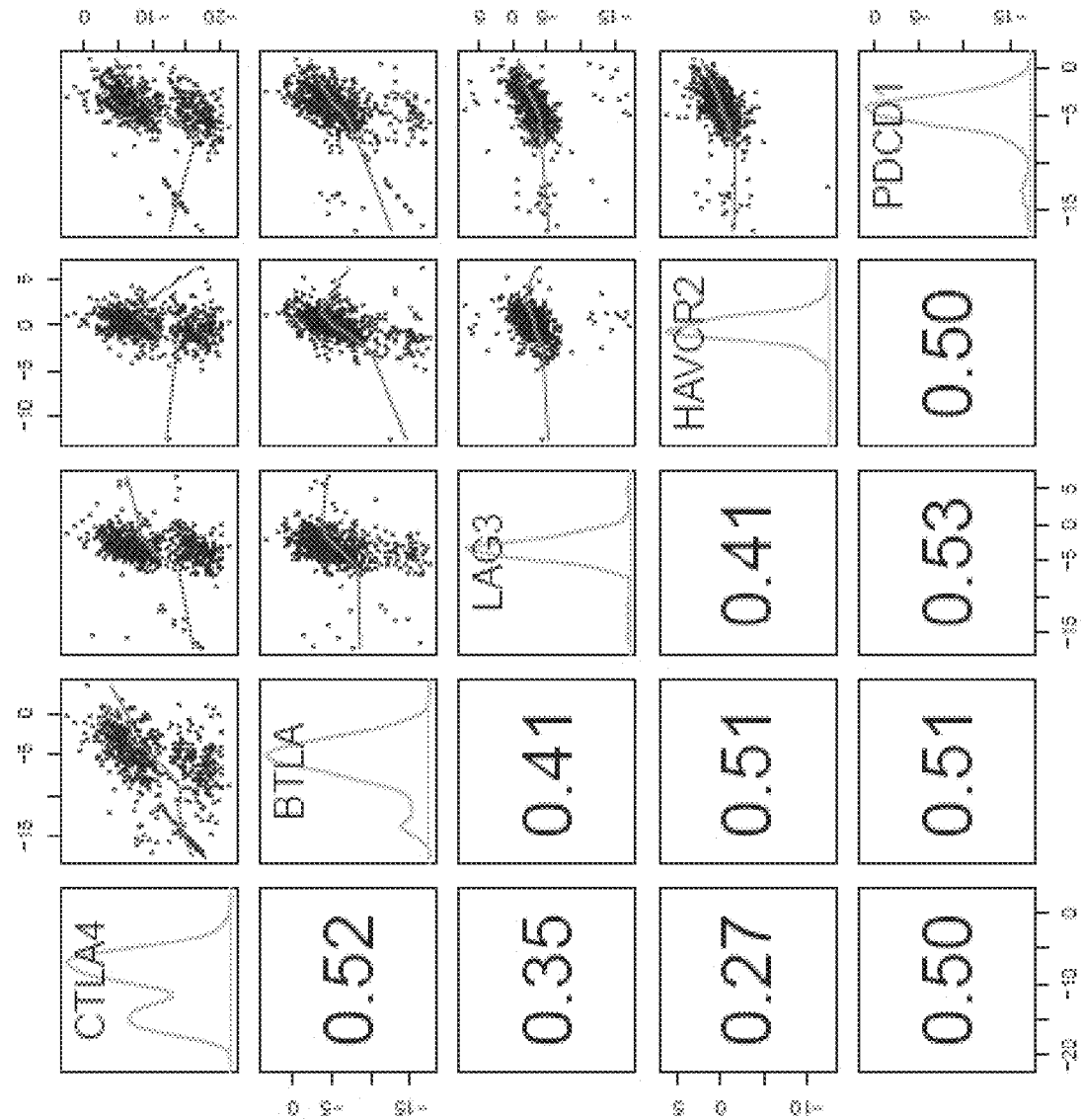
FIG. 5A is a Scattermatrix plot of T cell immune blocker (IB T cell) Signature 1 genes.
Figure 5B:
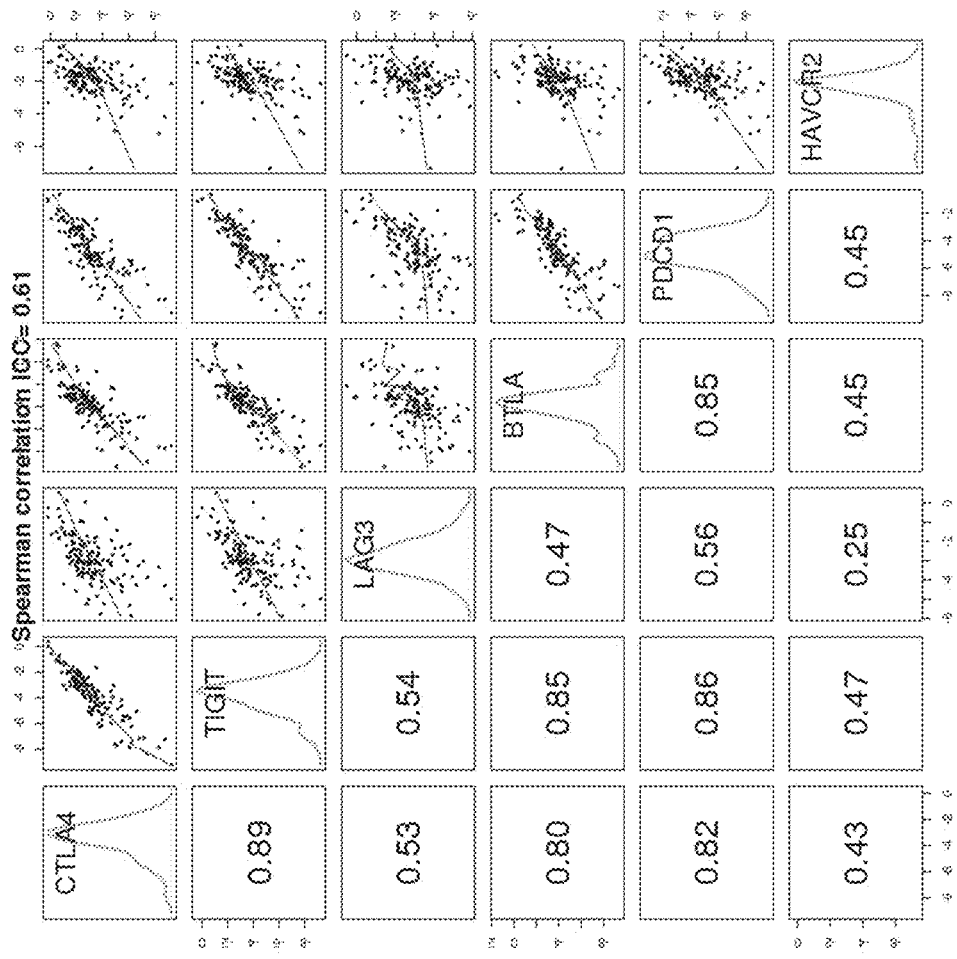
FIG. 5B is a Scattermatrix plot of IB T cell Signature 2 genes.
Figure 6A:
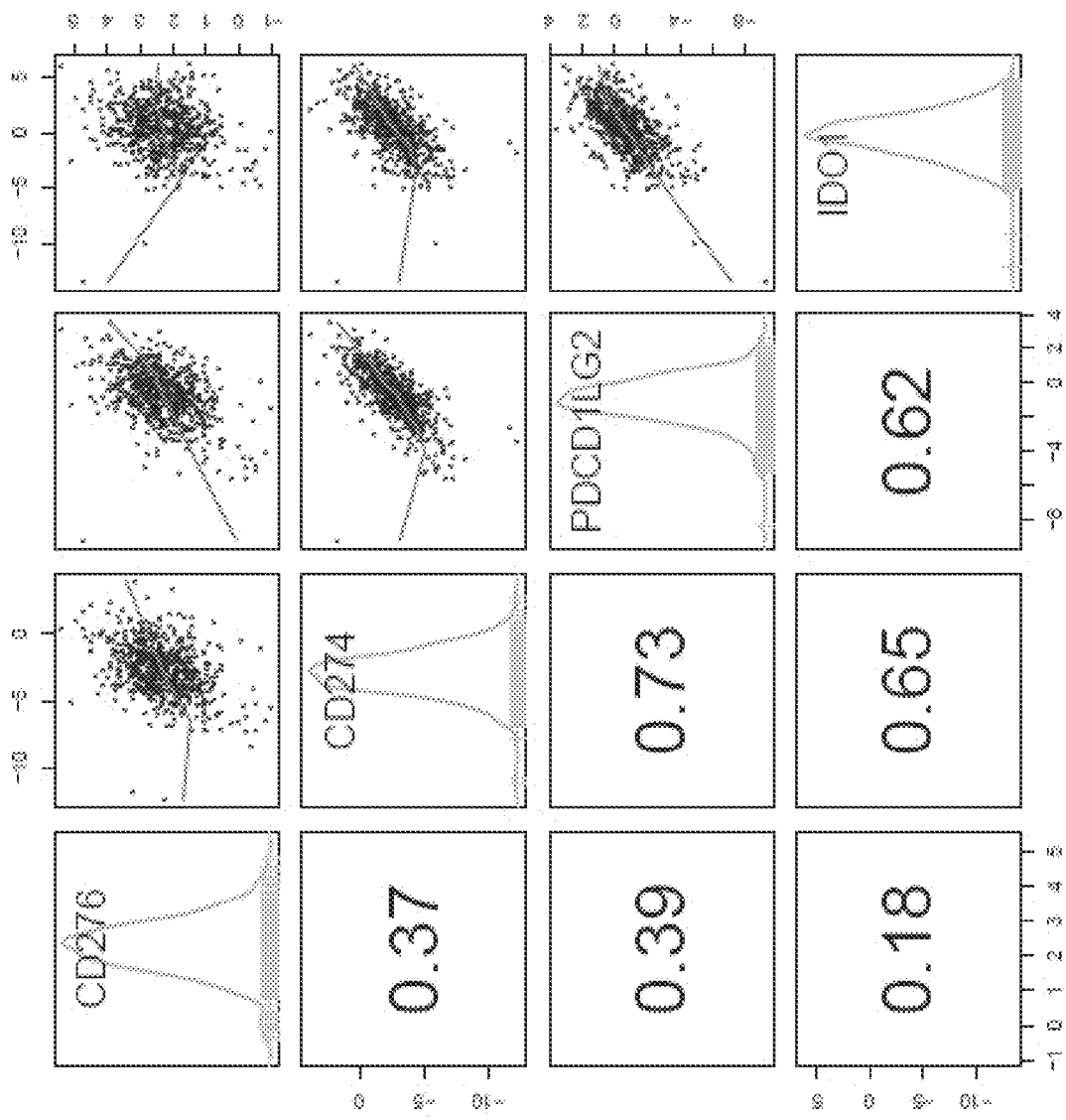
FIG. 6A is a Scattermatrix plot of APC immune blocker (IB APC) Signature 1 genes.
Figure 6B:
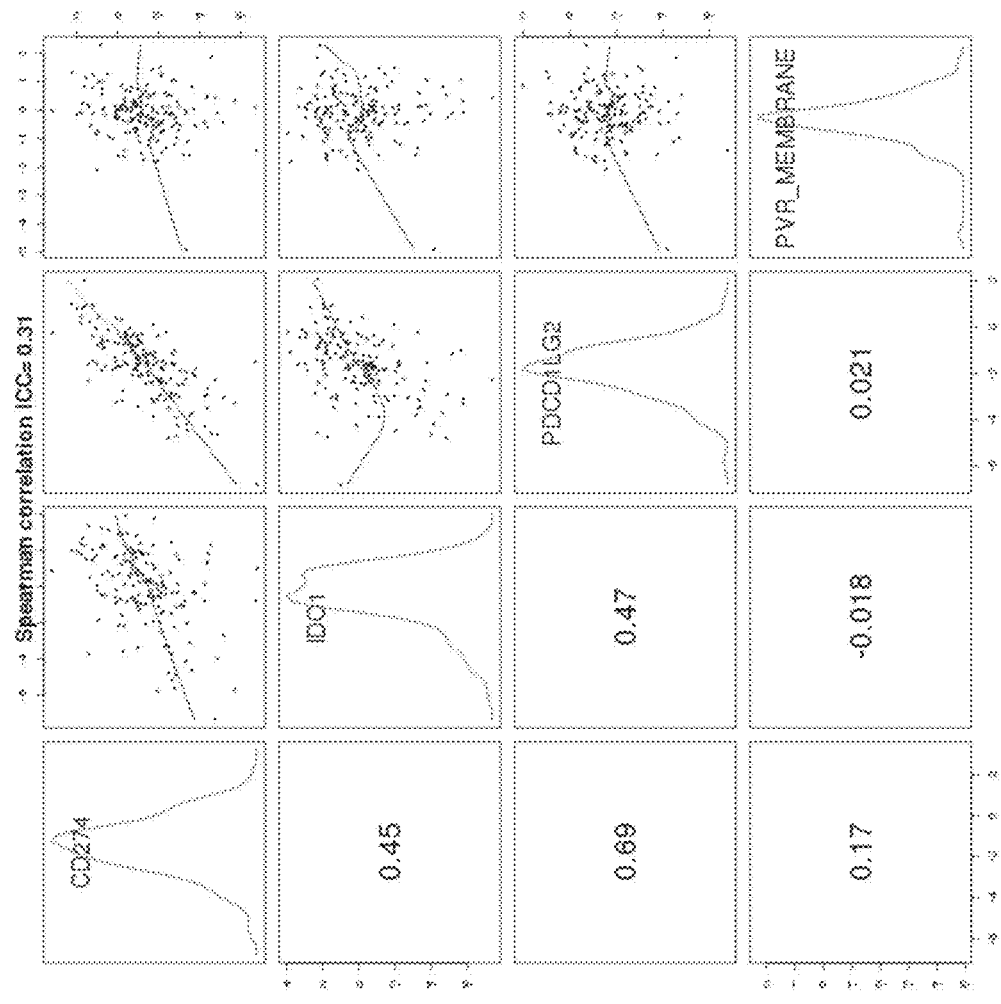
FIG. 6B is a Scattermatrix plot of IB APC Signature 2 genes.
Figure 7:
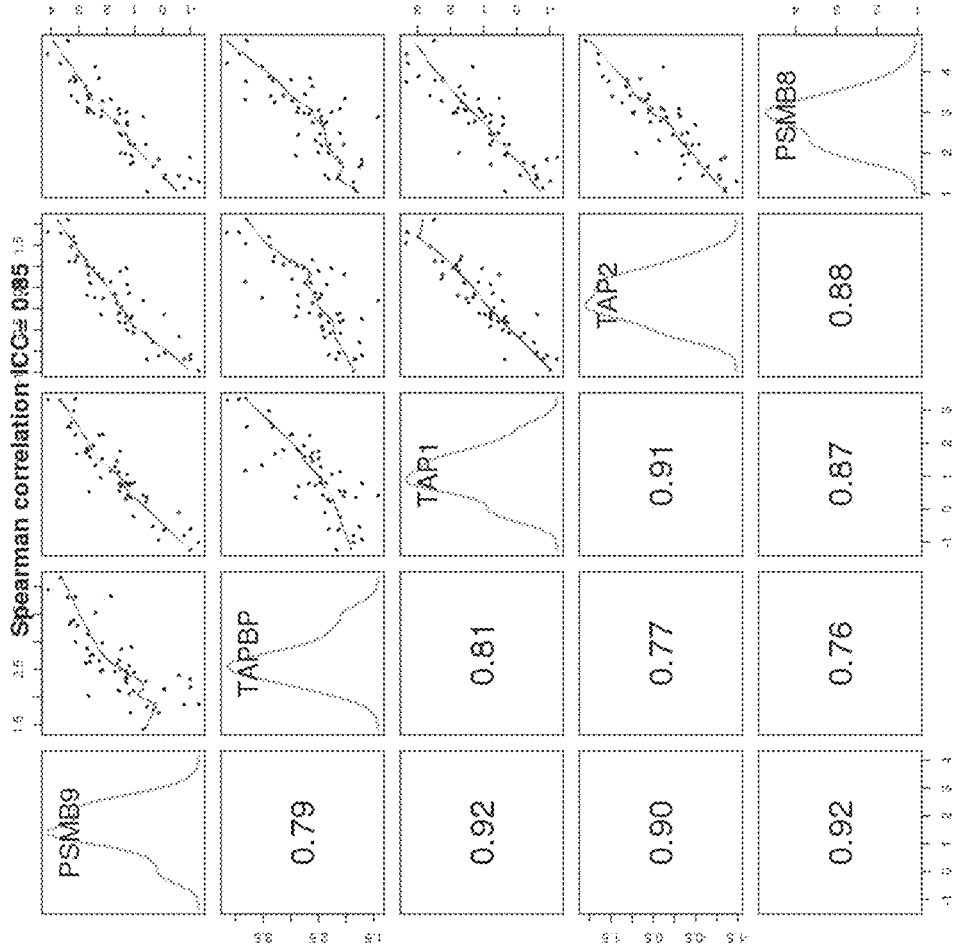
FIG. 7 is a Scattermatrix plot of antigen processing signature genes.
Figure 8:
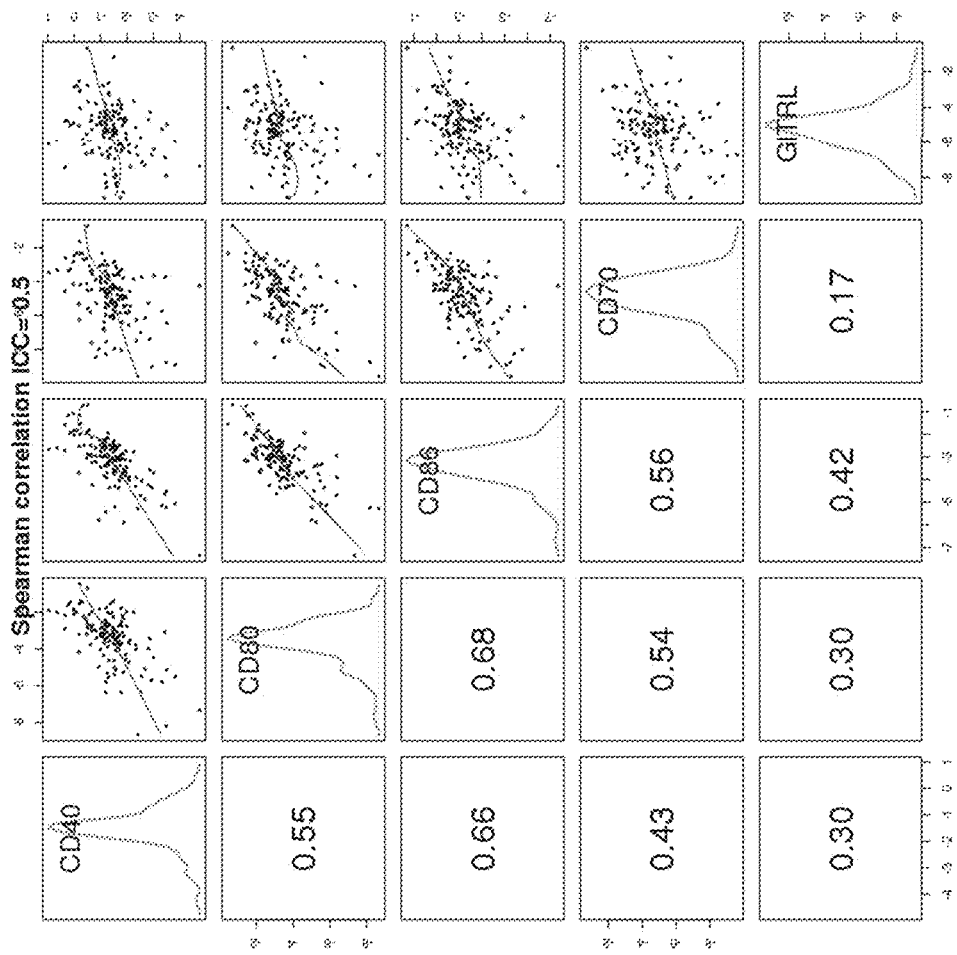
FIG. 8 is a Scattermatrix plot of costimulatory ligand signature genes.
Figure 9:
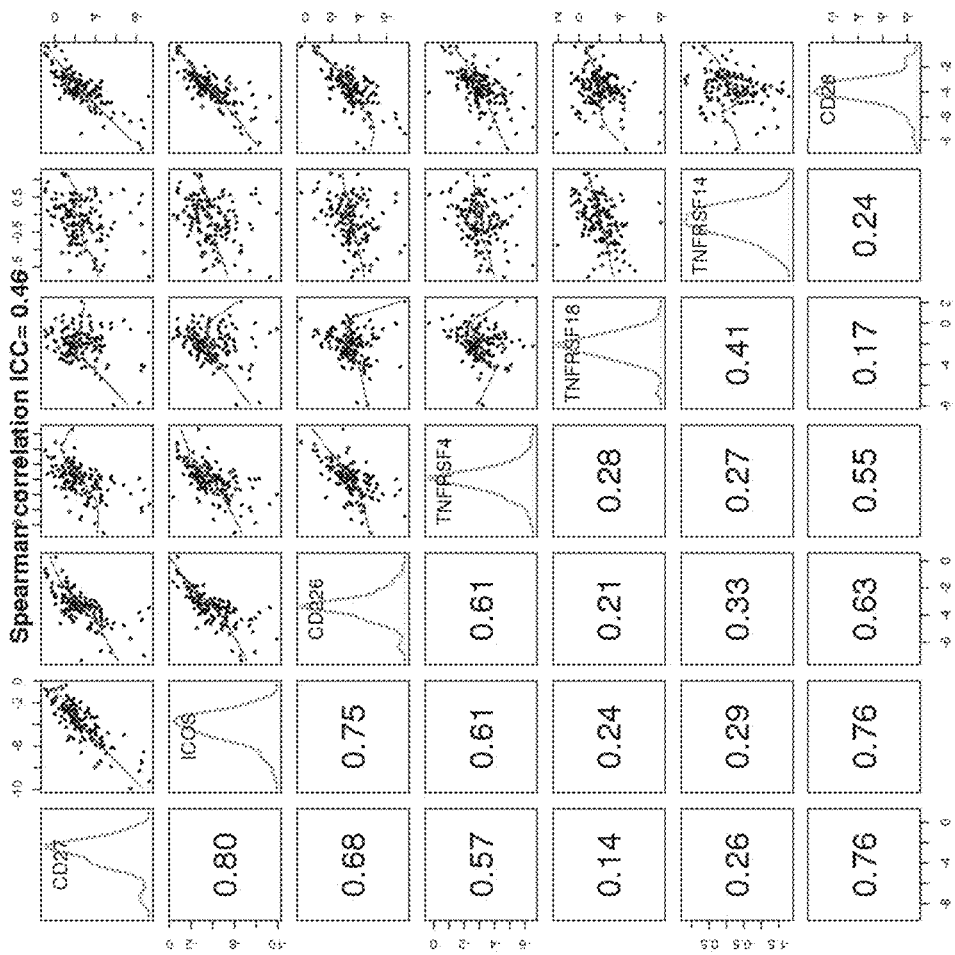
FIG. 9 is a Scattermatrix plot of costimulatory receptor signature genes.
Figure 10:
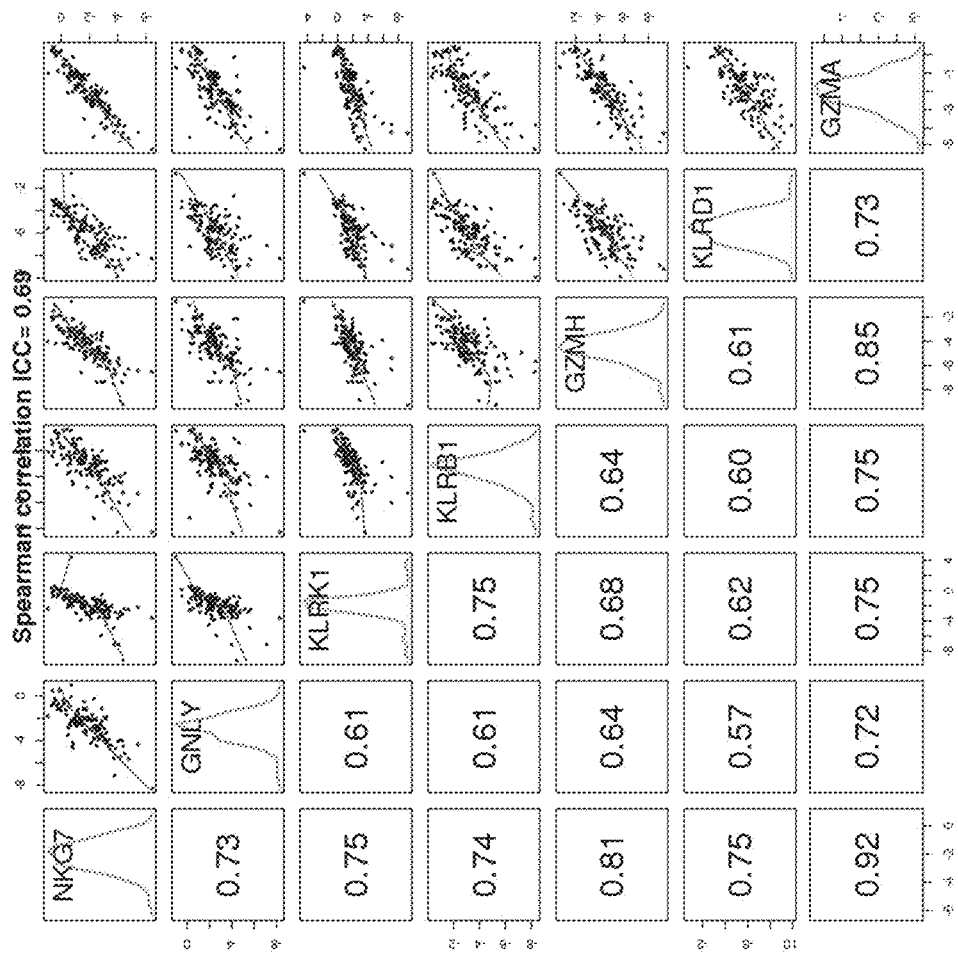
FIG. 10 is a Scattermatrix plot of cytolytic signature genes.
Figure 11:
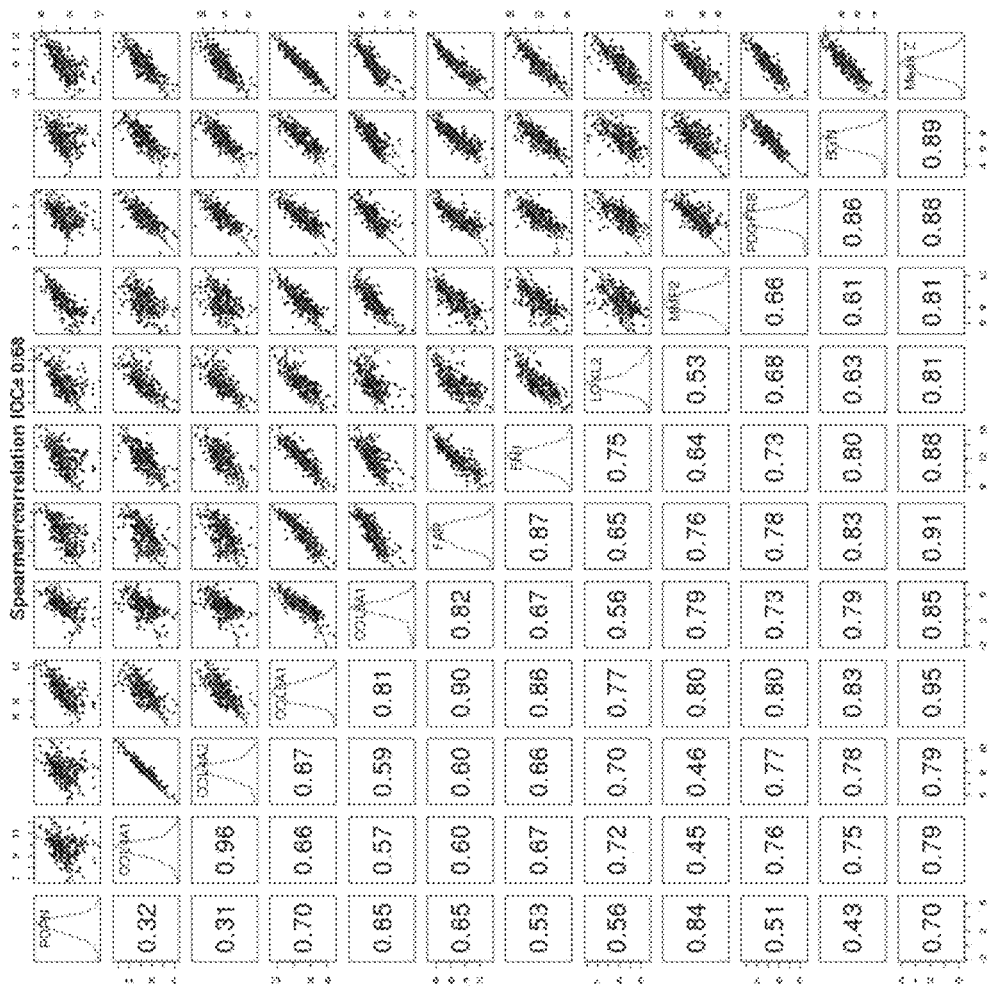
FIG. 11 is a Scattermatrix plot of active fibroblast signature genes.
Figure 19:
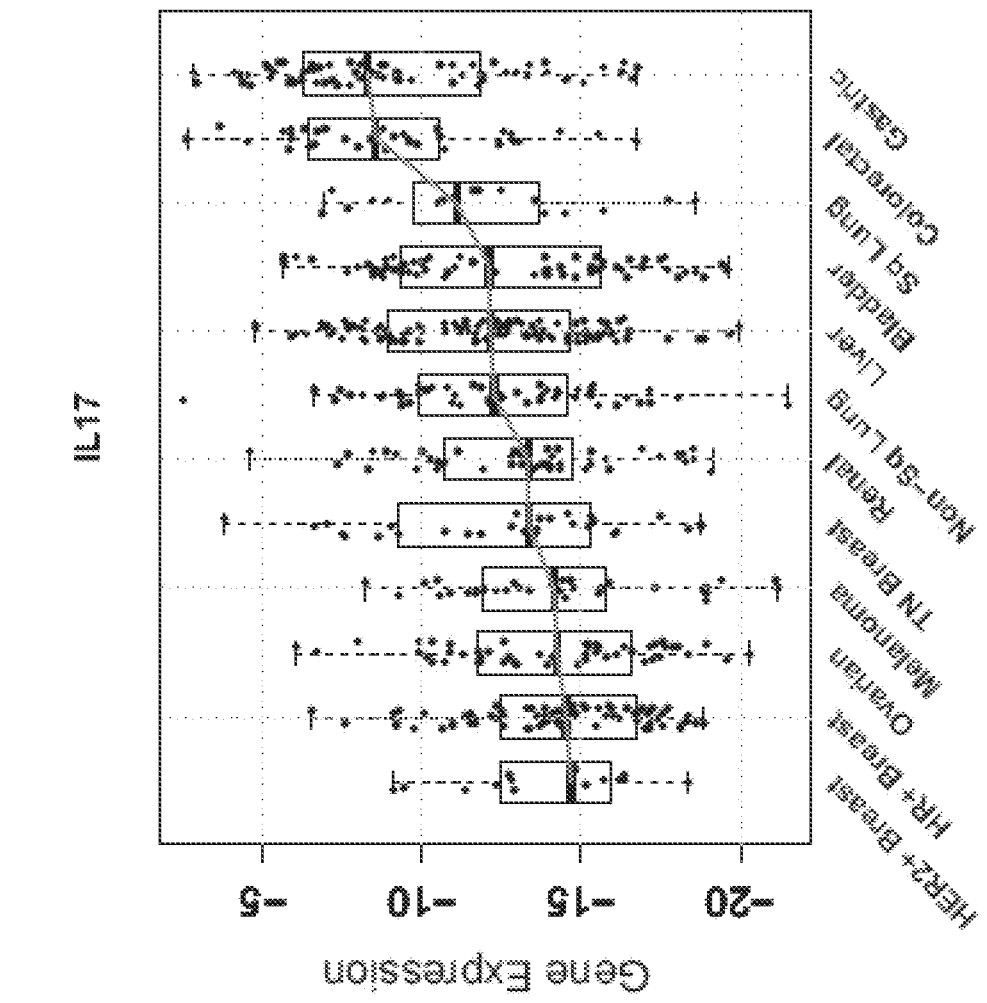
FIG. 19 is a plot of gene expression levels of Th17 (IL17) signature genes across indications.
Figure 20:
FIG. 20 shows multiple plots of IL17A/IL17F prevalence by indications. IL17 presence is determined by raw Ct<25. Sq- and Non-Sq Lung are collapsed into one group. HER2+ Breast was not evaluated due to small sample sizes.

While tumor infiltrating lymphocytes were shown to be associated with better prognosis in several cancer indications, production of IL-17A and IL-17F by Th17 cells was linked to worse prognosis in several tumors, such as CRC, TN BC (Couchad, 20123 Scientific Reports), and ovarian cancer. In some cases, production of IL-17A and IL-17F was associated with better prognosis in indications such as esophageal squamous carcinoma. Analysis of IL-17A and IL-17F across indications showed a complex distribution: tumors expressing IL-17A alone, IL-17F alone, IL-17A+/IL-17F+ and IL-17A−/IL-17F− (FIG. 20). The presence of single populations yielded to a gene signature index of 0.3 (FIG. 2A). Colorectal carcinoma is the indication with the highest levels of IL-17 genes, followed by squamous NSCLC, bladder and non squamous NSCLC (FIG. 19). Her2+ BC, HR+ BC, and OvCa were the indications with the lowest prevalence of IL-17 genes.

Figure 32:
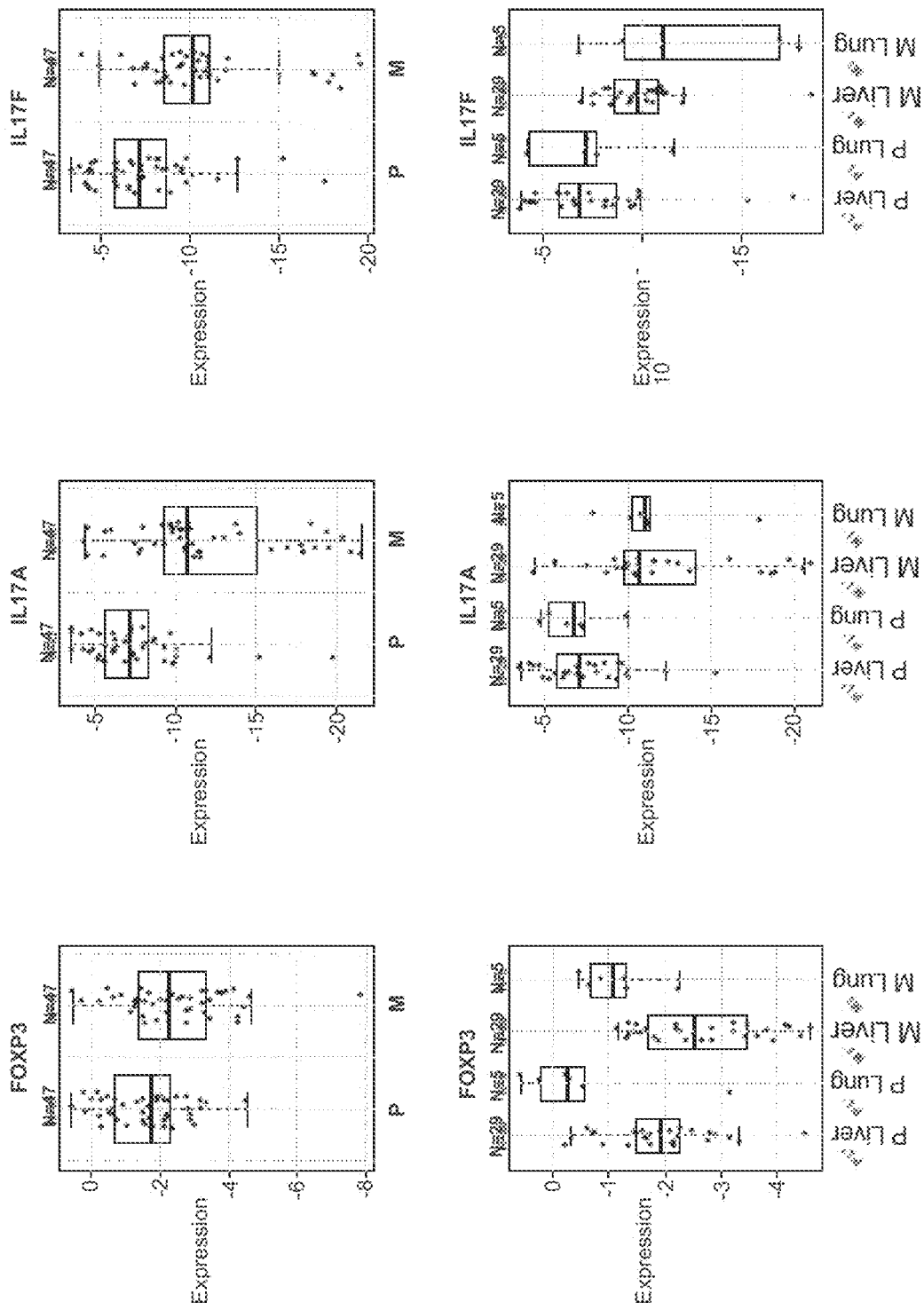
FIG. 32 shows Boxplots of gene set expression in association with primary vs. metastatic status.

When the prevalence of IL-17A and IL-17F was assessed in each indication, heterogeneity in the single and double gene distribution was observed. For instance, IL-17A and IL-17F were mainly co-expressed in CRC, squamous NSCLC, and bladder cancer, while Her2+ BC exhibited no IL-17A expression (FIG. 20). These results suggest that IL-17 biology may be distinct in each tumor type and that targeted therapies toward these cytokines may have to consider preponderance of the targeted tissue. For example, IL-17 signature was particularly overrepresented in primary CRC compared to all other tumor types. Th17 cells have been known to be associated with microbial dysbiosis in the colon. To examine if the high expression of Th17 signatures was unique to the primary tumor or if it was translated to distant metastases an analysis of matched primary tumors and metastases expression of IL-17 genes was assessed. Analysis of matched primary tumors and metastases showed that indeed the prevalence of Th17 signatures in CRC may be driven by the colon immunobiology rather than by characteristics of the tumor (FIG. 32). The liver is abundant in Kuppfer cells, sessile macrophages important in clearing cellular debris and gut derived microbial products. Considering that Arg1 and the myeloid markers are higher in CRC liver metastases, this suggested that resident organ microenvironment is an equally important determinant in contributing to the immunosuppressive microenvironment.

Example 6: Immune Response in the Tumor Microenvironment Changes Between Primary and Metastatic Sites The immune landscape in the tumor microenvironment may reflect either the endogenous immune responses characteristic of the organ or the specific recruitment by the tumor cells. Thus, it remains to be determined whether the tumor immune microenvironment is maintained when the tumor metastasizes. To test this possibility, the immune gene signatures were compared between 47 pairs of asynchronous matched primary and metastastic CRC tumors. Most of the metastases were located in the liver and lung (36 and 5, respectively) and the rest in other organs.

Differences of gene set expression between primary and metastatic pairs were evaluated using Wilcoxon signed-rank test, and multiplicity of the tests was adjusted using the Bonferroni approach. Table 12 shows log 2 fold change of primary over metastatic samples together with Wilcoxon signed-rank test p values (i.e., Table 12 shows the fold change of the gene signatures using metastases as denominator). A positive fold change indicates higher expression in the CR/PR group compared to the PD group. Boxplot of gene set expression in association with primary metastatic status is shown in FIG. 32.

TABLE 12

| Signature | log2FoldChange | raw p | Bonferroni corrected p |
|---|---|---|---|
| Teff | −0.36 | 0.13 | 1 |
| Treg | 0.74 | 0.00028 | 0.00224 |
| Inflammatory | 0.67 | 0.0085 | 0.068 |
| NKcell | 0.5 | 0.092 | 0.736 |
| Bcell | −0.08 | 0.55 | 1 |
| Myeloid | −0.49 | 0.025 | 0.2 |
| IL17 | 4 | 3.8e−07 | 3.04e−06 |
| Teff/Treg | −0.91 | 5.4e−08 | 4.32e−07 |

The IL-17 gene signature, characteristic of primary CRC tumors, was strikingly reduced in CRC metastases, irrespective of location in the liver or lung (−4 fold, p=3.04×10^−6). $T_{reg}$ were also significantly decreased in metastases (−0.76 fold, p=0.002272). While there were no significant differences in $T_{eff}$ between primary and metastases, the $T_{eff}$:$T_{reg}$ ratio was significantly increased in the metastases (+0.91 fold, p=4.344×10^−7). Finally, myeloid gene sets tend to be increased in the metastasis while the inflammatory signature is reduced (+0.49 and −67, p=0.1992 and 0.068, respectively).

Differences of immune gene expression between primary and metastatic pairs were evaluated using Wilcoxon signed-rank test for each of the 96 immune genes, and multiplicity of the tests were adjusted using the Bonferroni approach. Genes that were identified as significantly differentially expressed between primary and metastatic samples (Bonferroni corrected p≤0.05) were ARG1, IL17A, VTCN1, IL17F, IL1B, HLA.E, HAVCR2, CD70, FOXP3 and PTGS2.

Figure 33:
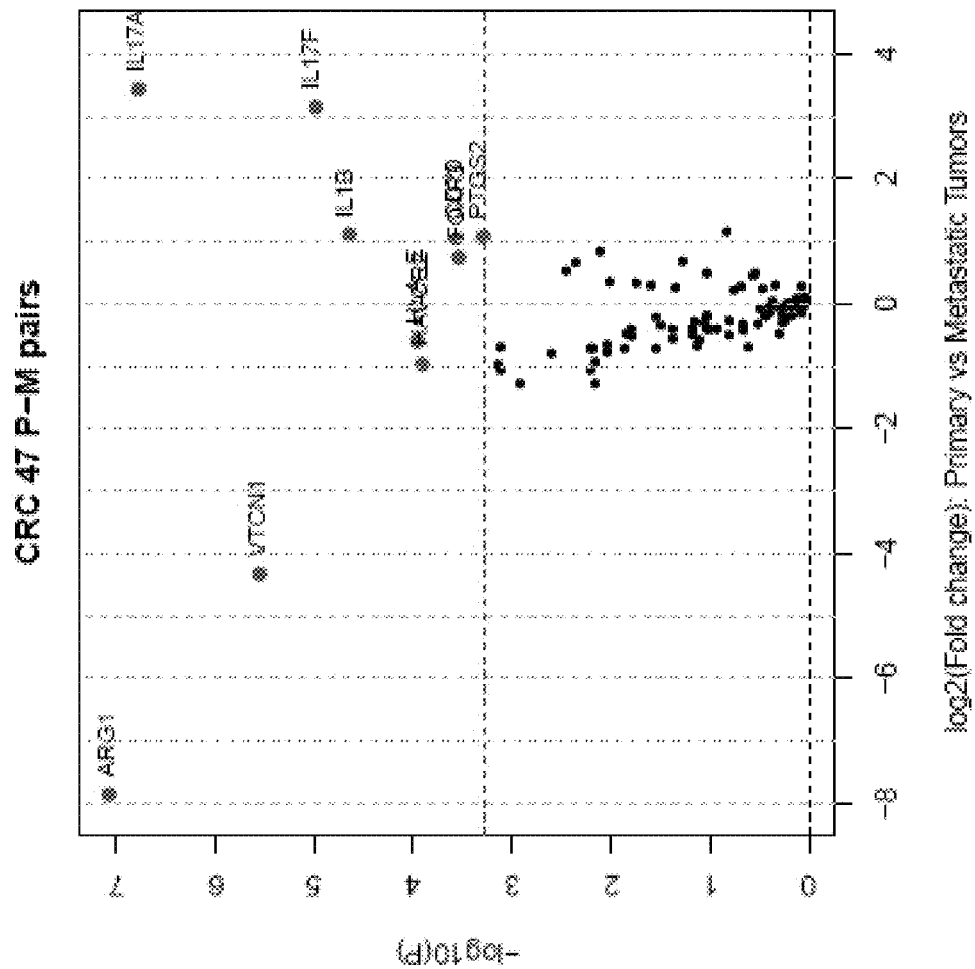
FIG. 33 is a Volcano plot for immune gene expression in association with CRC primary vs. metastatic status. Y axis is raw signed-rank Wicoxon p-value, and X axis is log 2 based fold change between primary and metastatic samples. Genes labeled had Bonferroni adjusted P≤0.05: ARG1, IL17A, VTCN1, IL17F, IL1B, HLA.E, HAVCR2, CD70, FOXP3 and PTGS2.

At the level of individual genes, Arg1, expressed in hepatocytes and anti-inflammatory macrophages, was the single highest upregulated gene between colon primary and liver metastases (FIG. 33). Taken together, these results suggest that the immune responses in the tumor microenvironment changes between primary and metastatic sites, mirroring the subjacent immune landscape of the organ rather than specific recruitment by tumor cells.

Example 7: Hormone Driven Tumors Display Reduced Inflammation

Figure 21:
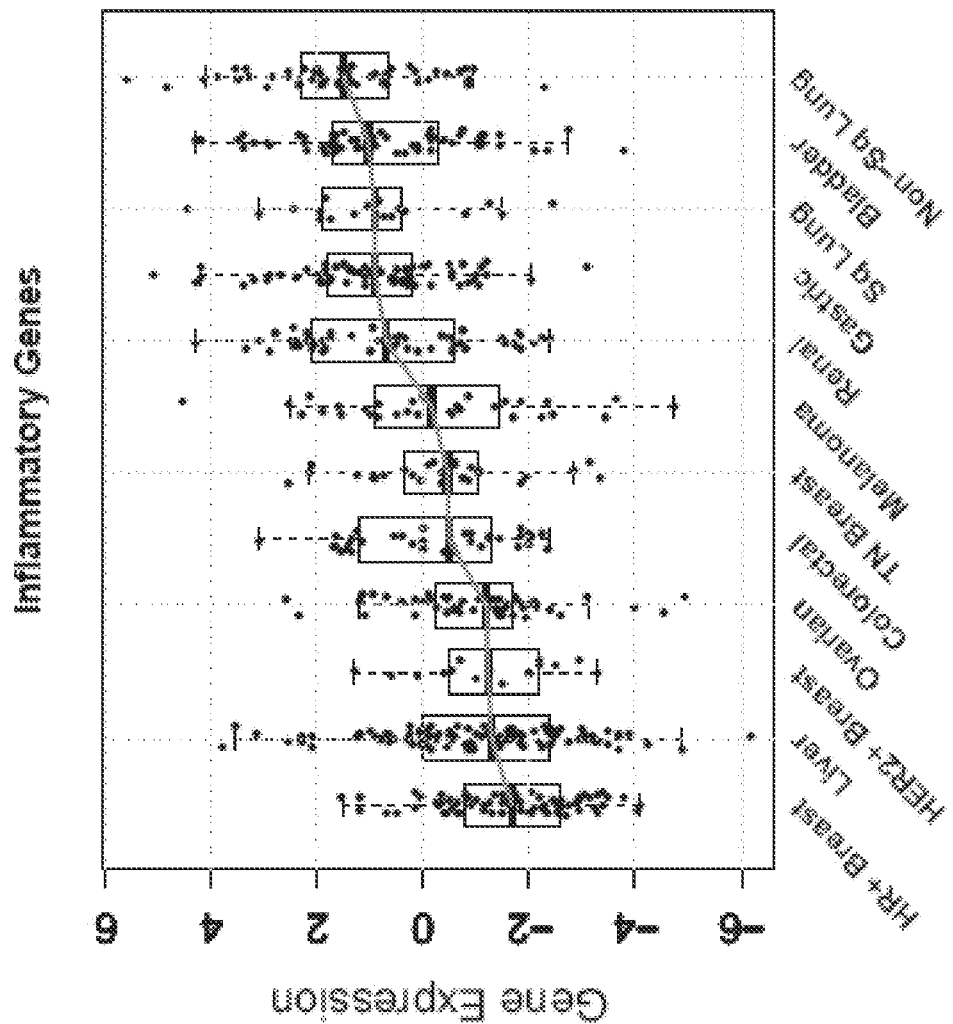
FIG. 21 is a plot of gene expression levels of inflammatory signature genes across indications.

Tumor-associated inflammation may promote tumor growth, angiogenesis, and recruitment of myeloid suppressor cells, which in turn switch off T cell mediated antitumoral response. Inflammasome products (IL-13 and IL-18), chemokines (CCL2, CCL22) and cytokines (IL-6, IL-8) were described to be part of this process in different indications. By using an inflammatory gene signature, it was observed that the overall inflammation varied across indications (FIG. 21). The most inflamed tumors were NSCLC, UBC, and RCC, while the least inflamed indications were HR+ BC, liver, Her2+ BC, and OvCa. These results suggest that hormone driven tumors display reduced local inflammation.

Figure 22:
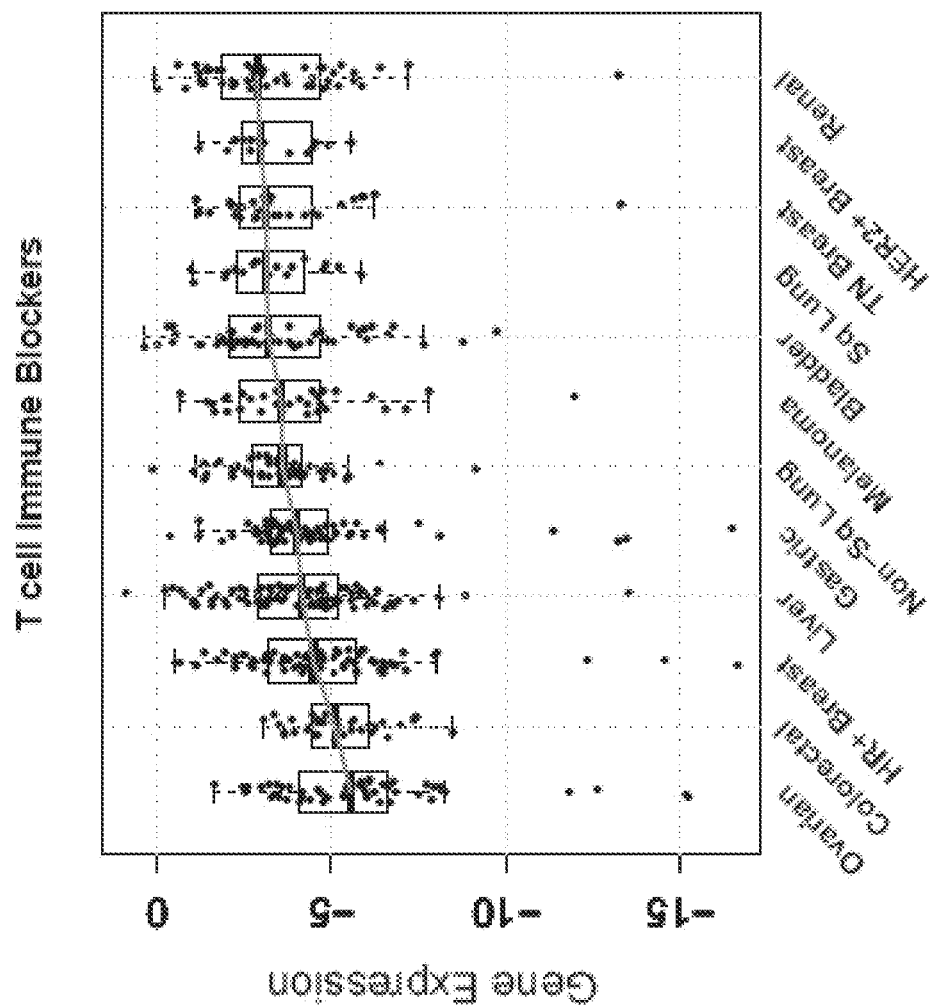
FIG. 22 is a plot of gene expression levels of immune blockers on T cells across indications.
Figure 26:
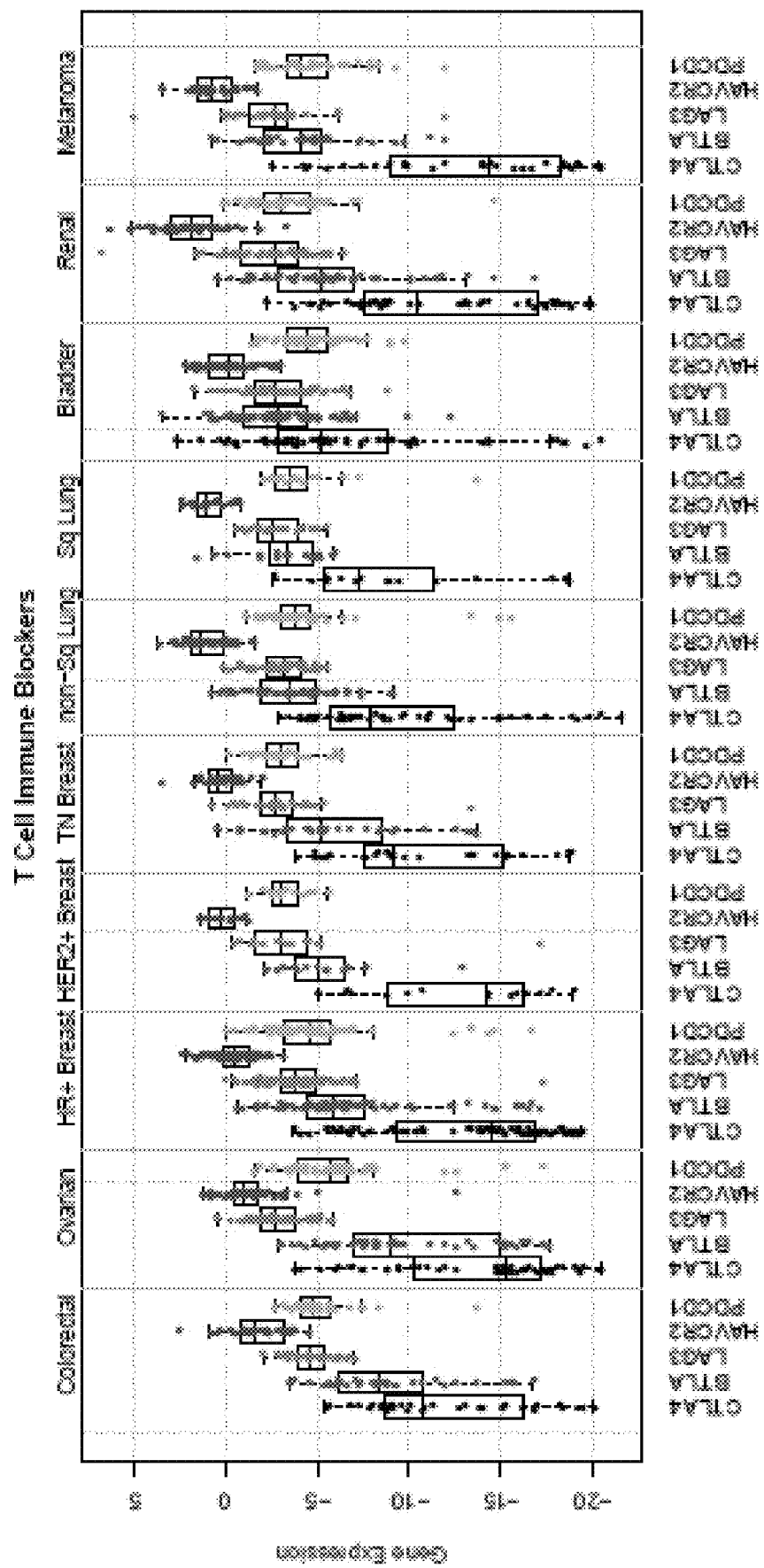
FIG. 26 is a plot showing gene expression levels of particular genes in the immune blockers on T cell signature genes across indications.

Example 8: The Presence of T Cell Immune Blockers Trails $T_{eff}$ Distribution Across Cancer Indications To prevent uncontrolled $T_{eff}$ activation, inhibitory receptors (IB) are upregulated on immune cells and/or tumor cells upon T cell activation. A mechanism of tumor escape is induction of the ligands for T cell IB, therefore turning off effective anti-tumor responses. To determine the possible impact of these receptor:ligand interactions, prevalence of IB T cell signatures and IB APC/tumor signatures were analyzed. Presence of T cell immune blockers trailed $T_{eff}$ distribution across indications (FIG. 22). In all indications, CTLA4 presented the lowest prevalence of IB T cell, while Tim3 (HVACR2) had the highest (FIG. 26). PD-1 and Lag3 were second in abundance in the IB T cell signature. Expression of BTLA was either reduced in OvCa and CRC or expressed similarly to PD1 and Lag3 in melanoma, RCC, UBC, BC, and NSCLC. These data suggest that, regardless of the tumor type, infiltrating $T_{eff}$ were similarly equipped with inhibitory receptors.

Figure 23:
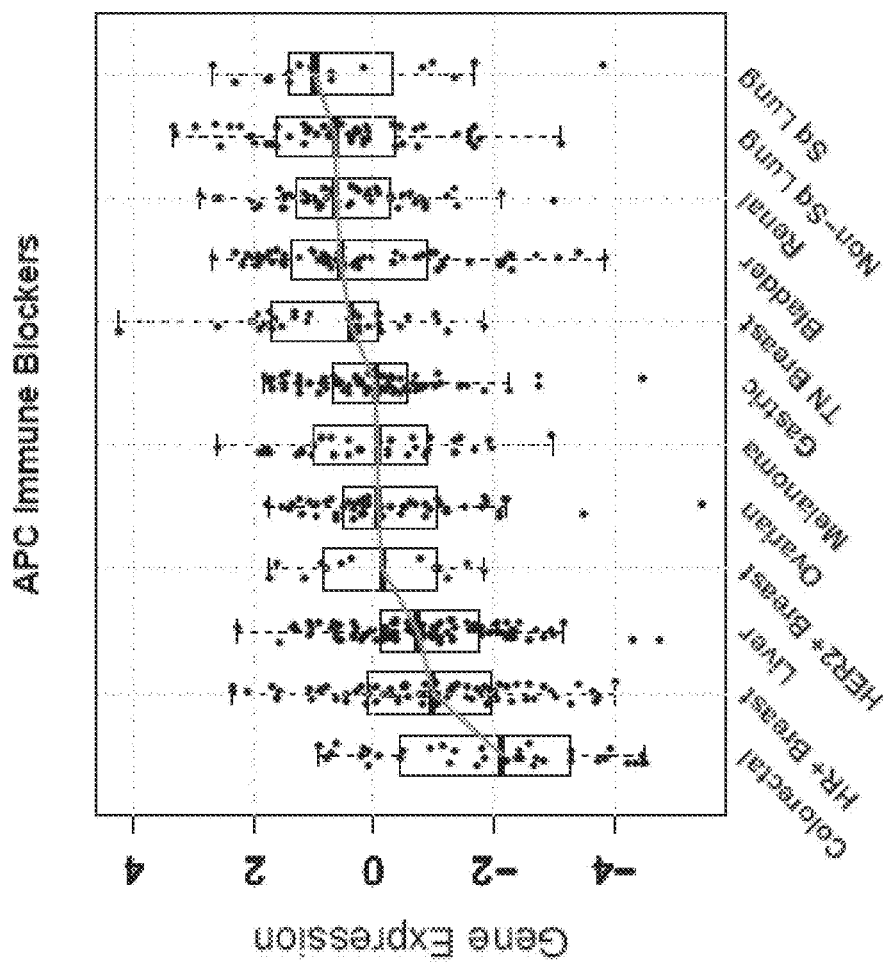
FIG. 23 is a plot of gene expression levels of immune blockers on APCs across indications.
Figure 24:
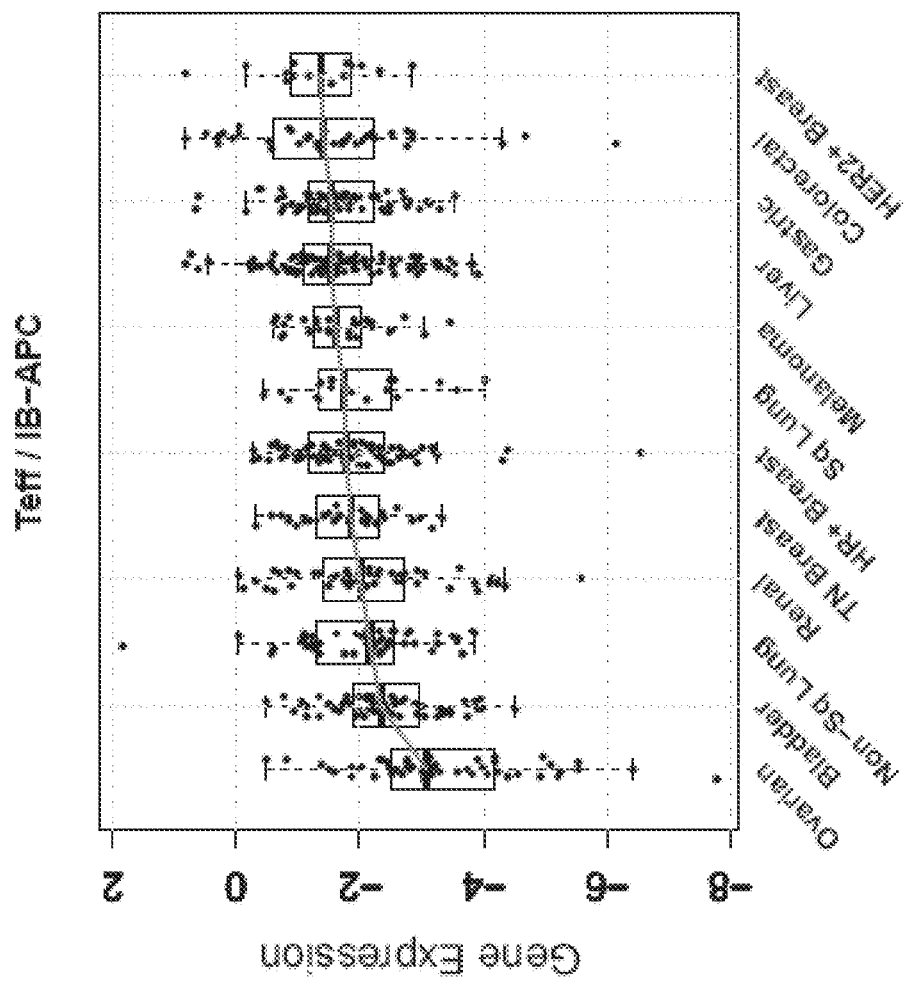
FIG. 24 is a plot of gene expression ratios of T effector vs. immune blockers on APC across indications.
Figure 25:
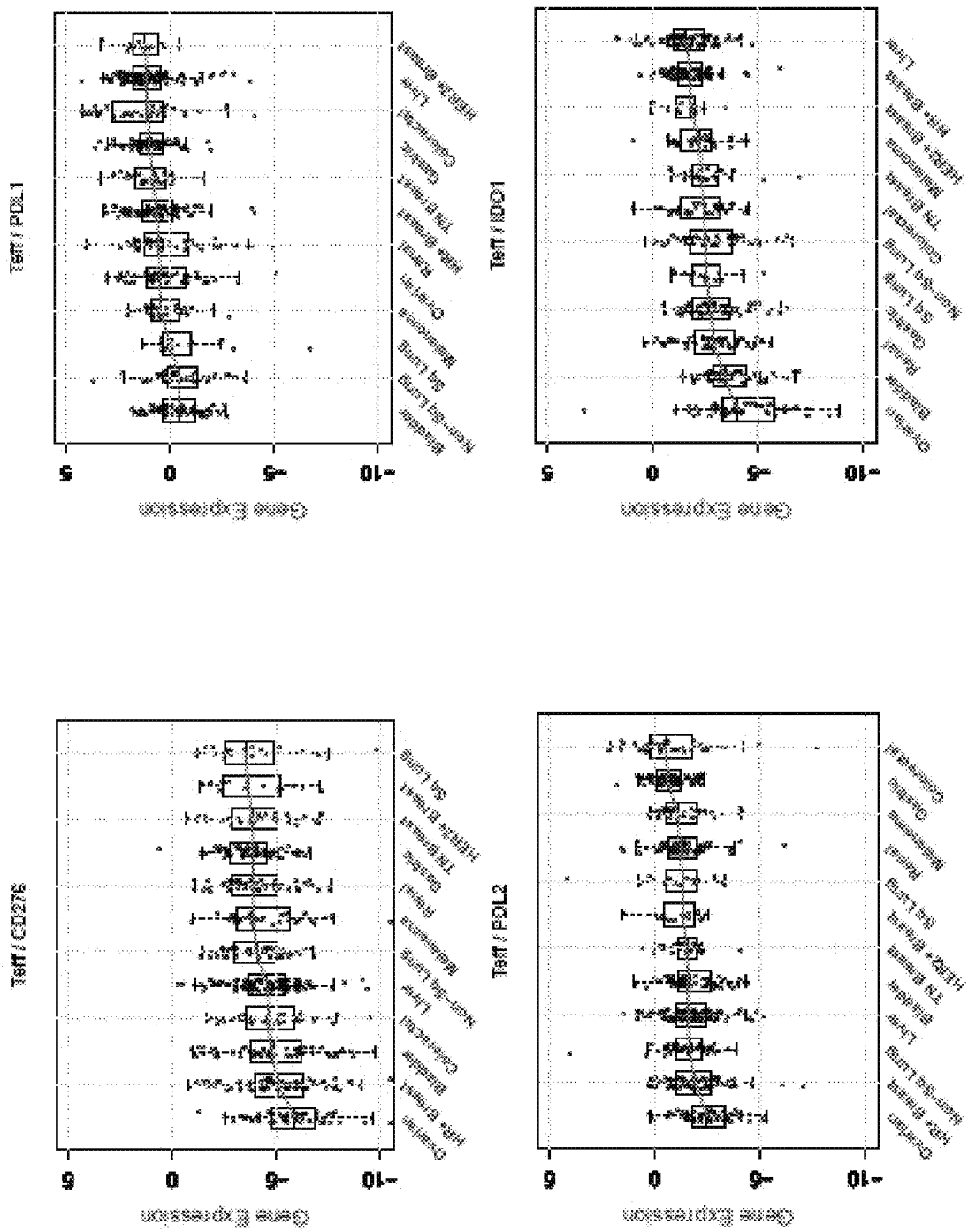
FIG. 25 shows multiple plots of gene expression ratios of T effector vs. particular genes in the immune blockers on APC signature genes across indications.
Figure 27:
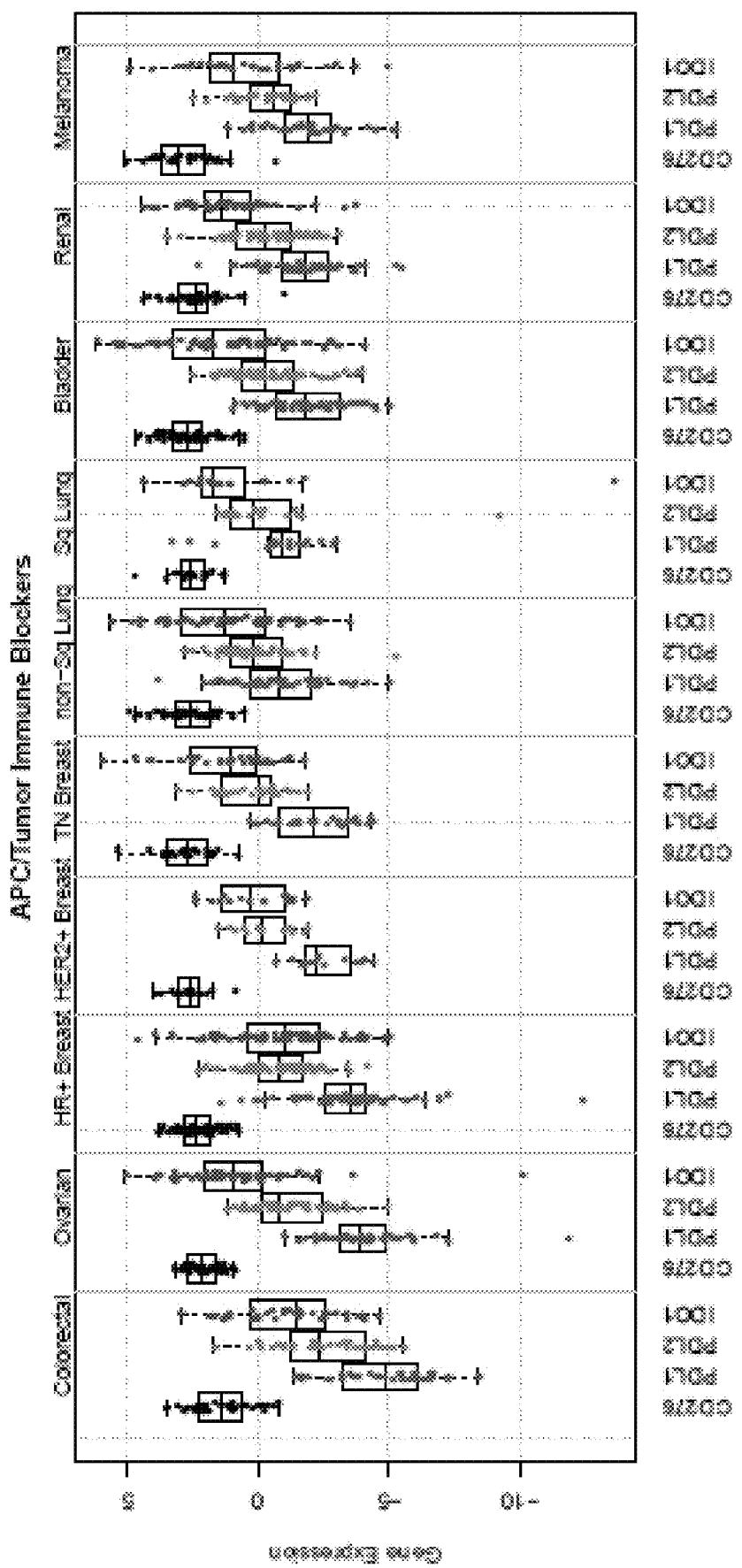
FIG. 27 is a plot showing gene expression levels of particular genes in the immune blockers on APC signature genes across indications.

Intratumoral antigen presenting cells (APC) and tumors express the inhibitory ligands for IB T cells as well as enzymes that produce catabolytes that inhibit T cell activation. To analyze the presence of IB APC/tumor, a gene signature was generated and analyzed across indications. Prevalence of APC-IB signature was similar among indications, except for a marked reduction in HR+ BC and CRC (FIG. 23). A granular analysis of genes was conducted to assess the relative expression patterns of individual APC-IB genes across cancer types (FIG. 27). Expression of CD276 was highest and differentiated from the other genes. PD-L1, PD-L2, and IDO1 were highly correlated (0.7). Of these genes, the highest expressed was IDO1 (FIG. 27). In addition, the ratio of gene expression of $T_{eff}$ gene signatures to APC-IB gene signatures was also determined across indications (FIG. 24). The ratio of gene expression of $T_{eff}$ gene signatures to each individual gene in the APC-IB gene signature was also determined across indications (FIG. 25). Of these, OvCa and HR+ BC had the lowest ratios of Teff/CD276 and Teff/PDL2, while OvCa alone had the lowest Teff/IDO1 ratio, suggesting that immunotherapy in OvCa may require the blockade of several immune inhibitors to trigger a treatment response.

Figure 28:
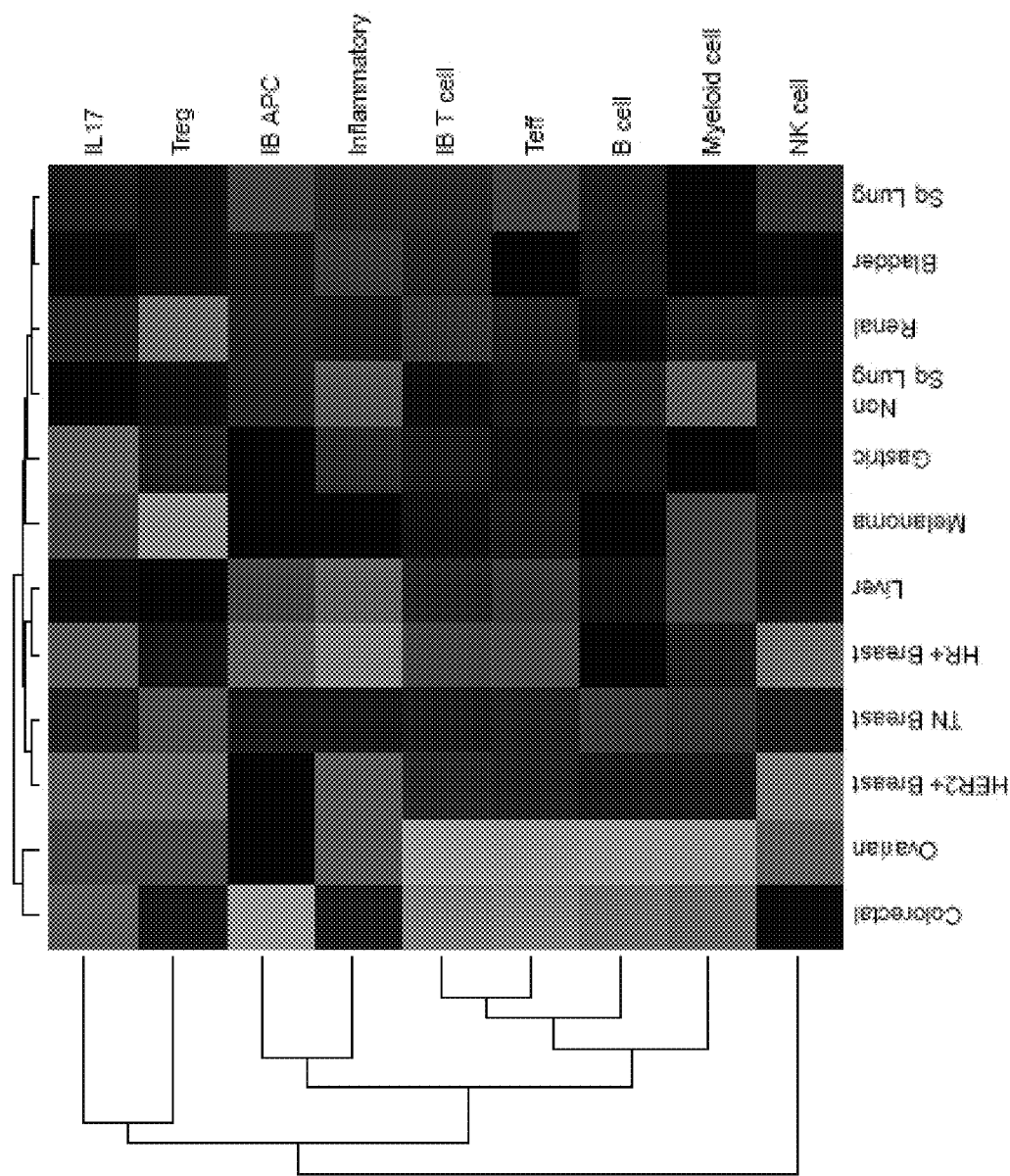
FIG. 28 is a plot showing the hierarchical clustering of immune gene signature expression across indications. Genes were median centered across the samples. Euclidean distance and complete linkage were used to generate the dendrogram. Red and green colors indicate higher and lower expression compared to median, respectively. Black indicates median expression.

Example 9: A High Degree of Heterogeneity is Present in the Immune Signature Gene Sets Across Cancer Indications A hierarchical clustering of the immune gene sets across indications was performed to analyze the immune landscape among tumor type. A high degree of heterogeneity was observed in the immune gene sets across indications, where some tumors showed a remarkable immune presence, while others were "immune deserts" (FIG. 28).

The unsupervised analysis clustered together the three types of breast cancer and the two types of lung tumors, suggesting that immunological similarities may arise from the tissue where the tumors grow. On the other hand, CRC and OvCa showed an immune desert cluster, devoid of immune gene signatures, except for IL17 and NK, respectively. Overall, the tumors with highest $T_{eff}$ infiltration were melanoma, RCC, NSCLC(Sq) and Her2+ and TN BC. However, the latter two cancers (i.e., Her2+ and TN BC) also exhibited a high incidence of $T_{reg}$, suggesting that the intratumoral immune responses in these tumors may be negated by the effects of $T_{reg}$. The most inflamed tumor was NSCLC-non squamous carcinoma, followed by NSCLC-squamous cell carcinoma, and UBC. The tumors with the highest incidence of IB APC/tumors were NSCLC, RCC, UBC, followed by melanoma, and TN BC. On the other hand, CRC, OvCa, HR+, and Her2+ BC had no signs of inflammation.

Considering the factors mentioned above, it is predicted that no single factor across indications contributes to responses to checkpoint inhibition but rather the complexity of the tumor immune microenvironment dictates the drivers of resistance or response to immunotherapy. Therefore, analyzing the differences in one or more immune cell gene signatures from multiple gene sets likely provides a more complete prognosis for resistance or response to immunotherapy.

Figure 34:
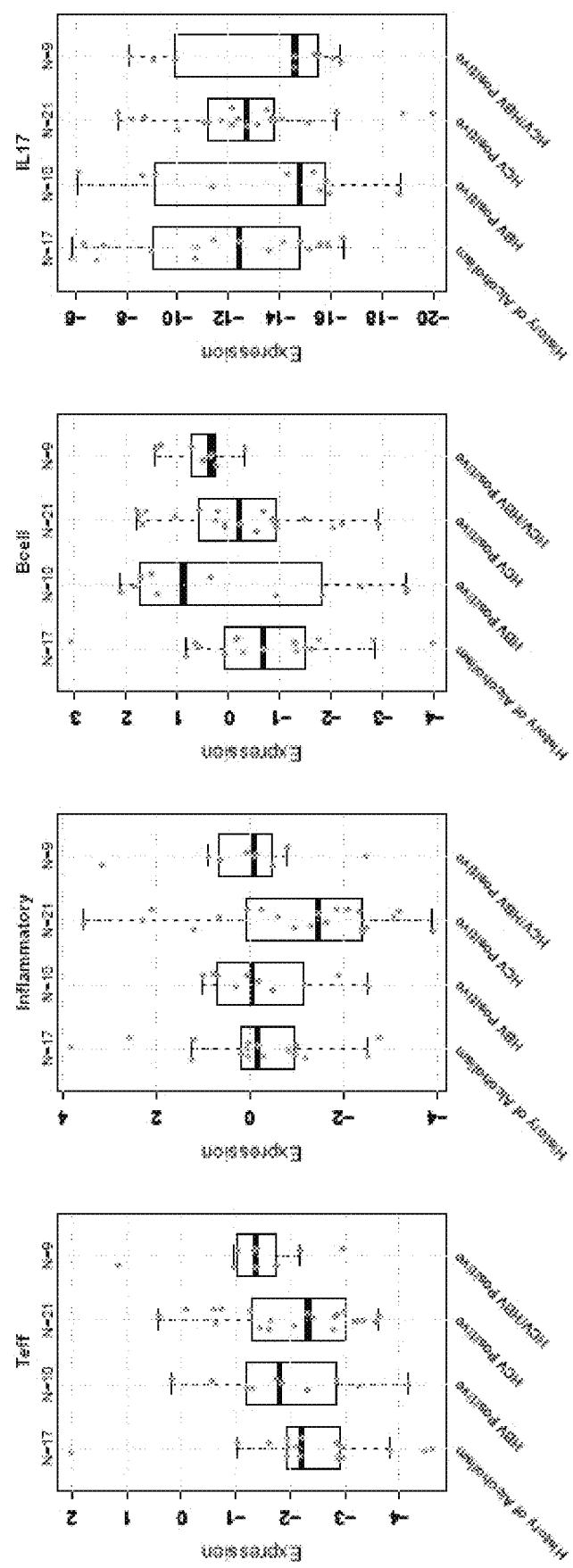
FIG. 34 shows Boxplots of gene set expression in association with etiology.
Figure 34:
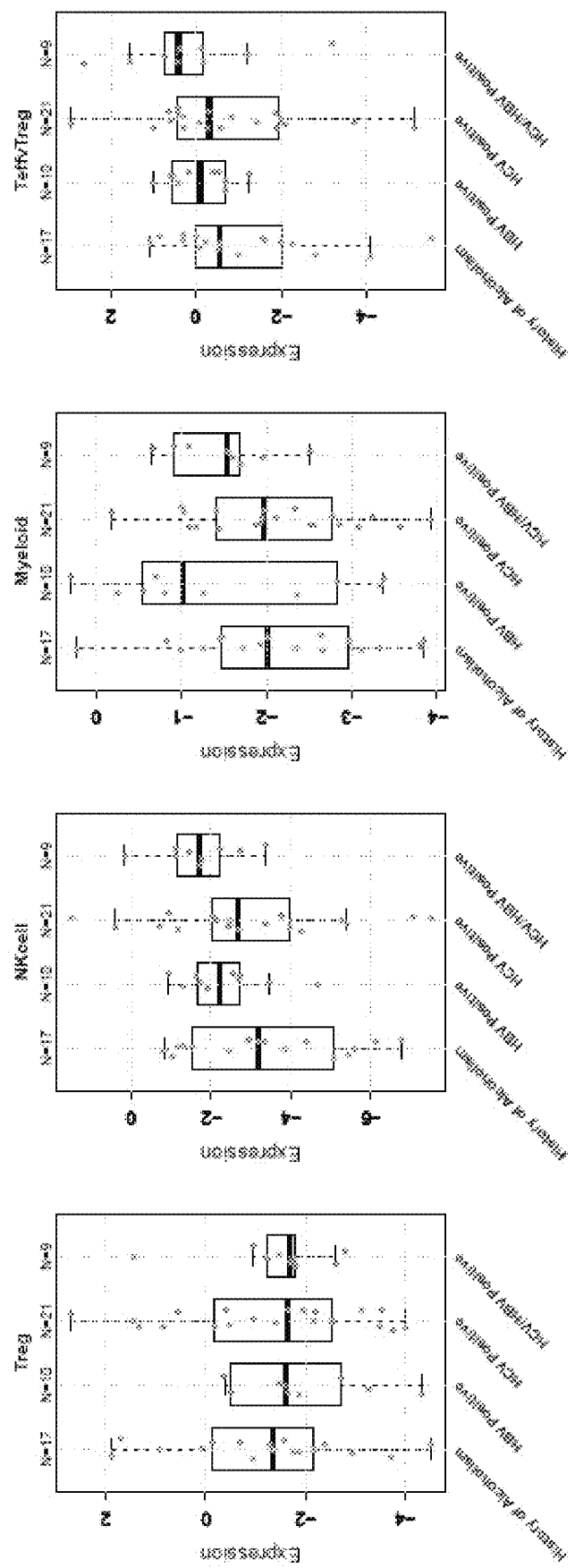
Figure 35:
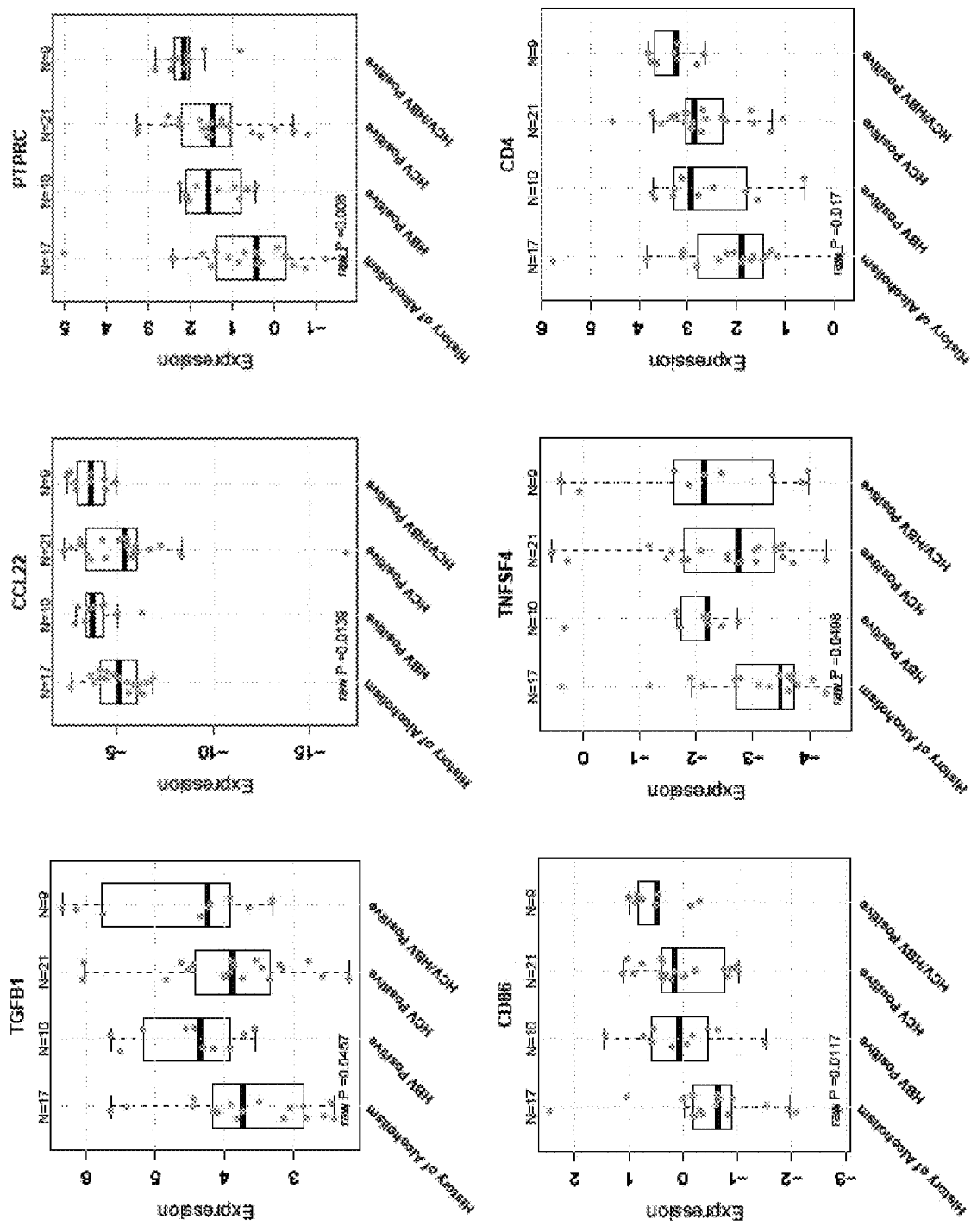
FIG. 35 shows Boxplots of immune genes having Kruskal Wallis P≤0.05 for association with etiology.
Figure 35:
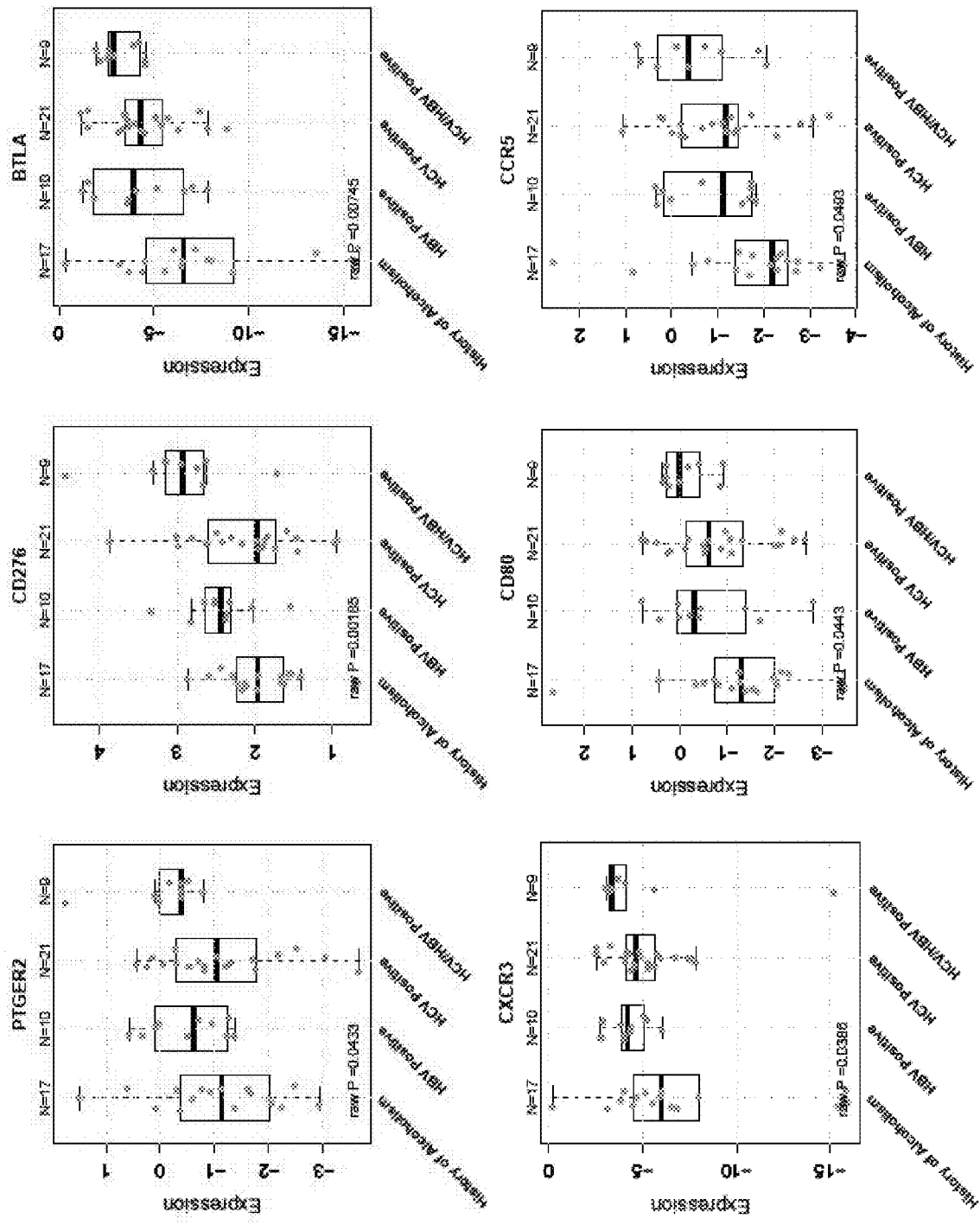
Figure 35:
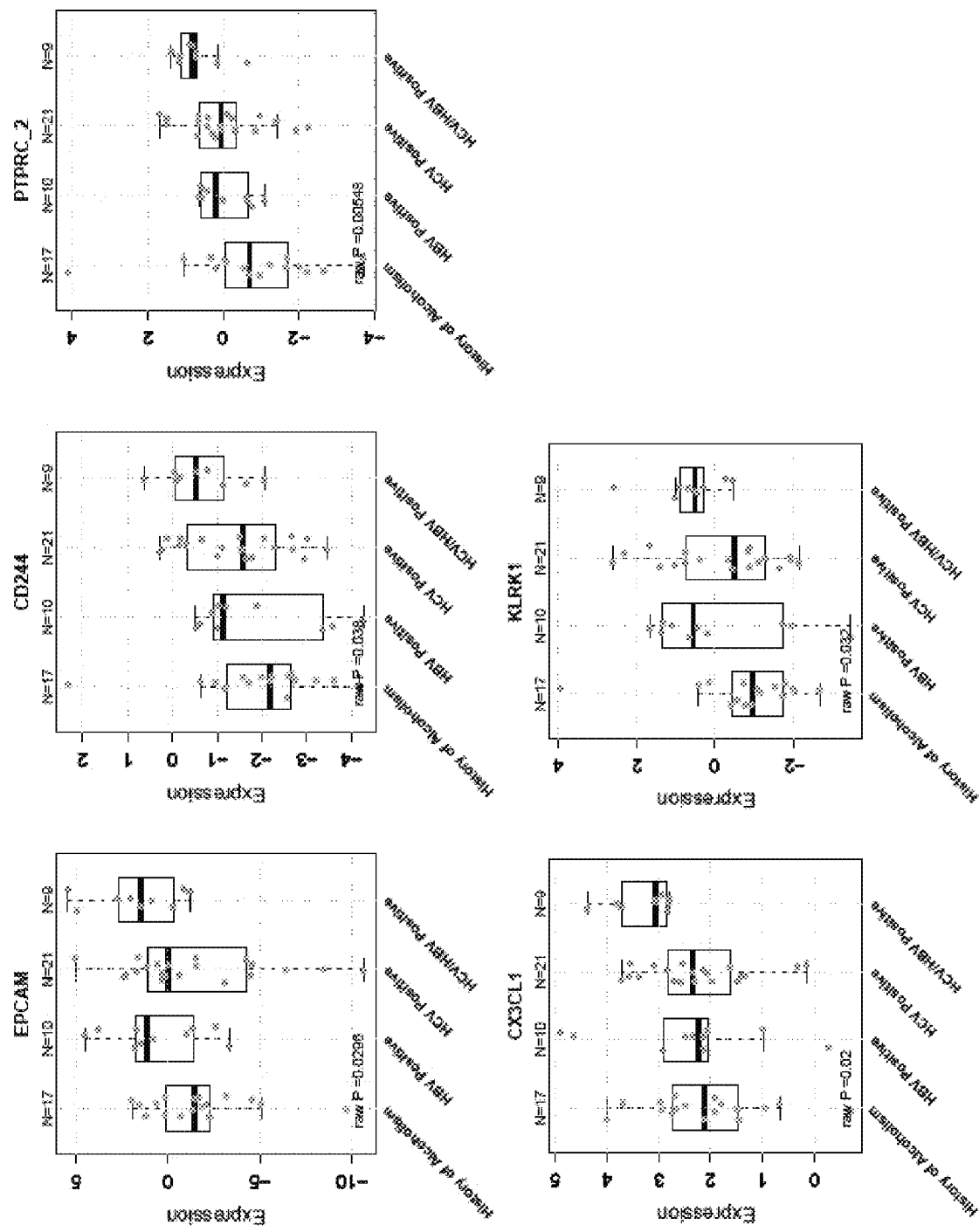

Example 10: Gene Set Expression is not Significantly Associated with Hepatocellular Carcinoma (HCC) Etiology Differences in gene set expression between the four etiology groups in HCC were evaluated using Kruskal Wallis tests, and multiplicity of the tests was adjusted using the Bonferroni approach. Table 13 shows median expression for each etiology group together with Kruskal-Wallis test p values. No immune subset was found to be significantly associated with HCC etiology although $T_{eff}$ subset was numerically higher in the virus double positive group (FIGS. 34 and 35). Differences of immune gene expression were evaluated using Kruskal-Wallis test for each of the 96 immune genes shown in Table 14 and no multiplicity correction was applied. These data suggest that despite disparate tumor etiologies, liver tumors share similar immune microenvironments.

Figure 36:
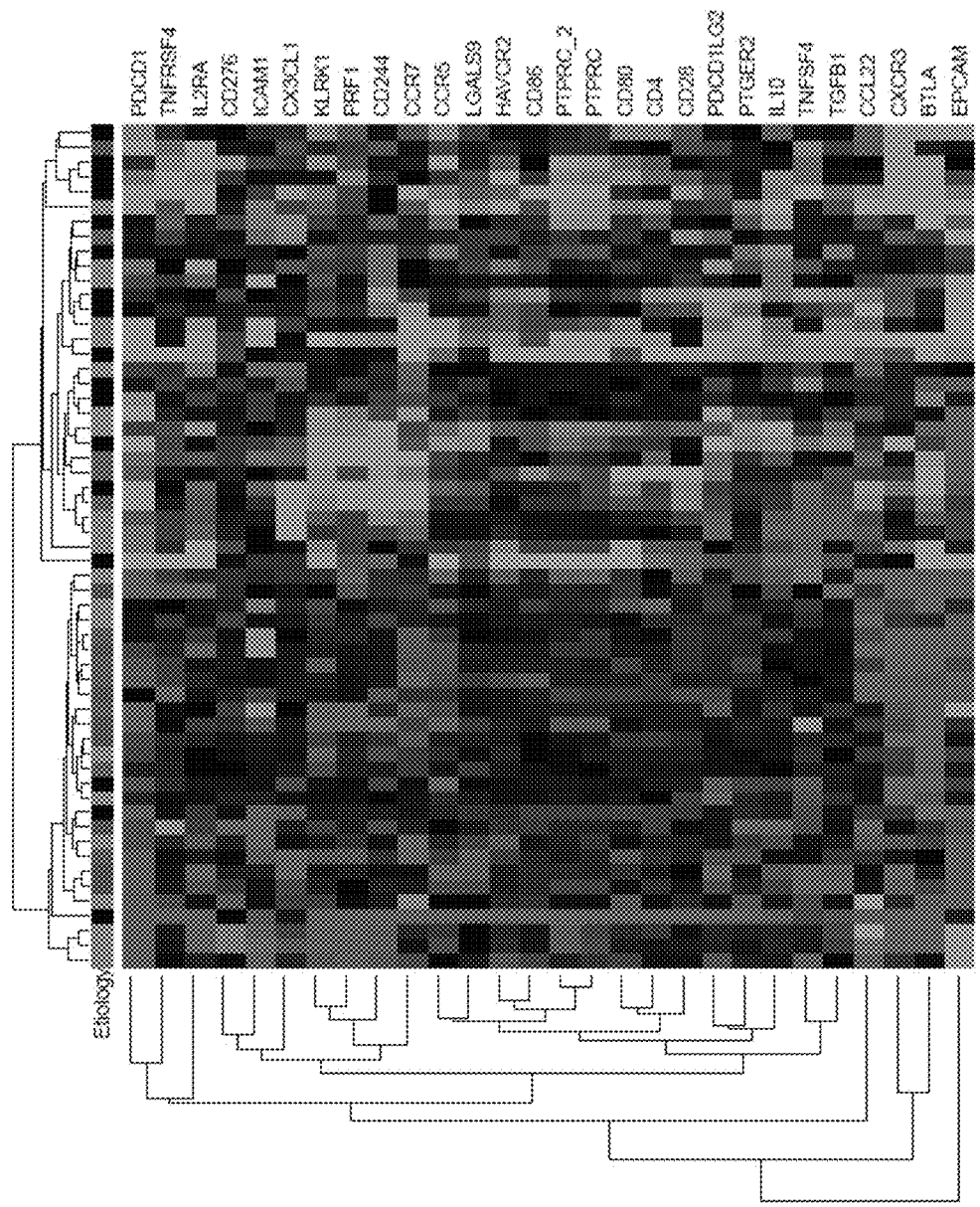
FIG. 36 is a hierarchical clustering of immune genes having p≤0.1 for etiology differences. Genes were median centered across the samples. Euclidean distance and complete linkage were used to generate the dendrogram. Red and green colors indicate higher and lower expression compared to median, respectively. Black indicates median expression. The following colors differentiate etiologies: black=history of Alcoholism; red=HBV+; green=HCV+; blue=HBV+ HCV+.

Hierarchical clustering of immune genes having P≤0:1 for etiology differences is shown in FIG. 36. Genes were median centered across the samples. Euclidean distance and complete linkage were used to generate the dendrogram. Red and green colors indicate higher and lower expression than median, respectively. Black indicates median expression. The following colors differentiate etiologies: black/History of Alcoholism; red/HBV+; green/HCV+; blue/HBV+ HCV+. A high degree of intraclass heterogeneity was present in HCC, with roughly half of tumors with high immune genes, but this difference could not be explained by HCC etiologic subtypes.

TABLE 13

| Signature | Alcoholism | HBV+ | HCV+ | HBV+ HCV+ | raw p | Bonferroni corrected p |
| --- | --- | --- | --- | --- | --- | --- |
| Teff | −2.22 | −1.8 | −2.33 | −1.36 | 0.14 | 1 |
| Treg | −1.36 | −1.6 | −1.64 | −1.68 | 0.882 | 1 |
| Inflammatory | −0.16 | −0.04 | −1.46 | −0.08 | 0.245 | 1 |
| NKcell | −3.18 | −2.23 | −2.69 | −1.7 | 0.142 | 1 |
| Bcell | −0.67 | 0.88 | −0.22 | 0.35 | 0.151 | 1 |
| Myeloid | −2 | −1.02 | −1.96 | −1.53 | 0.158 | 1 |
| IL17 | −12.4 | −14.77 | −12.7 | −14.61 | 0.58 | 1 |
| Teff/Treg | −0.56 | −0.1 | −0.32 | 0.41 | 0.201 | 1 |

TABLE 14

| | | | | | | | |
| --- | --- | --- | --- | --- | --- | --- | --- |
| ARG1 | BTLA | CCL2 | CCL22 | CCL28 | CCL5 | CCR5 | CCR7 |
| CD1C | CD244 | CD27 | CD274 | CD274_IvG | CD276 | CD28 | CD3E |
| CD4 | CD40 | CD40LG | CD48 | CD69 | CD70 | CD80 | CD8A |
| CD8B | CLEC4C | CSF2 | CTLA4 | CX3CL1 | CXCL10 | CXCL9 | CXCR3 |
| EOMES | EPCAM | FCRL5 | FOXP3 | GUSB | GZMA | GZMB | HAVCR2 |
| HLA_A | HLA_B | HLA_C | HLA_E | ICAM1 | ICOS | IDO1 | IFNγ |
| IL10 | IL12A | IL13 | IL17A | IL17F | IL1B | IL2 | IL2RA |
| IL4 | IL6 | IL7 | IL7R | IL8 | ITGAM | ITGAX | KLRK1 |
| LAG3 | LGALS9 | MAP4K1 | MICA | MICB | MS4A1 | NCAM1 | PDCD1 |
| PDCD1LG2 | PRF1 | PTGER2 | PTGER4 | PTGS2 | PTPRC | PTPRC_2 | RORC |
| SDHA | SP2 | TBX21 | TFRC | TGFB1 | TMEM55B | TNF | TNFRSF14 |
| TNFRSF4 | TNFSF9 | VCAM1 | VEGFA | VPS33B | VTCN1 | CD86 | TNFSF4 |

The invention claimed is:

1. A method of selecting treating a human patient having non-squamous non-small cell lung cancer (NSCLC), the method comprising:
  (i) determining the expression level of an immune cell gene signature in a tumor sample obtained from the patient, the immune cell gene signature comprising the following gene signature set:
    ITGAM, ITGAX, CD1C, and CLEC4C
  wherein an increase in the level of expression of each member of the immune cell gene signature relative to a median level identifies the patient for treatment with an immunotherapy; and
  (ii) administering the immunotherapy to the patient.

2. The method of claim 1, wherein the expression level of ITGAM, ITGAX, CD1C, and CLEC4C is correlated with the presence of myeloid cells in a tumor microenvironment of the tumor sample.

3. The method of claim 1, further comprising determining the ratio of Teff to Treg cells.

4. The method of claim 3, wherein if the ratio of Teff to Treg is high, the patient will likely benefit from an immunotherapy.

5. The method of claim 3, wherein if the ratio of Teff to Treg is low, the patient will likely benefit from an immunotherapy.

6. The method of claim 1, wherein the determining is carried out prior to administering the immunotherapy in order to provide a patient with a pre-administration prognosis for response.

7. The method of claim 1, wherein the non-squamous NSCLC is primary, advanced, refractory, or recurrent.

8. The method of claim 1, wherein expression of the immune cell gene signature in the tumor sample obtained from the patient is detected by measuring mRNA.

9. The method of claim 1, wherein the immunotherapy enhances tumor immunogenicity.

10. The method of claim 1, wherein the immunotherapy comprises treatment with a CD28, OX40, GITR, CD137, CD27, ICOS, HVEM, NKG2D, MICA, or 2B4 agonist or treatment with a CTLA-4, PD-1 axis, TIM-3, BTLA, VISTA, LAG-3, B7H4, CD96, TIGIT, or CD226 antagonist.

11. The method of claim 10, wherein the immunotherapy comprises treatment with a PD-1 axis binding antagonist.

12. The method of claim 11, wherein the PD-1 axis binding antagonist is a PD-L1 binding antagonist, a PD-1 binding antagonist, or a PD-L2 binding antagonist.

13. A method of treating a human patient having non-squamous NSCLC, the method comprising administering an immunotherapy to the patient, wherein the expression level of an immune cell gene signature in a tumor sample obtained from the patient has been determined to have an increase in the level of expression of each member of the immune cell gene signature relative to a median level, the immune cell gene signature comprising the following gene signature set: ITGAM, ITGAX, CD1C, and CLEC4C.

* * * * *